(12) United States Patent
Liu et al.

(10) Patent No.: US 10,934,258 B2
(45) Date of Patent: Mar. 2, 2021

(54) MATERIALS FOR USE IN AN AQUEOUS ORGANIC REDOX FLOW BATTERY

(71) Applicants: Tianbiao Liu, Logan, UT (US); Bo Hu, Logan, UT (US); Camden DeBruler, Logan, UT (US); Jian Luo, Logan, UT (US)

(72) Inventors: Tianbiao Liu, Logan, UT (US); Bo Hu, Logan, UT (US); Camden DeBruler, Logan, UT (US); Jian Luo, Logan, UT (US)

(73) Assignee: Utah State University, Logan, UT (US)

(*) Notice: Subject to any disclaimer, the term of this patent is extended or adjusted under 35 U.S.C. 154(b) by 228 days.

(21) Appl. No.: 15/659,593

(22) Filed: Jul. 25, 2017

(65) Prior Publication Data

US 2018/0072669 A1    Mar. 15, 2018

Related U.S. Application Data

(60) Provisional application No. 62/366,458, filed on Jul. 25, 2016.

(51) Int. Cl.
| | |
|---|---|
| *H01M 8/18* | (2006.01) |
| *H01M 8/04276* | (2016.01) |
| *H01M 8/04746* | (2016.01) |
| *C07D 213/22* | (2006.01) |
| *C07D 211/94* | (2006.01) |

(52) U.S. Cl.
CPC .......... *C07D 213/22* (2013.01); *C07D 211/94* (2013.01); *H01M 8/04276* (2013.01); *H01M 8/04746* (2013.01); *H01M 8/188* (2013.01); *Y02E 60/50* (2013.01)

(58) Field of Classification Search
CPC ............... H01M 8/18; H01M 8/04276; H01M 8/04746; C07D 213/22; C07D 211/94
See application file for complete search history.

(56) References Cited

U.S. PATENT DOCUMENTS

| | | | | |
|---|---|---|---|---|
| 2013/0273459 | A1 | 10/2013 | Xu et al. | |
| 2014/0028260 | A1* | 1/2014 | Goeltz | H01M 8/188 320/127 |
| 2014/0370405 | A1* | 12/2014 | Zhang | H01M 8/20 429/418 |
| 2015/0236543 | A1 | 8/2015 | Brushett et al. | |

FOREIGN PATENT DOCUMENTS

| | | |
|---|---|---|
| CN | 104300167 A | 1/2015 |
| CN | 103000924 B | 2/2015 |
| WO | 2014150210 A1 | 9/2014 |

OTHER PUBLICATIONS

Liu et al., A Total Organic Aqueous Redox Flow Battery Employing Low Cost and Sustainable Methyl Viologen (MV) Anolyte and 4-HO-TEMPO Catholyte, 6 Advanced Energy Materials 1-8 (2016).

* cited by examiner

*Primary Examiner* — Osei K Amponsah

(57) ABSTRACT

Described herein are aqueous organic redox flow batteries that include a first redox active material that can include a metallocene or a salt thereof, and a second redox active material that can include a viologen or a salt thereof. The aqueous organic redox flow batteries may further include a first aqueous electrolyte, a second aqueous electrolyte, and a separator between the first and second aqueous electrolytes. In addition, disclosed herein are methods of making the metallocene and viologen compounds.

22 Claims, 118 Drawing Sheets
(114 of 118 Drawing Sheet(s) Filed in Color)

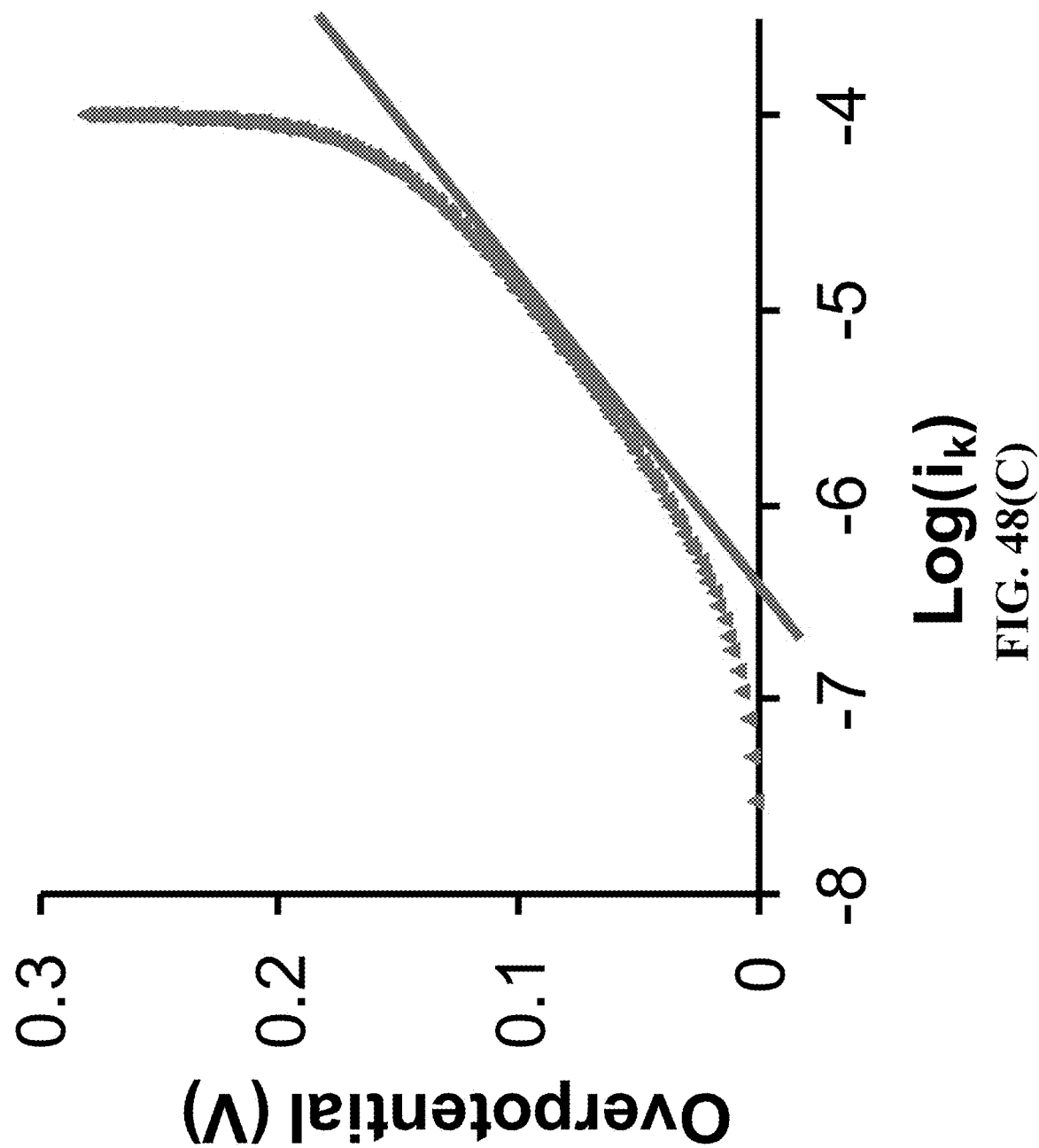

MATERIALS FOR USE IN AN AQUEOUS ORGANIC REDOX FLOW BATTERY

CROSS-REFERENCE TO RELATED APPLICATION(S)

This application claims priority to U.S. Provisional Application No. 62/366,458 filed on Jul. 25, 2016, which is incorporated fully herein by reference.

TECHNICAL FIELD

The present disclosure relates generally to redox active metallocene- and viologen-based materials and more particularly to aqueous organic redox flow batteries that include metallocene- and viologen-based redox active materials, and methods of making metallocene- and viologen-based redox active materials.

BACKGROUND

Redox flow batteries (RFBs) have been recognized as a viable renewable energy technology for large-scale energy storage. A redox flow battery generally includes a positive electrode electrolyte and a negative electrode electrolyte supplied to a battery element having a membrane interposed between a positive electrode and a negative electrode. An aqueous solution containing a metal ion having a valence which changes by oxidation-reduction is representatively used as the electrolytes. Traditional RFBs often suffer from drawbacks, such as expensive and resource limited redox active materials, corrosive and hazardous electrolytes, low current performance, and expensive system costs.

SUMMARY

In some aspects, the present disclosure provides a redox flow battery comprising a first redox active material comprising a metallocene or a salt thereof; and a second redox active material. The metallocene may have formula (I),

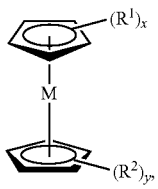

(I)

or a salt thereof, wherein: M is Fe, Co, Ni, Mn, Cr, Ti, Mo, or W; $R^1$ and $R^2$, at each occurrence, are each independently selected from the group consisting of hydrogen, halogen, alkyl, cycloalkyl, heterocyclyl, aryl, heteroaryl, —CN, —$NO_2$, —$OR^a$, —$SR^a$, -alkyl-N($R^a$)$_z$, —N($R^a$)$_z$, —C(O)$R^a$, —C(O)O$R^a$, —S(O)$_z R^a$, —S(O)$_z OR^a$, and —OP(O)(O$R^a$)$_2$; $R^a$, at each occurrence, is independently selected from the group consisting of hydrogen, alkyl, cycloalkyl, heterocyclyl, aryl, heteroaryl, alkyl-N($R^b$)$_z$, an oxygen protecting group, and a nitrogen protecting group; $R^b$, at each occurrence, is independently selected from the group consisting of hydrogen, alkyl, cycloalkyl, heterocyclyl, aryl, heteroaryl, an oxygen protecting group, and a nitrogen protecting group; x is 1, 2, 3, 4, or 5; y is 0, 1, 2, 3, 4, or 5; and z, at each occurrence, is independently 2 or 3.

In some aspects, the present disclosure provides an aqueous organic redox flow battery including a first redox active material including a metallocene or a salt thereof of formula (I) and a second redox active material including a viologen of formula (V):

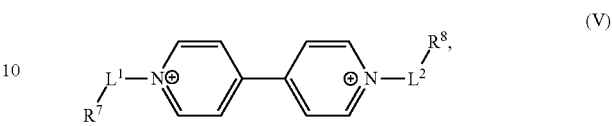

(V)

or a salt thereof, wherein $L^1$ and $L^2$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-(OCH$_2$CH$_2$)$_m$; $R^7$ and $R^8$ are each independently selected from the group consisting of —$CH_3$, —$NO_2$, —$OR^d$, —N($R^d$)$_m$, —C(O)$R^d$, —C(O)O$R^d$, —S(O)$_m$, —$PO_3$, —S(O)$_m R^d$, —S(O)$_m OR^d$, —OP(O)(O$R^d$)$_2$, —$OCH_3$, —(C$R^d{}_2$)$_m$CN, substituted aryl, and substituted heteroaryl; $R^d$, at each occurrence, is independently selected from the group consisting of hydrogen, alkyl, cycloalkyl, heterocyclyl, aryl, heteroaryl, alkyl-N($R^e$)$_m$, alkyl-S(O)$_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; and m, at each occurrence, is independently 2 or 3.

In some aspects, the present disclosure provides a redox flow battery comprising a first redox active material; and a second redox active material comprising a viologen or a salt thereof. The viologen may have formula (VI),

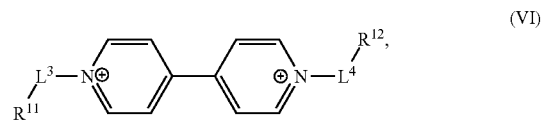

(VI)

or a salt thereof, wherein $L^3$ and $L^4$ are each independently selected from the group consisting of bond, $C_1$-$C_{12}$ alkylenyl, $C_1$-$C_{12}$ alkenylenyl, $C_1$-$C_{12}$ alkynylenyl, and $C_1$-$C_4$ alkylenyl-(OCH$_2$CH$_2$)$_m$; $R^{11}$ is selected from the group consisting of, —$NO_2$, —$OR^g$, —N($R^g$)$_q$, —C(O)$R^g$, —C(O)O$R^g$, —S(O)$_q$, —$PO_3$, —S(O)$_q R^g$, —S(O)$_q OR^g$, —OP(O)(O$R^g$)$_2$, —$OCH_3$, —(C$R^d{}_2$)$_m$CN, substituted aryl, and substituted heteroaryl; $R^{12}$ is selected from the group consisting of —$CH_3$, —$NO_2$, —$OR^g$, —C(O)$R^g$, —C(O)O$R^g$, —S(O)$_q$, —$PO_3$, —S(O)$_q R^g$, —S(O)$_q OR^g$, —OP(O)(O$R^g$)$_2$, OC$H_3$, —(C$R^d{}_2$)$_m$CN, substituted aryl, and substituted heteroaryl; $R^g$, at each occurrence, is independently selected from the group consisting of hydrogen, alkyl, cycloalkyl, heterocyclyl, aryl, heteroaryl, alkyl-N($R^h$)$_q$, alkyl-S(O)$_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; and q, at each occurrence, is independently 2 or 3.

In some aspects, the present disclosure provides a redox flow battery comprising a first redox active material; and a second redox active material comprising a viologen or a salt thereof. The viologen may have formula (VII),

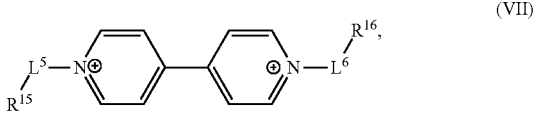

(VII)

or a salt thereof, wherein $L^5$ and $L^6$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_j$, $R^{15}$ and $R^{16}$ are each independently selected from the group consisting of —$OR^j$, —$C(O)R^j$, —$C(O)OR^j$, —$S(O)_j$, —$PO_3$, —$S(O)_jR^j$, —$S(O)_jOR^j$, —$OP(O)(OR^j)_2$, —$(CR^j_2)_jCN$, substituted aryl, and substituted heteroaryl; $R^j$, at each occurrence, is independently selected from the group consisting of alkyl-$S(O)_j$, and an oxygen protecting group; and j, at each occurrence, is independently 2 or 3.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 30(A) is a schematic of the $(NPr)_2V/[FcN^{Et}]Br$ AORFB with structural drawings showing the cell reactions of the $(NPr)_2V$ anolyte and the $[FcN^{Et}]Br$ catholyte. FIG. 30(B) shows a cyclic voltammogram of $[FcN^{Et}]Br$ (0.60 V) and $(NPr)_2V$ (−0.35 V, −0.72 V) combined in 0.5 M NaCl aqueous electrolyte. The dashed curve is a cyclic voltammogram of only the 0.5 M NaCl electrolyte, with labels for the onset potentials for the hydrogen evolution reaction (−1.00 V) and oxygen evolution reaction (1.50 V). Experiment conditions: 4.0 mM $[FcN^{Et}]Br$, 4.0 mM (NPr)$_2$V, 100 mV/s scan rate, glassy carbon working electrode, glassy carbon counter electrode, Ag/AgCl reference electrode.

FIGS. 31(A)-31(I) show operational data of a (NPr)$_2$V/[FcN$^{Et}$]Br AORFB (0.25 M/0.50 M) utilizing both electrons and individual electron of (NPr)$_2$V. Plots of battery capacity over cycling numbers for two-electron process (FIG. 31(A)), the 1$^{st}$ electron (FIG. 31(D)) and the 2$^{nd}$ electron (FIG. 31(G)). Charge and discharge curves of AORFB at current densities from 40 mA/cm$^2$ to 100 mA/cm$^2$ for two-electron (FIG. (B)), the 1$^{st}$ electron (FIG. 31(E)) and the 2$^{nd}$ electron (FIG. 31(H)); Plots of average coulombic efficiency (ce), energy efficiency (ee), and voltage efficiency (ye) at varying operational current densities for two-electron (FIG. 31(C)), the 1$^{st}$ electron (FIG. 31(F)) and the 2$^{nd}$ electron (FIG. 31(I)).

Figure 32:
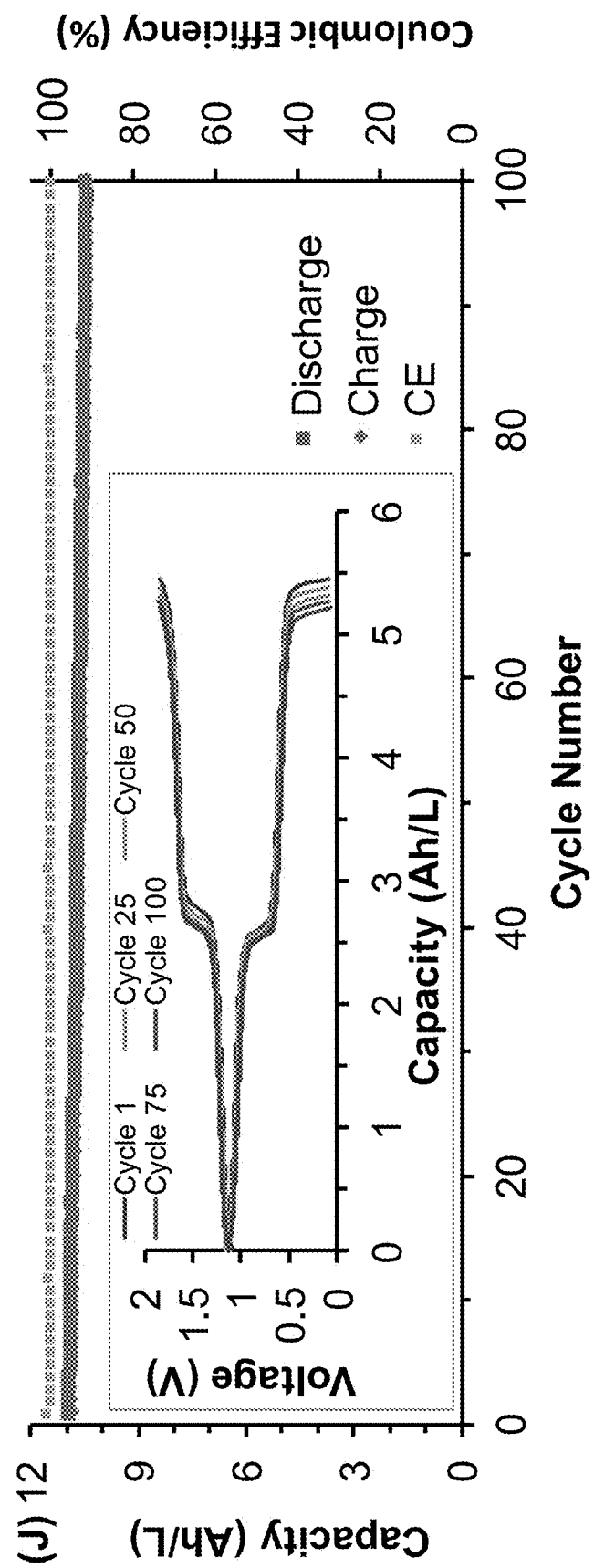

FIG. 32 shows the extended 100 cycle data of a (NPr)$_2$V/[FcN$^{Et}$]Br AORFB depicting charge capacity, discharge capacity, and coulombic efficiency versus cycle number at 60 mA/cm$^2$ current density. Inset: Charge and discharge curves of several cycles from the experiment. Conditions: Cathode: 12 mL of 0.50 M [FcN$^{Et}$]Br in 2.0 M NaCl; Anode: 12 mL of 0.25 M (NPr)$_2$V in 2.0 M NaCl; AMV anion exchange membrane.

Figure 33:
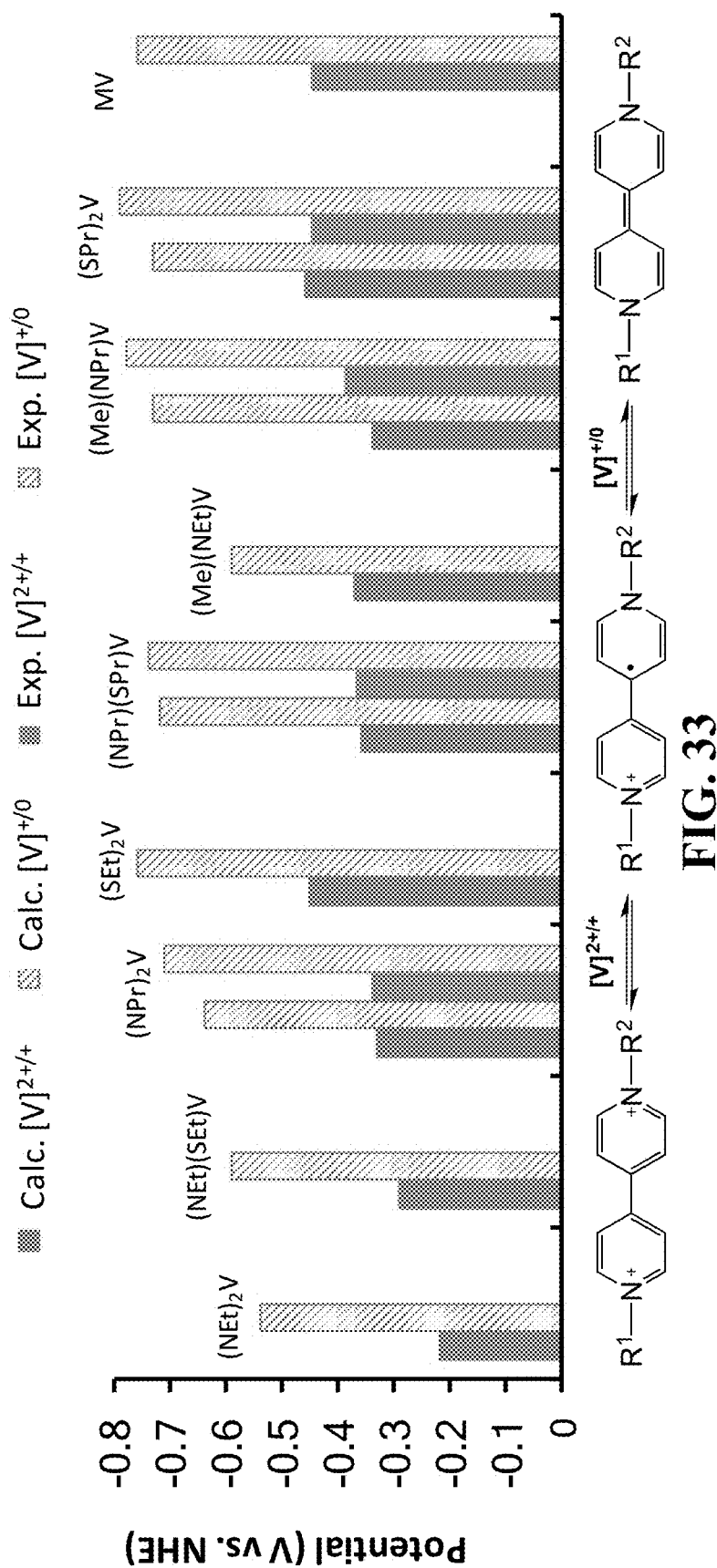

FIG. 33 shows DFT calculations of redox potentials of viologen compounds. Experimental redox potentials of several viologens were plotted for comparison. Bottom: a general scheme for two stepwise one-electron reductions for viologens.

Figure 34:
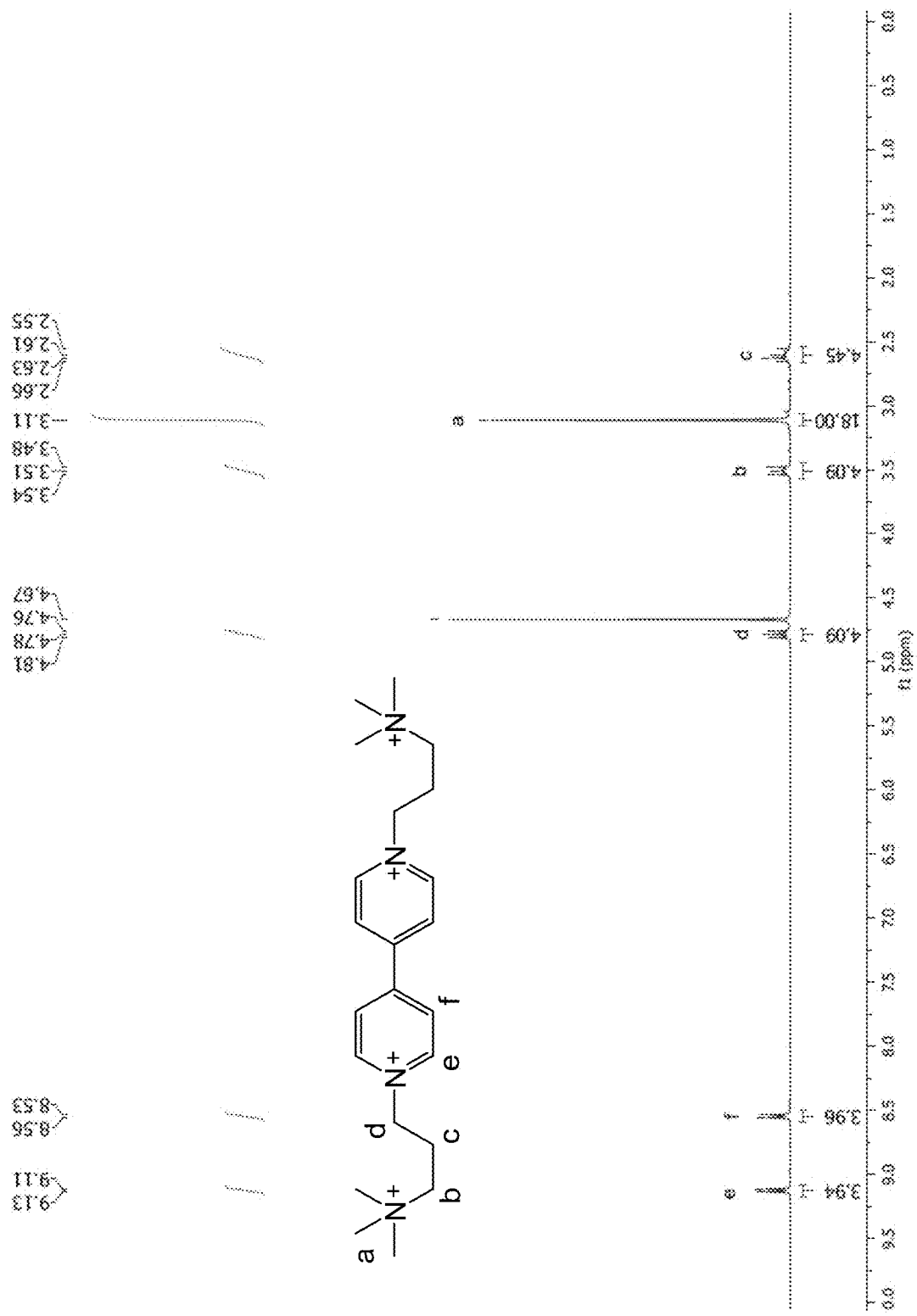

FIG. 34 shows $^1$H NMR spectrum of (NPr)$_2$V. Conditions: 500 MHz field strength, 25° C., D$_2$O solvent. The residual HOD solvent peak is observed ~4.67 ppm. The structure has been labeled, assigning each individual peak in the spectrum.

Figure 35:
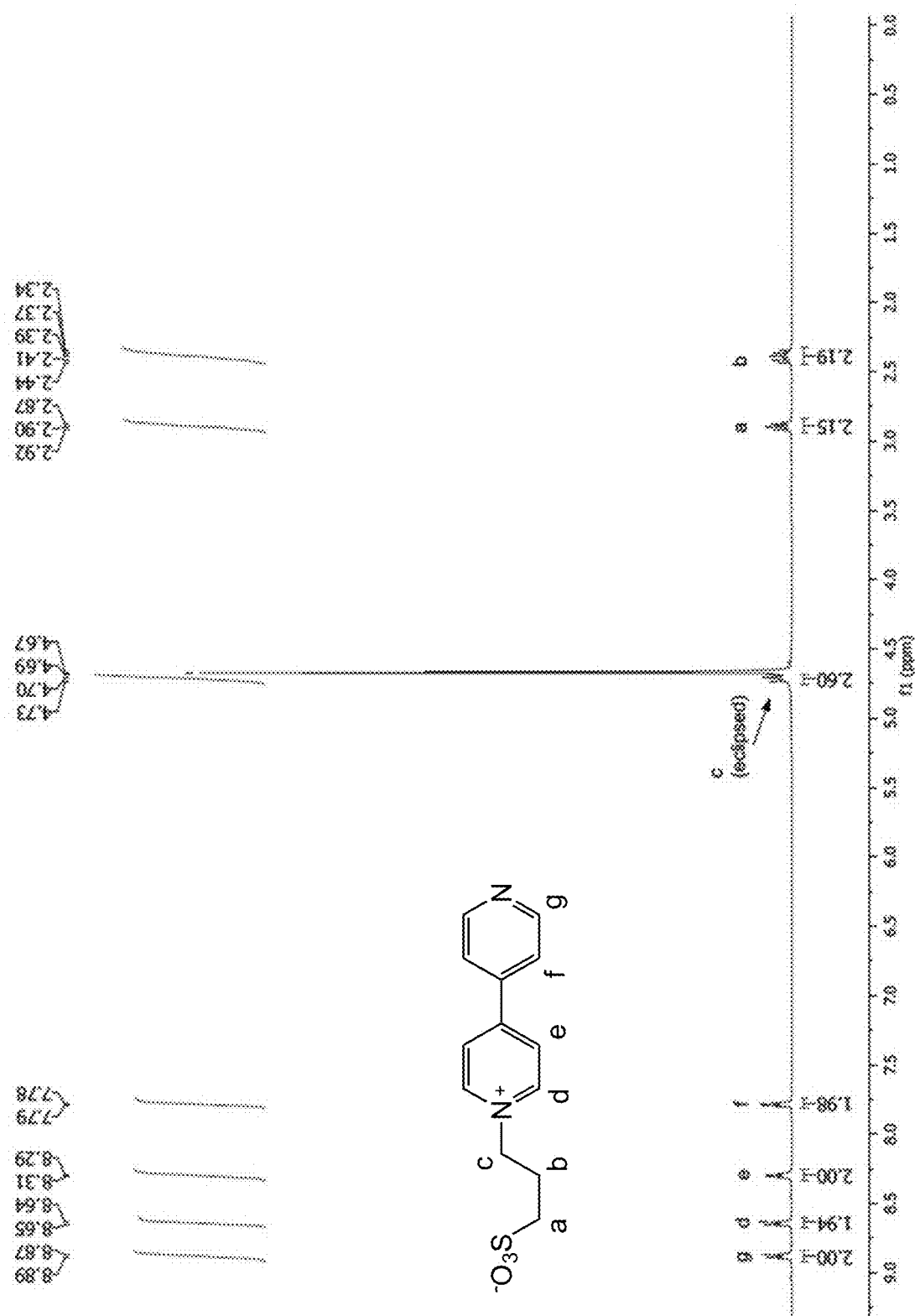

FIG. 35 shows $^1$H NMR spectrum of 4'-pyridine-[3-sulfonatopropyl-4-pyrdinium (SPy). Conditions: 500 MHz field strength, 25° C., D$_2$O solvent. The residual HOD solvent peak is observed 4.67 ppm. The structure has been labeled, assigning each individual peak in the spectrum.

Figure 36:
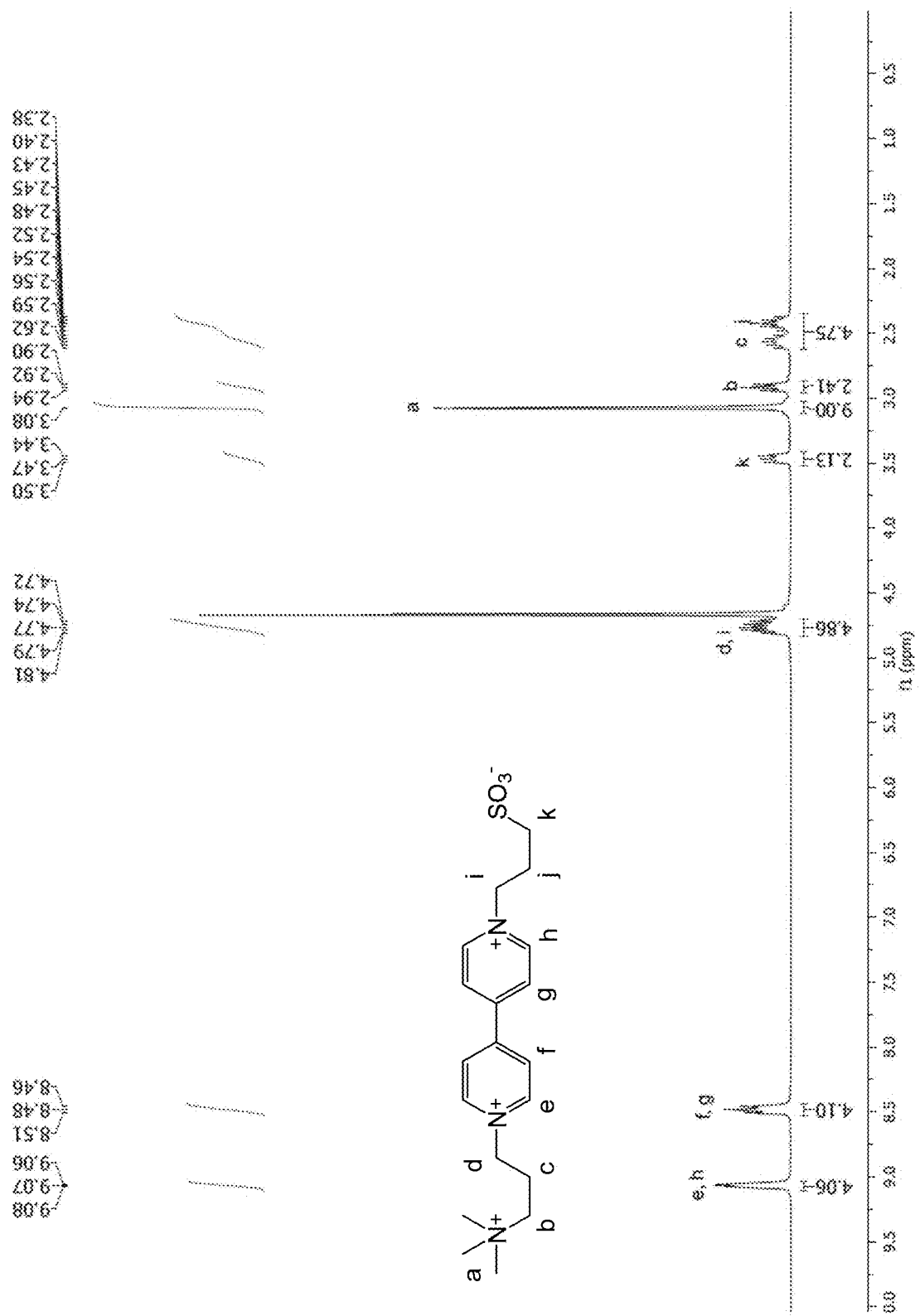

FIG. 36 shows $^1$H NMR spectrum of 1'-[3-(trimethylammonium)propyl]-4'-pyridinium-1-[3-sulfonatopropyl]-4-pyridinium dibromide ((NPr)(SPr)V). Conditions: 500 MHz field strength, 25° C., D$_2$O solvent. The residual HOD solvent peak is observed 4.67 ppm. The structure has been labeled, assigning each individual peak in the spectrum.

Figure 37:

FIG. 37 shows $^1$H NMR spectrum of 4'-pyridine-methyl-4-pyrdinium iodide (MeBpy). Conditions: 500 MHz field strength, 25° C., D$_2$O solvent. The residual HOD solvent peak is observed 4.7 ppm. The structure has been labeled, assigning each individual peak in the spectrum.

Figure 38:
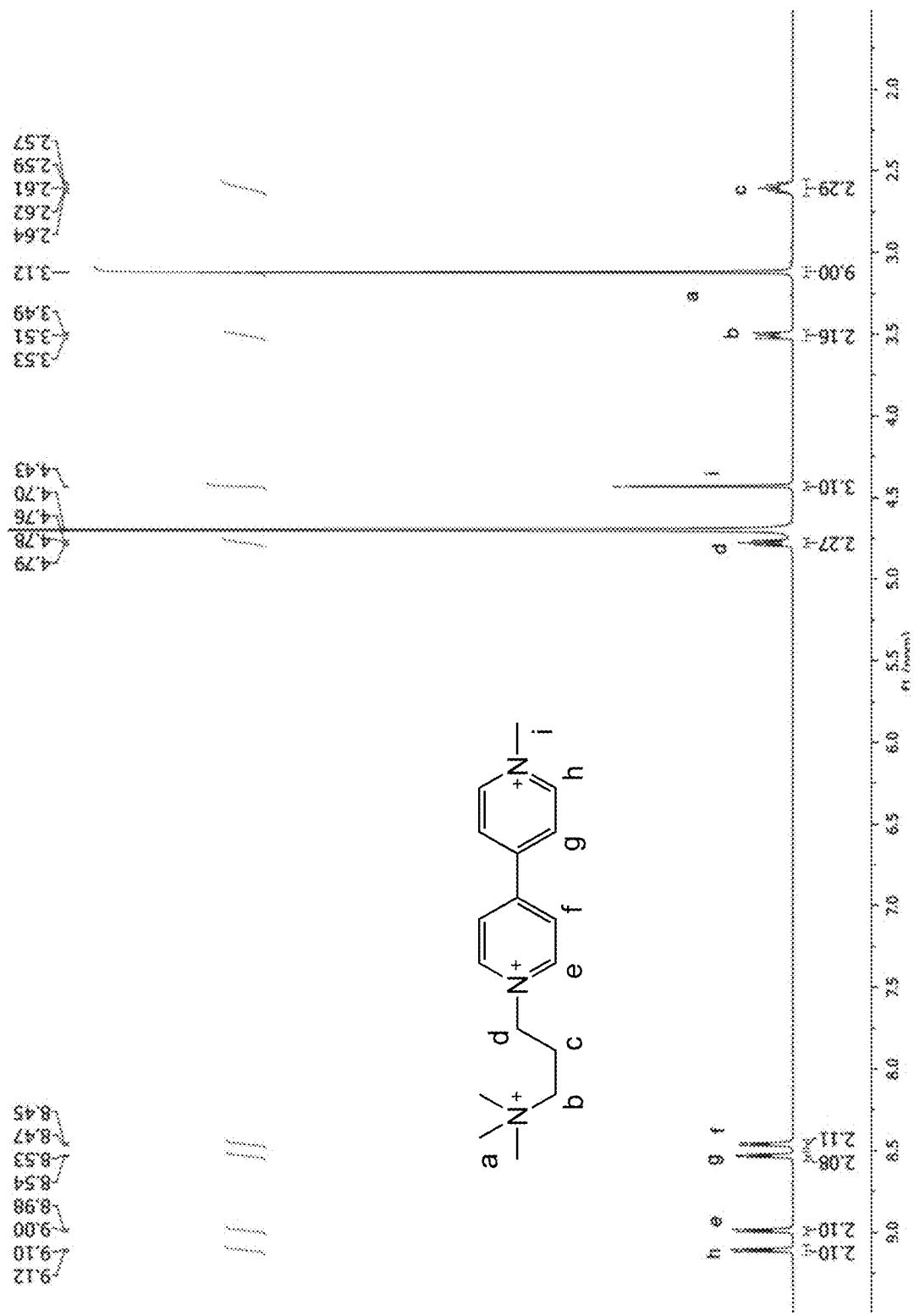

FIG. 38 shows $^1$H NMR spectrum of l'-methyl-4'-pyridinium-1-[3-(trimethylaminium)propyl]-4-pyridinium trichloride ((Me)(NPr)V). Conditions: 500 MHz field strength, 25° C., D$_2$O solvent. The residual HOD solvent peak is observed 4.7 ppm. The structure has been labeled, assigning each individual peak in the spectrum.

Figure 39:
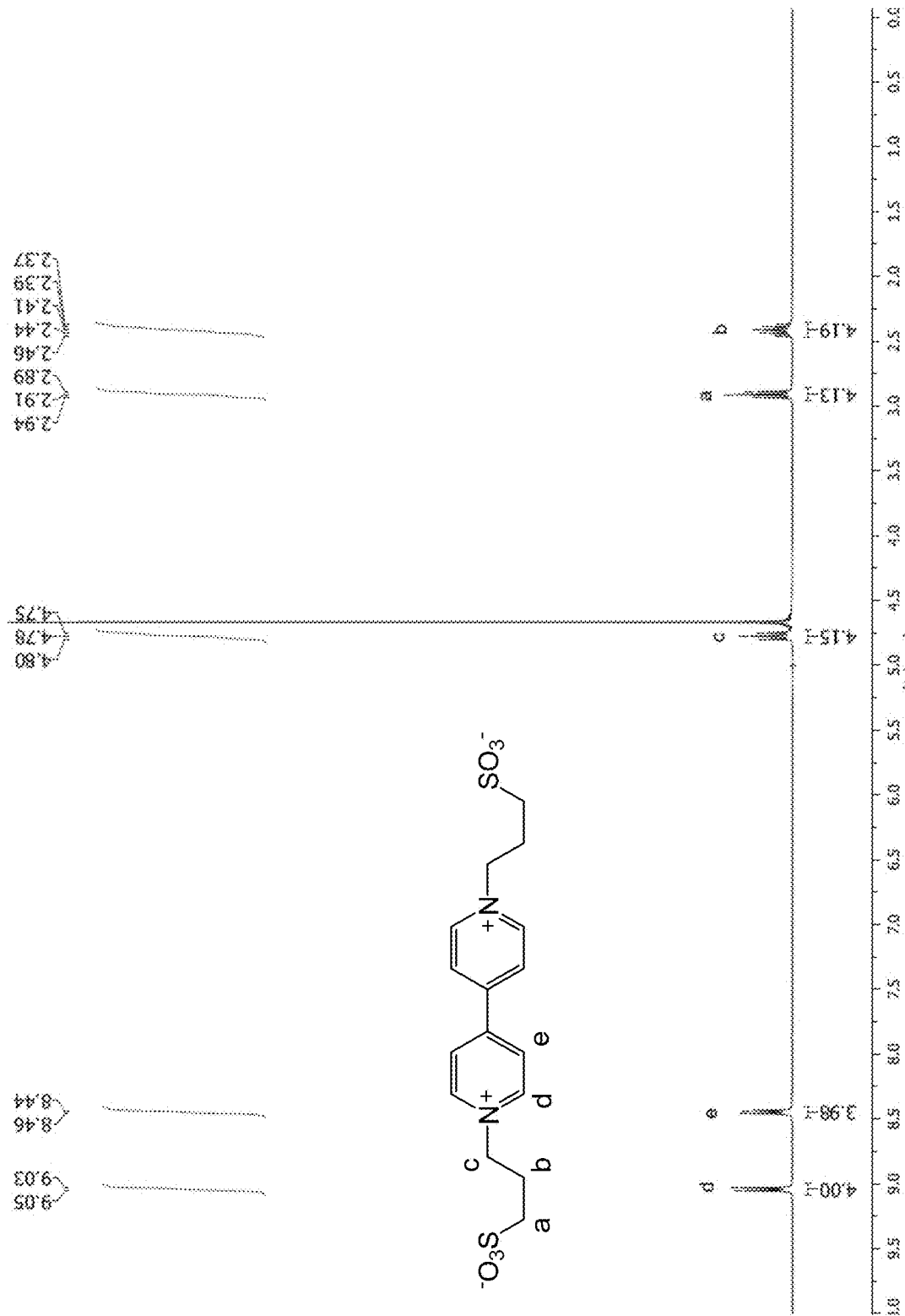

FIG. 39 shows $^1$H NMR spectrum of 1,1'-bis[3-sulfonatopropyl]-4,4'-bipyridinium ((SPr)$_2$V). Conditions: 500 MHz field strength, 25° C., D$_2$O solvent. The residual HOD solvent peak is observed 4.75 ppm. The structure has been labeled, assigning each individual peak in the spectrum.

Figure 40:
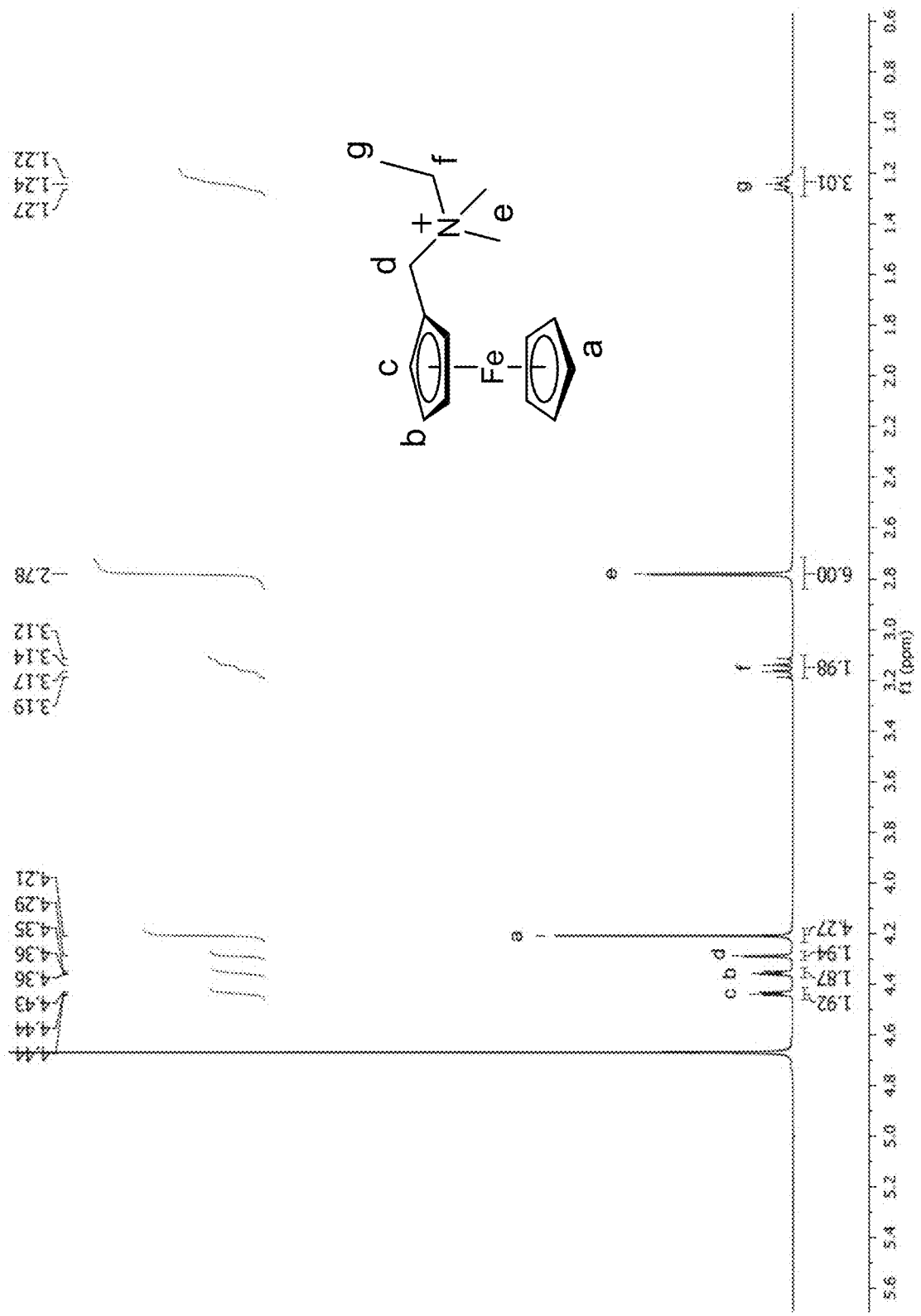

FIG. 40 shows $^1$H NMR spectrum of [FcN$^{Et}$]Br. Conditions: 500 MHz field strength, 25° C., D$_2$O solvent. The residual HOD solvent peak is observed 4.67 ppm. The structure has been labeled, assigning each individual peak in the spectrum.

Figure 41A:
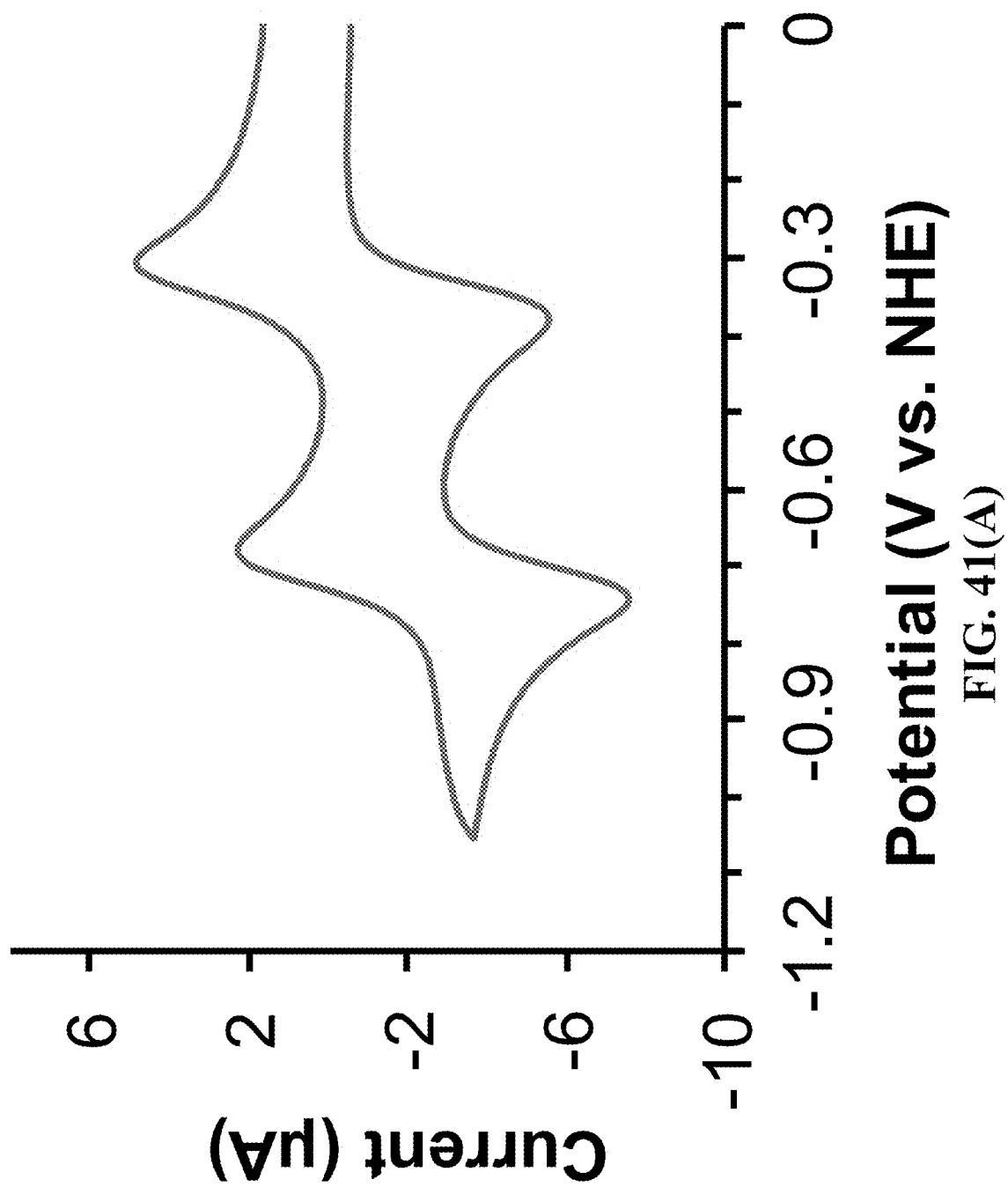
Figure 41B:
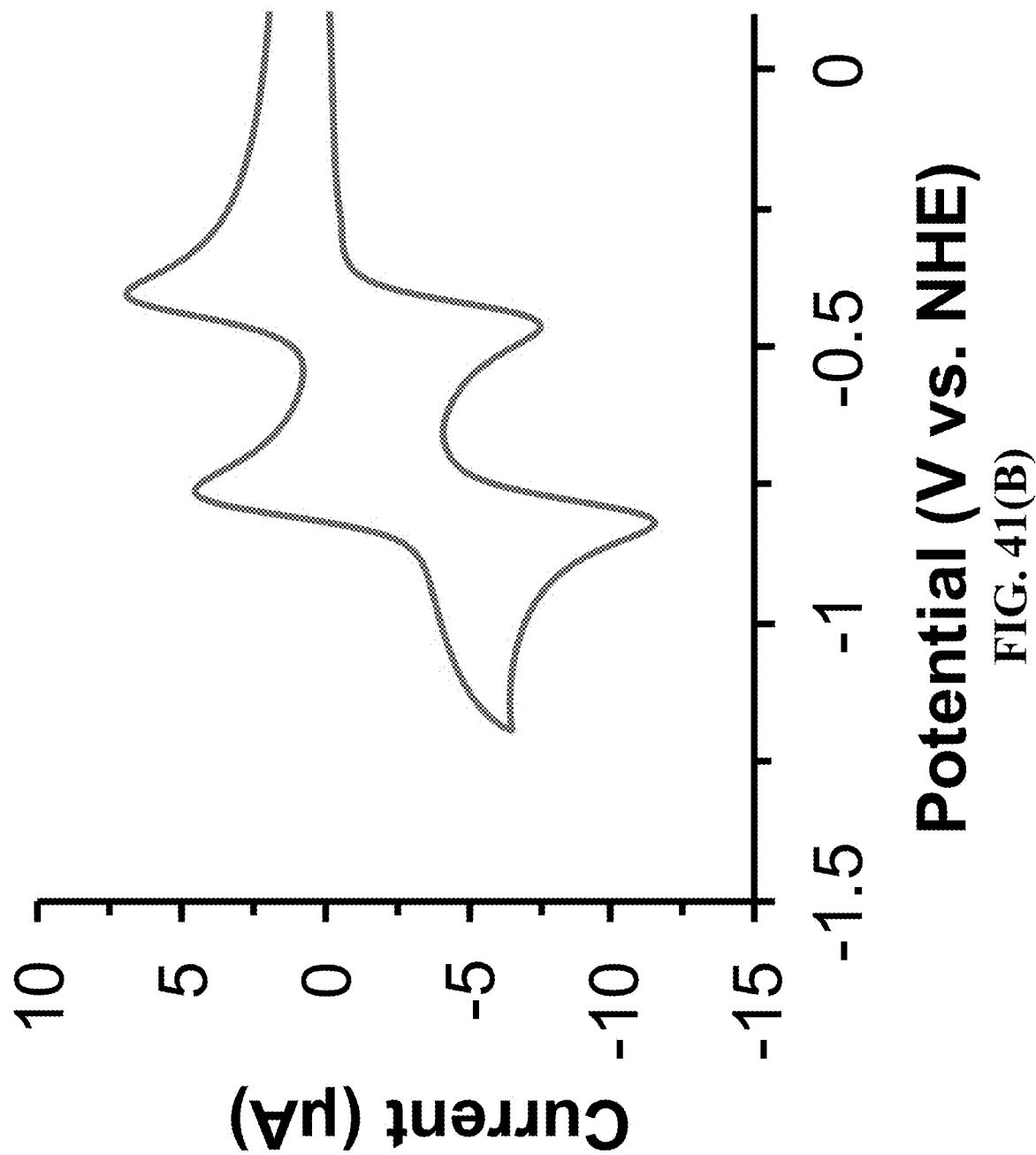
Figure 41C:
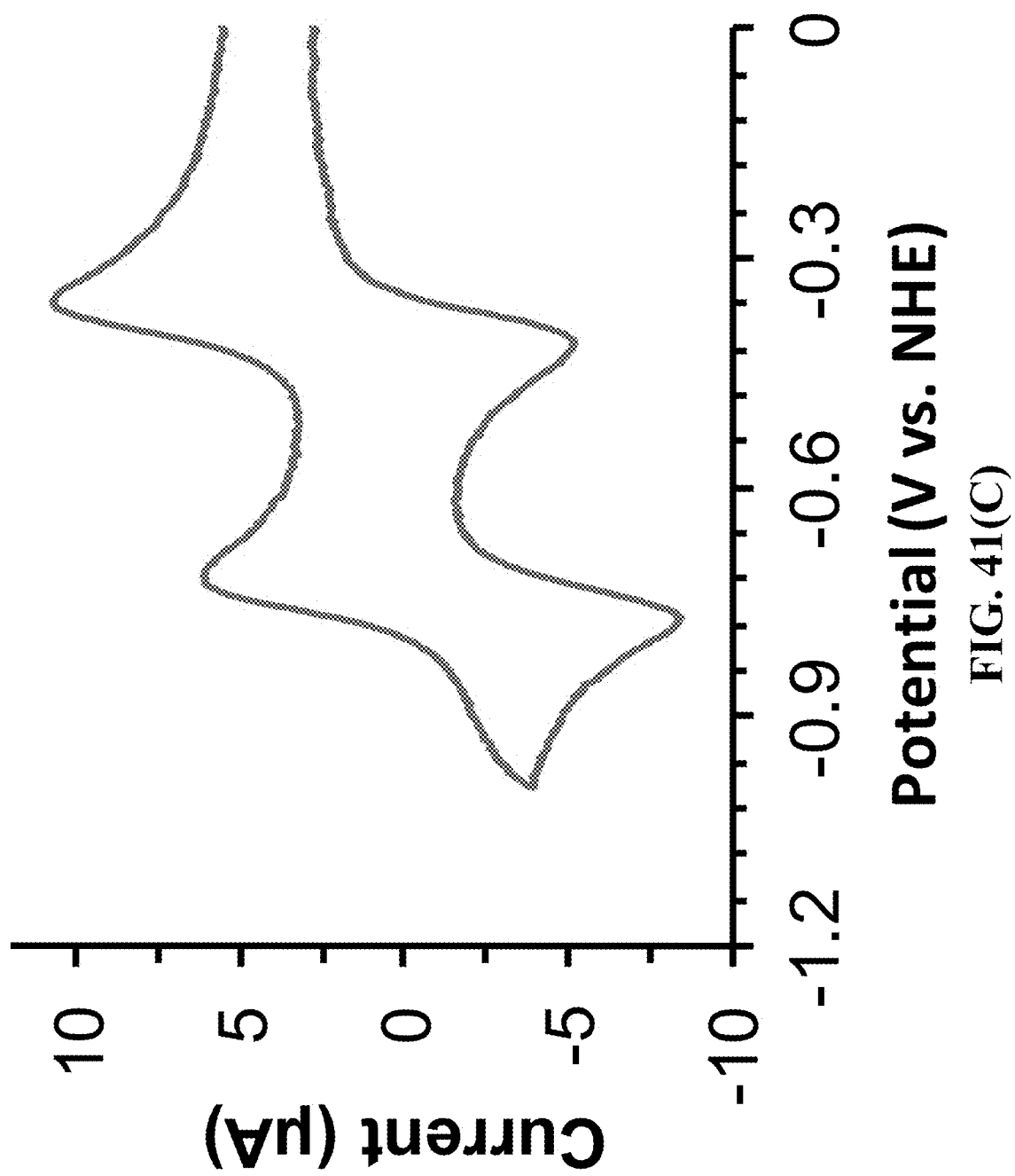
Figure 41D:
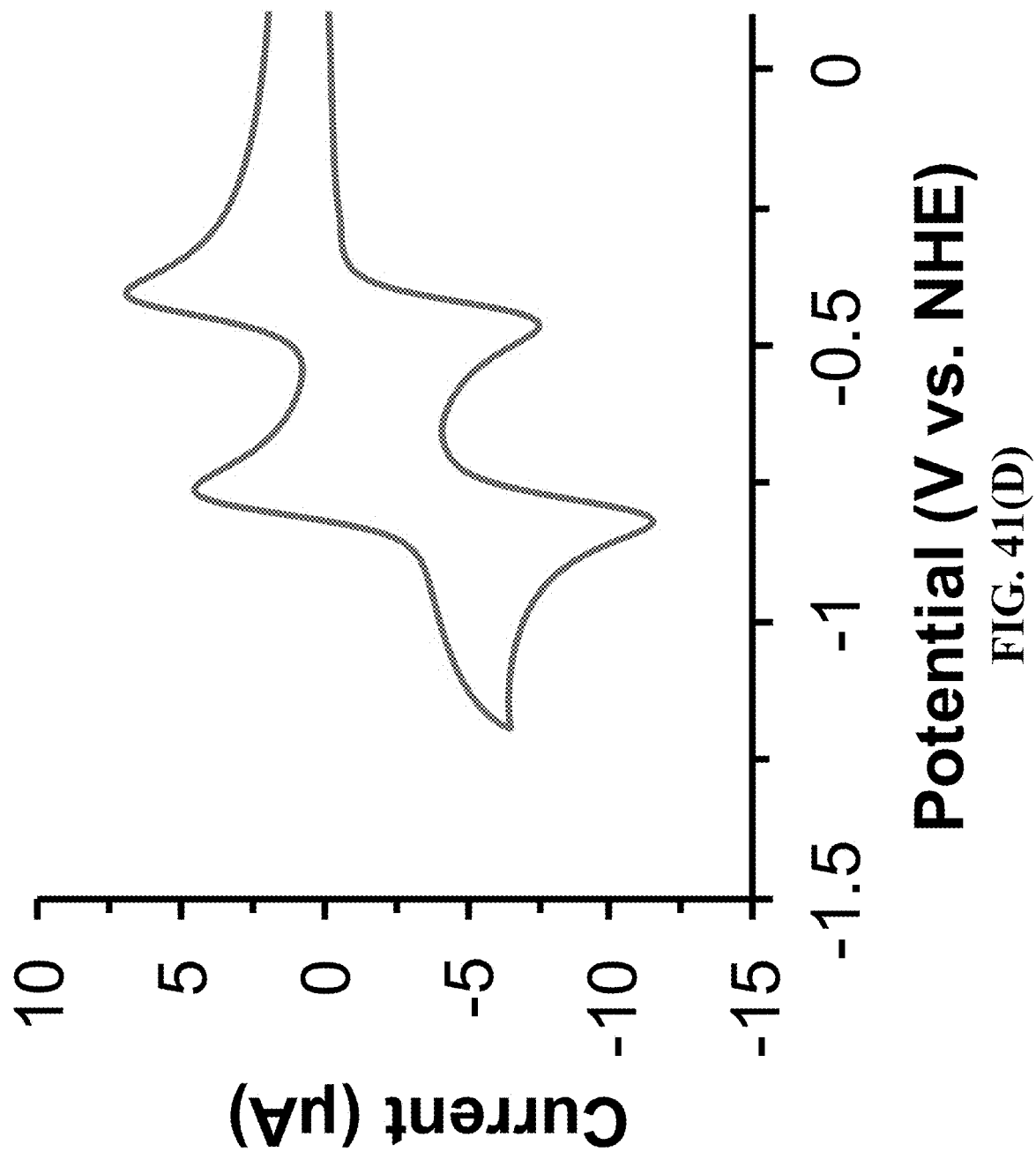
Figure 41E:
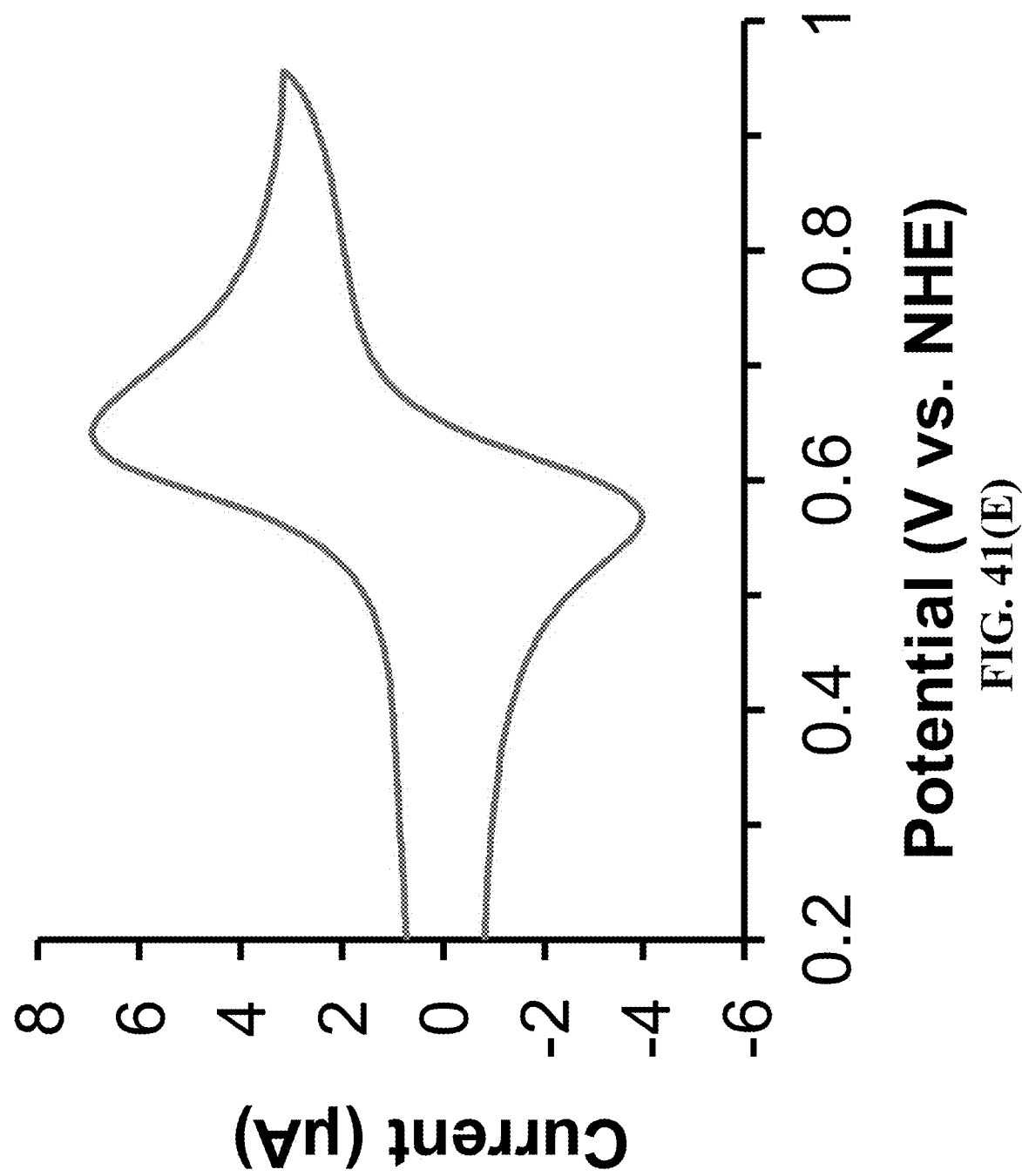

FIGS. 41(A)-(E) show cyclic voltammetry curves for redox-active materials as follows: FIG. 41(A) (NPr)$_2$V; FIG. 41(B) (NPr)(SPr)V; FIG. 41(C) (Me)(NPr)V; FIG. 41(D) (SPr)$_2$V; FIG. 41(E) [FcN$^{Et}$]Br. Experiment conditions for all: 4.0 mM active material in 0.5 M NaCl electrolyte, glassy carbon working electrode, glassy carbon counter electrode, Ag/AgCl reference electrode, 100 mV/s scan rate.

Figure 42A:
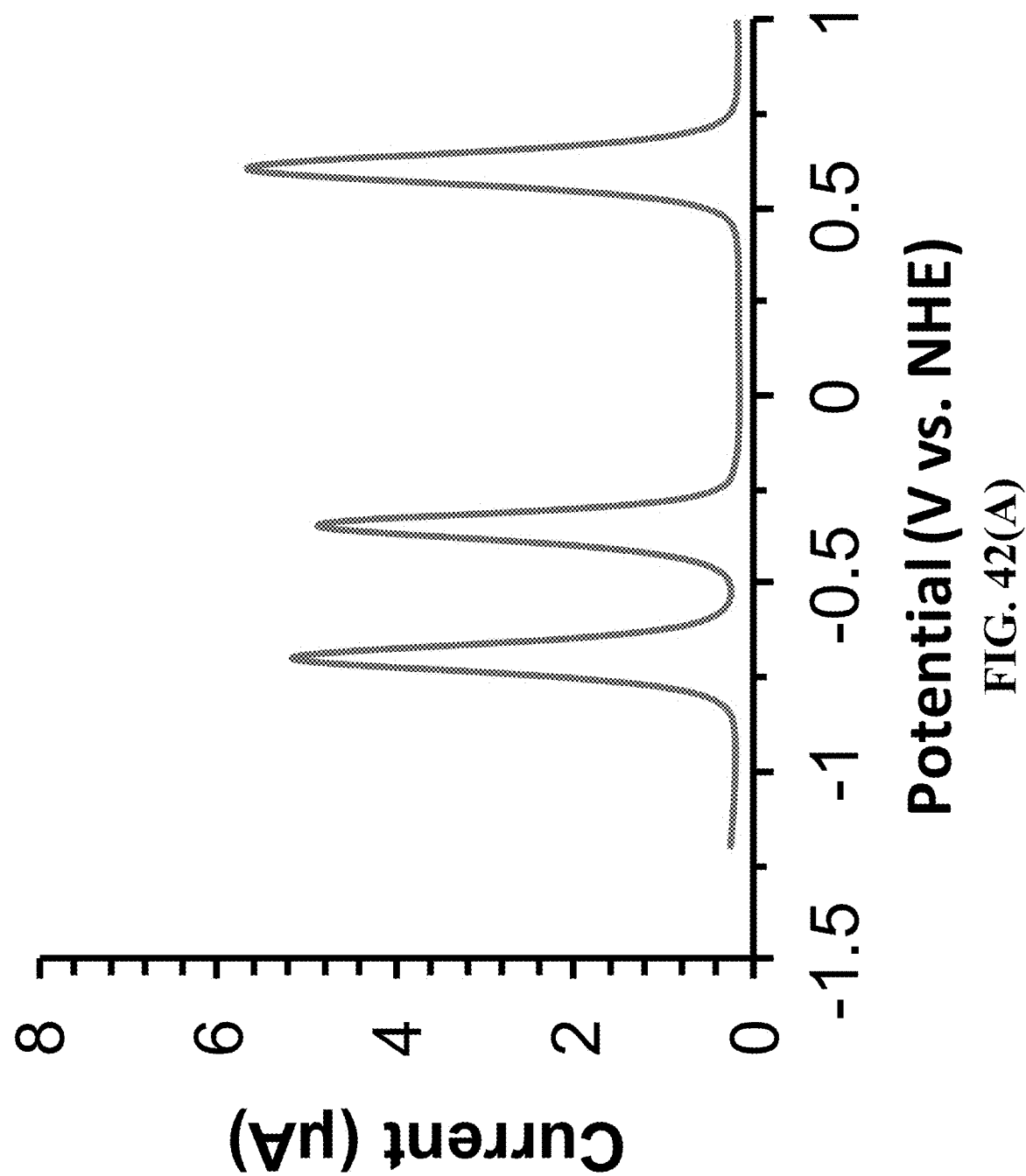
Figure 42B:
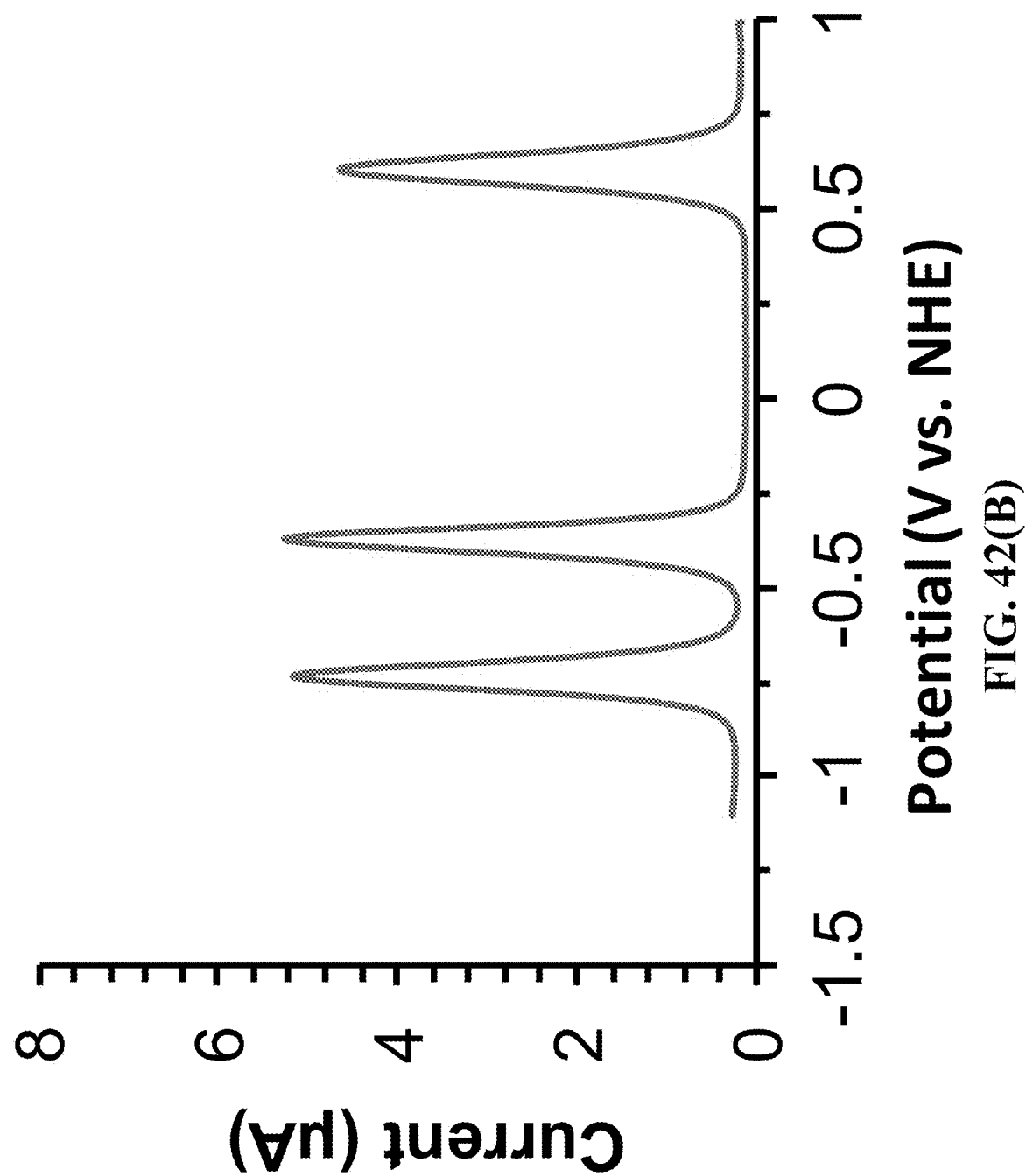
Figure 42C:
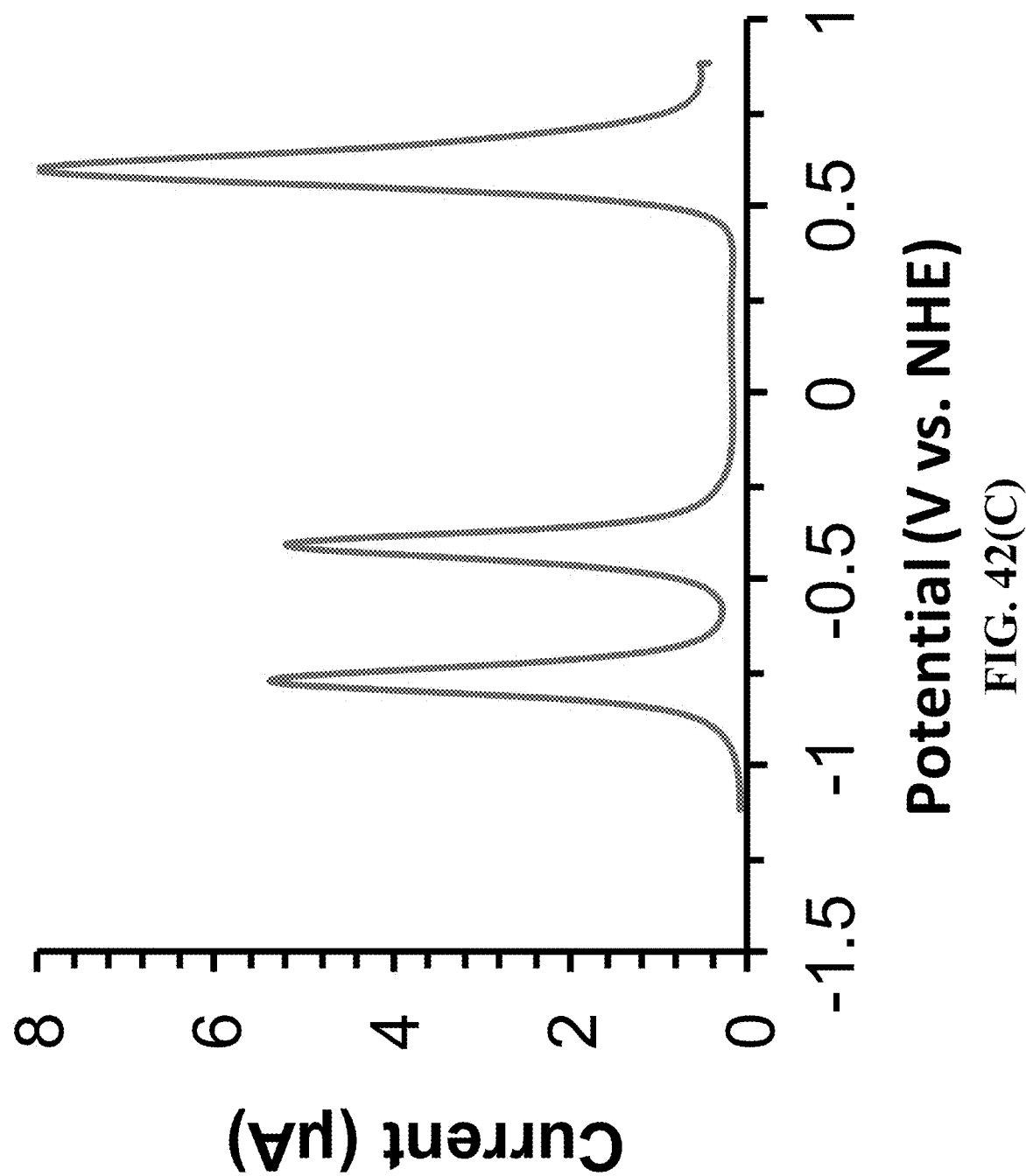
Figure 42D:
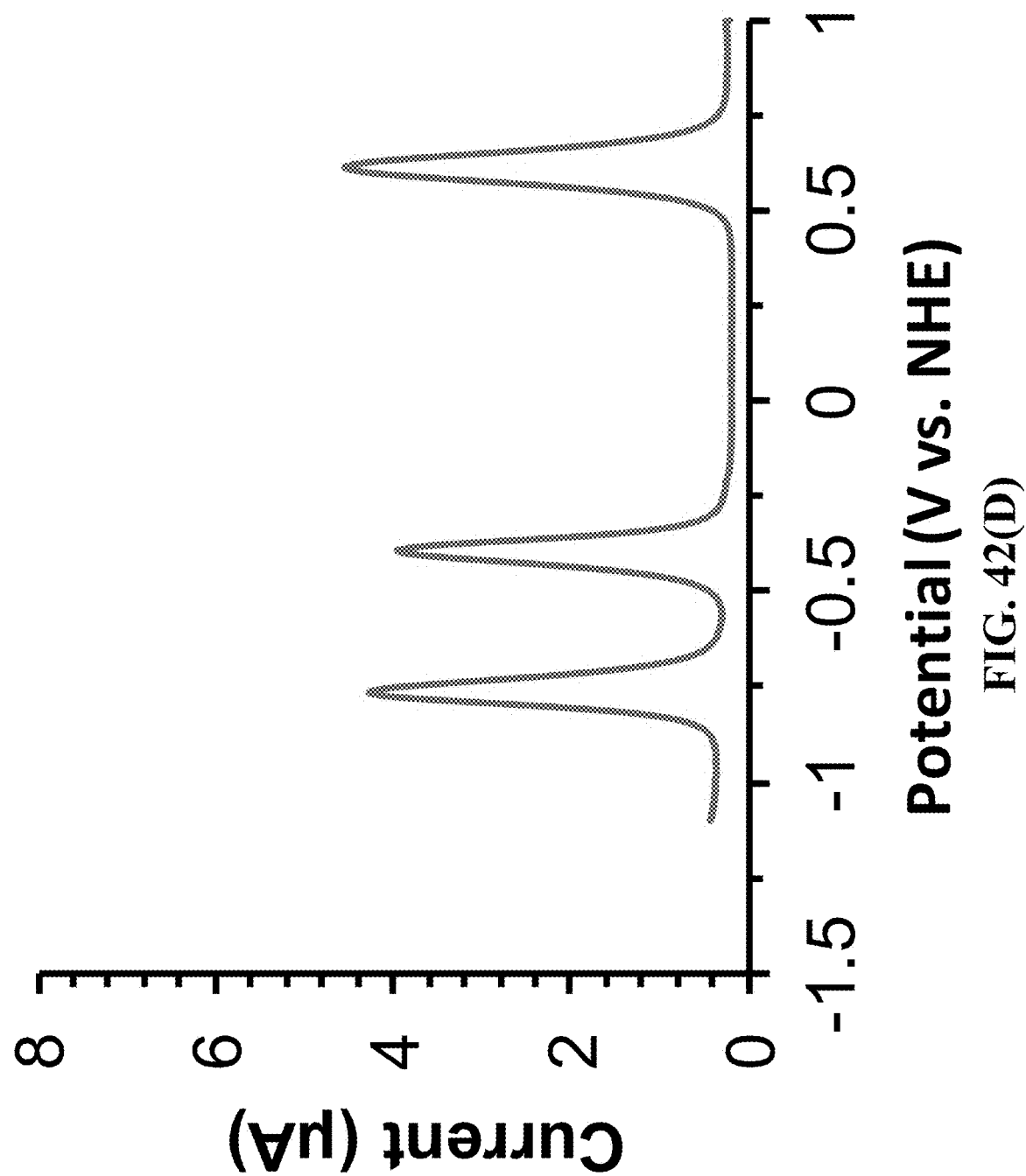
Figure 42E:
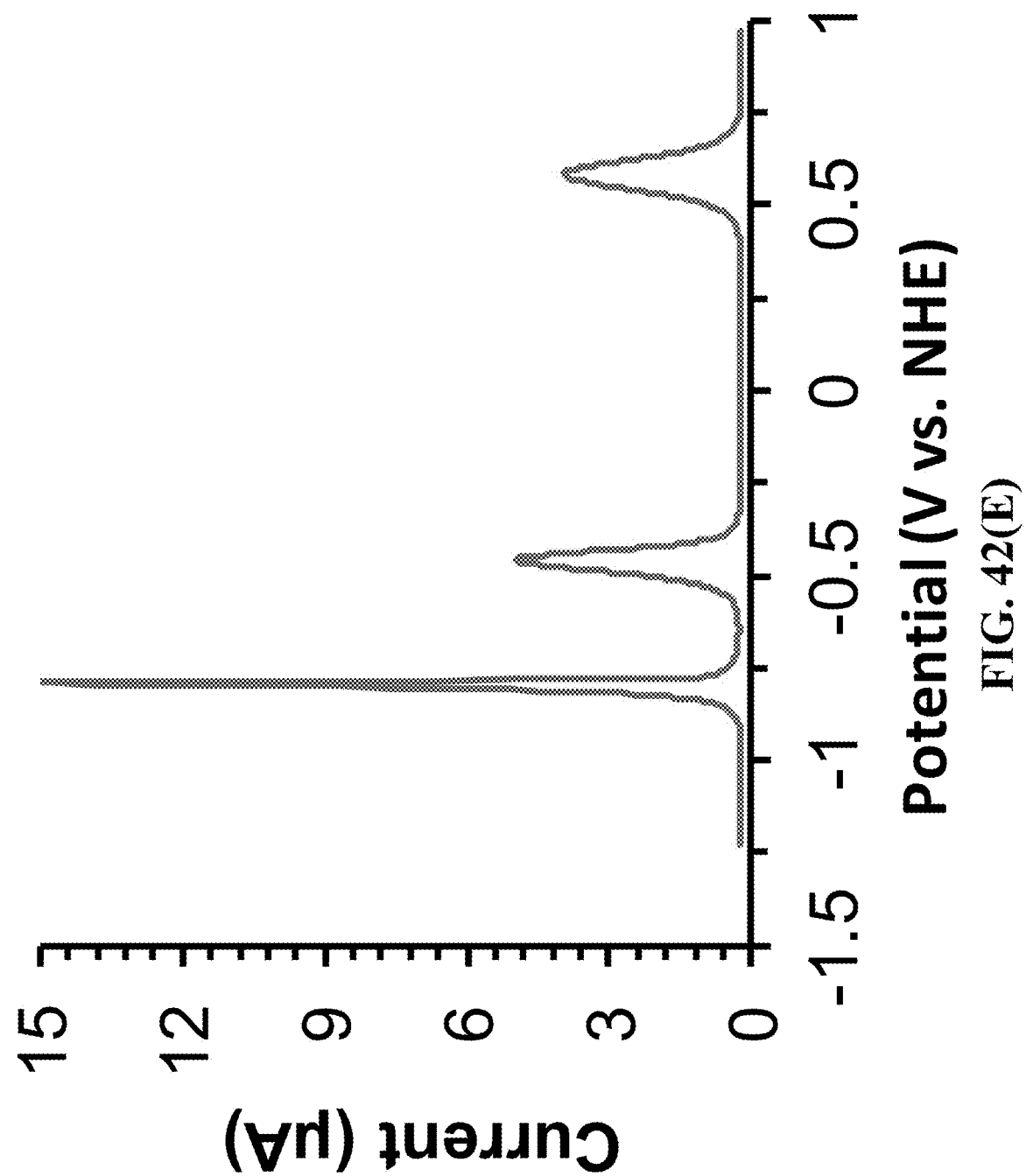
Figure 43A:
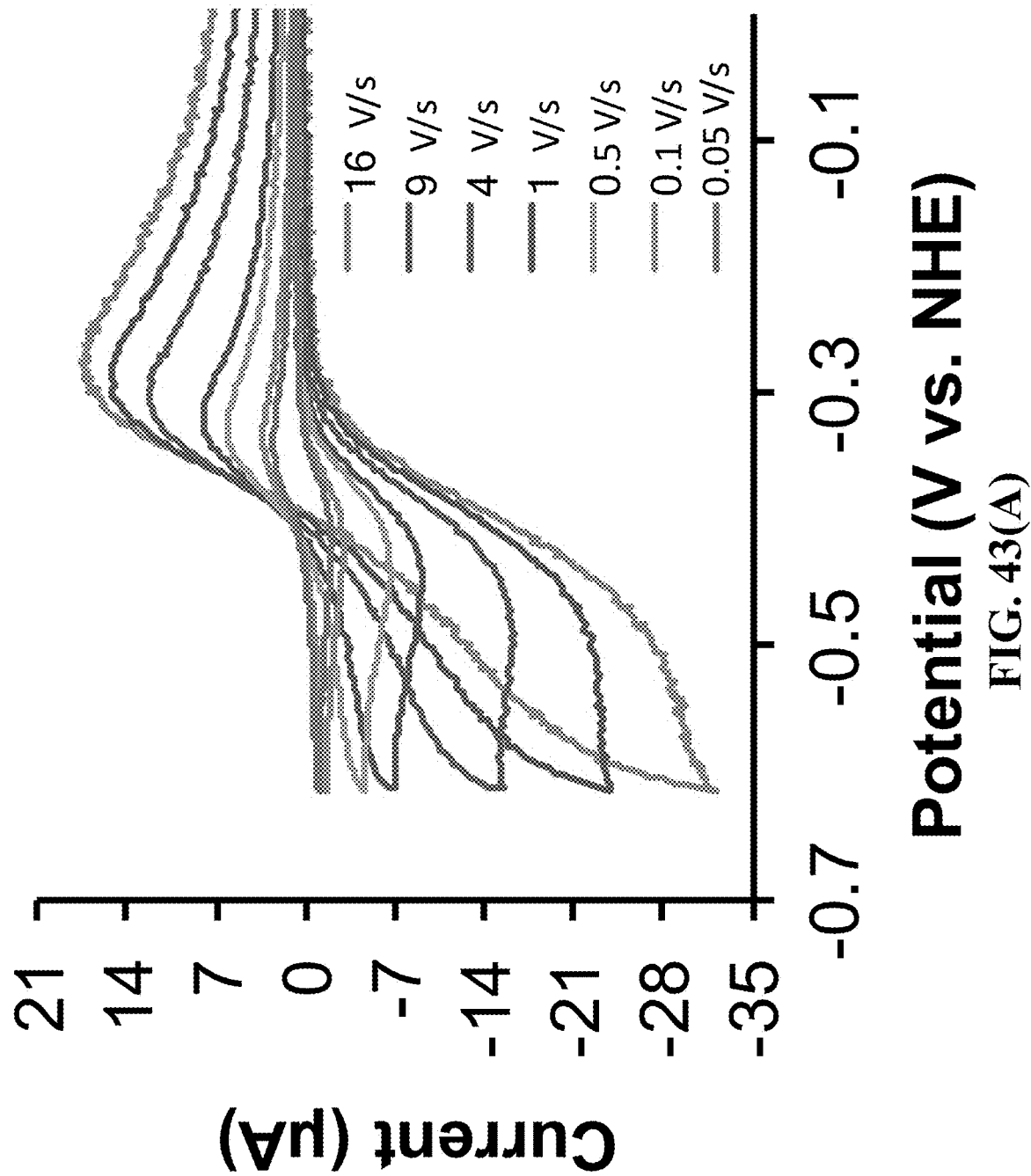
Figure 43B:
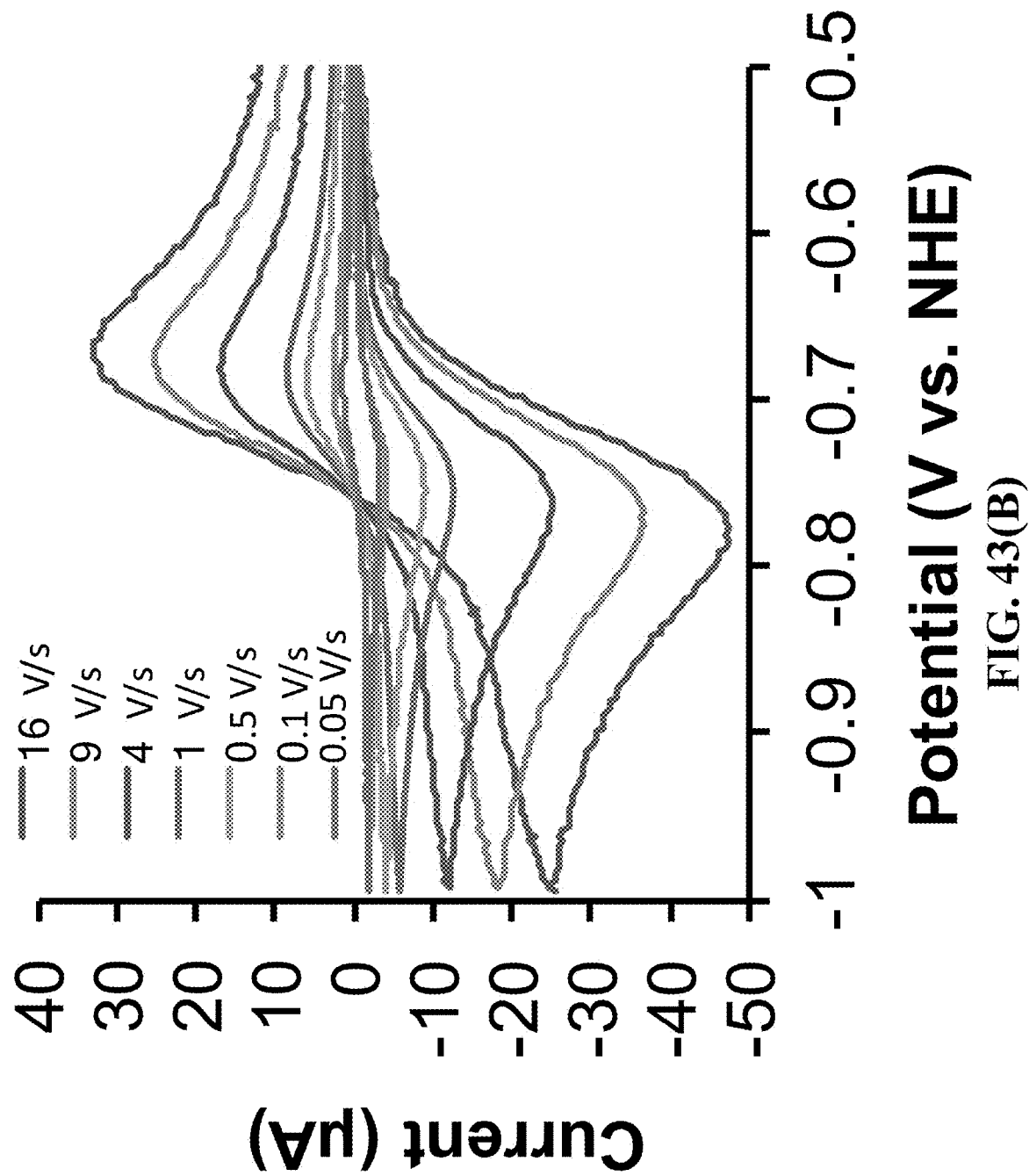
Figure 43C:
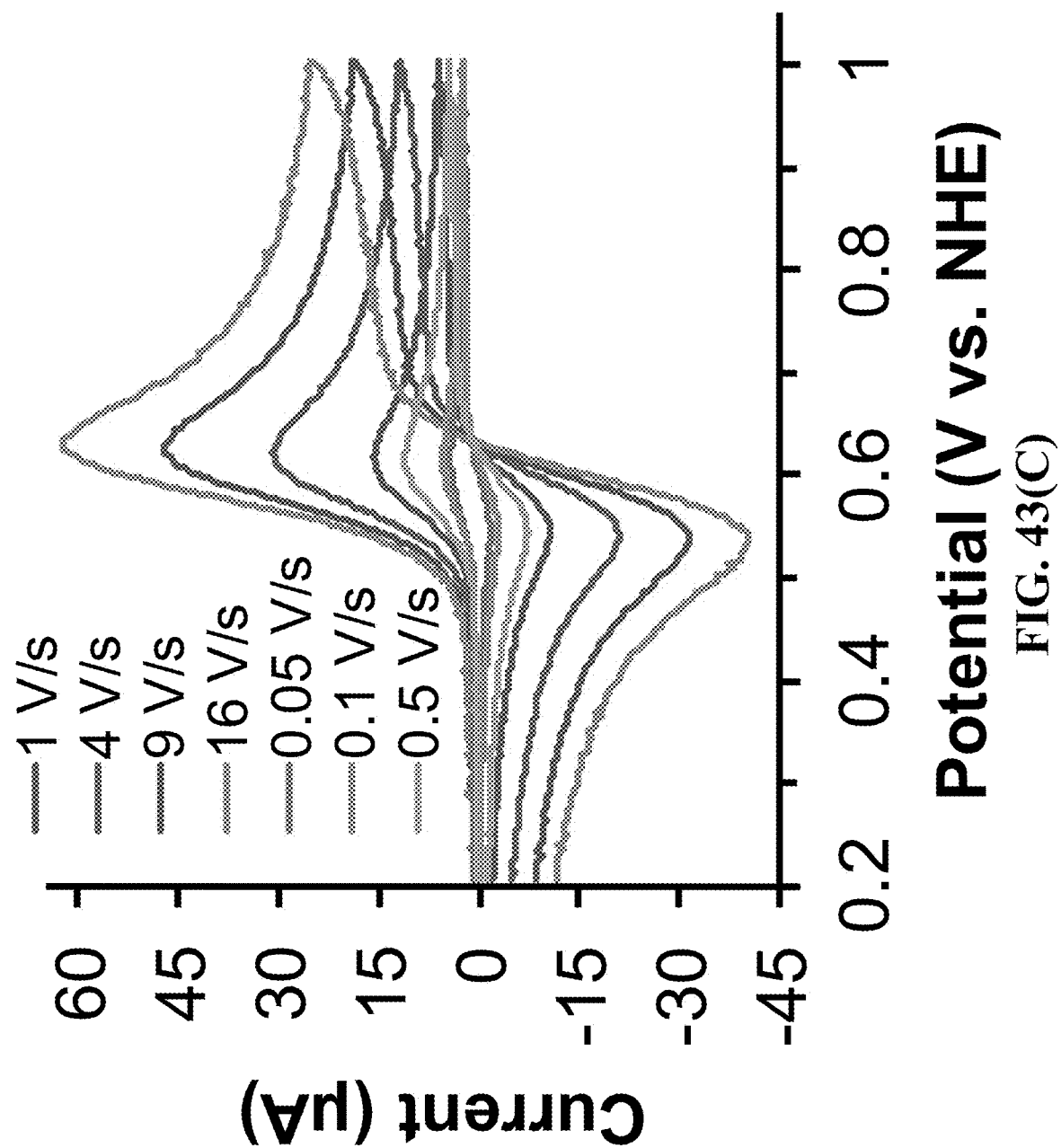
Figure 43D:
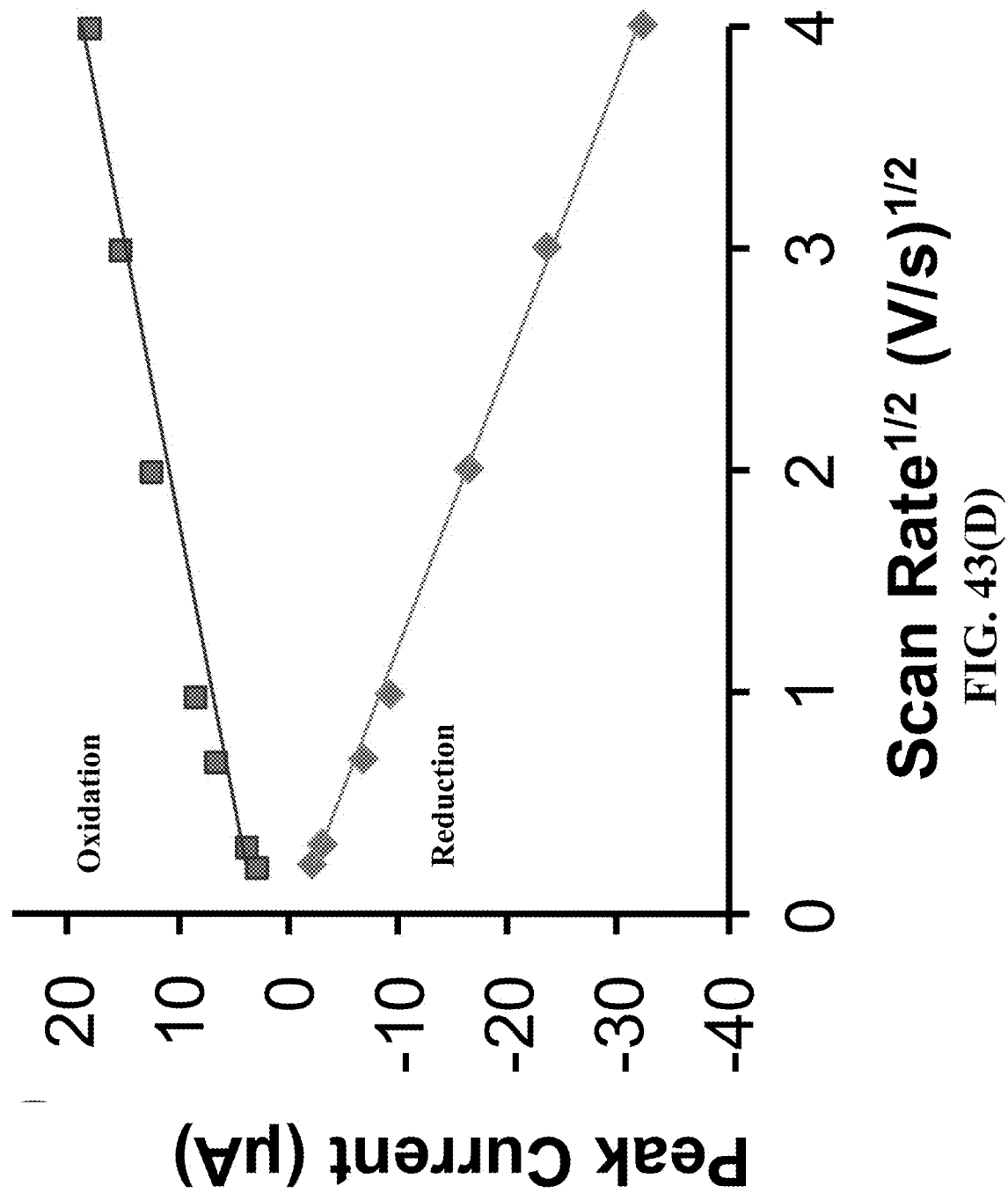
Figure 43E:
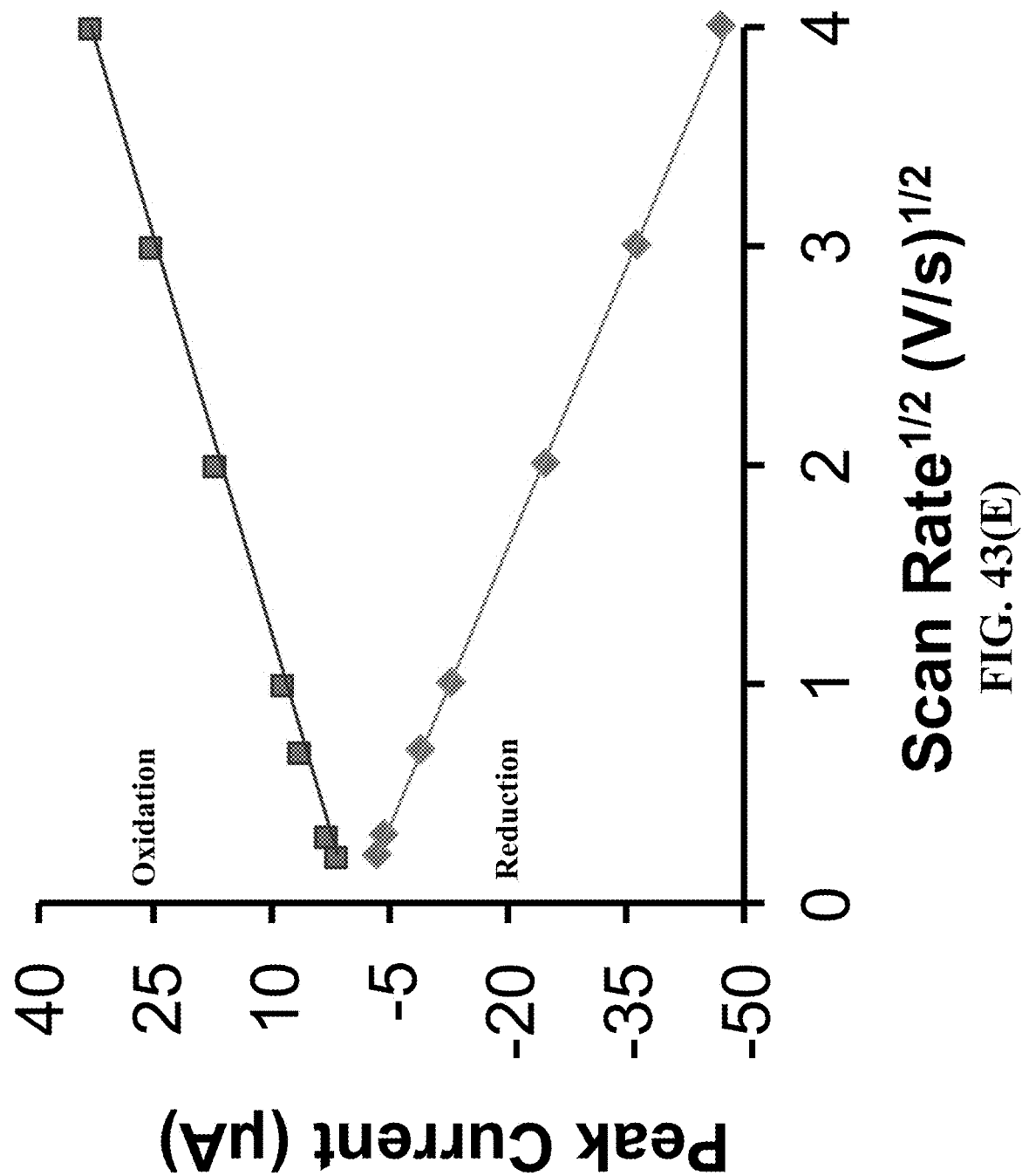
Figure 43F:
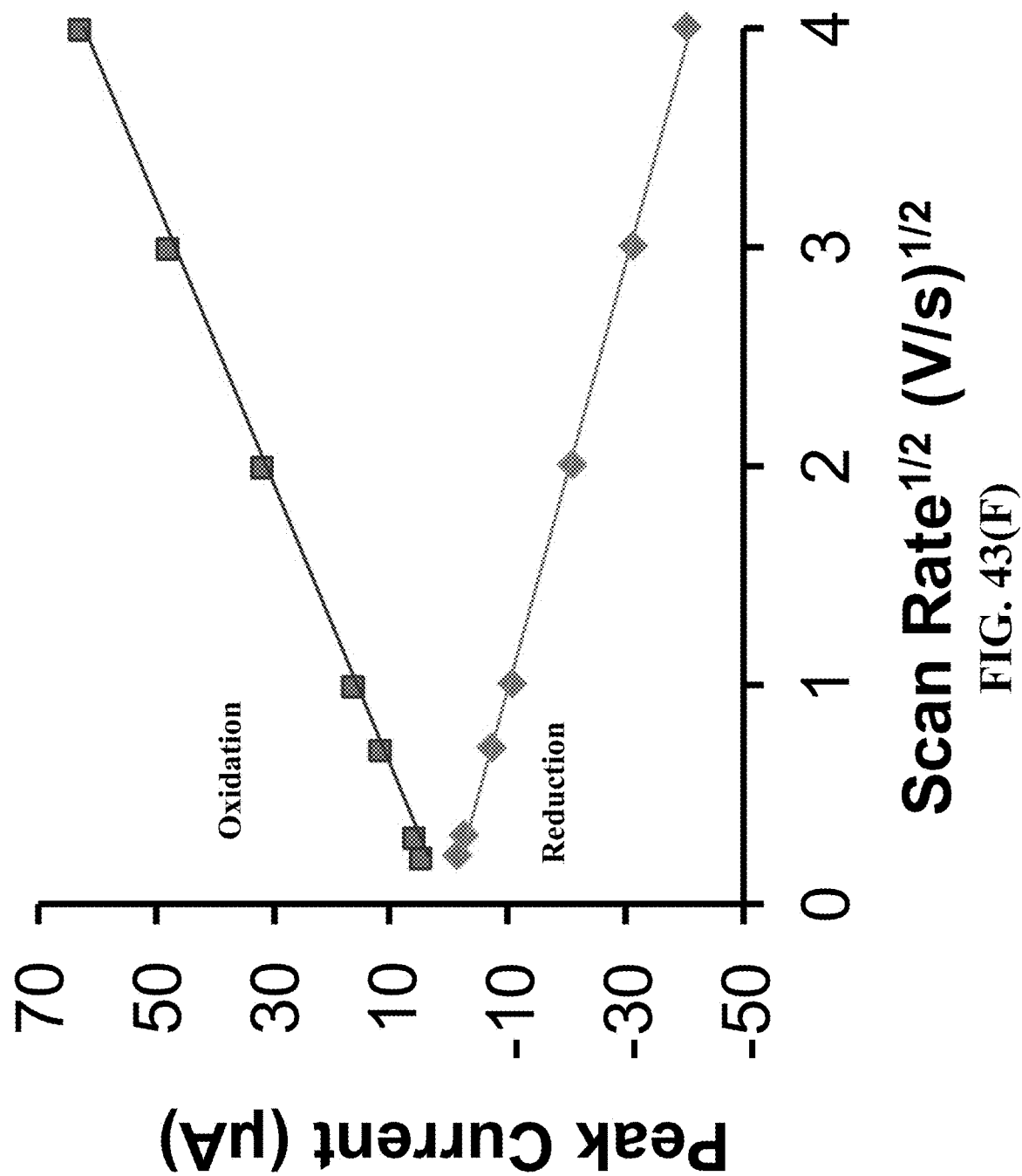
Figure 44A:
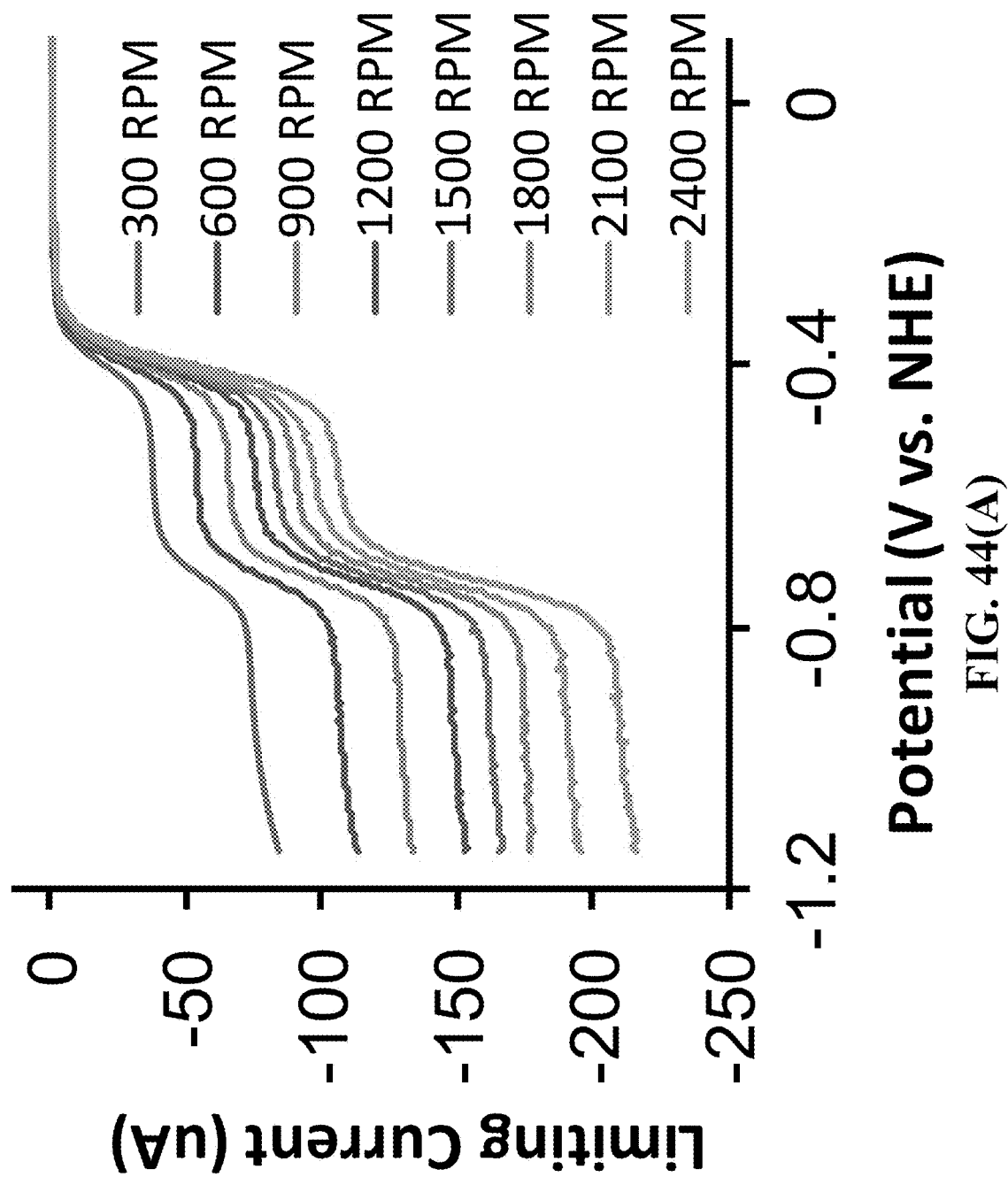
Figure 44B:
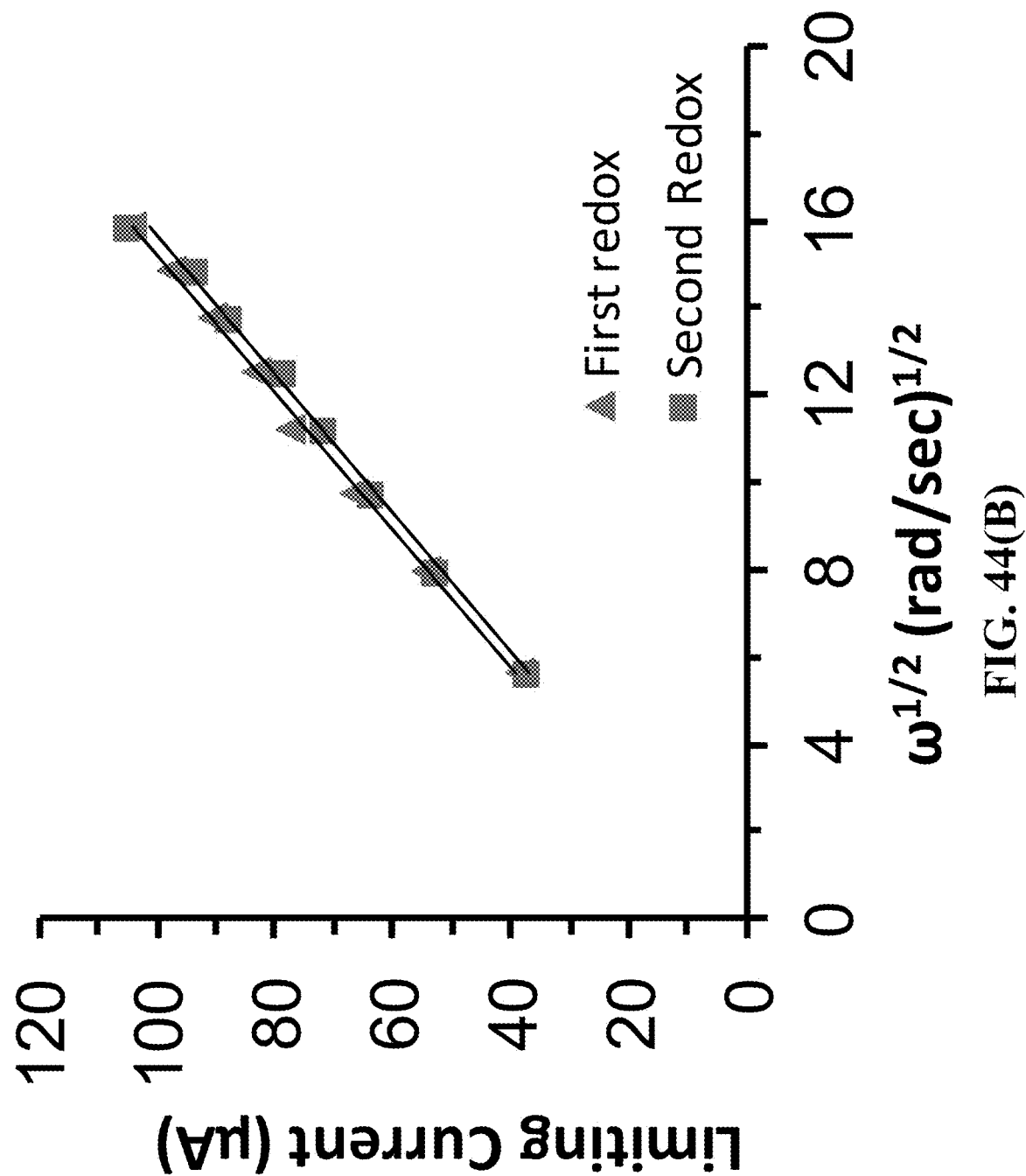
Figure 44C:
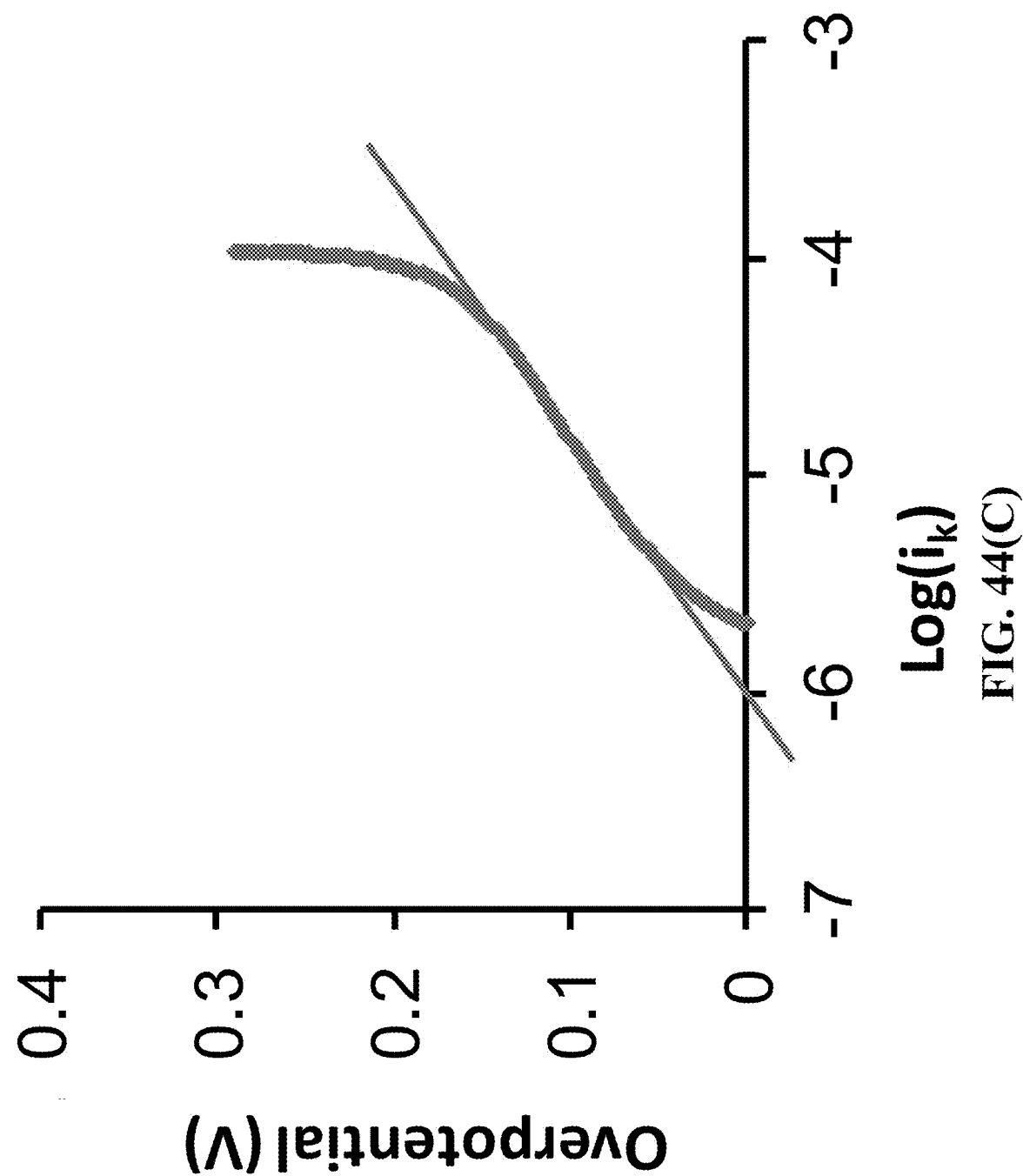
Figure 44D:
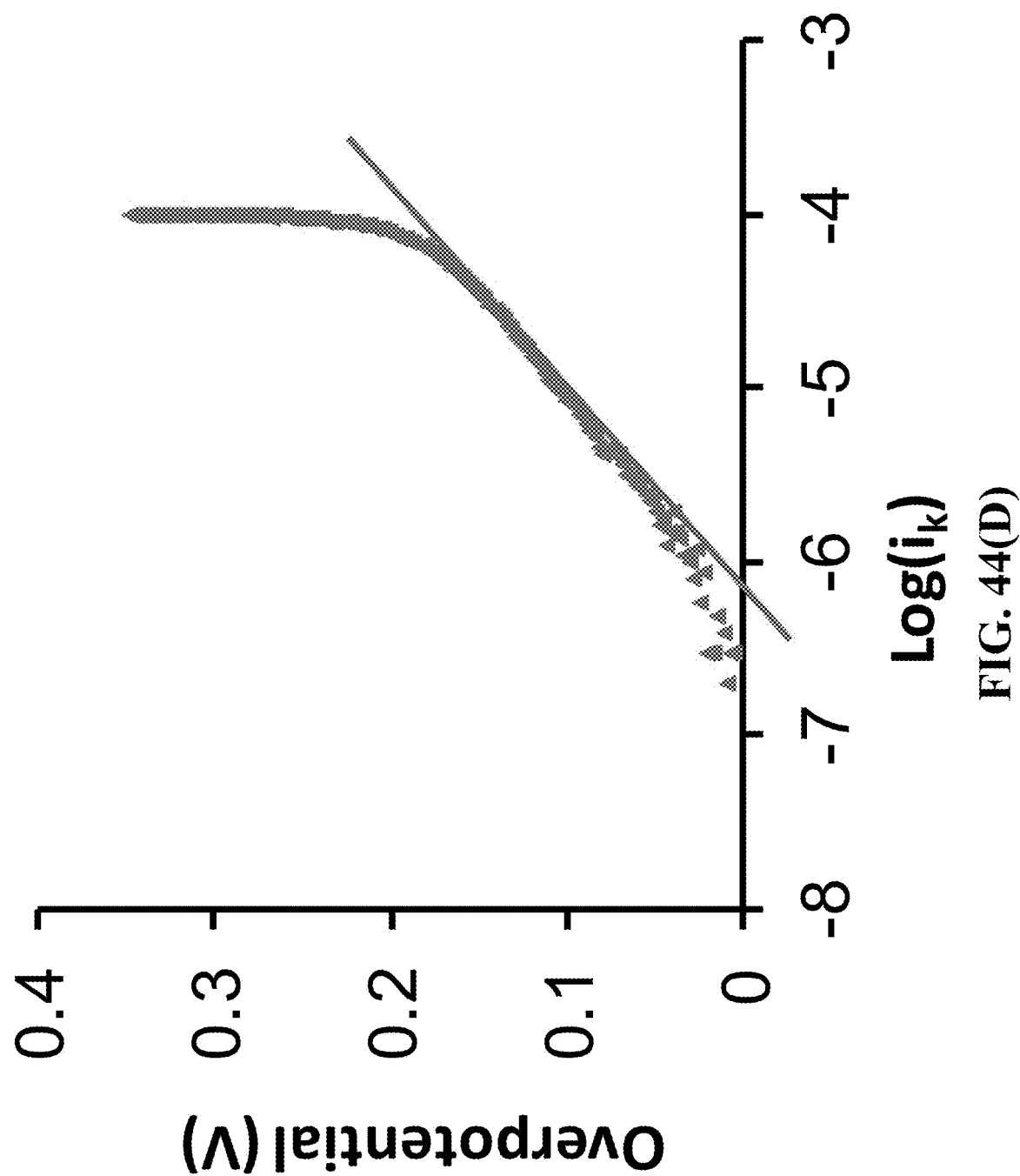

FIGS. 42(A)-(E) show square wave voltammetry curves for viologens as follows with [FcN$^{Et}$]Br as internal reference at 0.60 V vs. NHE: FIG. 42(A) (NPr)$_2$V; FIG. 42(B) (NPr)(SPr)V; FIG. 42(C) (Me)(NPr)V; FIG. 42(D) (SPr)$_2$V; FIG. 42(E) MV. Experiment conditions for all: 4 mM viologen with 4 mM [FcN$^{Et}$]Br in 0.5 M NaCl supporting electrolyte. 1.0 V initial potential, −1.2 V final potential, 25 mV pulse width, 25 Hz frequency, glassy carbon working electrode, glassy carbon counter electrode, Ag/AgCl reference electrode.

FIGS. 43(A)-(F) show cyclic voltammetry curves of (NPr)$_2$V and [FcN$^{Et}$]Br at variable scan rate. CV of (NPr)$_2$V's first redox (FIG. 43(A)), second redox (FIG. 43(B)) and [FcN$^a$]Br's redox (FIG. 43(C)). Plots of is and is versus the square root of scan rate for (NPr)$_2$V's first redox (FIG. 43(D)), second redox (FIG. 43(E)), and [FcN$^a$]Br's redox (FIG. 43(F)). The linear relationships show both oxidation and reduction as diffusion controlled processes for all three redox events. Experiment conditions for all: 4.0 mM active material in 0.5 M NaCl, glassy carbon working electrode, glassy carbon counter electrode, Ag/AgCl reference electrode. Scan rates from 0.05 V/s to 16 V/s.

FIGS. 44 (A)-(D) show rotating disk electrode (RDE) data and analysis for (NPr)$_2$V. FIG. 44(A) LSV scans with rotating working electrode. FIG. 44(B) Levich analysis for each reduction. Tafel analysis for the first (FIG. 44(C)) and second (FIG. 44(D)) reductions. Experiment conditions: 1.0 mM (NPr)$_2$V in 0.5 M NaCl electrolyte; 5 mV/s scan rate; 300 rpm to 2400 rpm rotation rate; 0.196 cm$^2$ electrode area; glassy carbon rotating disk working electrode, glassy carbon counter electrode, Ag/AgCl reference electrode.

Figure 45A:
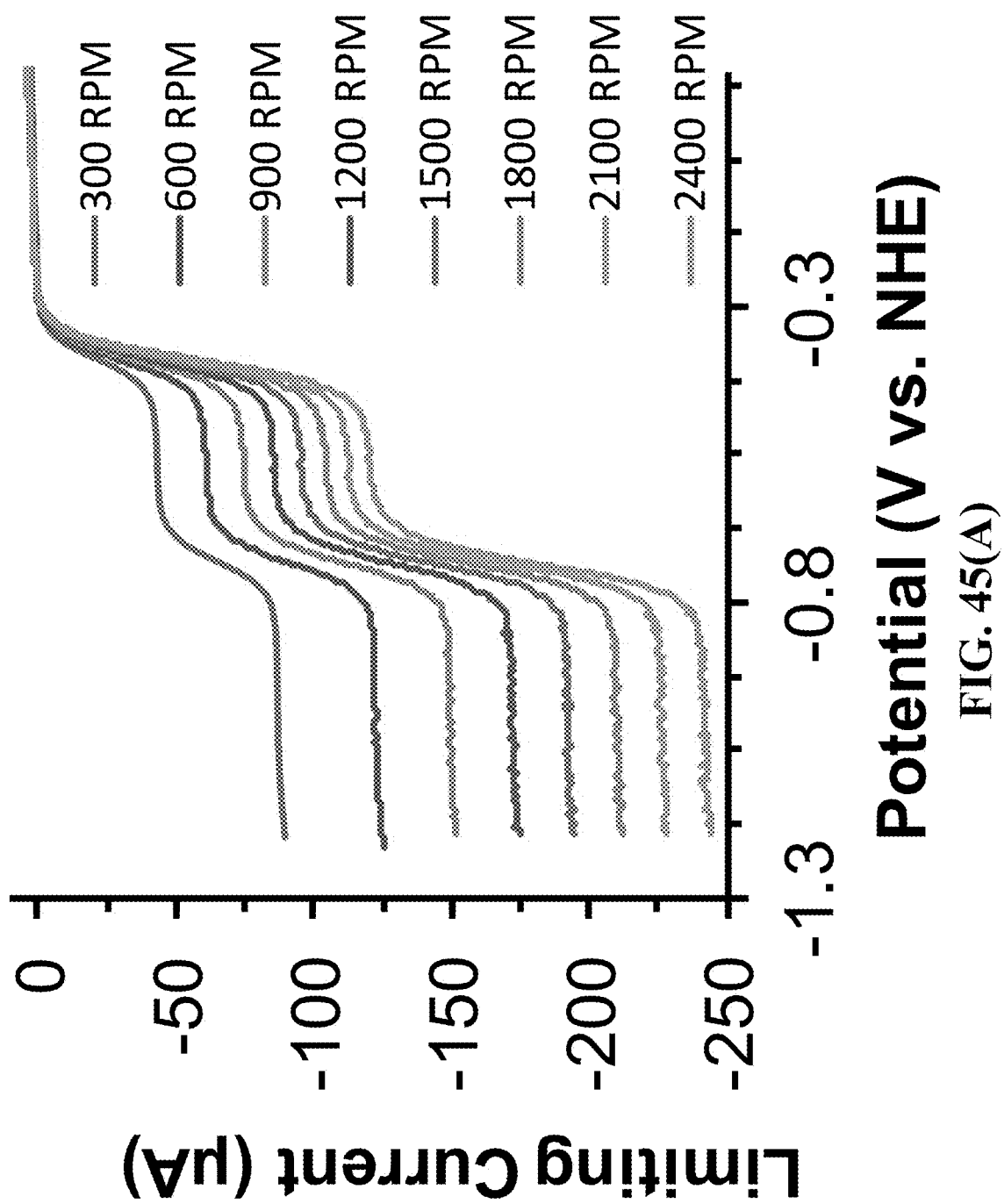
Figure 45B:
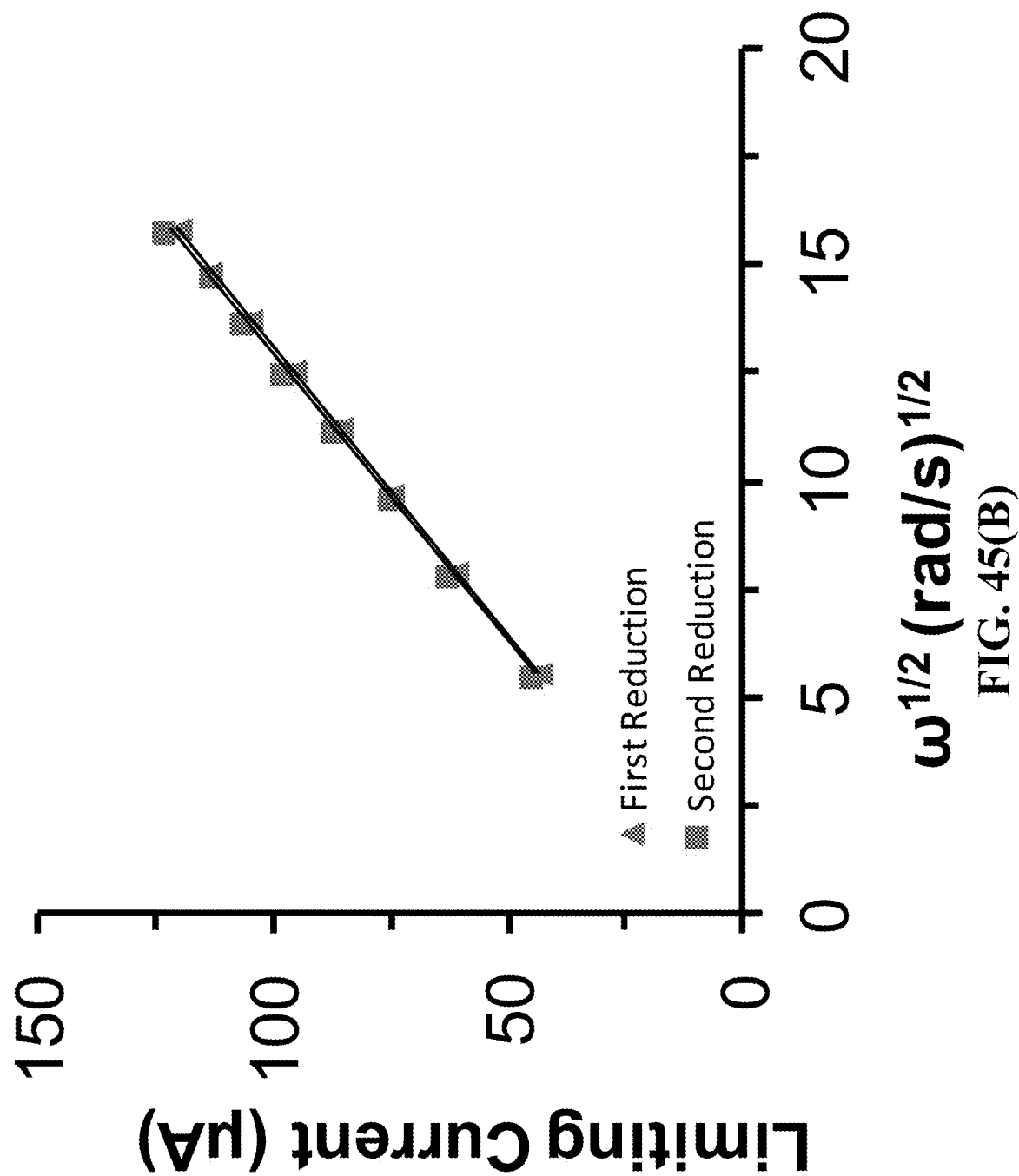
Figure 45C:
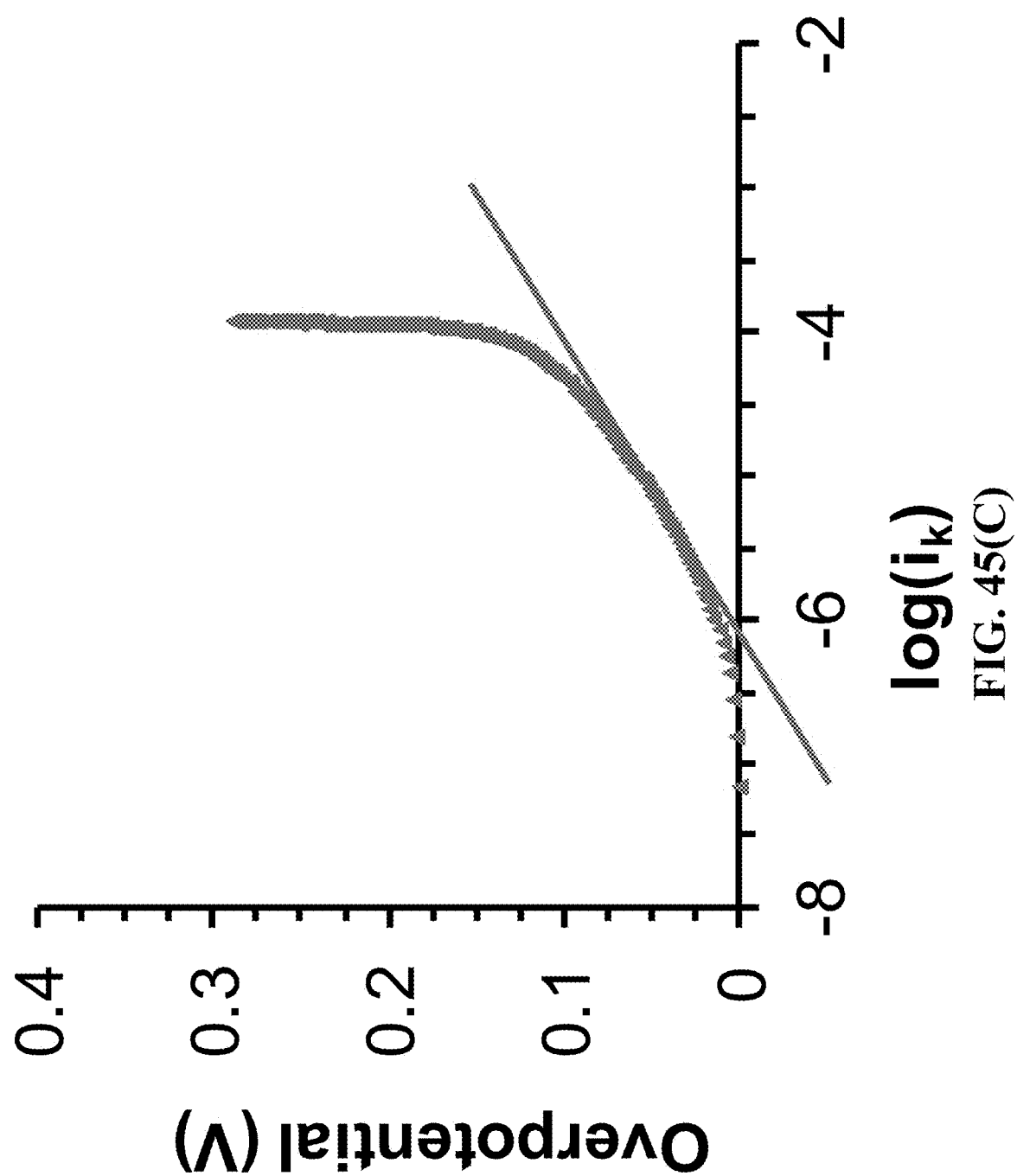
Figure 45D:
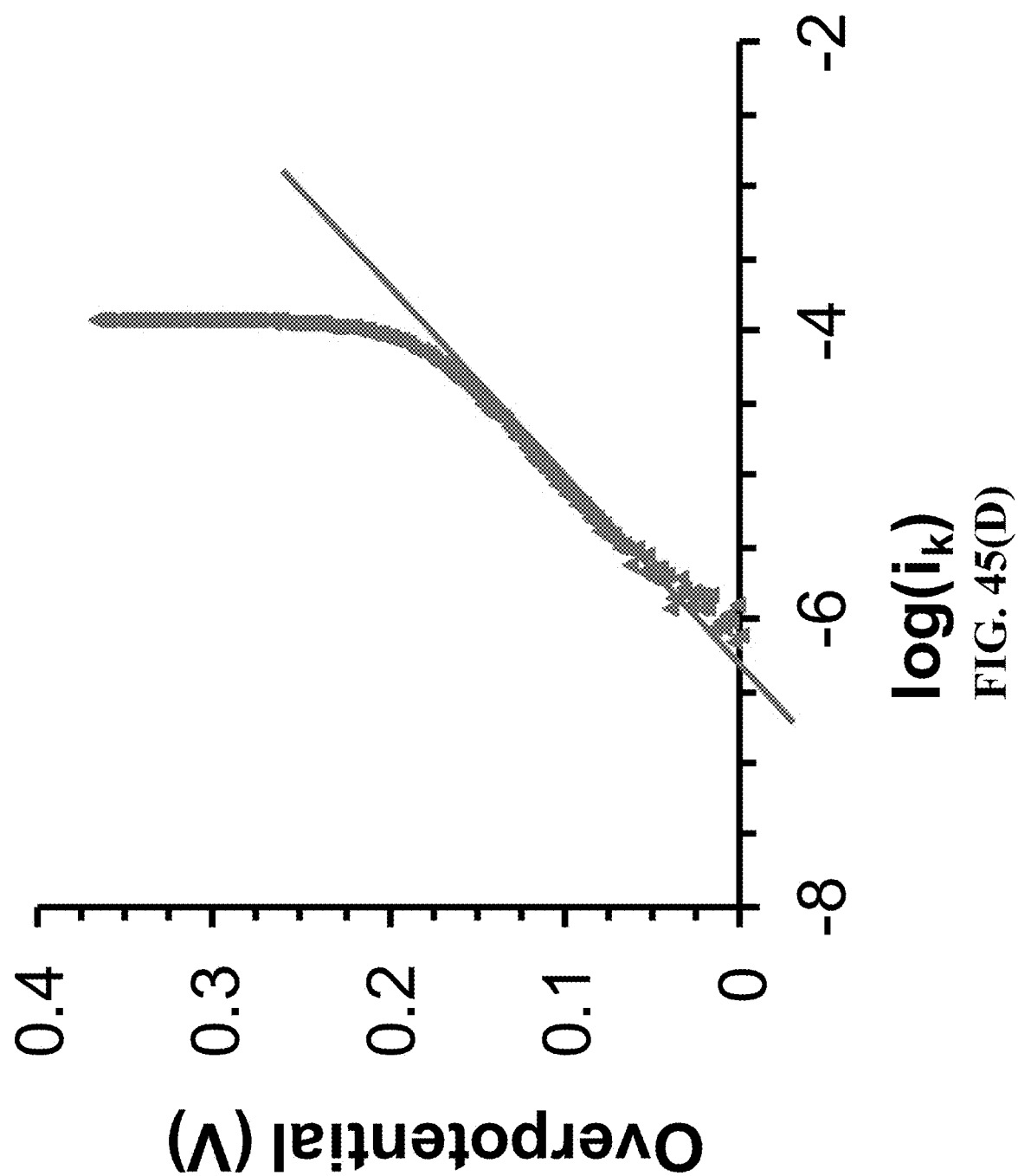

FIGS. 45(A)-(D) show RDE data and analysis for (NPr)(SPr)V. FIG. 45(A) LSV scans with rotating working electrode. FIG. 45(B) Levich analysis for each reduction. Tafel analysis for the first (FIG. 45(C)) and second (FIG. 45(D)) reductions. Experiment conditions: 1.0 mM (NPr)(SPr)V in 0.5 M NaCl electrolyte; 5 mV/s scan rate; 300 rpm to 2400 rpm rotation rate; 0.196 cm$^2$ electrode area; glassy carbon rotating disk working electrode, glassy carbon counter electrode, Ag/AgCl reference electrode.

Figure 46A:
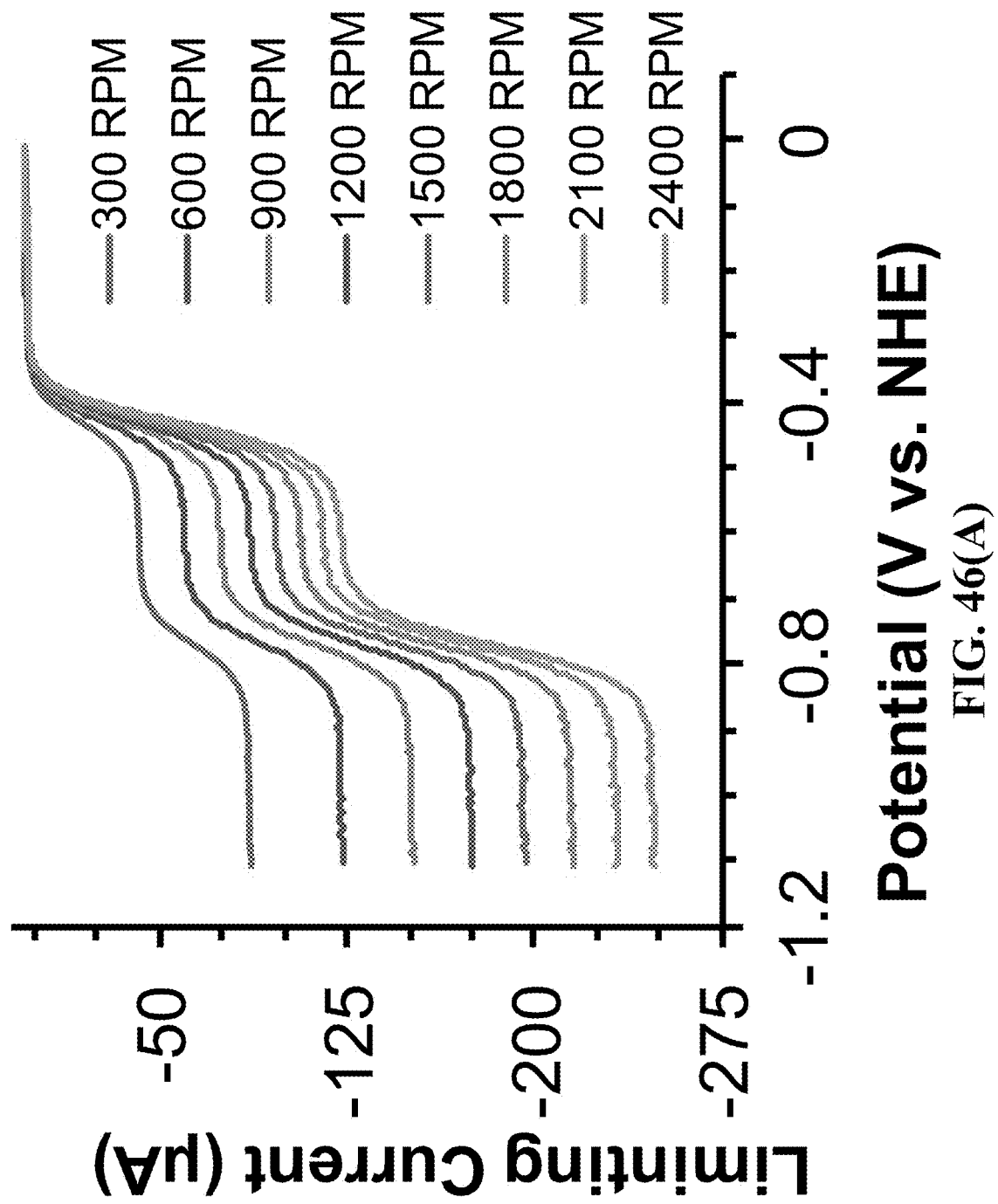
Figure 46B:
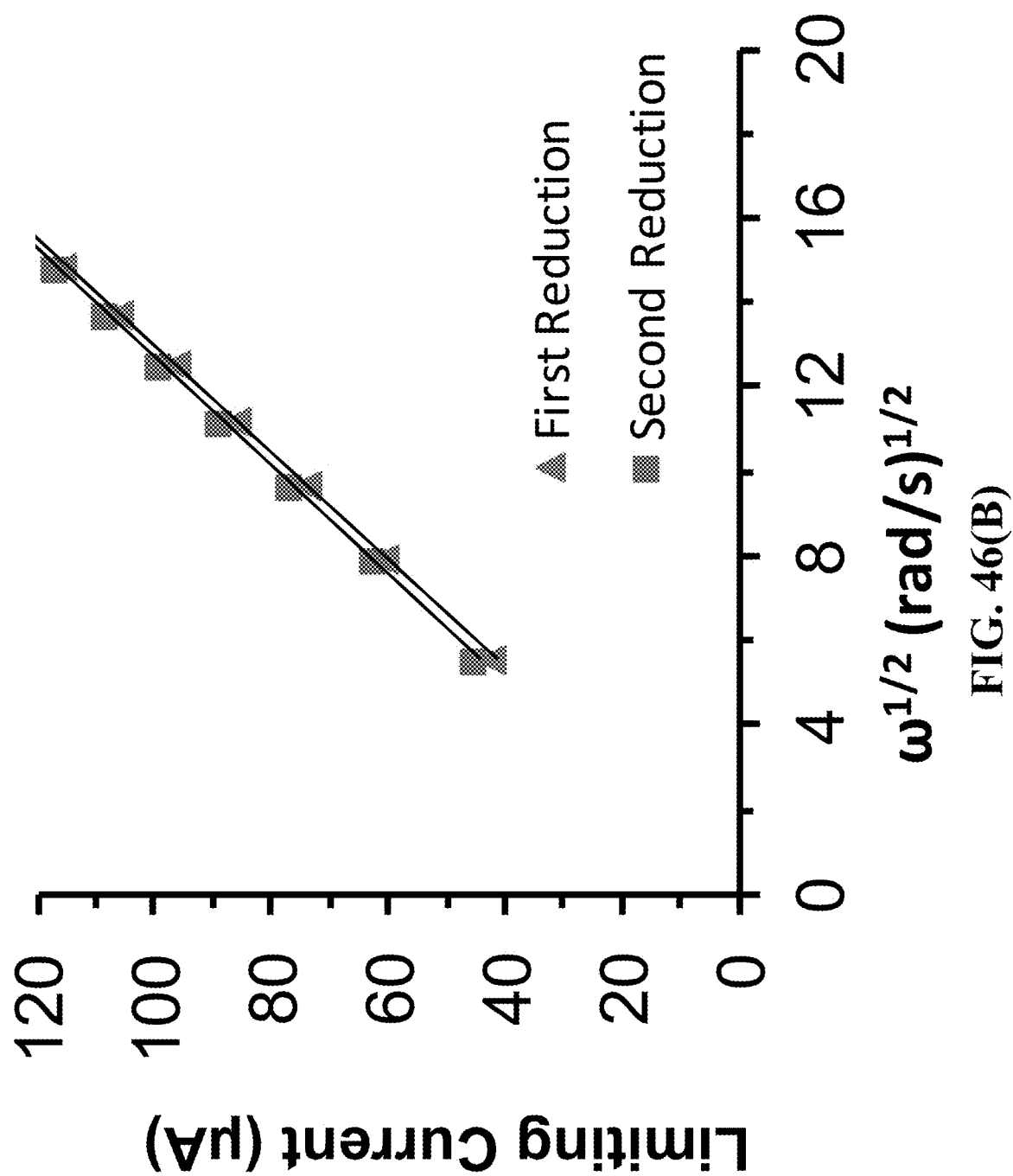
Figure 46C:
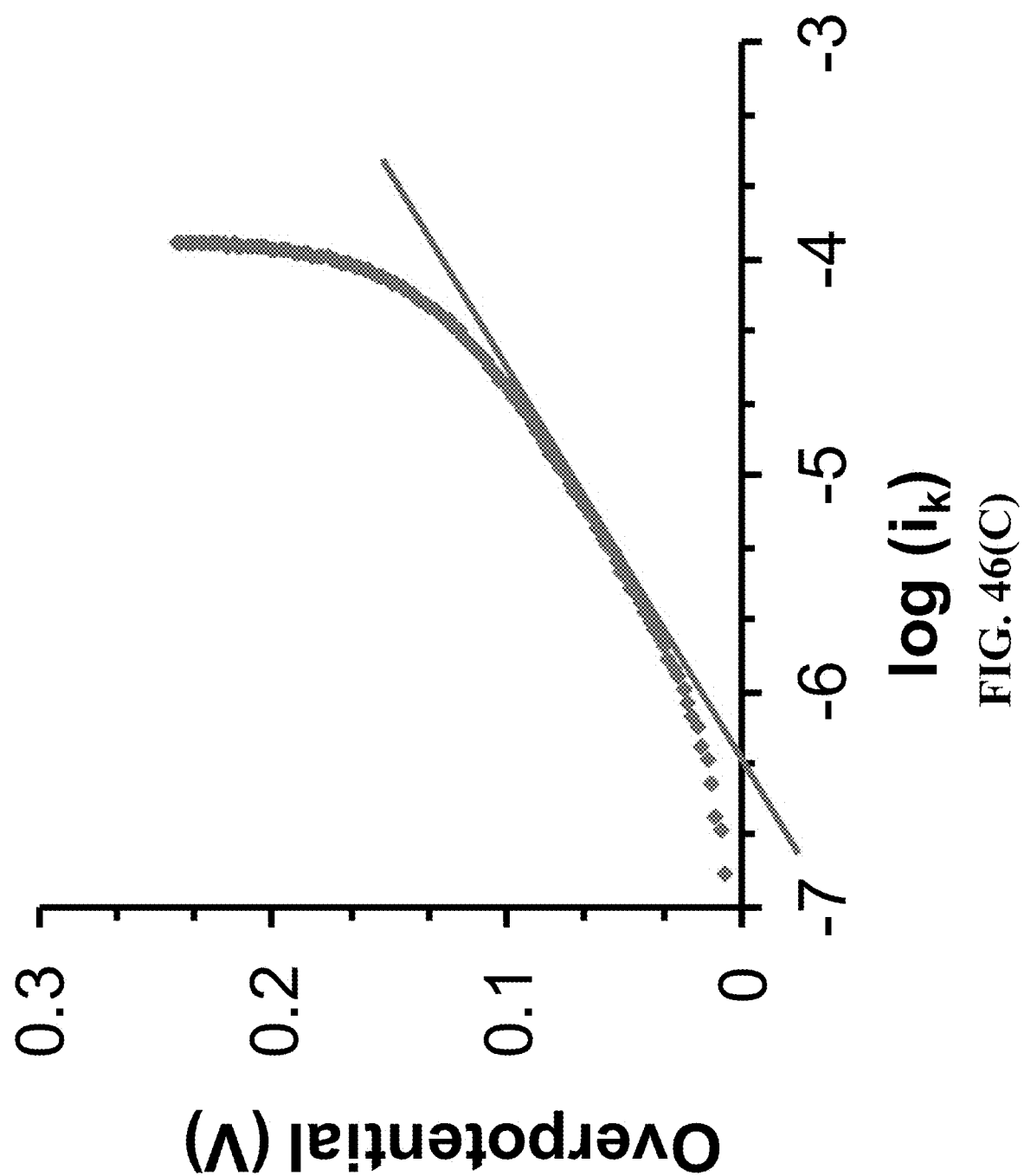
Figure 46D:
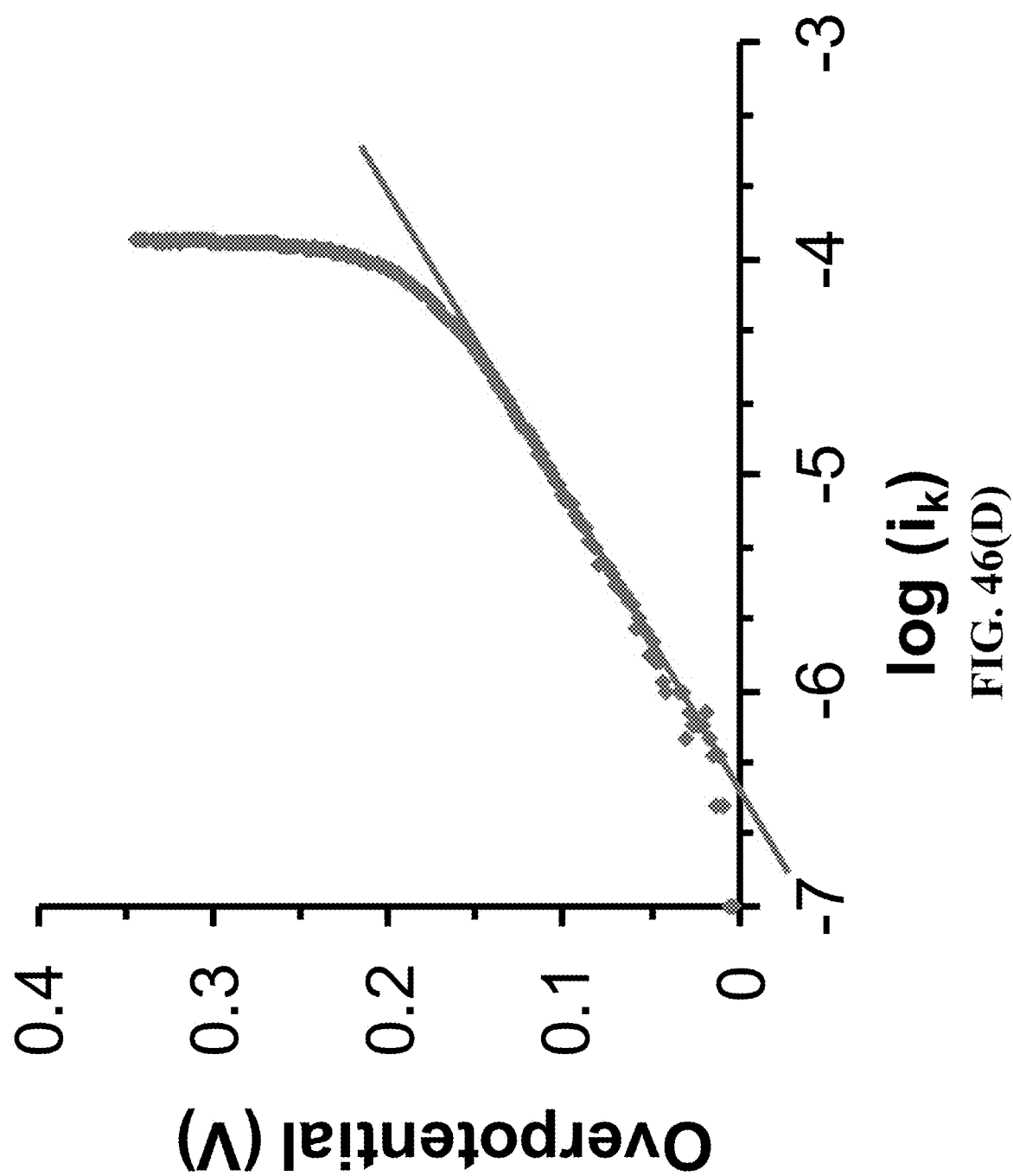

FIGS. 46(A)-(D) show RDE data and analysis for (Me)(NPr)V. FIG. 46(A) LSV scans with rotating working electrode. FIG. 46(B) Levich analysis for each reduction. Tafel analysis for the first (FIG. 46(C)) and second (FIG. 46(D)) reductions. Experiment conditions: 1.0 mM (Me)(NPr)V in 0.5 M NaCl electrolyte; 5 mV/s scan rate; 300 rpm to 2400 rpm rotation rate; 0.196 cm$^2$ electrode area; glassy carbon rotating disk working electrode, glassy carbon counter electrode, Ag/AgCl reference electrode.

Figure 47A:
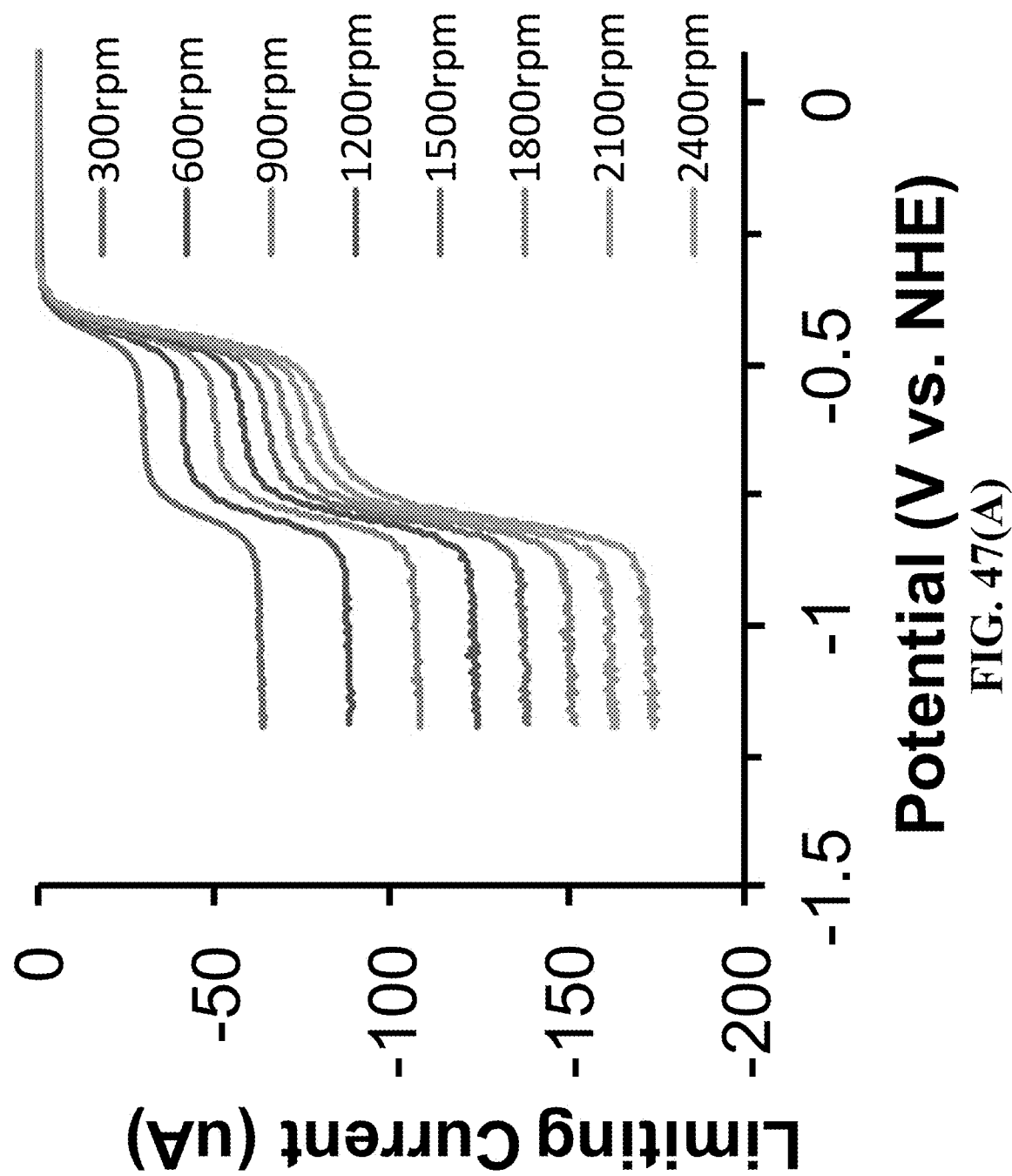
Figure 47B:
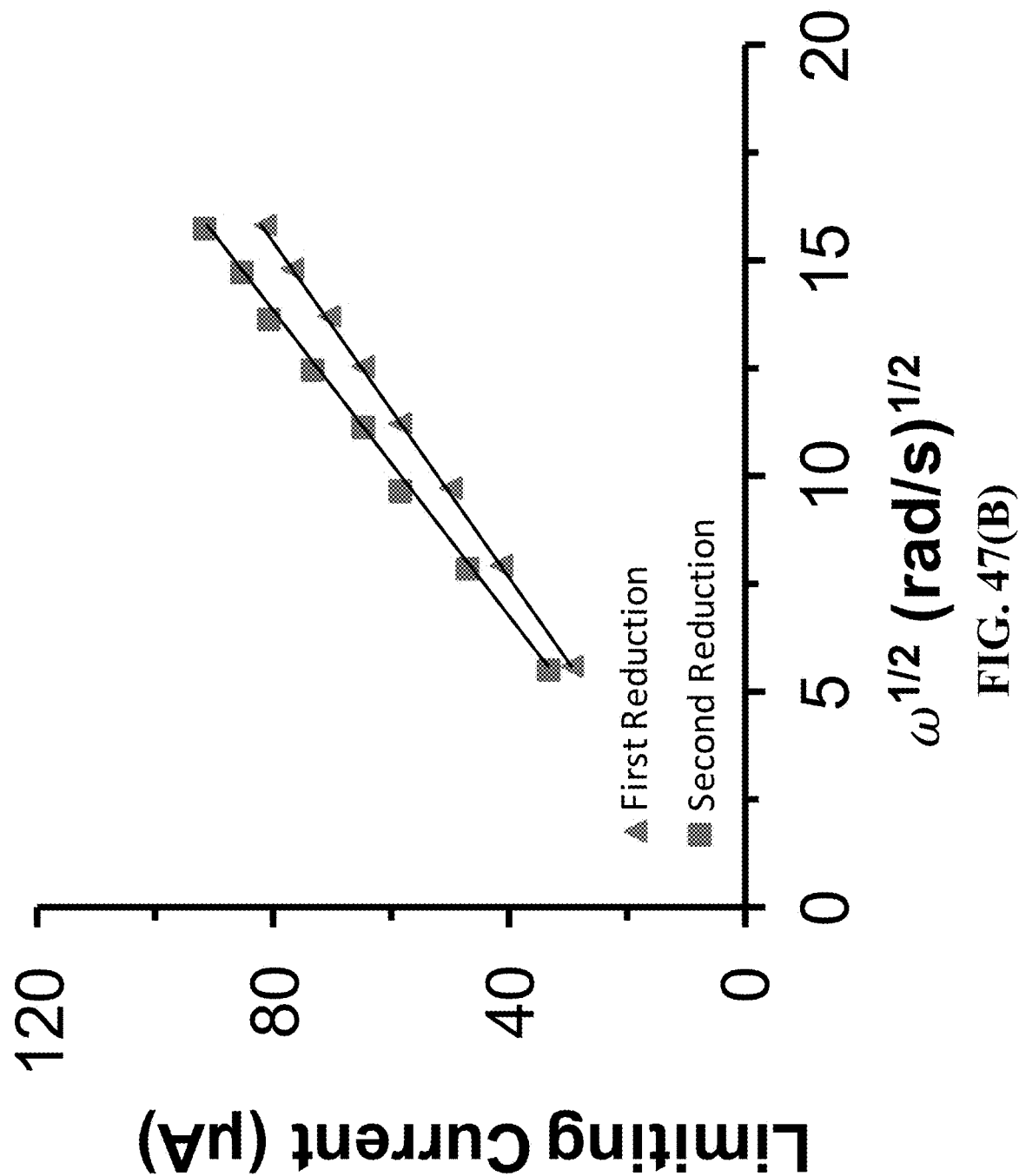
Figure 47C:
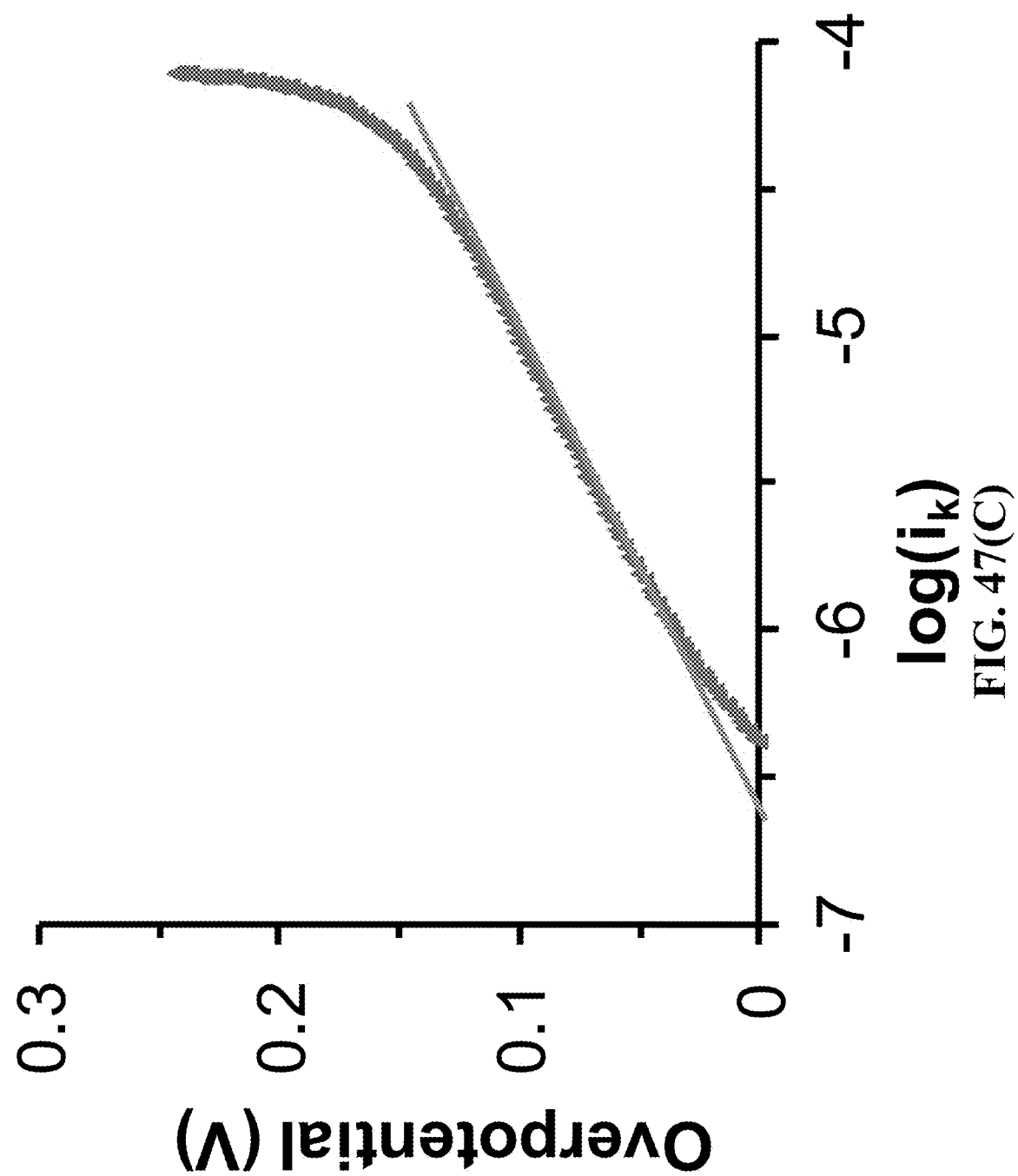
Figure 47D:
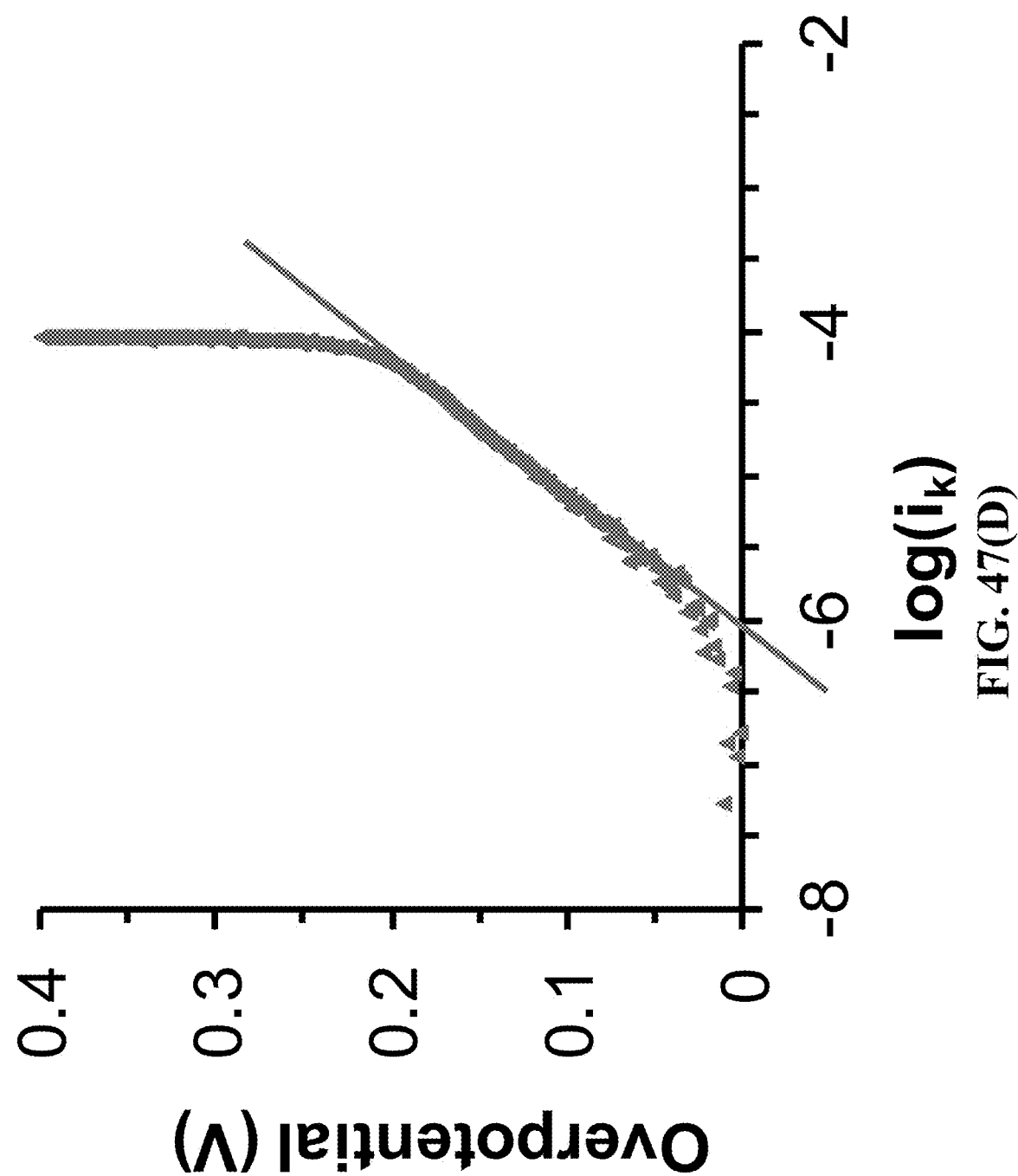

FIGS. 47(A)-(D) show RDE data and analysis for (SPr)$_2$V. FIG. 47(A) LSV scans with rotating working electrode. FIG. 47(B) Levich analysis for each reduction. Tafel analysis for the first (FIG. 47(C)) and second (FIG. 47(D)) reductions. Experiment conditions: 1.0 mM (SPr)$_2$V in 0.5 M NaCl electrolyte; 5 mV/s scan rate; 300 rpm to 2400 rpm rotation rate; 0.196 cm$^2$ electrode area; glassy carbon rotating disk working electrode, glassy carbon counter electrode, Ag/AgCl reference electrode.

Figure 48A:
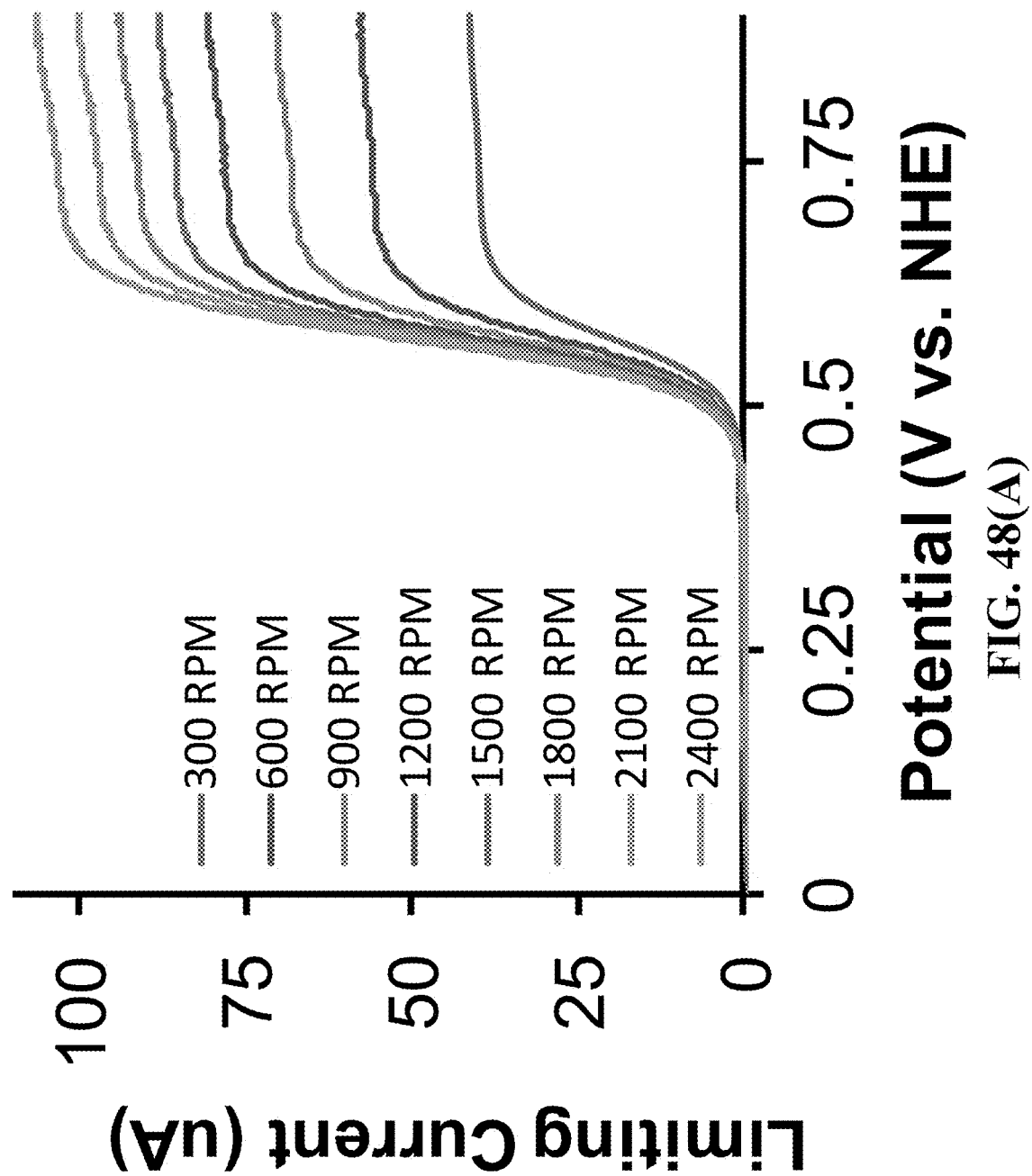
Figure 48B:
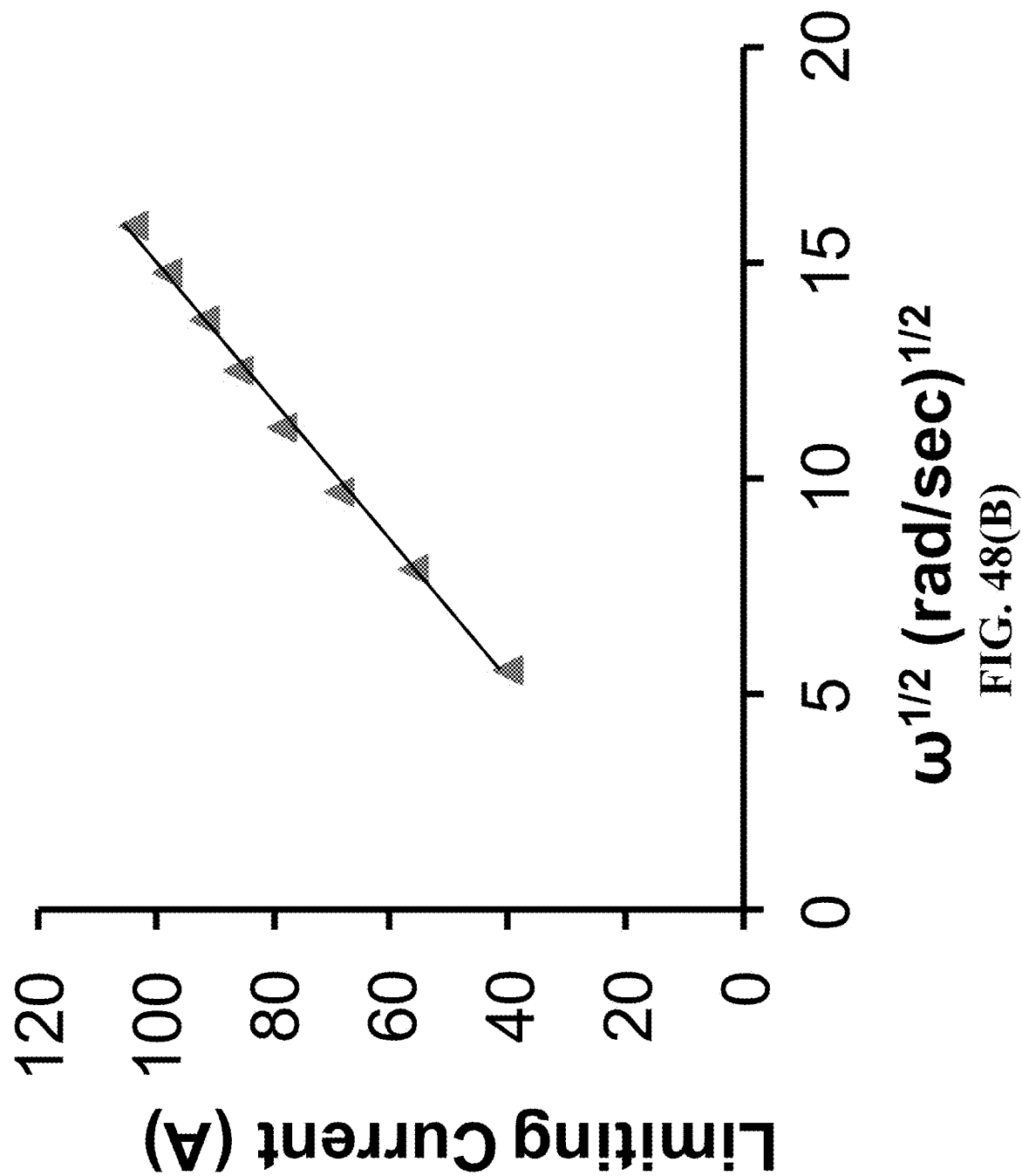

FIGS. 48(A)-(C) show RDE data and analysis for [FcN$^{Et}$]Br. FIG. 48(A) LSV scans with rotating working electrode.

FIG. 48(B) Levich analysis. FIG. 48(C) Tafel analysis. Experiment conditions: 1.0 mM [FcN$^{Et}$]Br in 0.5 M NaCl electrolyte; 5 mV/s scan rate; 300 rpm to 2400 rpm rotation rate; 0.196 cm$^2$ electrode area; glassy carbon rotating disk working electrode, glassy carbon counter electrode, Ag/AgCl reference electrode.

Figure 49A:
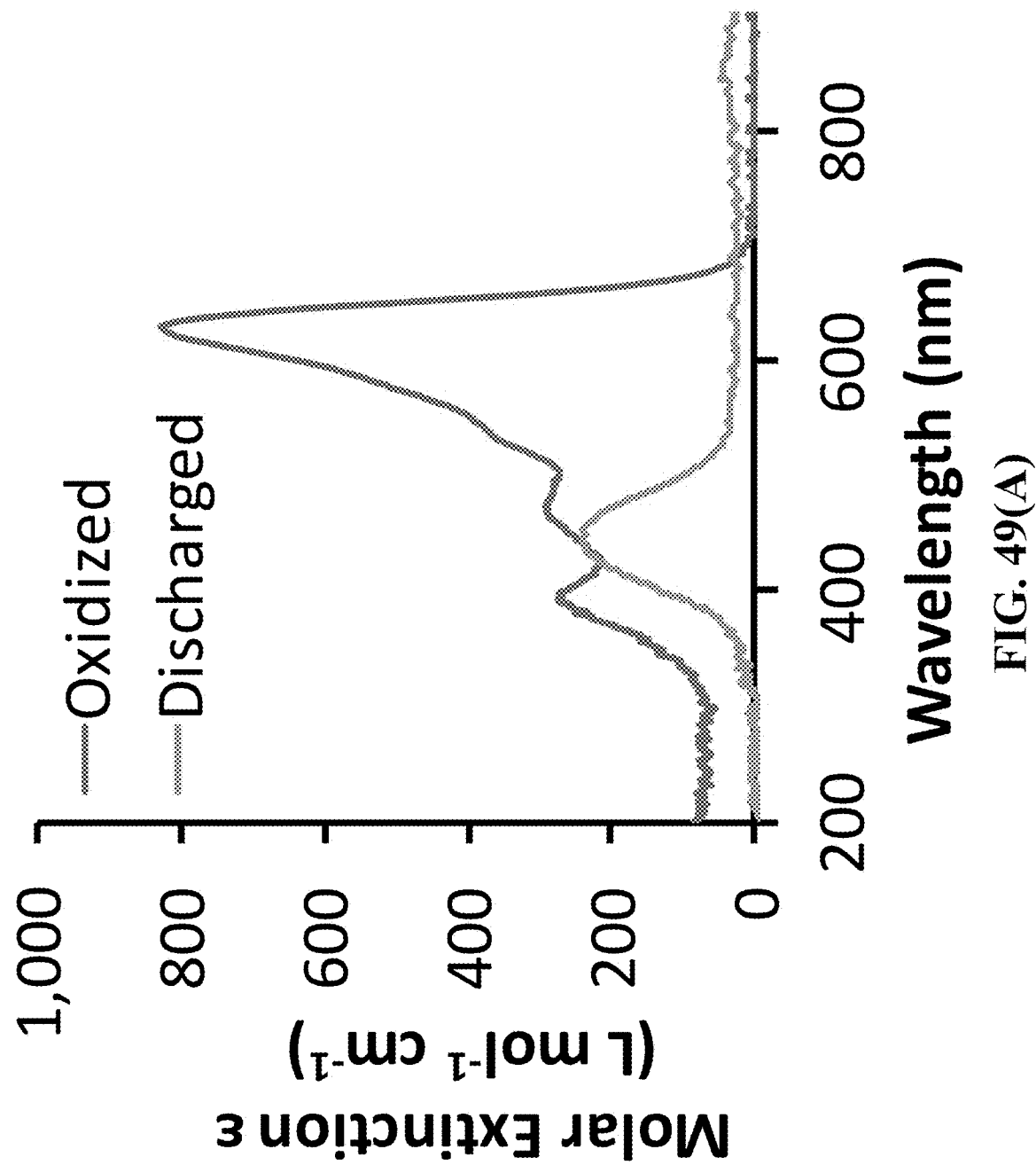
Figure 49B:
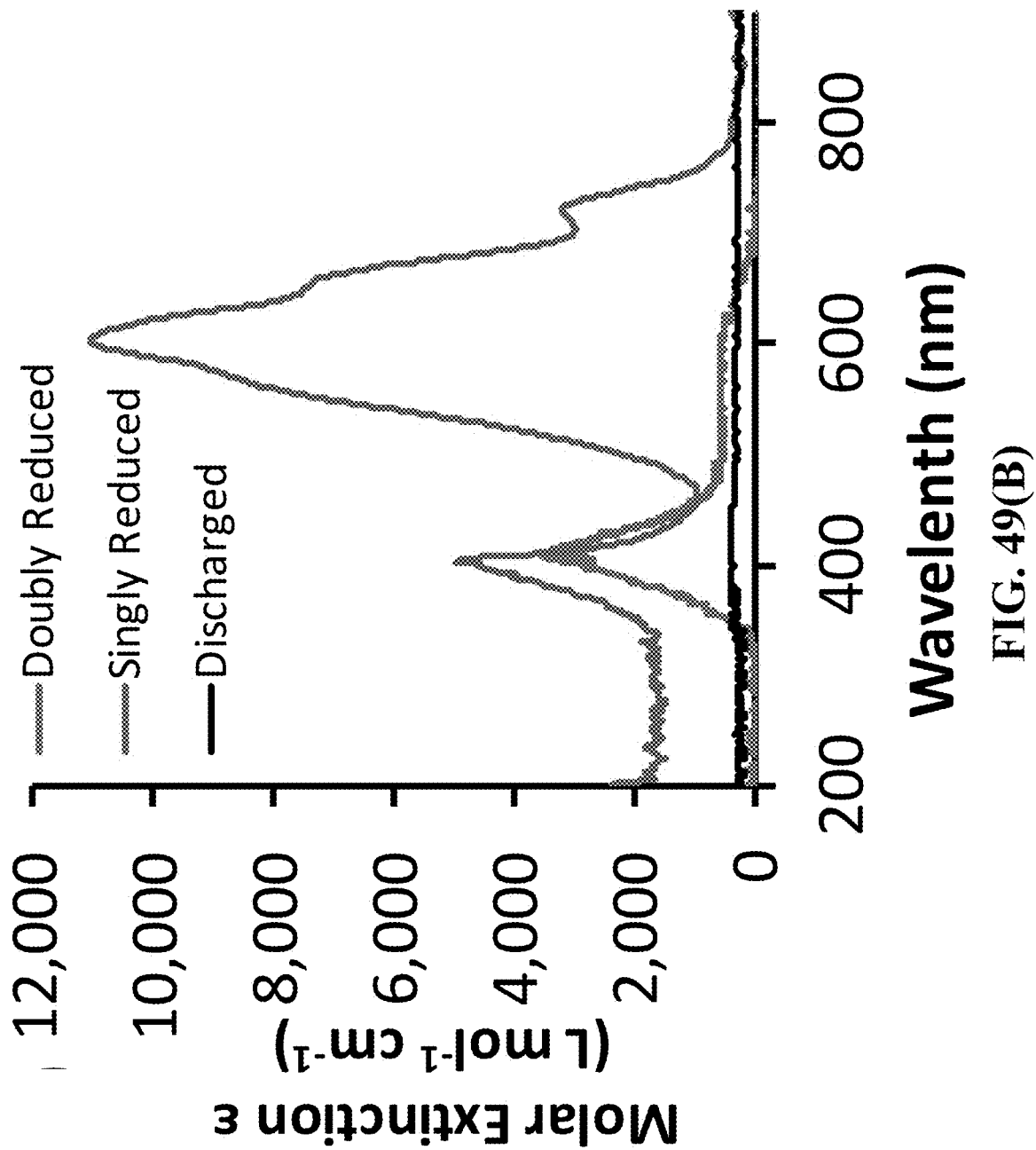
Figure 49C:
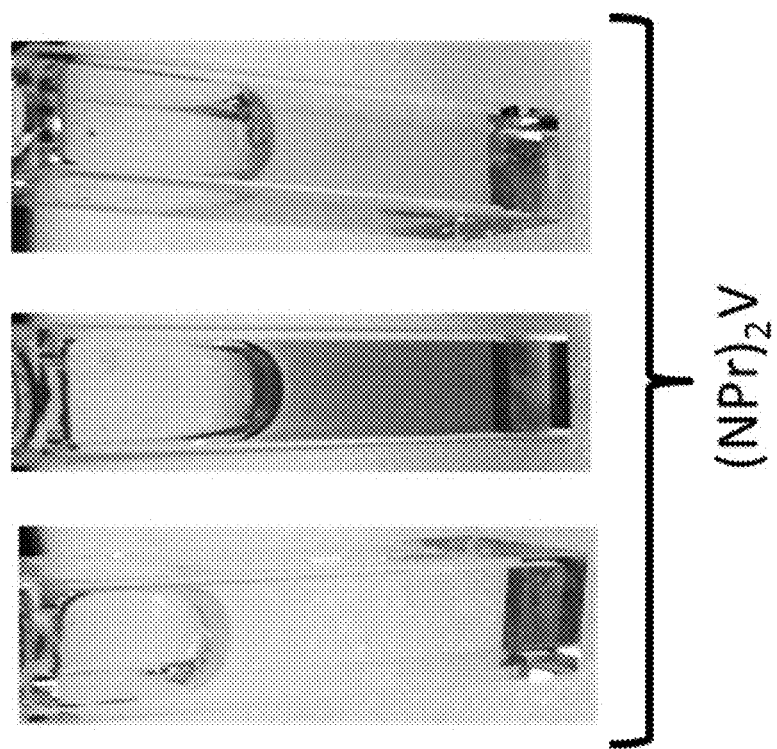
Figure 49C:
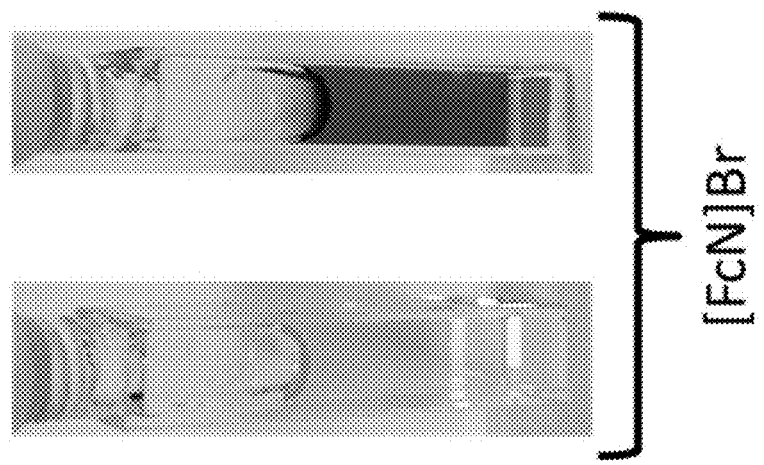

FIG. 49(A) shows UV-Vis spectra of the two redox states of [FcN$^{Et}$]Br with corresponding photos showing solution color FIG. 49(C) (left: discharged, right: fully oxidized). Conditions: 1.25 mM [FcN$^{Et}$]Br in 2.0 M NaCl aqueous solution. FIG. 49(B) shows UV-Vis spectra of the three redox states of (NPr)$_2$V with corresponding photos showing solution color FIG. 49(C) (left: discharged, center: singly reduced, right: doubly reduced). Conditions: 0.125 mM (NPr)$_2$V in 2.0 M NaCl aqueous solution.

Figure 50:
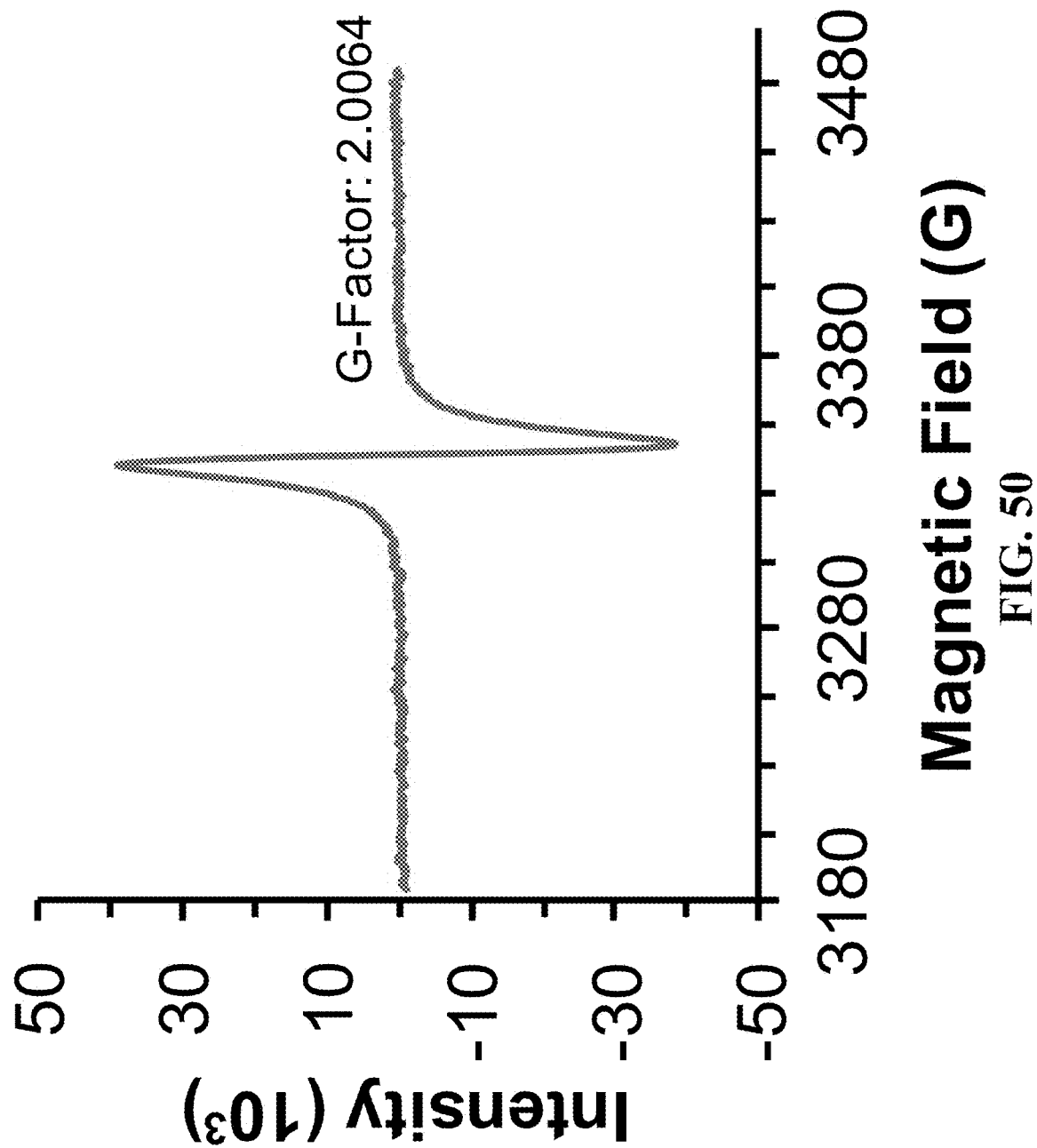

FIG. 50 shows an electron paramagnetic resonance (EPR) Spectrum of the singly reduced [(NPr)$_2$V]$^{3+}$ radical. Sample preparation: 1 mL of 1 mM [(NPr)$_2$V]$^{3+}$ radical in 2.0 M NaCl was removed from an AORFB, and adhered to glass wool by immersing the wool in the solution and vacuuming off the H$_2$O solvent in an argon glove box.

Figure 51:
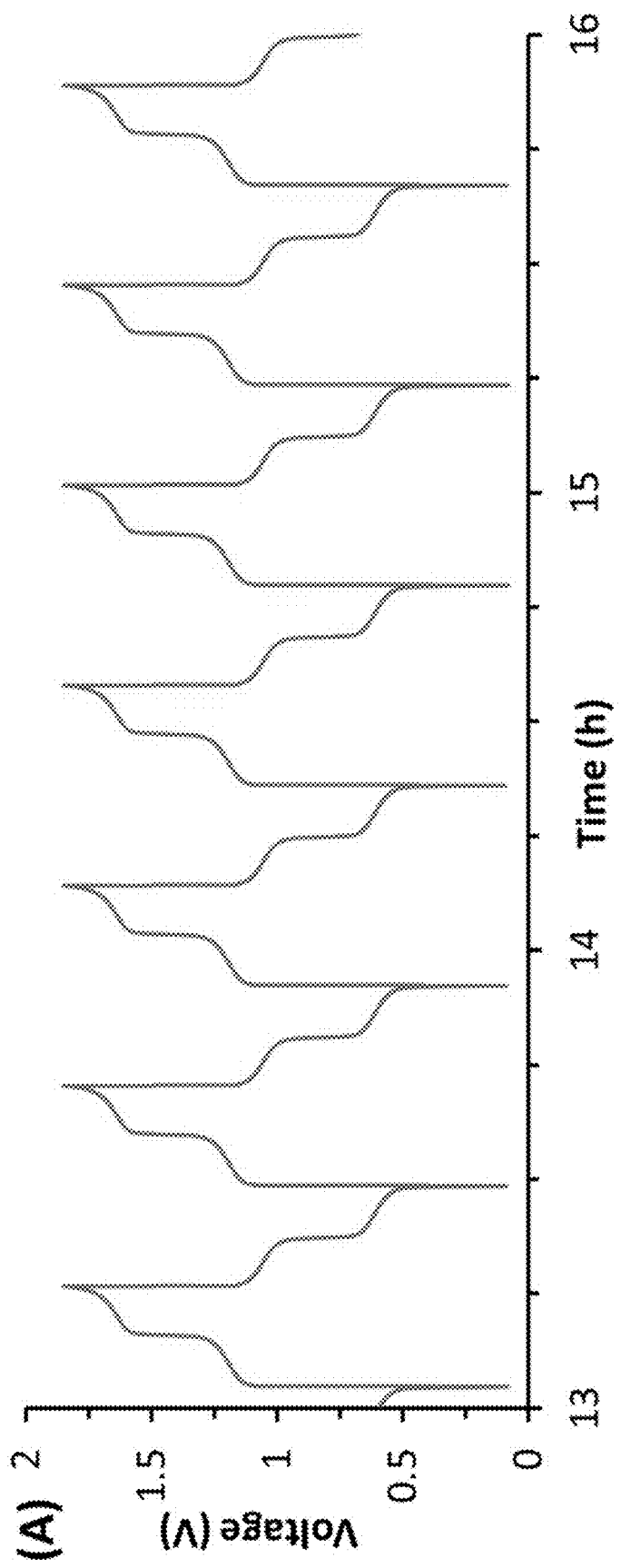

FIG. 51 shows representative charge/discharge voltage profiles over time for a 0.25 M (NPr)$_2$V and 0.5 M [FcN$^{Et}$]Br AORFB at 60 mA/cm$^2$ current density. Battery was operated using both redox from (NPr)$_2$V.

Figure 52:
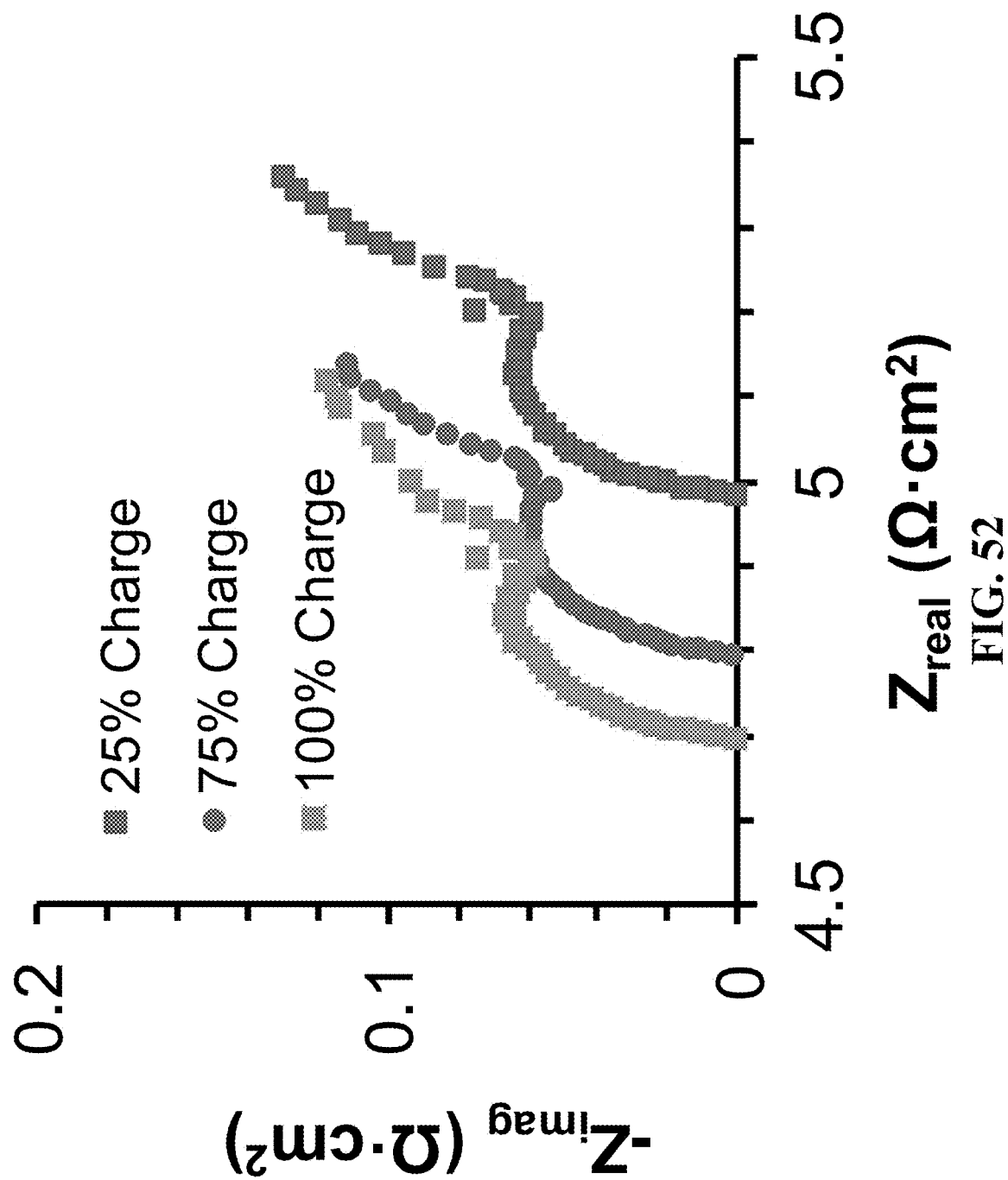

FIG. 52 shows Nyquist plots of a (NPr)$_2$V/[FcN$^{Et}$]Br AORFB recorded at 25%, 75%, and 100% state of charge (SOC).

Figure 53:
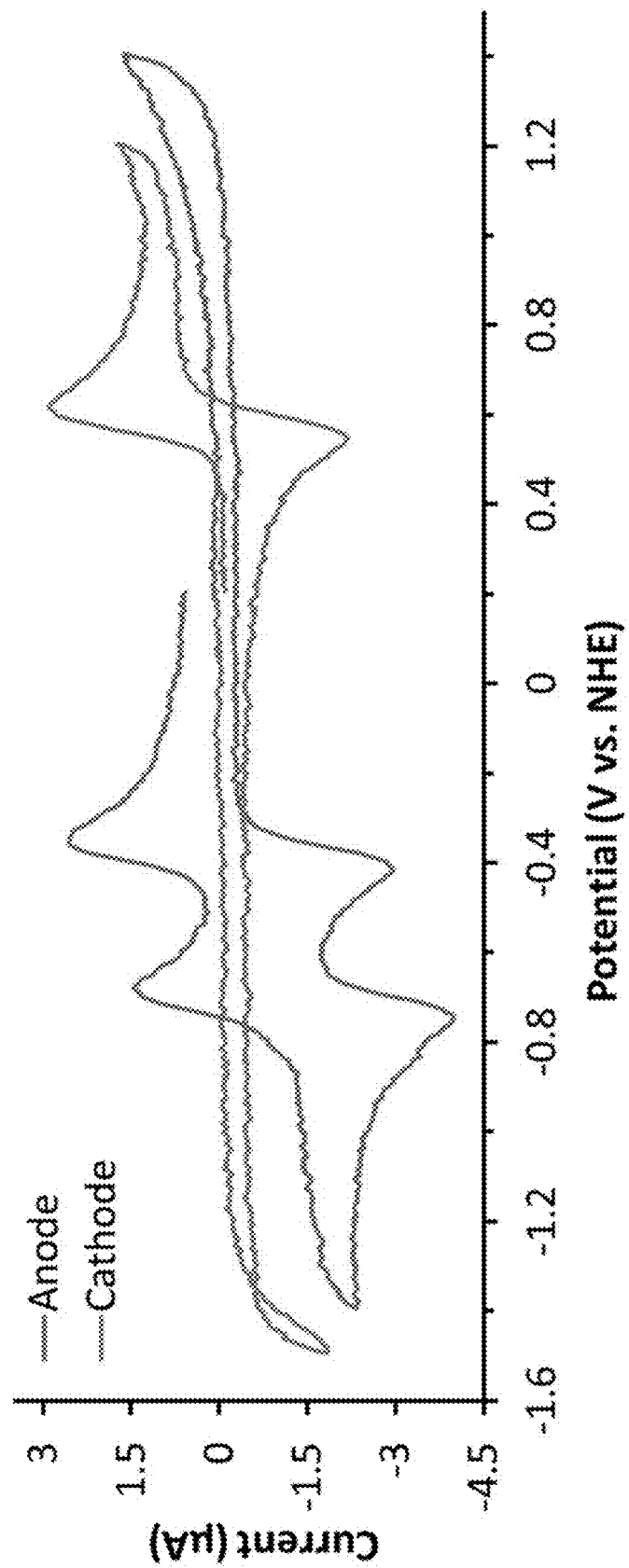

FIG. 53 shows post-cell CV analysis of the (NPr)$_2$V anode and [FcN$^{Et}$]Br cathode solutions after 100 cycles indicating no electrolyte crossover. Each CV shows redox waves belonging to only one individual compound. No [FcN$^{Et}$]Br was detected in the anode solution, and no (NPr)$_2$V was detected in the cathode solution. Experiment conditions: 4 mM [FcN$^{Et}$]Br, 4 mM (NPr)$_2$V, 0.5 M NaCl aqueous electrolyte, glassy carbon working electrode, glassy carbon counter electrode, Ag/AgCl reference electrode.

Figure 54:
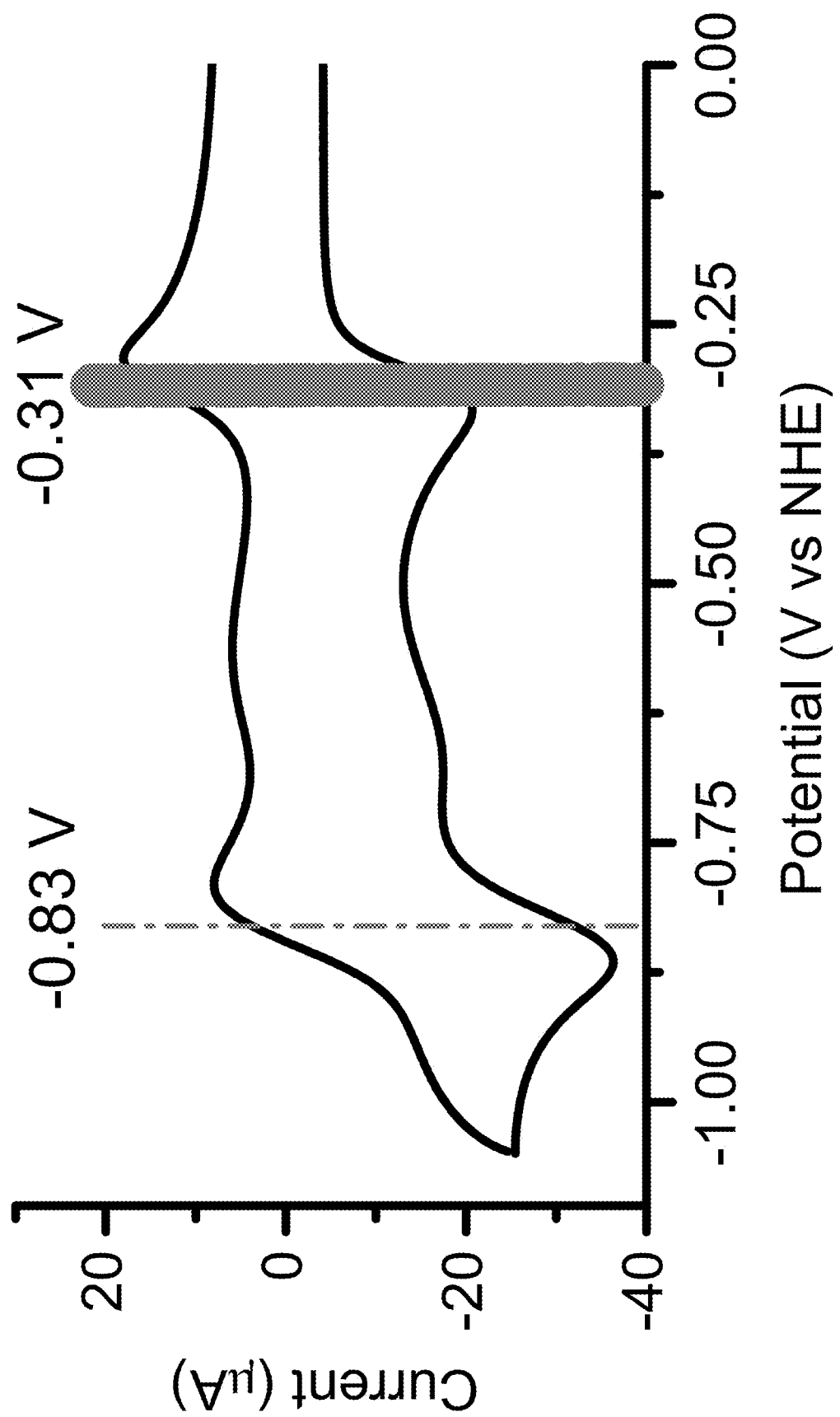

FIG. 54 shows a cyclic voltammogram of 1, bis[(3, 5,-bisulfonato-4-hydroxyphenyl) methyl]-4, 4'-Bipyridinium (S4V) (4 mM) in NaCl (0.5 M) solution. Conditions: scan rate, 100 mV/s; working electrode, glassy carbon; reference electrode, Ag/AgCl; counter electrode, glassy carbon.

Figure 55:
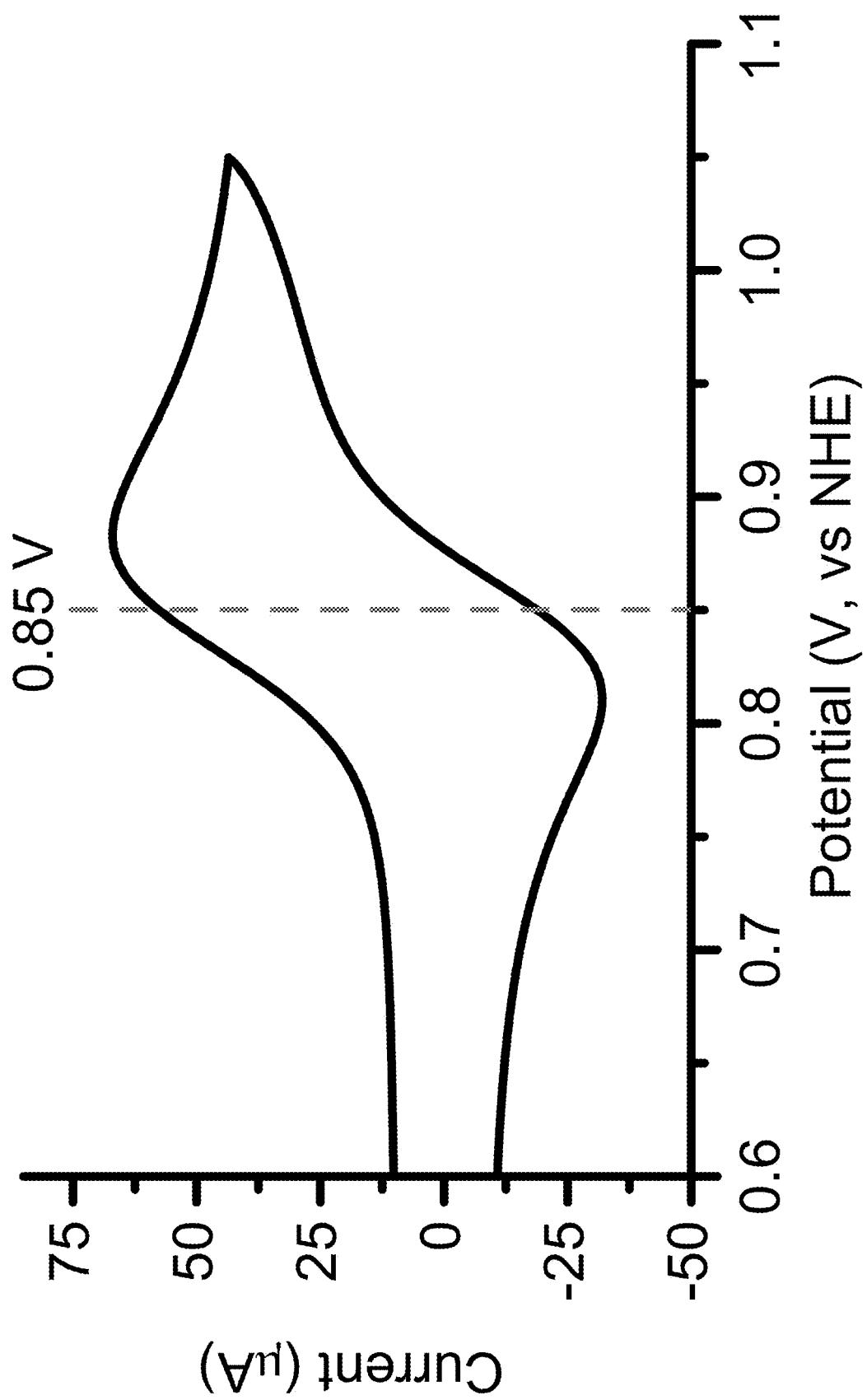

FIG. 55 shows a cyclic voltammogram of FcN2 (4 mM) in NaCl (0.5 M) solution. Conditions: scan rate, 100 mV/s; working electrode, glassy carbon; reference electrode, Ag/AgCl; counter electrode, glassy carbon.

Figure 56:
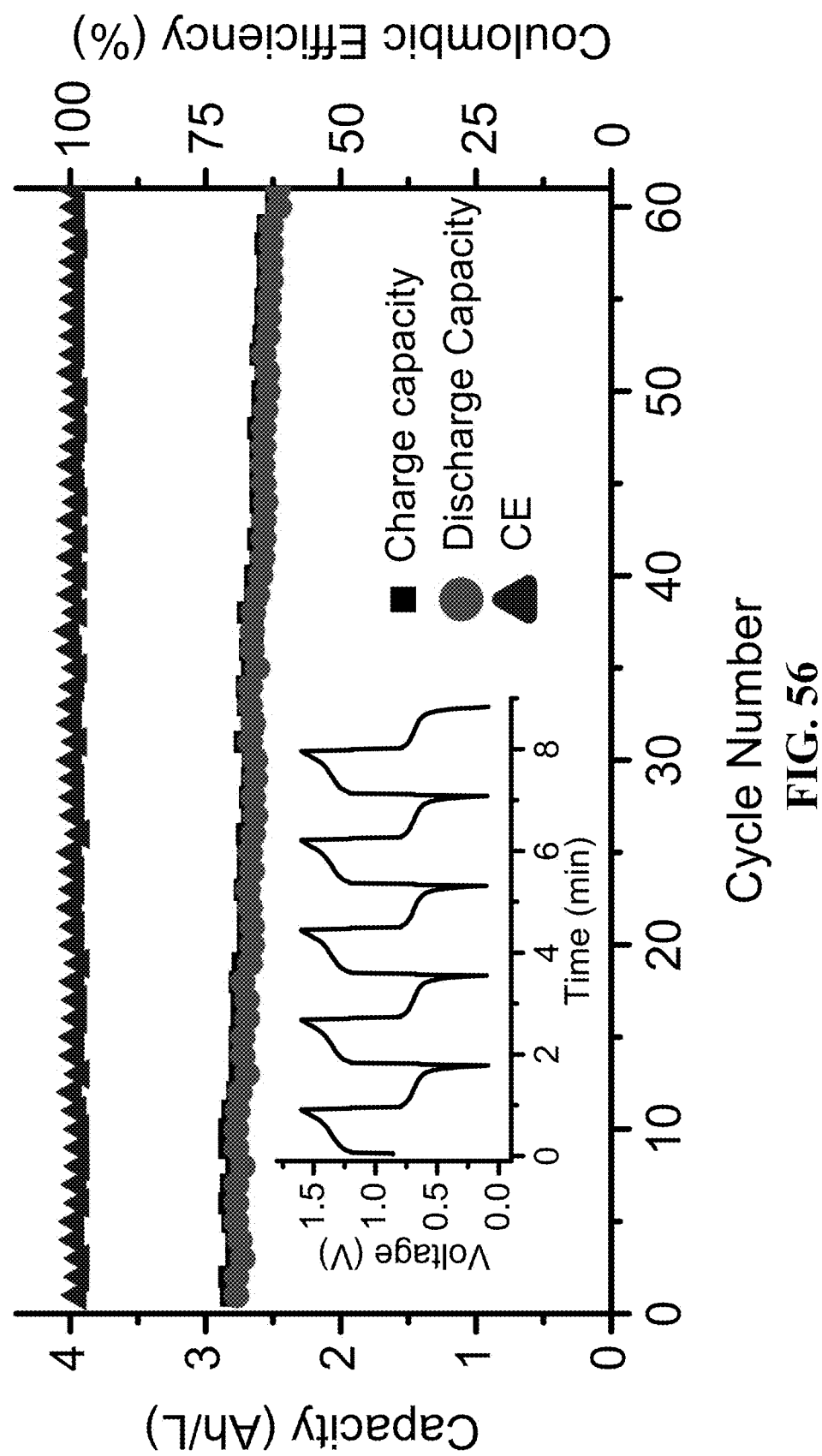

FIG. 56 shows cycling performance for a FcN2-MV AORFB. Conditions: 0.15 M FcN in 2.0 M NaCl solution; 0.15 mM MV in 2.0 M NaCl solution; charge and discharge rate, 20 mA/cm$^2$.

Figure 57:
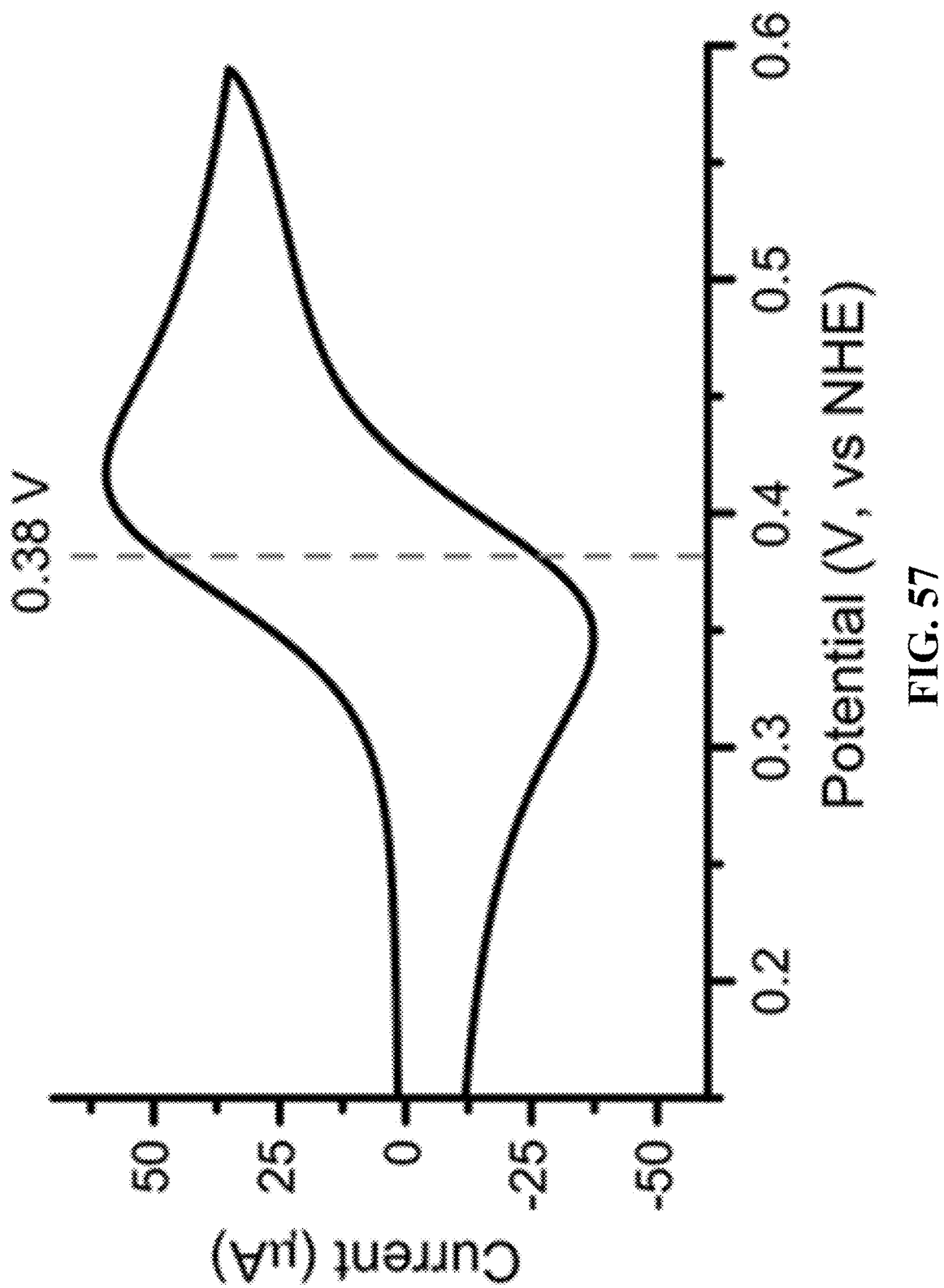

FIG. 57 shows CV of (ferrocenylpropyl)trimethylammonium chloride (prop-FcNCl) having a solubility of approximately 2.2 M in H$_2$O.

Figure 58:
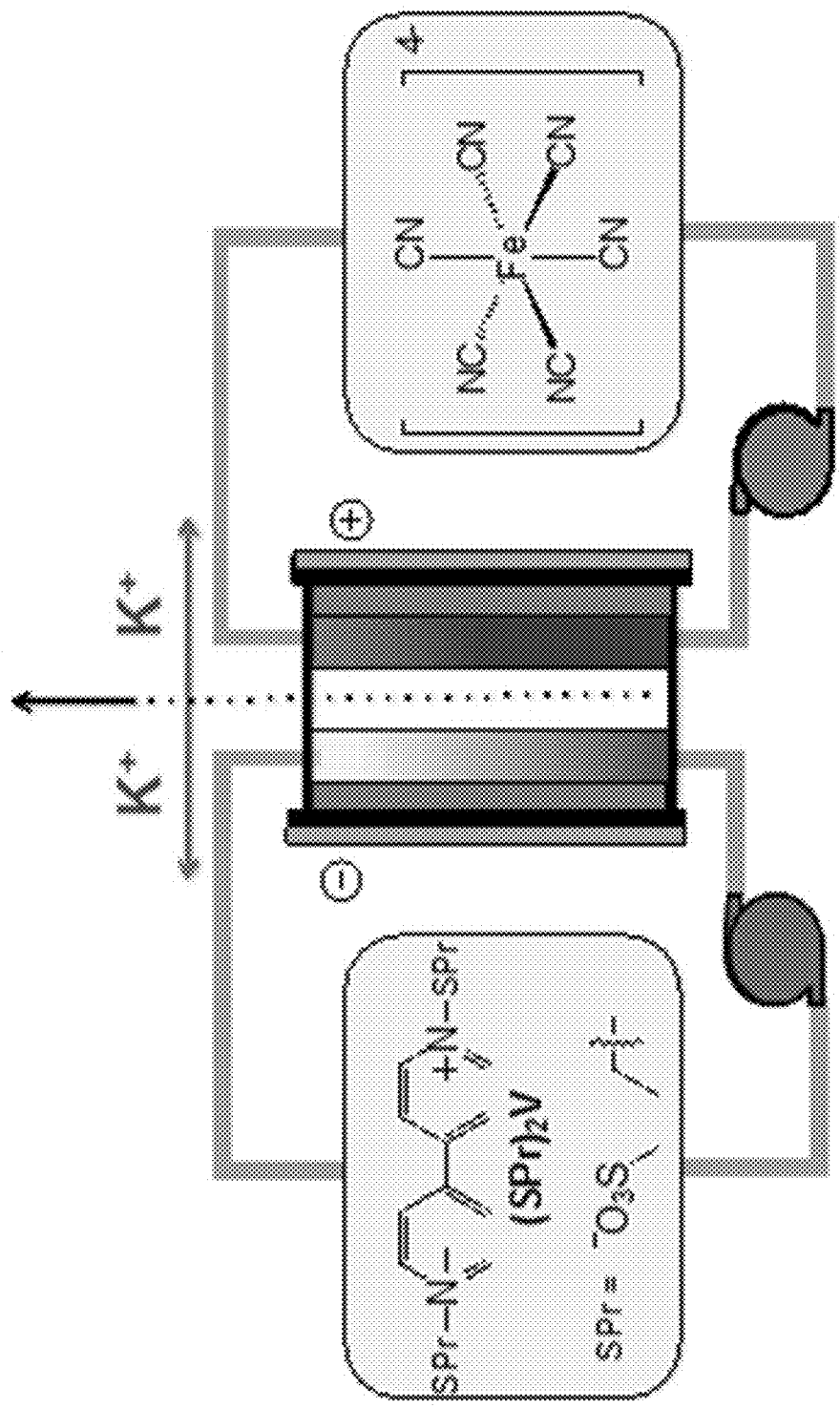

FIG. 58 shows an exemplary schematic of battery design for cation exchange viologen AORFBs.

Figure 59A:
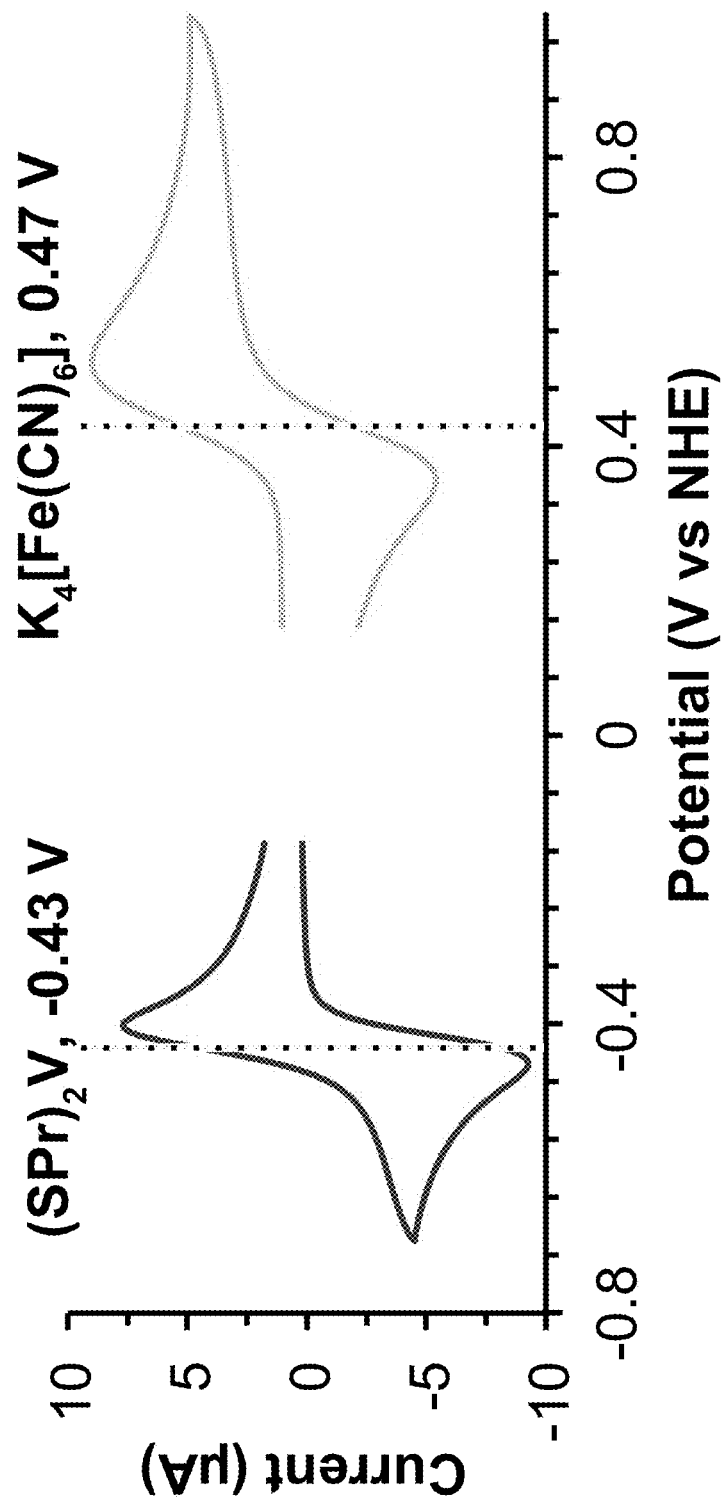
Figure 59B:
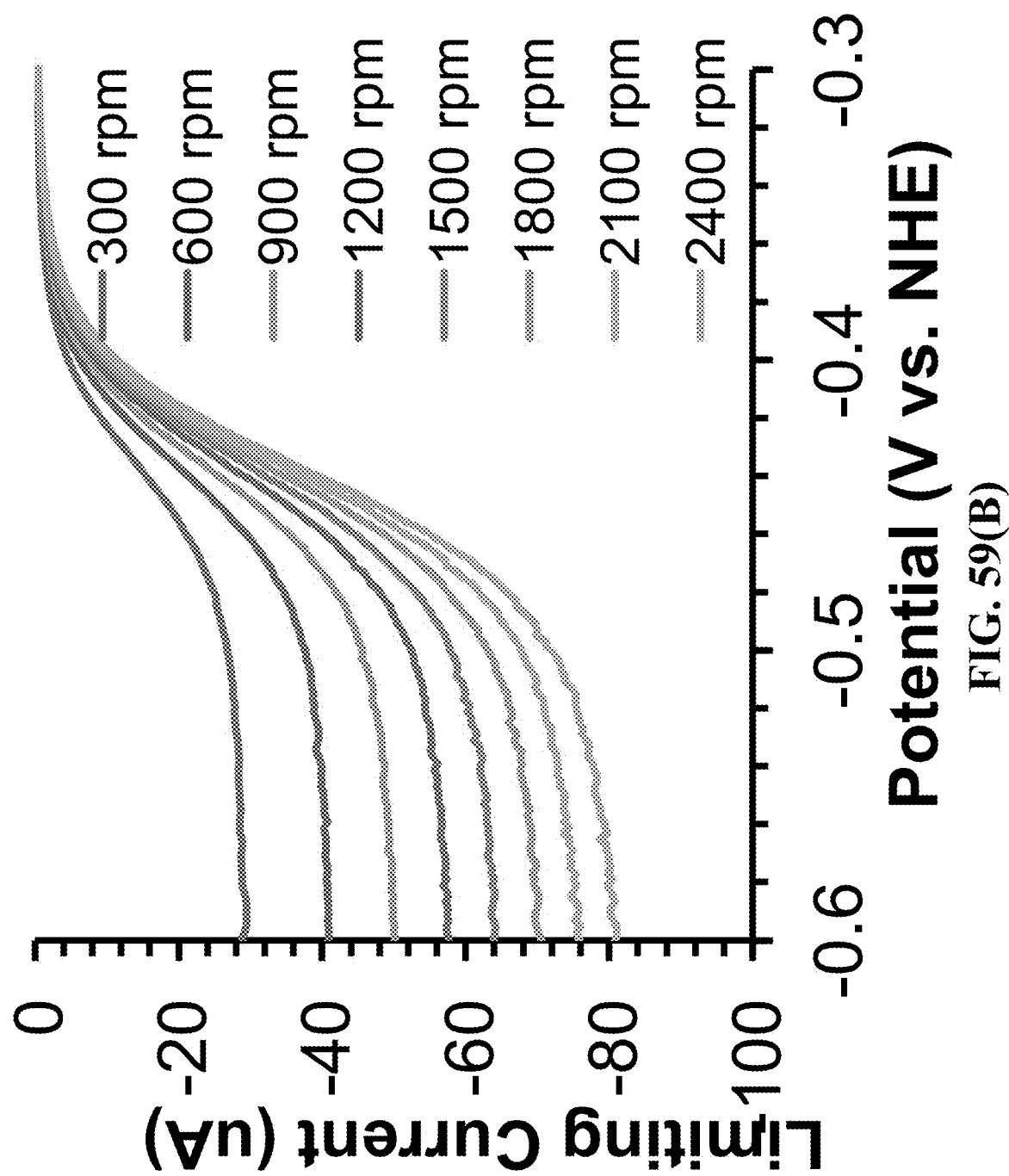
Figure 59C:
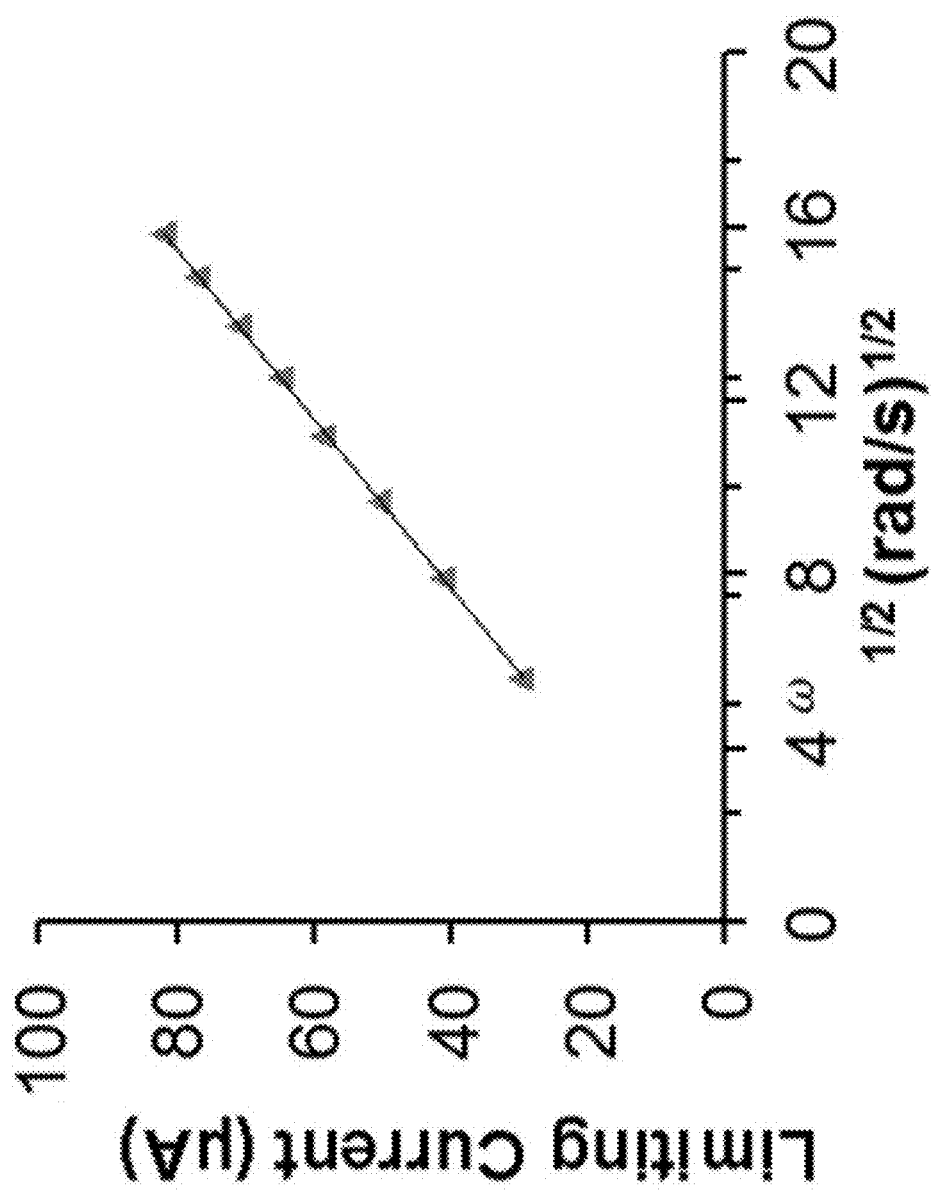
Figure 59D:
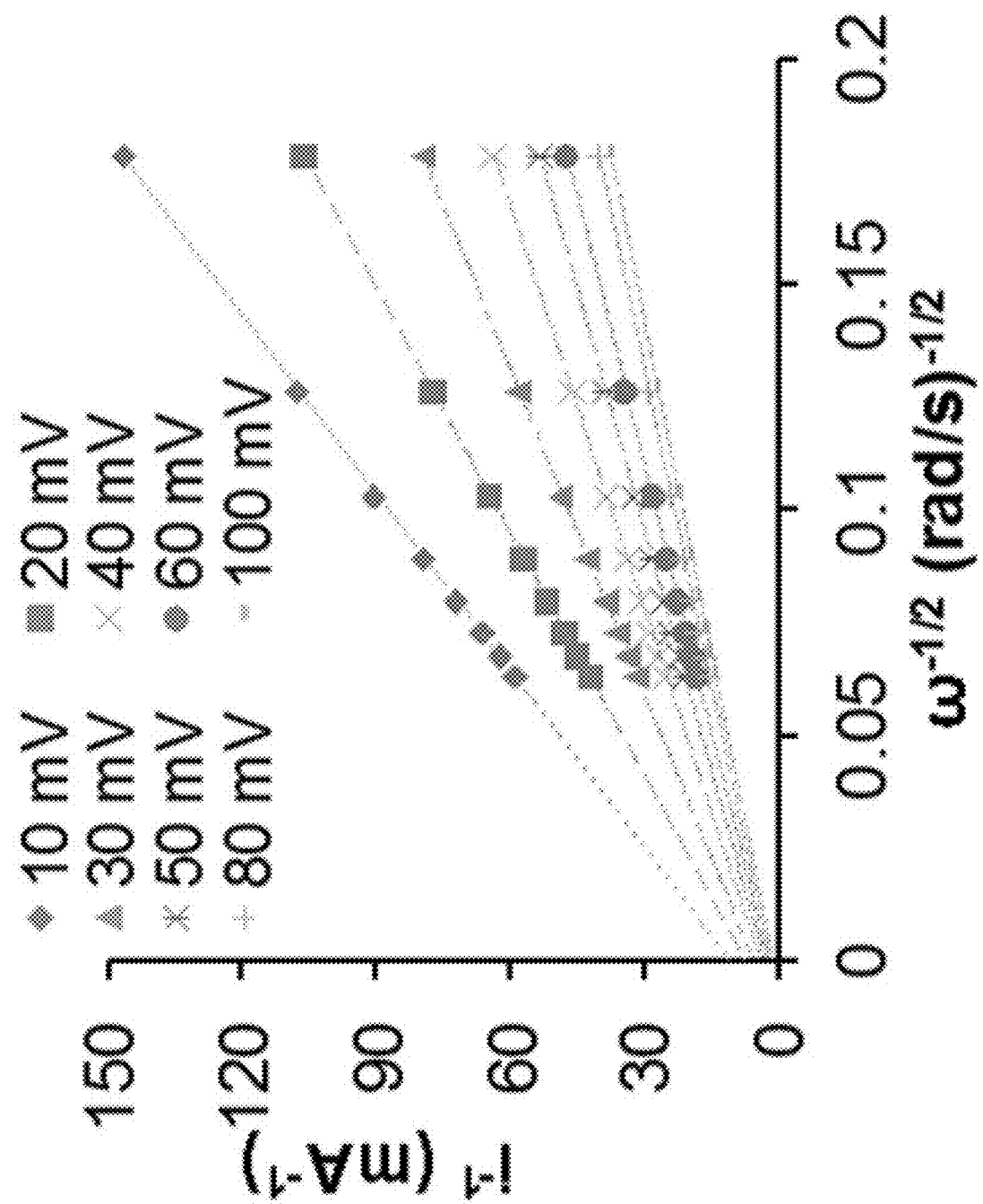

FIG. 59(A) shows Cyclic voltammogram of (SPr)$_2$V (−0.43 V) and K$_4$[Fe(CN)$_6$] in 0.5 M KCl aqueous electrolyte. Experiment conditions: 4.0 mM (SPr)$_2$V or K$_4$[Fe(CN)$_6$], 100 mV/s scan rate, glassy carbon working electrode, glassy carbon counter electrode, Ag/AgCl reference electrode. FIG. 59(B) shows LSV scans with rotating working electrode for the reduction of (SPr)$_2$V. FIG. 59(C) shows a Levich plot for the reduction of (SPr)$_2$V. FIG. 59(D) shows a Koutechy-Levich analysis for the reduction. FIG. 59(E) shows a linear Tofel plot fit of overpotential versus log(i$_k$) extrapolated to infinite rotation rate. The x-intercept of the best fit lines in FIG. 59(D) was used to calculate k$^0$ for the first and second reductions respectively.

Figure 60:
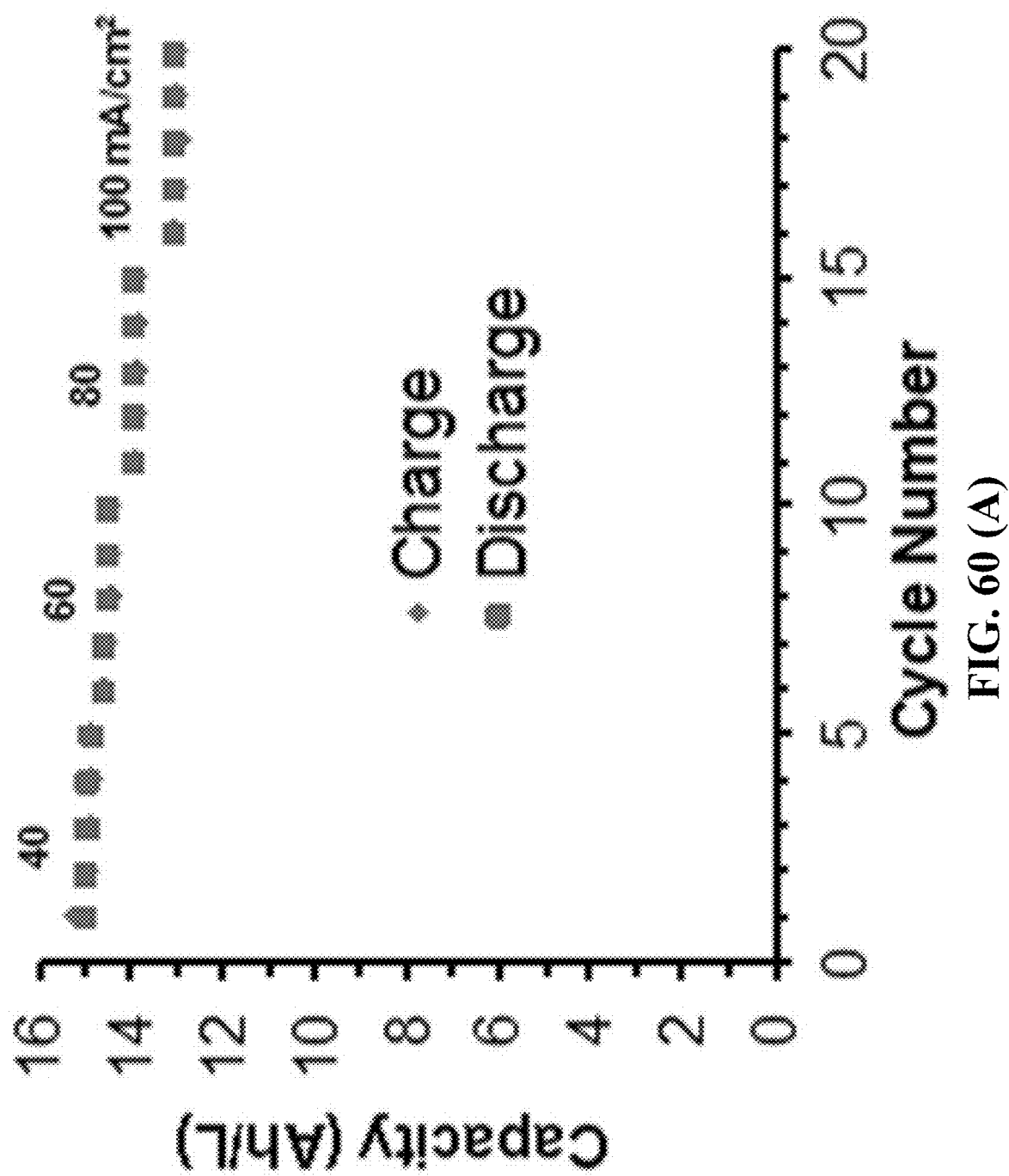
Figure 60B:
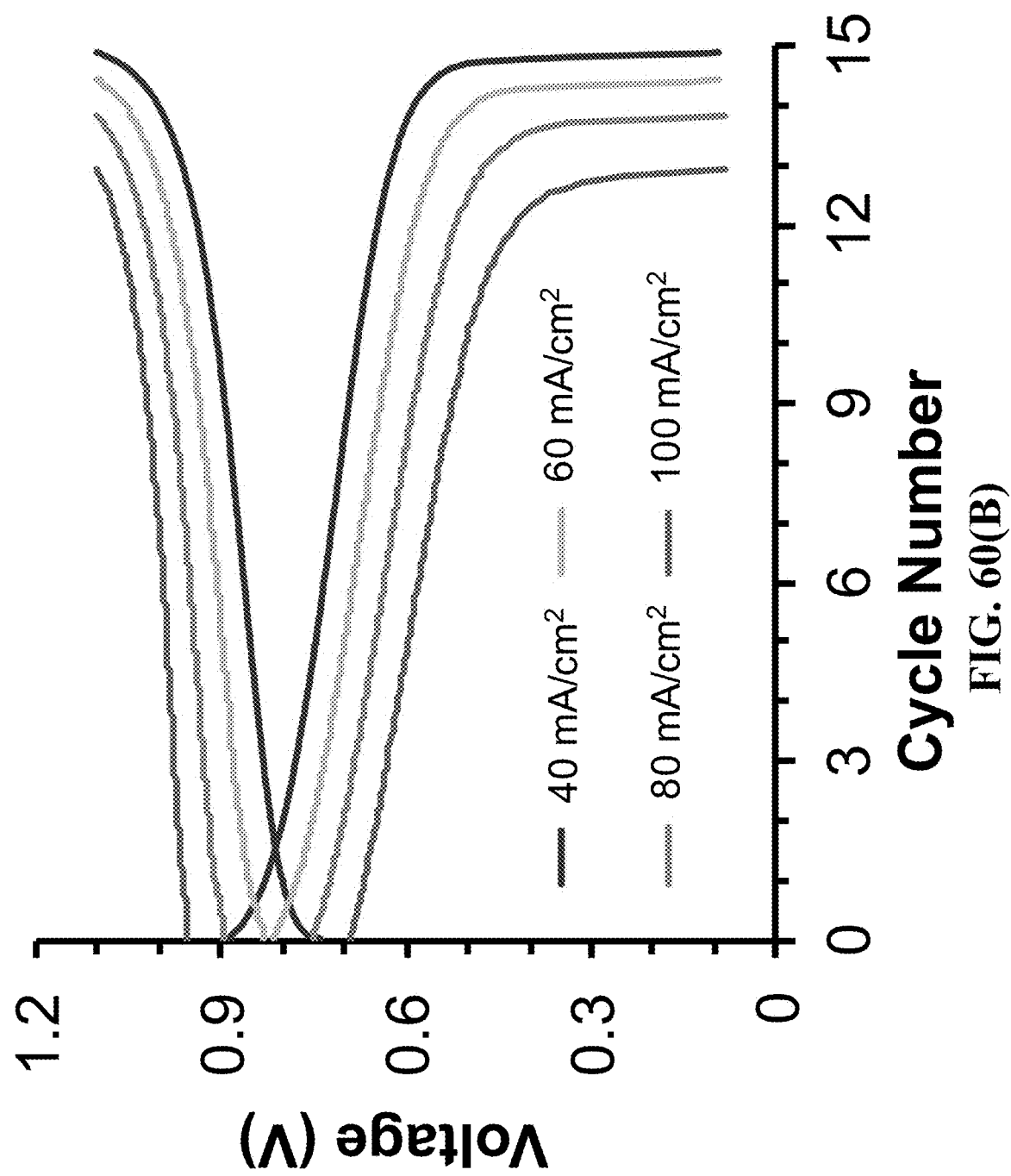
Figure 60C:
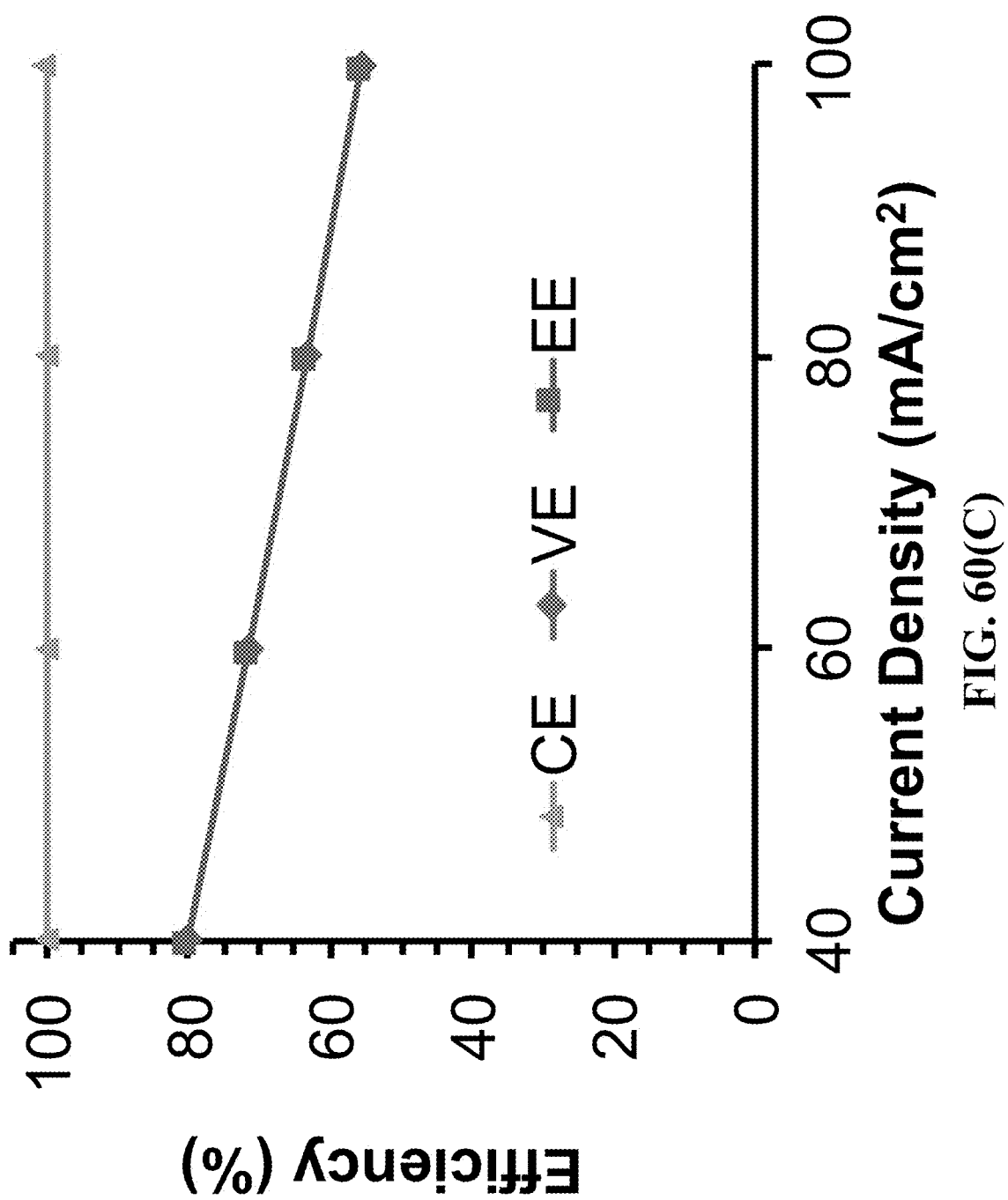
Figure 60D:
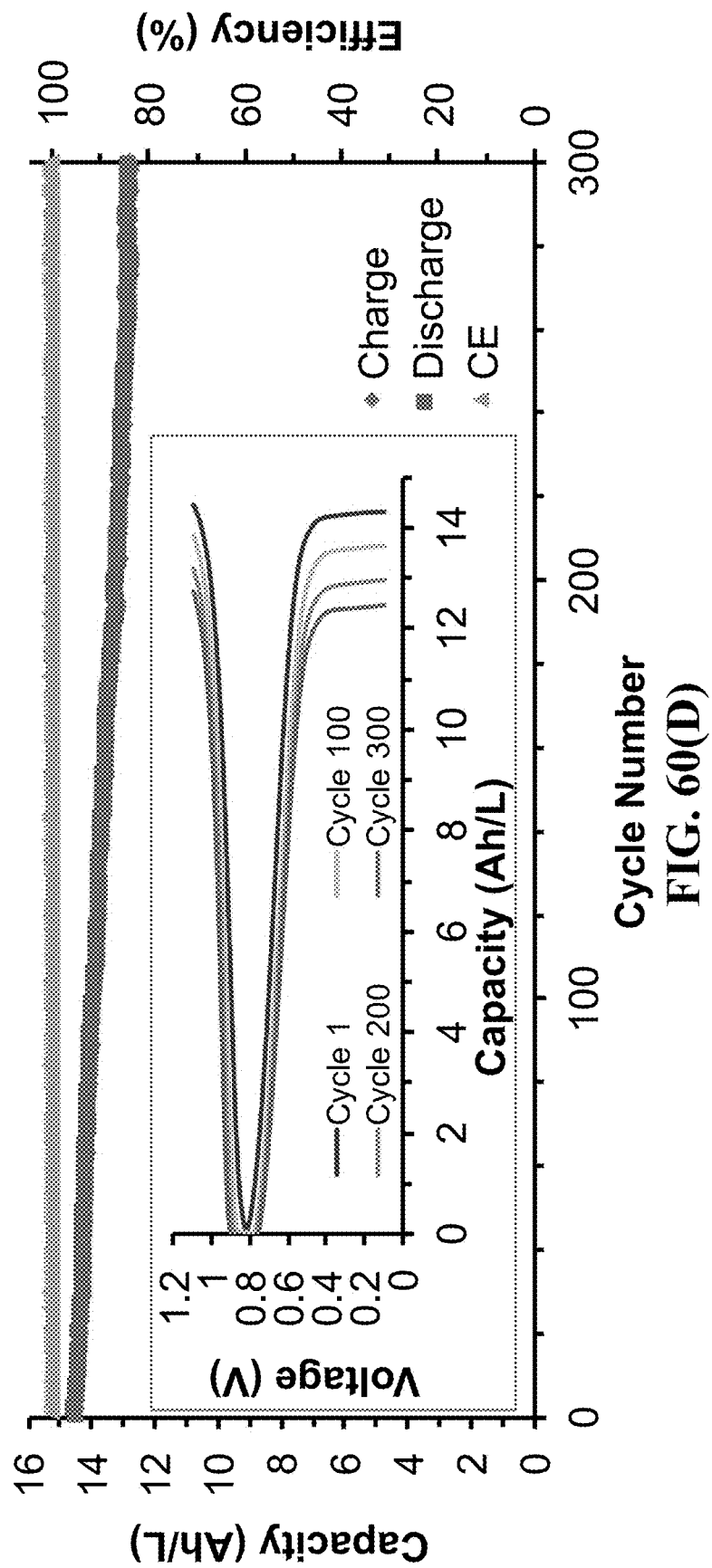
Figure 60E:
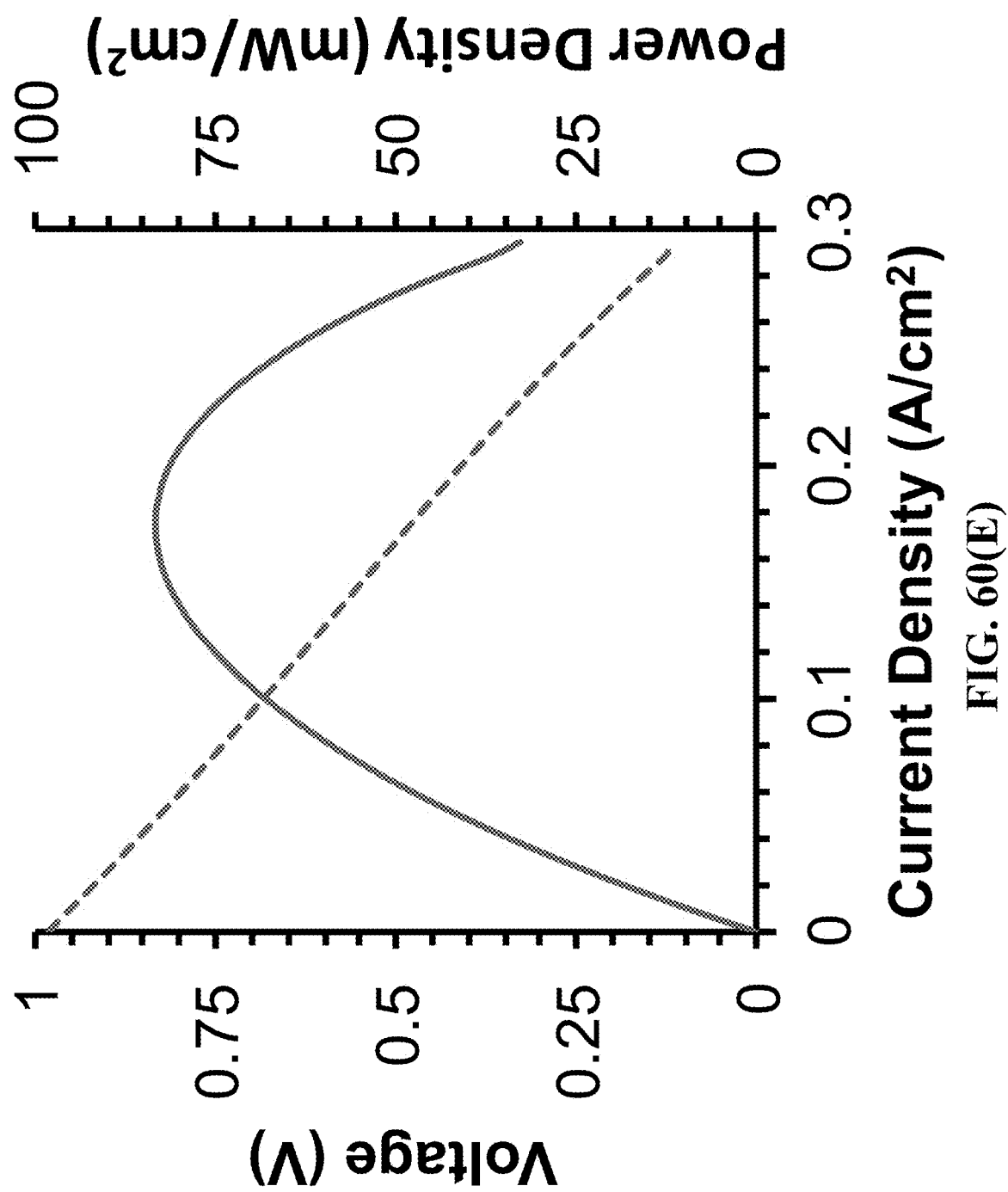
Figure 60F:
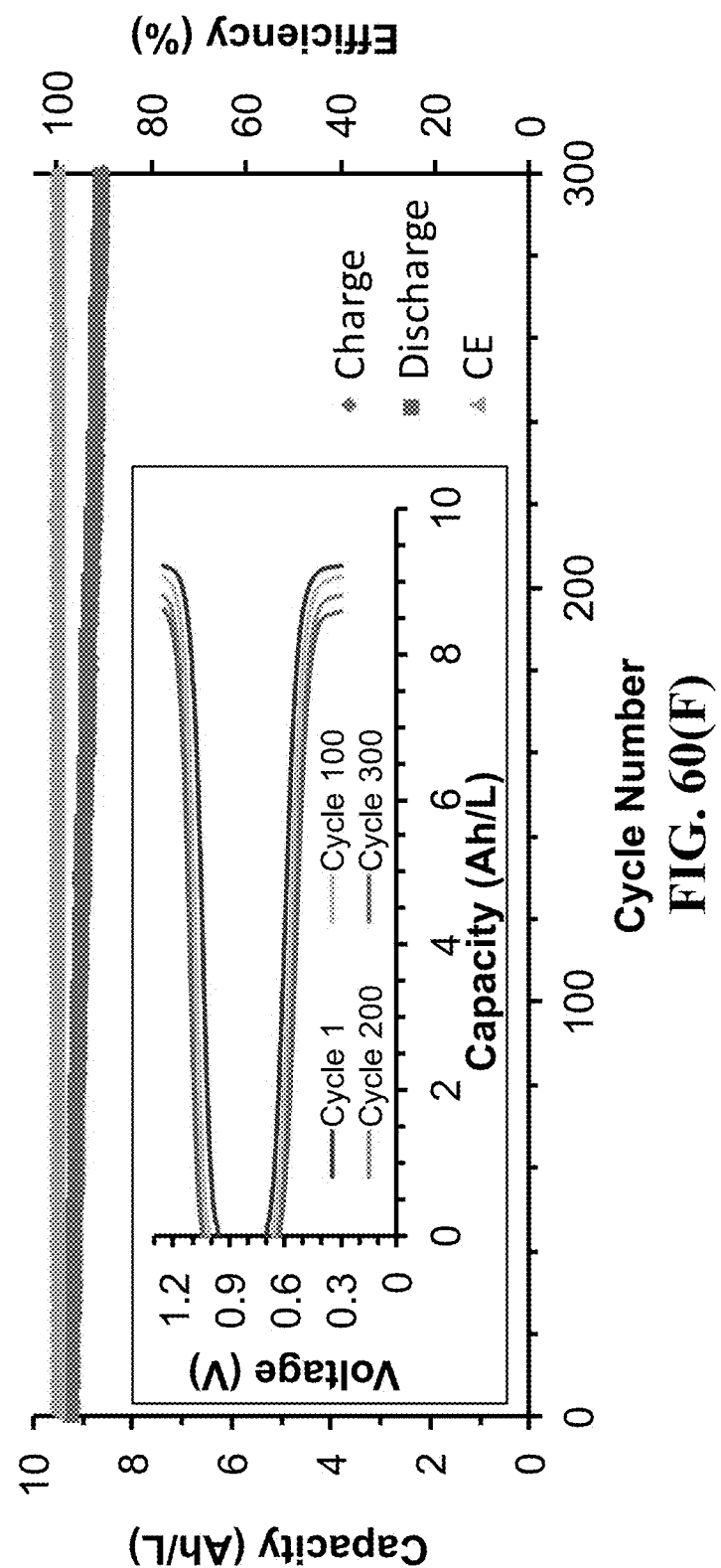
Figure 60G:
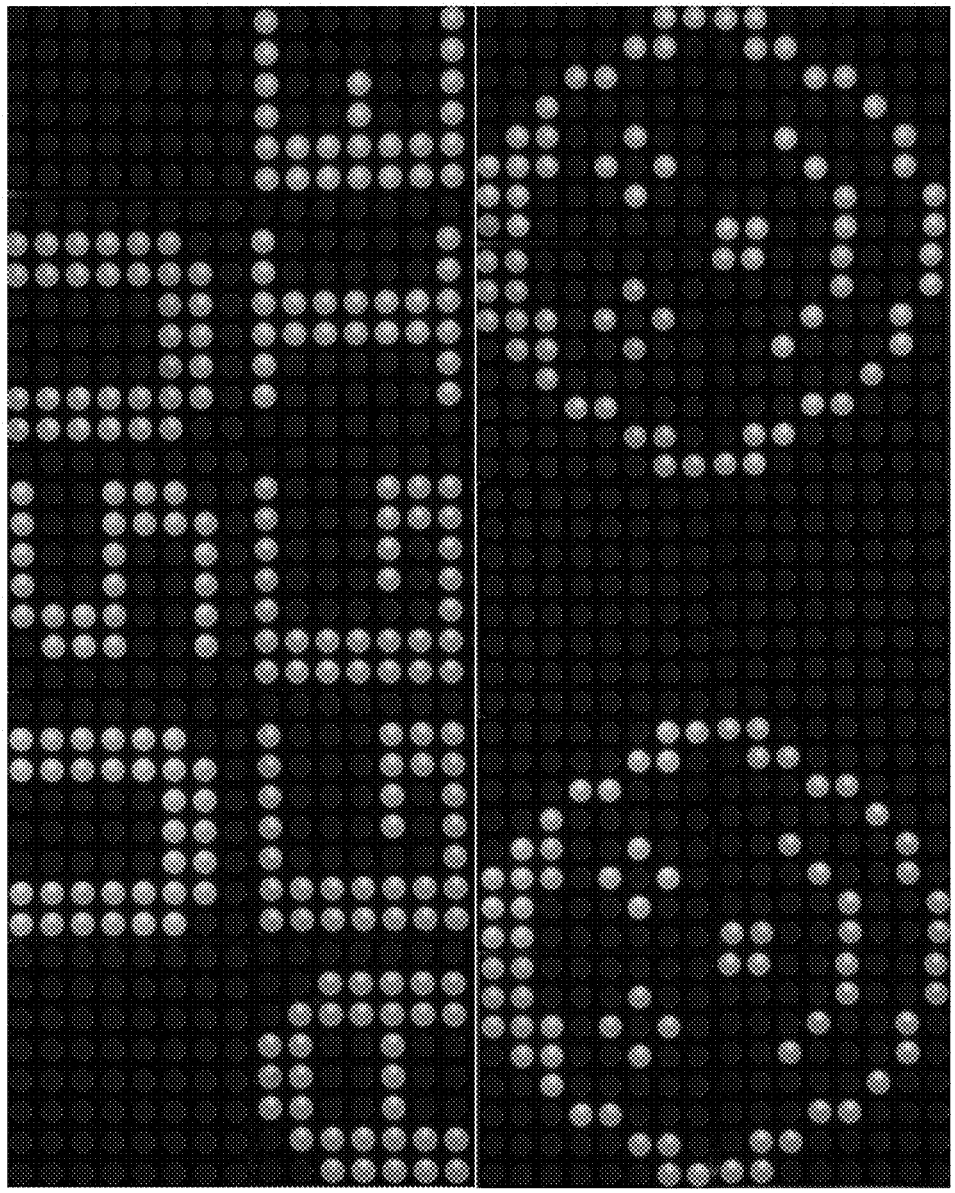

FIG. 60(A) shows a plot of battery capacity versus cycling numbers of a (SPr)$_2$V/K$_4$[Fe(CN)$_6$] AORFB at current densities from 40 mA/cm$^2$ to 100 mA/cm$^2$. FIG. 60(B) shows representative charge and discharge curves at current densities from 40 mA/cm$^2$ to 100 mA/cm$^2$. FIG. 60(C) shows plots of average coulombic efficiency, energy efficiency, and voltage efficiency at different operational current densities. FIG. 60(D) shows extended 300 cycle data showing charge capacity, discharge capacity, and coulombic efficiency versus cycle number at 60 mA/cm$^2$ current density. Inset: Representative charge and discharge curve. FIG. 60(E) shows polarization and power density data collected at 100% state of charge. Conditions: anolyte: 0.6 M (SPr)$_2$V in 1.5 M KCl; catholyte: 0.6 M K$_4$[Fe(CN)$_6$]$_6$; Nafion 211 cation exchange membrane. FIG. 60(F) shows extended 300 cycle data of a (SPr)$_2$V/KI AORFB showing charge capacity, discharge capacity, and coulombic efficiency versus cycle number at 60 mA/cm$^2$ current density. Inset: Representative charge and discharge curve. Conditions: anolyte: 0.5 M (SPr)$_2$V in 1.5 M KCl; catholyte: 2.0 M KI and 2.0 M KCl; Nafion 212 cation exchange membrane. FIG. 60(G) shows red LED array lighted up by a (SPr)$_2$V/K$_4$[Fe(CN)$_6$] AORFB.

Figure 61A:
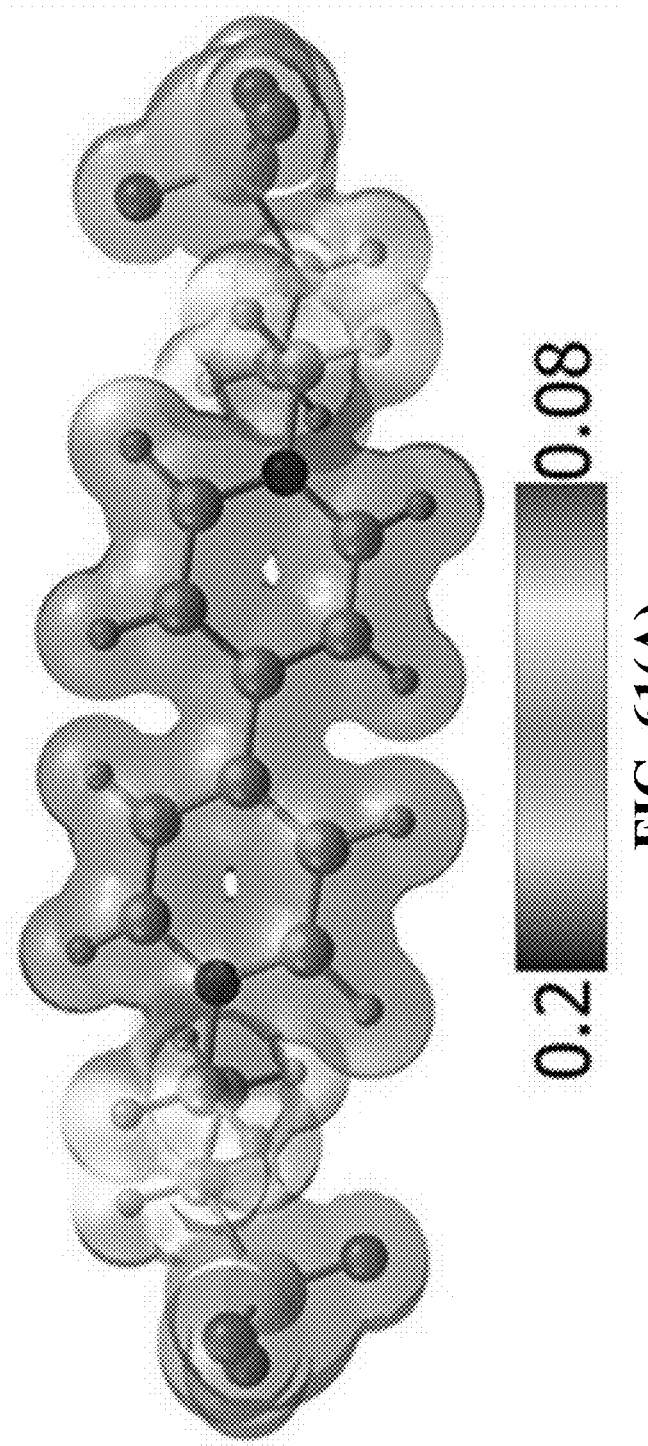
Figure 61B:
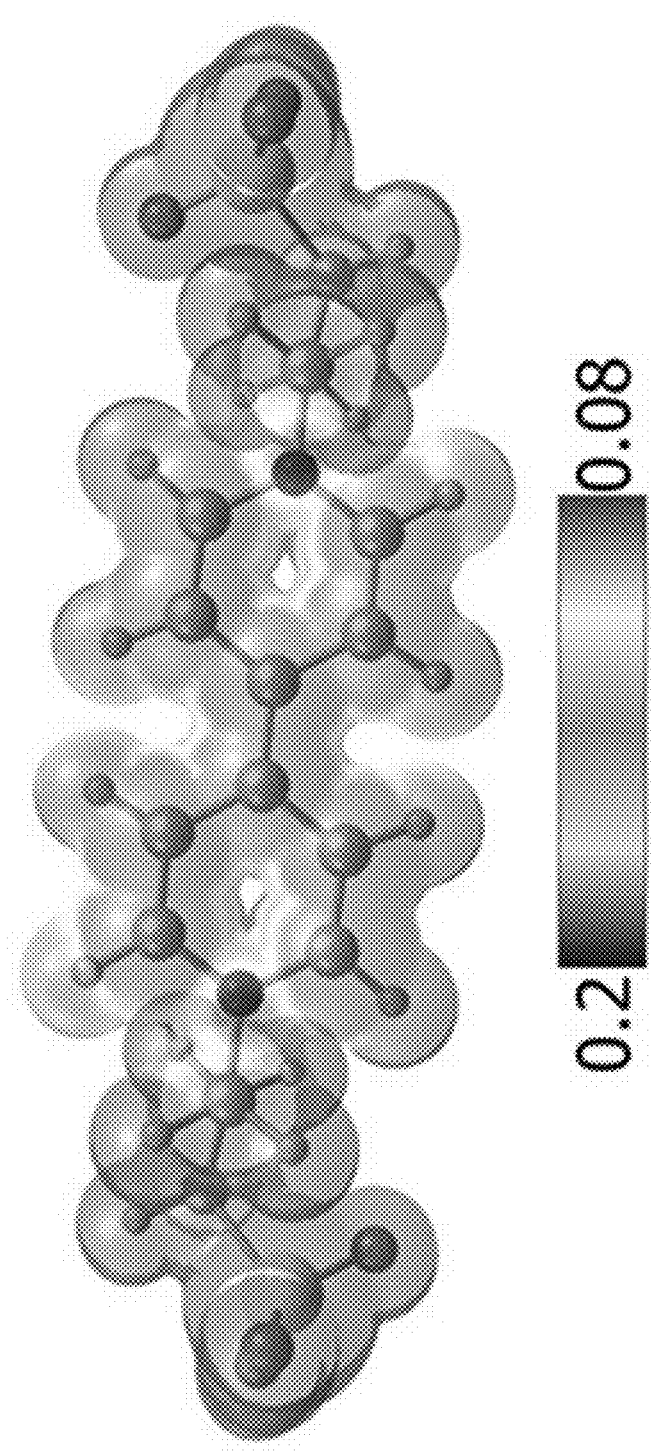
Figure 61C:
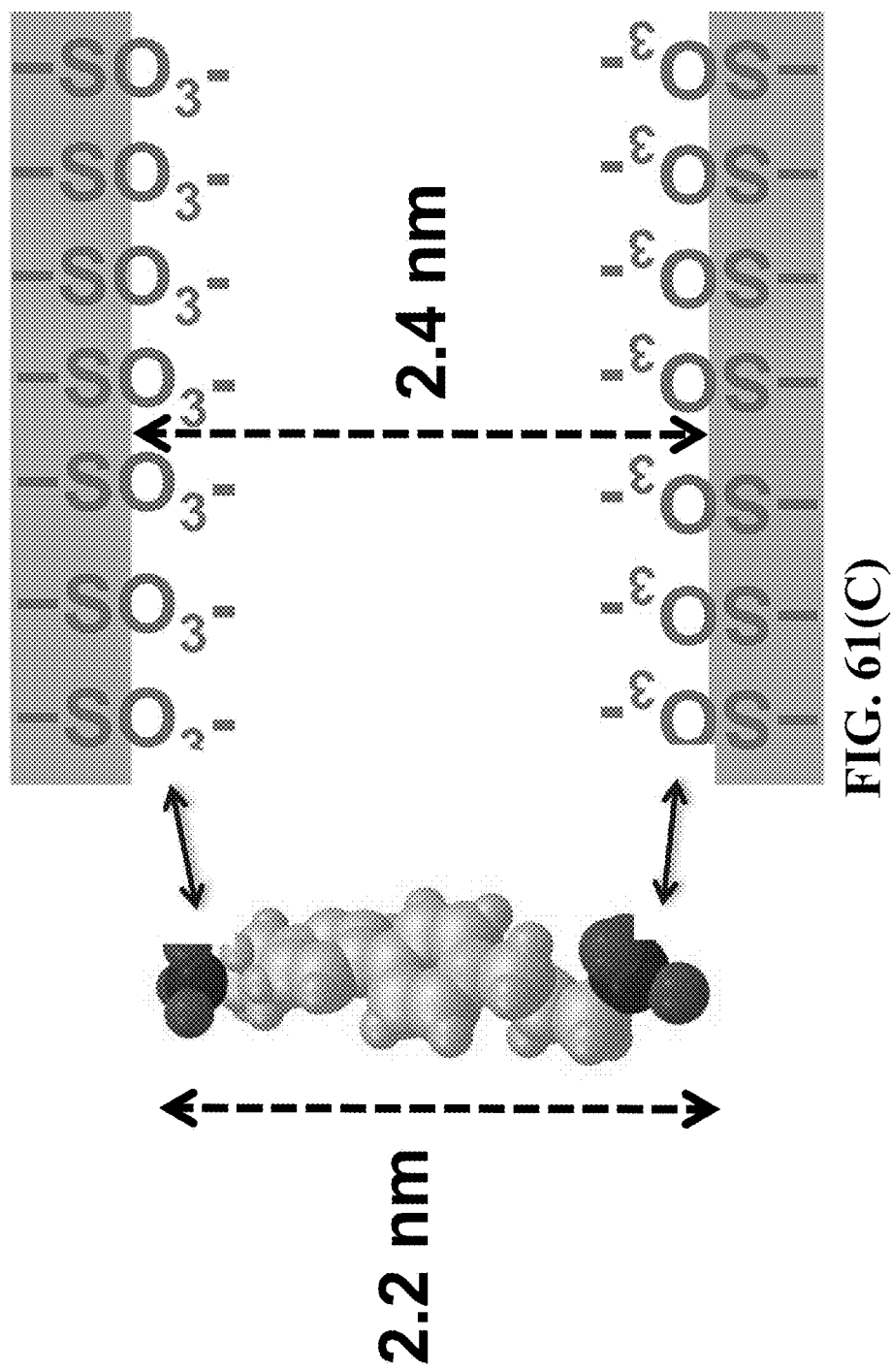
Figure 61D:
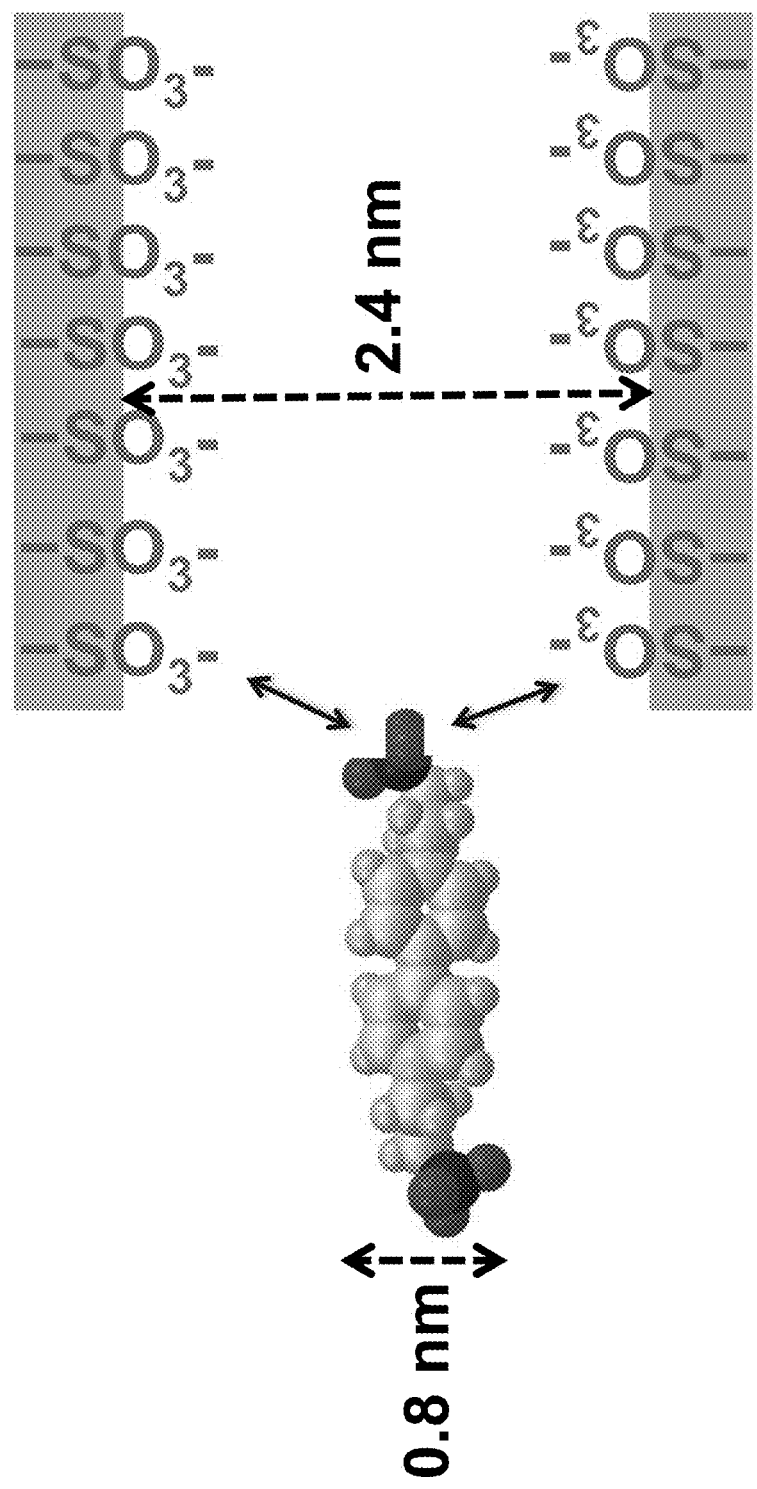

FIG. 61(A) shows electrostatic charge surface of the optimized ground state structure of (SPr)$_2$V. FIG. 61(B) shows electrostatic charge surface of the optimized ground state structure of [(SPr)$_2$V]$^-$. FIG. 61(C) shows the proposed interaction of (SPr)$_2$V represented in a space-filling model adopting perpendicular orientation with a Nafion membrane. FIG. 61(D) shows the proposed interaction of (SPr)$_2$V represented in a space-filling model adopting parallel orientation with a Nafion membrane. The blue double-headed arrows indicate the negative charge repulsion.

Figure 62A:
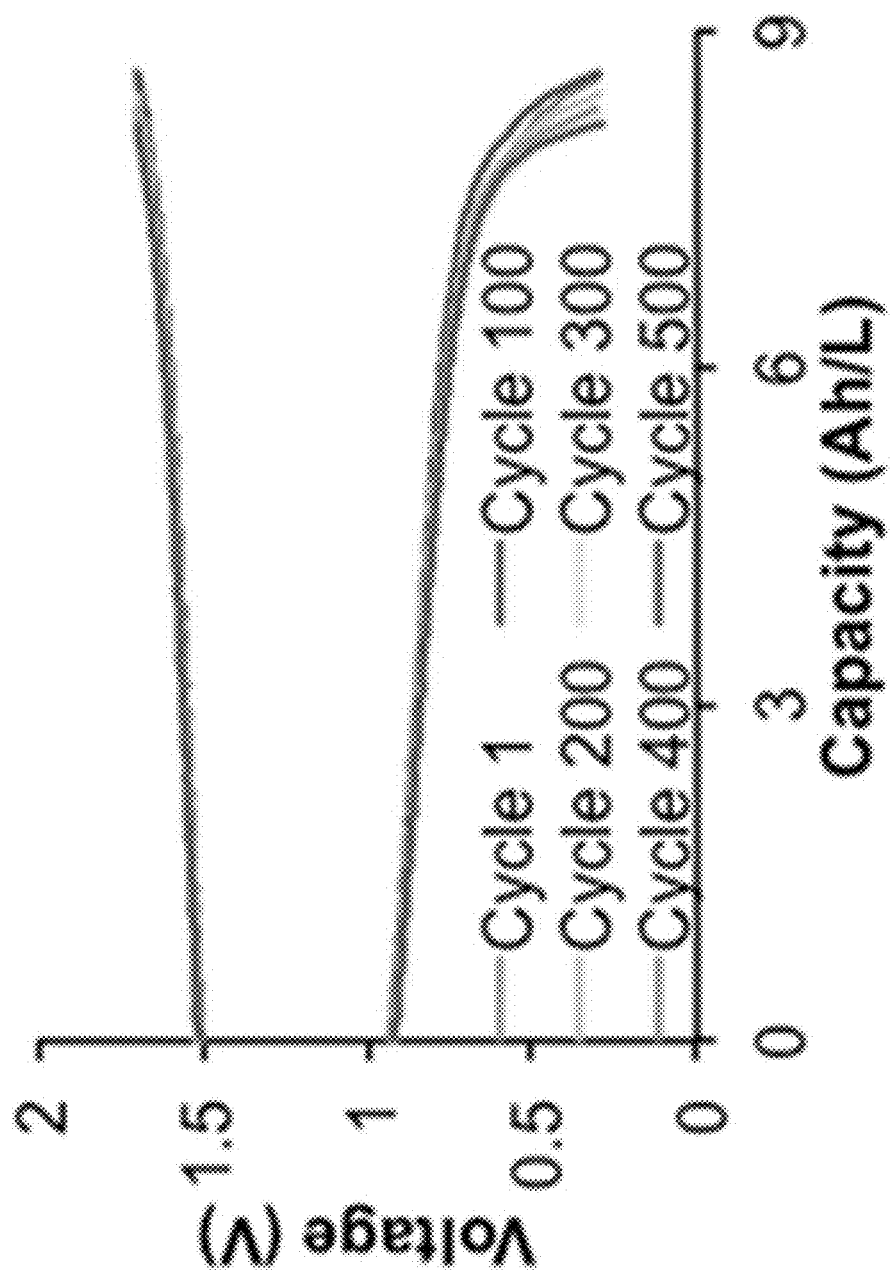
Figure 62B:
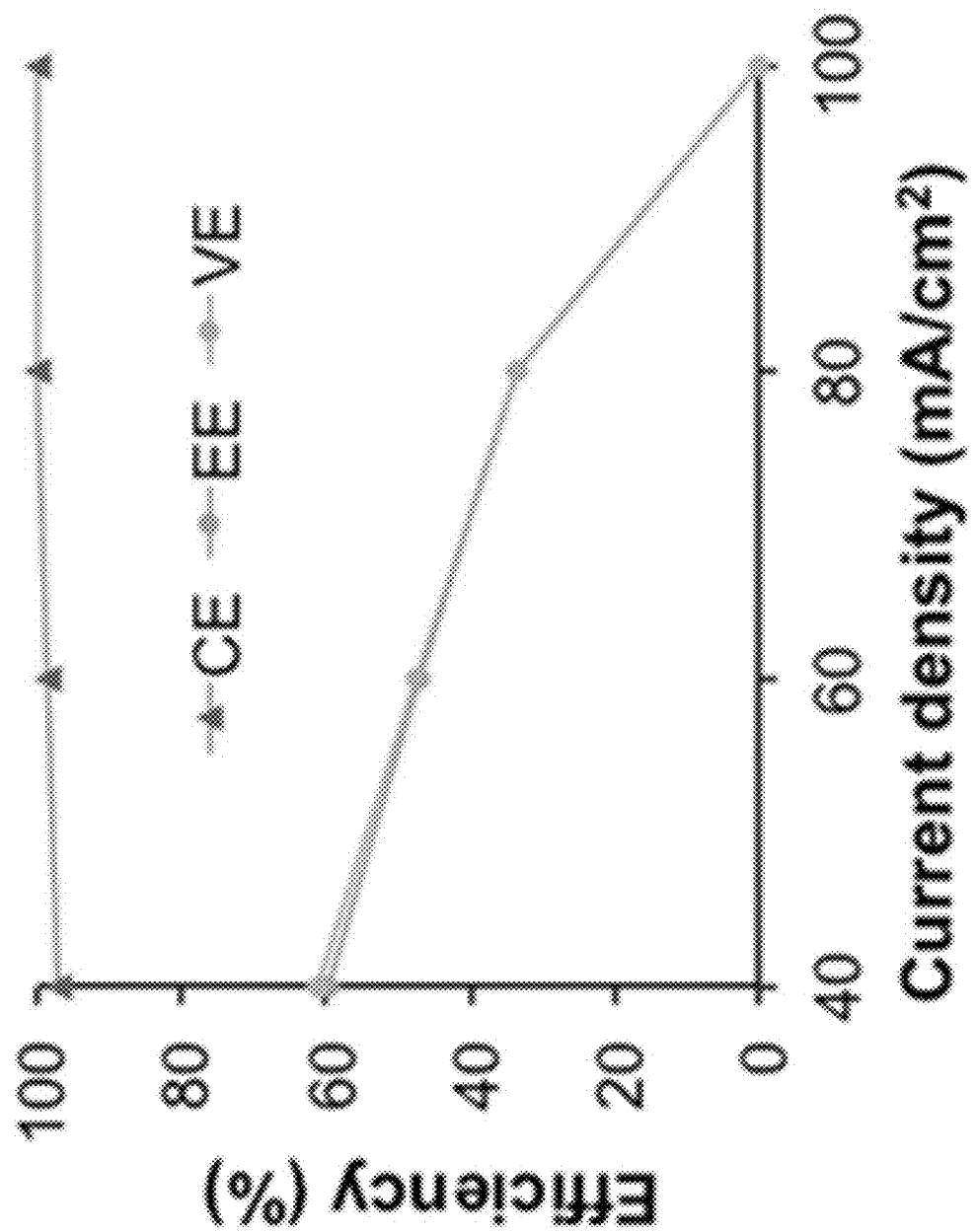
Figure 62C:
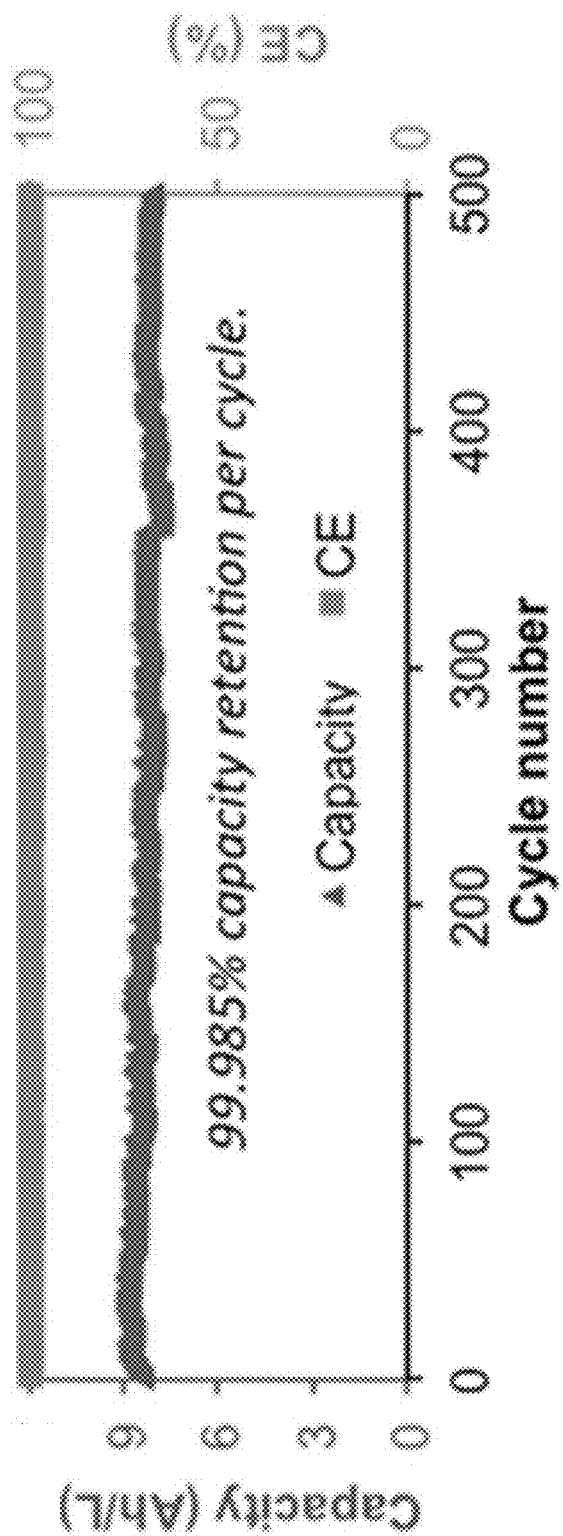

FIGS. 62(A)-(C) show operational data of a 0.5 M (NPr)$_2$VCl/4-N$^{me}$-TEMPO AORFB. FIG. 62(A) shows selected charge and discharge curves at 60 mA/cm$^2$. FIG. 62(B) shows plots of average coulombic efficiency, energy efficiency, and voltage efficiency at varying operational current densities from 40 to 100 mA/cm$^2$. FIG. 62(C) shows extended 500 cycle data of a (NPr)$_2$VCl$_4$/4-N$^{Me}$-TEMPO AORFB showing discharge capacity and coulombic efficiency versus cycle number at 60 mA/cm$^2$.

Figure 63A:
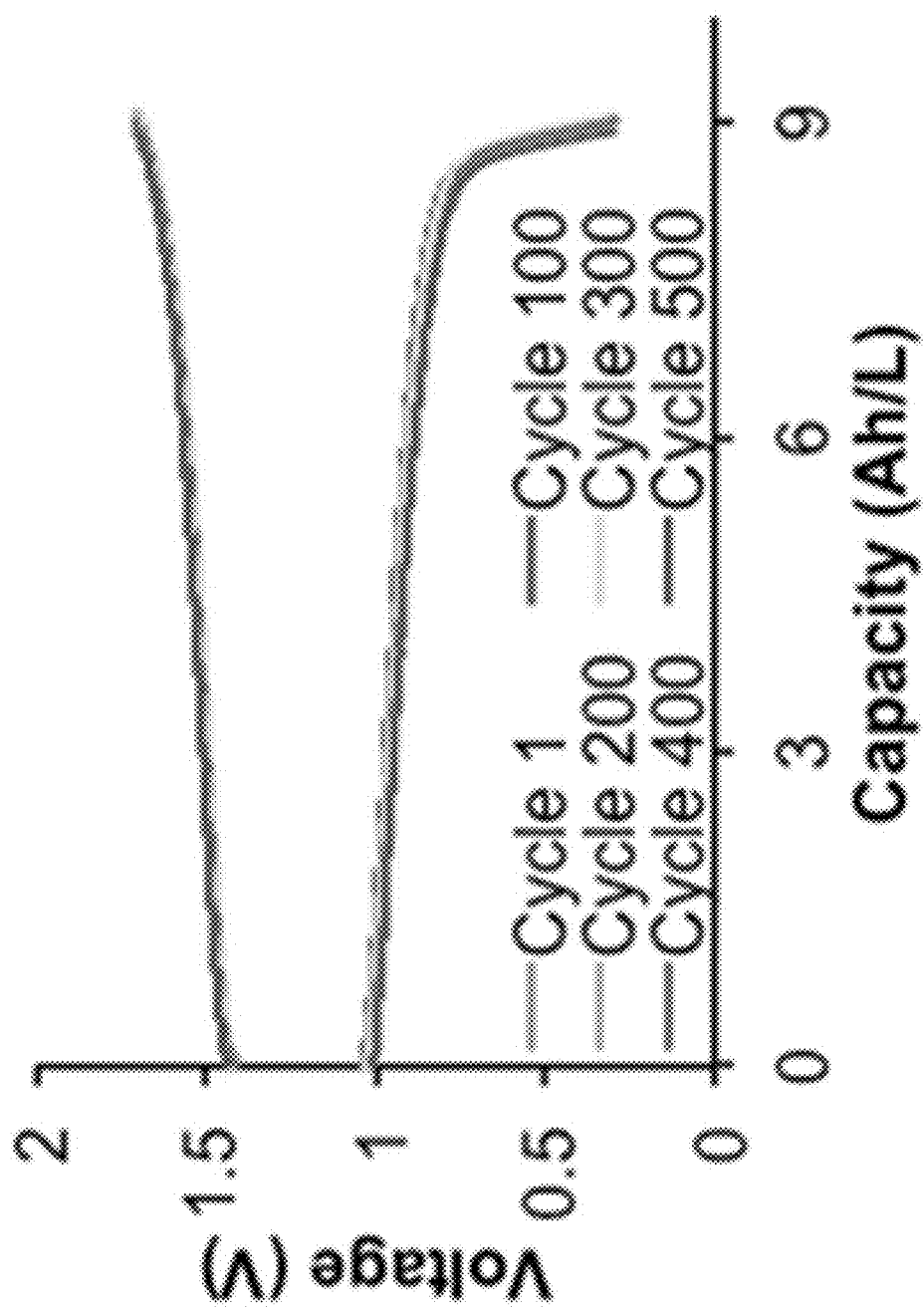
Figure 63B:
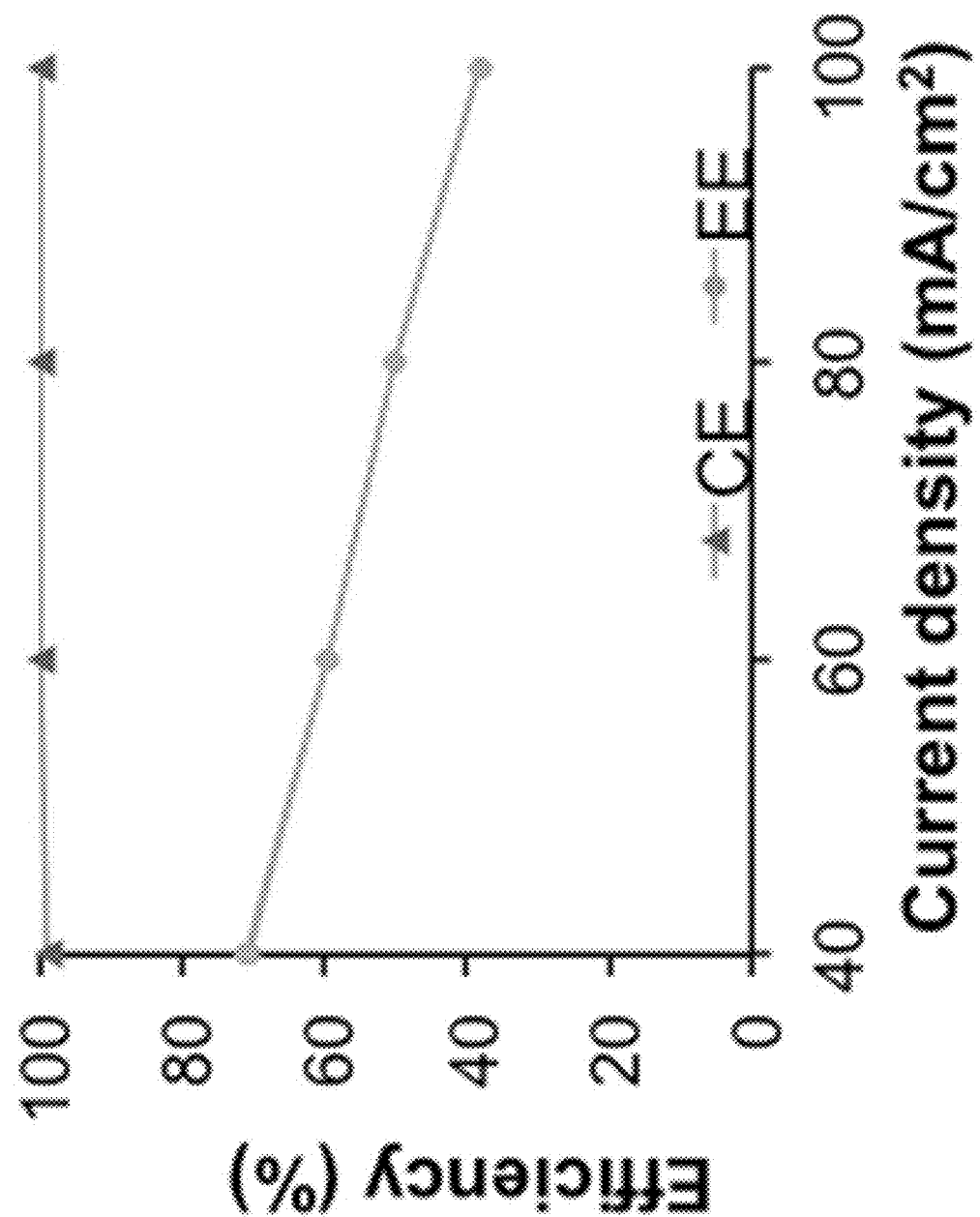
Figure 63C:
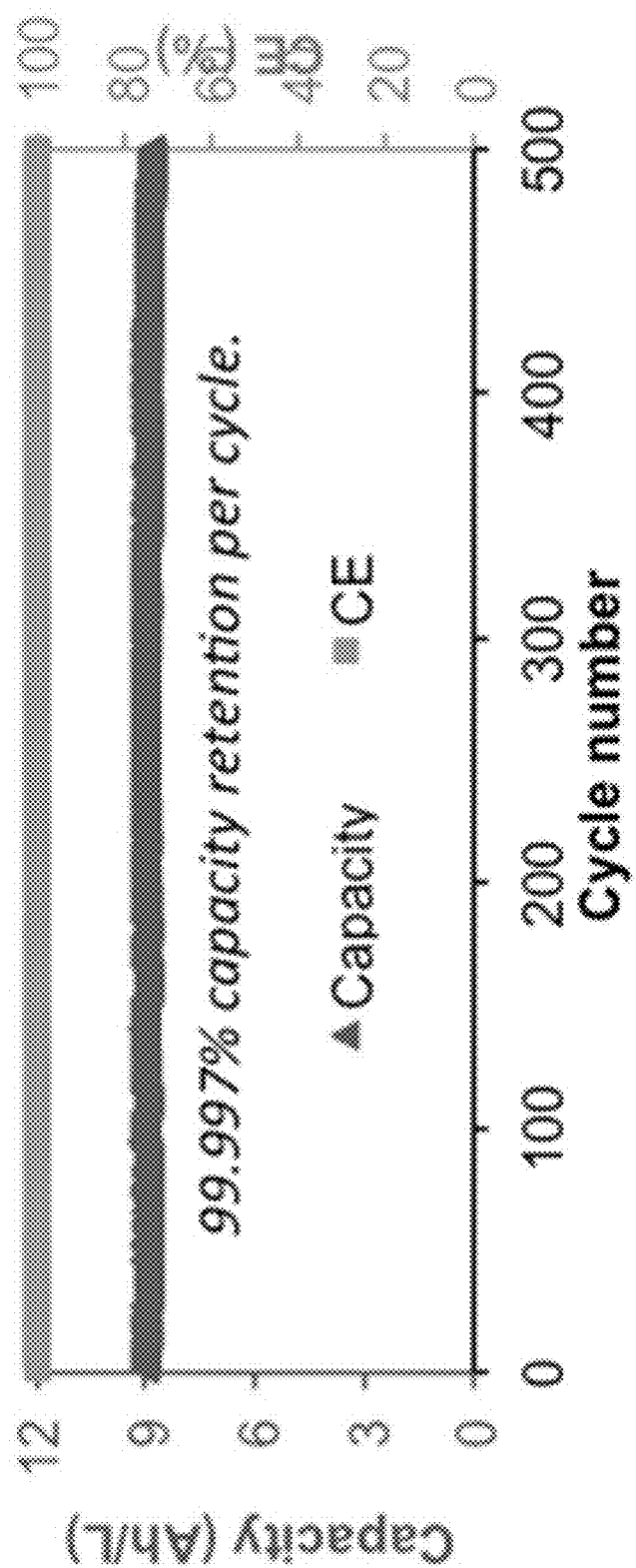

FIGS. 63(A)-(C) show operational data of a 0.5 M (NPr)$_2$VCl/4-N$^{NPr}$-TEMPO AORFB. FIG. 63(A) shows selected charge and discharge curves at 60 mA/cm$^2$. FIG. 63(B) shows plots of average coulombic efficiency, energy efficiency, and voltage efficiency at varying operational current densities from 40 to 100 mA/cm$^2$. FIG. 63(C) shows extended 500 cycle data of a (NPr)$_2$VCl$_4$/4-N$^{Pr}$-TEMPO AORFB showing discharge capacity and coulombic efficiency versus cycle number at 60 mA/cm$^2$.

DETAILED DESCRIPTION

Disclosed herein are redox active metallocenes and viologens (and salts thereof). The compounds may be useful as redox mediators in a variety of applications. Also disclosed herein are methods of preparing metallocene- and viologen-based redox active materials. The methods may be performed at ambient conditions and can be scaled up using common commercial precursors, thereby being economically efficient.

Also disclosed herein are aqueous organic redox flow batteries. The batteries can employ sustainable and non-corrosive redox active electrolyte materials based on earthabundant elements (e.g., C, H, N, and Fe). In certain embodiments, the AORFBs include a metallocene-based redox active material, a viologen-based redox active material or a combination thereof. The metallocene- and viologen-based redox active materials may be highly soluble in aqueous liquids and may demonstrate advantageous electrochemical properties.

The disclosed AORFBs can exhibit excellent electrochemical performance as evidenced by one or more of energy density, energy efficiency, capacity retention, and battery operation parameters (e.g., current density). For example, cycling performance indicates that the disclosed AORFBs may be a promising technology to meet the system capital cost target of below $100/kWh for electrochemical storage projected by the US Department of Energy. Accordingly, the disclosed AORFBs provide both an economically and environmentally friendly source of renewable energy, while providing high performance.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's *Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "active material" or "redox active material" refers to materials which undergo a change in oxidation state during operation of an electrochemical system, such as a flow battery. In certain embodiments, types of active materials comprise species dissolved in a liquid electrolyte. A type of redox active material may comprise a single species or may comprise multiple species.

The term "alkylenyl," as used herein, refers to a divalent group derived from a straight or branched chain hydrocarbon of 1 to 50 carbon atoms, for example, of 2 to 5 carbon atoms. Representative examples of alkylenyl include, but are not limited to, —$CH_2$—$CH_2$—, —$CH_2$—$CH_2$—$CH_2$—, —$CH_2$—$CH_2$—$CH_2$—$CH_2$—, and —$CH_2$—$CH_2$—$CH_2$—$CH_2$—$CH_2$—.

The term "alkenylenyl," as used herein, refers to a divalent group derived from a straight or branched chain hydrocarbon of 1 to 50 carbon atoms, wherein at least one carbon-carbon bond is a double bond. Representative examples of alkenylenyl include, but are not limited to, —CH=CH—, —CH=CH—$CH_2$—, —$CH_2$—CH=CH—$CH_2$—, and —$CH_2CH_2$—CH=CH—$CH_2$—.

The term "alkynylenyl," as used herein, refers to a divalent group derived from a straight or branched chain hydrocarbon of 1 to 50 carbon atoms, wherein at least one carbon-carbon bond is a triple bond. Representative examples of alkynylenyl include, but are not limited to, —C≡C—, —C≡C—$CH_2$—, —C≡C—$CH_2$—$CH_2$— and —$CH_2$—C≡C—$CH_2$—.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "aqueous electrolyte" as used herein, refers to an aqueous solution in which at least one kind of such a substance is dissolved. In some cases, the aqueous electrolyte is a solvent, wherein solvent comprises at least about 50% water, at least about 75% weight water, at least about 80% weight water, at least about 85% weight water, at least 90% weight water, or at least 95% weight water, based on the total weight of the solvent. For the purpose of this calculation, any co-solvents are included in the weight of the solvent but any type of redox active material, buffer, or other supporting electrolyte is not considered a solvent, even if such species is a liquid. When a co-solvent is present, the co-solvent may be soluble, miscible, or partially miscible with water.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "halogen" or "halo" as used herein, means Cl, Br, I, or F.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocyclyl" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an OH group.

The term "hydroxyalkyl" as used herein, means an alkyl group, as defined herein, in which one, two, three, four, five, six, seven or eight hydrogen atoms are replaced by a hydroxyl group.

The term "metallocene" as used herein, refers to a compound comprising at least one $\eta^3$ to $\eta^5$-cycloalkadienyl-type moiety, wherein $\eta^3$ to $\eta^5$-cycloalkadienyl moieties include cyclopentadienyl, indenyl, fluorenyl, and the like, including saturated or substituted derivatives or analogs of any of these. An example of a metallocene is ferrocene.

The term "nitrogen protecting group" as used herein refers to substituents that can be introduced to protect nitrogen-containing functional groups (e.g., —NH$_2$ or NHR) from undesired reactions. Exemplary nitrogen protecting groups include, but are not limited to, p-methoxyphenyl ("PMP"), benzyl, methyl, triphenylmethyl, pivaloyl, pyrrolidinylmethyl, t-butoxycarbonyl, silyl, acetyl, benzyloxycarbonyl (Cbz) and trimethylsilyethoxymethyl (SEM).

The term "oxygen protecting group" as used herein refers to substituents that can be introduced to protect oxygen-containing functional groups (e.g., —OH) from undesired reactions. Exemplary oxygen protecting groups include, but are not limited to, silyl ethers, methyl ethers, alkyl ethers, benzyl ethers, esters, benzoates, carbonates, and sulfonates.

The term "substituted" as used herein refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy (e.g., —OH), hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, sulfonatyl (e.g., $-SO_3^-$, $-SO_3H$, etc.), $-PO_3^{-2}$, $-PO_3H^-$—COOH, ketone, amide, carbamate, and acyl.

The term "viologen" as used herein refers to a compound that includes a 4,4'-bypyridyl core structure. An example includes, but is not limited to, methyl viologen.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Aqueous Organic Redox Flow Batteries

Aqueous organic redox flow batteries (AORFBs) have potential for being affordable, and safe, and can have a high theoretical energy density. An aqueous organic redox flow battery may be thought of as a rechargeable battery with a continuous flow of one aqueous reactant past its negative, or low potential, electrode and a continuous flow of another aqueous reactant past its positive, or high-potential, electrode. The reactants can be stored in separate tanks and pumped to and from a power-converting device, such as an electrochemical cell stack, when charging (absorbing excess electricity from the power source) or discharging (delivering electricity to the power source). Present AORFBs are often limited by the solubility of the redox active materials, as well as the need to use corrosive acids and bases, which ultimately limit their commercial potential. Accordingly, there is a need for improved materials and AORFBs that utilize these improved materials.

The disclosed aqueous organic redox flow batteries can include a first redox active material that includes a water-soluble metallocene, and a second redox active material. In other embodiments, the disclosed organic redox flow batteries can include a second redox active material that includes a viologen compound, and a first redox active material that can (but is not limited to) a metallocene compound. The batteries may further include an aqueous electrolyte(s) (e.g., a first and second aqueous electrolyte), a separator, a first electrode, and a second electrode.

Figure 1:
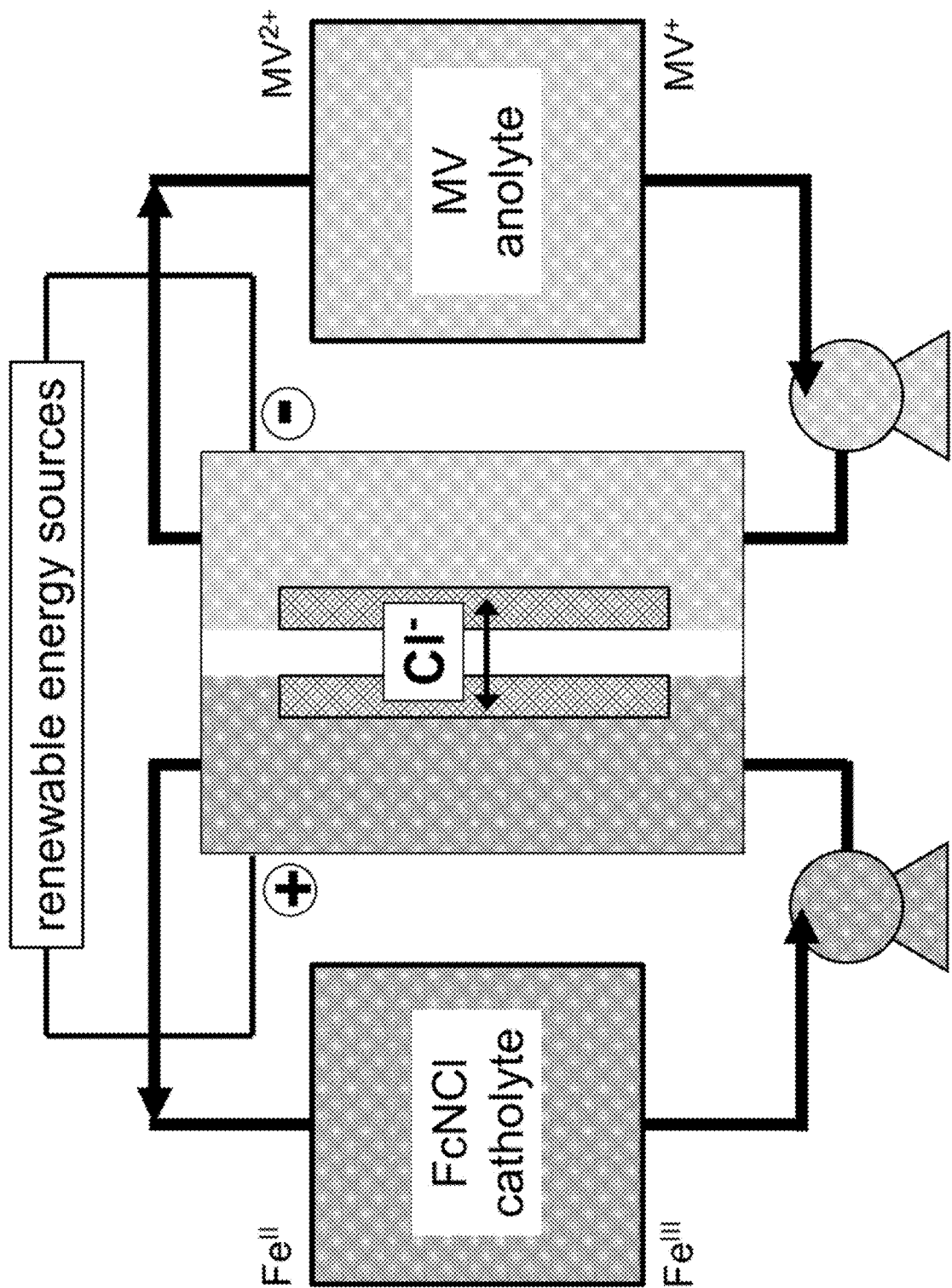
FIG. 1 shows a schematic of a disclosed aqueous organic redox flow battery (AORFB).

FIG. 1 shows one exemplary AORFB including a first electrolyte comprising FcNCl as a first redox active material, and a second electrolyte comprising methyl viologen (MV) as a second redox active material, where an anion (e.g., Cl$^-$) exchanges between the first and second electrolytes to balance electroneutrality. During charge the redox material FcNCl is oxidized (i.e., gives up an electron) and redox material MV is reduced (i.e., accepts an electron). To balance the charge from this electron transfer, an anion (e.g., Cl$^-$) is transported across the physical separator or anion-selective membrane. During discharge, when electricity is utilized from the battery, the current direction is reversed and redox materials FcNCl and MV are reformed.

In certain embodiments, the AORFB may balance electroneutrality through a cation exchange mechanism. For example, an AORFB using neutral viologen compounds can operate through a cation (e.g., K$^-$) being exchanged between the first and second electrolytes. Whether the AORFB operates through a cation or anion exchange can depend on the different redox active materials being used.

In certain embodiments, the AORFB includes a first circulation loop including a first storage tank containing the first aqueous electrolyte, piping for transporting the first aqueous electrolyte, a chamber in which the first electrode is in contact with the first aqueous electrolyte, and a pump to circulate the first aqueous electrolyte through the first circulation loop; a second circulation loop including a second storage tank containing the second aqueous electrolyte, piping for transporting the second aqueous electrolyte, a chamber in which the second electrode is in contact with the second aqueous electrolyte, and a pump to circulate the second aqueous electrolyte through the second circulation loop; and optionally control hardware and software.

FIG. 1 shows an exemplary system of an AORFB with two circulation paths, each including a tank, pump, piping, and one or more chambers within an electrochemical stack. The electrochemical stack may include one or more electrochemical cells, wherein each electrolyte contacts either a positive or negative electrode and a separator divides the two electrolytes. In some embodiments, the separator is permeable to and/or conductive to ions.

The disclosed aqueous organic redox flow batteries may be both charged and discharged. In certain embodiments, during charge, the first redox active material present in a first aqueous electrolyte undergoes oxidation, and the second redox active material present in a second aqueous electrolyte undergoes reduction, whereas during discharge, the first redox active material present in the first aqueous electrolyte undergoes reduction, and the second redox active material present in the second aqueous electrolyte undergoes oxidation. In still other embodiments, the roles of the electrolytes are reversed, such that during charge the first redox active material present in the first aqueous electrolyte undergoes reduction, and the second redox active material present in the second aqueous electrolyte undergoes oxidation, whereas during discharge, the first redox active material present in the first aqueous electrolyte undergoes oxidation, and the second redox active material present in the second aqueous electrolyte undergoes reduction.

A. Redox Active Materials

The disclosed AORFBs include first and second redox active materials. The redox active materials may have one or more redox potentials. In certain embodiments, the redox potentials of the first redox active material and second redox active material may be the same or different. When the potentials are different the type of redox active material with the higher potential is the "positive redox active material", and the corresponding electrolyte and electrode may be referred to as the "positive electrolyte" and "positive electrode". Likewise, the redox active material with the lower potential is the "negative redox active material", and the corresponding electrolyte and electrode may be referred to as the "negative electrolyte" and "negative electrode". During charge the positive redox active material present in the positive electrolyte undergoes oxidation, and the negative redox active material present in the negative electrolyte undergoes reduction, whereas during discharge, the positive redox active material present in the positive electrolyte undergoes reduction, and the negative redox active material present in the negative electrolyte undergoes oxidation.

i. Metallocene Compounds

The first redox active material may include a metallocene or a salt thereof, and may be included as part of the catholyte of the disclosed AORFBs. The metallocene or salt thereof may have advantageous properties that make it useful as a redox active material. For example, the high aqueous solubility of the disclosed metallocene compounds is a surprising finding that affords the disclosed AORFBs a significantly higher theoretical capacity.

In certain embodiments, the metallocene or salt thereof may have an aqueous solubility of ≥1 M, ≥1.5 M, ≥2 M, ≥2.5 M, ≥3 M, ≥3.5 M, or ≥4 M. In certain embodiments, the metallocene or salt thereof may have an aqueous solubility of from about 1M to about 10 M, such as from about 1M to about 8 M, from about 2M to about 6 M, or from about 3 M to about 5 M. In certain embodiments, the metallocene or salt thereof may have an aqueous solubility of about 4 M.

In certain embodiments, the metallocene or salt thereof may have a reversible redox coupling at a potential of from about 0.5 V vs NHE to about 1.5 V vs NHE (at 50 mV/s in 0.5 M aqueous electrolyte). In certain embodiments, the metallocene or salt thereof may have a reversible redox coupling at a potential of about 0.6 V vs NHE (at 50 mV/s in 0.5 M aqueous electrolyte).

In certain embodiments, the metallocene or salt thereof may include a hydrophilic functional group, such as a quaternary ammonium salt.

In certain embodiments, the metallocene has formula (I):

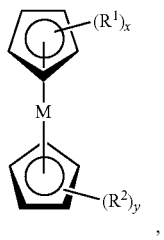

(I)

or a salt thereof, wherein: M is Fe, Co, Ni, Mn, Cr, Ti, Mo, V, or W; $R^1$ and $R^2$, at each occurrence, are each independently selected from the group consisting of hydrogen, halogen, alkyl, cycloalkyl, heterocyclyl, aryl, heteroaryl, —CN, —$NO_2$, —$OR^a$, —$SR^a$, -alkyl-N($R^a$)$_z$, —N($R^a$)$_z$, —C(O)$R^a$, —C(O)O$R^a$, —S(O)$_z$$R^a$, —S(O)$_z$O$R^a$, and —OP(O)(O$R^a$)$_2$; $R^a$, at each occurrence, is independently selected from the group consisting of hydrogen, alkyl, cycloalkyl, heterocyclyl, aryl, heteroaryl, alkyl-N($R^b$)$_z$, an oxygen protecting group, and a nitrogen protecting group; $R^b$, at each occurrence, is independently selected from the group consisting of hydrogen, alkyl, cycloalkyl, heterocyclyl, aryl, heteroaryl, an oxygen protecting group, and a nitrogen protecting group; x is 1, 2, 3, 4, or 5; y is 0, 1, 2, 3, 4, or 5; and z, at each occurrence, is independently 2 or 3.

In certain embodiments, the metallocene has formula (I-a):

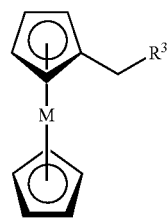

(I-a)

or a salt thereof, wherein: M is Fe, Co, Ni, Mn, Cr, Ti, Mo, V, or W; $R^3$ is —$NO_2$, —$OR^a$, —N($R^a$)$_z$, —C(O)$R^a$, —C(O)O$R^a$, —S(O)$_z$$R^a$, —S(O)$_z$O$R^a$, or —OP(O)(O$R^a$)$_2$; $R^a$, at each occurrence, is independently selected from the group consisting of hydrogen, alkyl, cycloalkyl, heterocyclyl, aryl, heteroaryl, alkyl-N($R^b$)$_z$, an oxygen protecting group, and a nitrogen protecting group; $R^b$, at each occurrence, is independently selected from the group consisting of hydrogen, alkyl, cycloalkyl, heterocyclyl, aryl, heteroaryl, an oxygen protecting group, and a nitrogen protecting group; and z is 2 or 3.

In certain embodiments, the metallocene has formula (I-b):

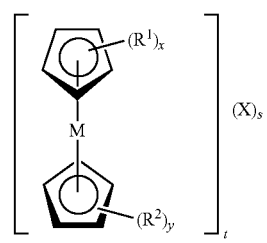

(I-b)

wherein M is Fe, Co, Ni, Mn, Cr, Ti, Mo, V, or W; $R^1$ and $R^2$, at each occurrence, are each independently selected from the group consisting of hydrogen, halogen, alkyl, cycloalkyl, heterocyclyl, aryl, heteroaryl, —CN, —$NO_2$, —$OR^a$, —$SR^a$, -alkyl-N($R^a$)$_z$, —N($R^a$)$_z$, —C(O)$R^a$, —C(O)O$R^a$, —S(O)$_z$$R^a$, —S(O)$_z$O$R^a$, and —OP(O)(O$R^a$)$_2$; $R^a$, at each occurrence, is independently selected from the group consisting of hydrogen, alkyl, cycloalkyl, heterocyclyl, aryl, heteroaryl, alkyl-N($R^b$)$_z$, an oxygen protecting group, and a nitrogen protecting group; $R^b$, at each occurrence, is independently selected from the group consisting of hydrogen, alkyl, cycloalkyl, heterocyclyl, aryl, heteroaryl, an oxygen protecting group, and a nitrogen protecting group; x is 1, 2, 3, 4, or 5; y is 0, 1, 2, 3, 4, or 5; z, at each occurrence, is independently 2 or 3; and X, at each occurrence, is independently $F^-$, $Cl^-$, $Br^-$, $I^-$, $SO_4^{2-}$, $OH^-$, $CO_3^{2-}$, $ClO_4^-$, $H_2PO_4^-$, $HPO_4^{2-}$, $PO_4^{3-}$, $NO_3^-$, $N_3^-$, $CN^-$, $N(CN)_2^-$, $SCN^-$, or a combination thereof; s is ≥1 (e.g., 1, 2, or 3); and t is ≥1 (e.g., 1, 2, or 3). In certain embodiments, t is 1, and s is 1 (e.g., t is 1, s is 1, and X is $Cl^-$). In certain embodiments, t is 2, and s is 1 (e.g., t is 2, s is 1, and X is —$SO_4^{2-}$). In certain embodiments, t is 3, and s is 1 (e.g., t is 3, s is 1, and X is $PO_4^{3-}$). In certain embodiments, t is 1, and s is 2 (e.g., t is 1 when one of $R^4$, $R^5$ or $R^6$ contain an additional cationic charge, s is 2, and X is $Br^-$).

In certain embodiments, the metallocene has formula (I-b-1):

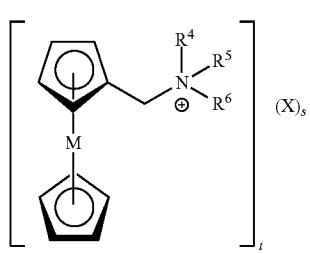

(I-b-1)

wherein: M is Fe, Co, Ni, Mn, Cr, Ti, Mo, V, or W; $R^4$, $R^5$, and $R^6$ are each independently selected from the group consisting of hydrogen, $C_1$-$C_6$-alkyl, and alkyl-$N(R^b)_2$; $R^b$, at each occurrence, is independently selected from the group consisting of hydrogen, alkyl, cycloalkyl, heterocyclyl, aryl, heteroaryl, an oxygen protecting group, and a nitrogen protecting group; X, at each occurrence, is independently halide (e.g., $F^-$, $Cl^-$, $Br^-$, $I^-$), $SO_4^{2-}$, $OH^-$, $CO_3^{2-}$, $ClO_4^-$, $H_2PO_4^-$, $HPO_4^{2-}$, $PO_4^{3-}$, $NO_3^-$, $N_3^-$, $CN^-$, $N(CN)_2^-$, $SCN^-$, or a combination thereof; s is ≥1 (e.g., 1, 2, or 3); and t is ≥1 (e.g., 1, 2, or 3). In certain embodiments, t is 1, and s is 1 (e.g., t is 1, s is 1, and X is $Cl^-$). In certain embodiments, t is 2, and s is 1 (e.g., t is 2, s is 1, and X is —$SO_4^{2-}$). In certain embodiments, t is 3, and s is 1 (e.g., t is 3, s is 1, and X is $PO_4^{3-}$). In certain embodiments, t is 1, and s is 2 (e.g., t is 1 when one of $R^4$, $R^5$ or $R^6$ contain an additional cationic charge, s is 2, and X is $Br^-$).

In certain embodiments, the metallocene has formula (I-c):

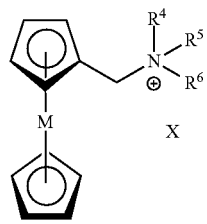

(I-c)

wherein: M is Fe, Co, Ni, Mn, Cr, Ti, Mo, V, or W; $R^4$, $R^5$, and $R^6$ are each independently selected from the group consisting of hydrogen and $C_1$-$C_6$-alkyl; and X is $F^-$, $Cl^-$, $Br^-$, $I^-$, or a combination thereof.

In certain embodiments, the metallocene has formula (I-d):

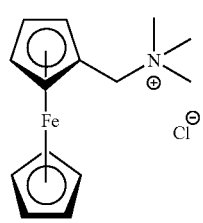

(I-d)

In certain embodiments, the metallocene has formula (I-e):

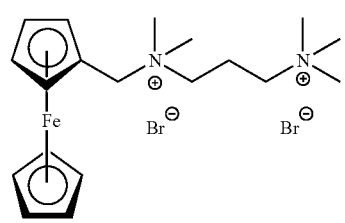

(I-e)

In certain embodiments, the metallocene has formula (I-f):

(I-f)

In certain embodiments, the metallocene has formula (I-g):

(I-g)

In certain embodiments, the metallocene has formula (I-h):

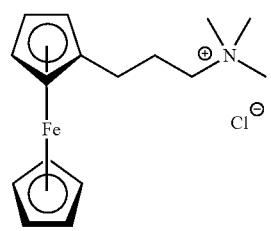

(I-h)

In certain embodiments, the metallocene has formula (I-i):

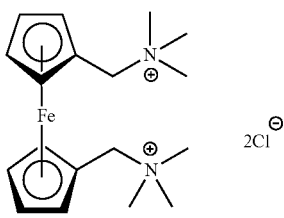

(I-i)

In certain embodiments, the metallocene has formula (I-j):

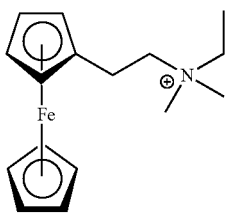

(I-j)

The disclosed metallocene compounds may exist in various salt forms. The term "salt thereof" refers to salts or zwitterions of the compounds. The salt may be, for example, a monosalt, disalt, trisalt or tetrasalt. Mixed salts may also exist. The salts may be prepared during the final isolation and purification of the compounds or separately by reacting a functional group of the compounds with a suitable acid, base, or alkylating agent. The amino groups of the compounds may be quaternized with alkyl chlorides, bromides and iodides such as methyl, ethyl, propyl, isopropyl, butyl, lauryl, myristyl, stearyl and the like. Suitable counterions include, but are not limited to, halide ($F^-$, $Cl^-$, $Br^-$, $I^-$), $SO_4^{2-}$, $OH^-$, $CO_3^{2-}$, $ClO_4^-$, $H_2PO_4^-$, $HPO_4^{2-}$, $PO_4^{3-}$, $-NO_3^-$, $N_3^-$, $CN^-$, $N(CN)_2^-$, and $SCN^-$. Basic addition salts may be prepared during the final isolation and purification of the disclosed compounds by reaction of a carboxyl group for example, with a suitable base such as the hydroxide, carbonate, or bicarbonate of a metal cation such as lithium, sodium, potassium, calcium, magnesium, or aluminum, or an organic primary, secondary, or tertiary amine.

For example, where a disclosed metallocene compound is in a salt form, one or more of the hydrogens represented by variable IV may be replaced by a Li, Na, or K (e.g., one or more $R^1$ and $R^2$ variables may be a group such as —C(O)ONa, —S(=O)ONa, —S(O)$_2$ONa, —OP(O)(OH)(ONa), or —OP(O)(ONa)$_2$). As another example, where a disclosed metallocene compound is in a salt form, one or more of the alkyl-N($R^a$)$_z$ and N($R^a$)$_z$ groups represented by the $R^1$ and $R^2$ variables may be quaternized (z=3) and can include a suitable negatively charged counterion X (e.g., halide ($F^-$, $Cl^-$, $Br^-$, $I^-$), $SO_4^{2-}$, $OH^-$, $CO_3^{2-}$, $ClO_4^-$, $H_2PO_4^-$, $HPO_4^{2-}$, $PO_4^{3-}$, —$NO_3^-$, $N_3^-$, $CN^-$, $N(CN)_2^-$, $SCN^-$, or any negative charged species).

a. Synthesis Methods of Metallocene Compounds

Compounds of formula (I) may be synthesized as shown in Schemes 1-3.

Abbreviations which have been used in the descriptions of Schemes 1-3 that follow are: $CH_3CN$ for acetonitrile; Br($CH_2$)$_3$NMe$_3$Br for (3-bromopropyl)trimethylammonium bromide; R.T. for room temperature; $H_2SO_4$ for sulfuric acid; and NaOH for sodium hydroxide.

Scheme 1:

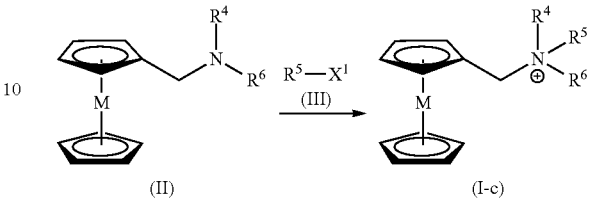

As shown in scheme 1, a compound of formula (I-c), wherein M is Fe, Co, Ni, Mn, Cr, Ti, Mo, V, or W; $R^4$, $R^5$, and $R^6$ are each independently selected from the group consisting of hydrogen and $C_1$-$C_6$-alkyl; $X^1$ is F, Cl, Br, or I; and X is $F^-$, $Cl^-$, $Br^-$ or $I^-$, may be synthesized by a one-step alkylation by mixing a compound of formula (II) with a compound of formula (III). In certain embodiments, the reaction of scheme 1 can be performed at room temperature in a solvent that includes acetonitrile.

In certain embodiments, the reaction of scheme 1 can yield 90% or greater of the compound of formula (I-c). In other embodiments, the reaction of scheme 1 can yield 90% or greater of the compound of formula (I-c) at a scale of 15 grams or greater.

Scheme 2:

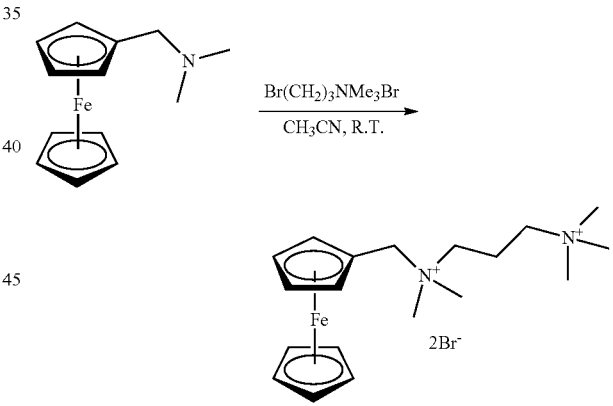

As shown in scheme 2, a metallocene diammonium bromide salt may be synthesized by a one-step alkylation by mixing a (ferrocenylmethyl)dimethylamine with $CH_3CN$ and Br($CH_2$)$_3$NMe$_3$Br at room temperature.

Scheme 3:

Scheme 3:

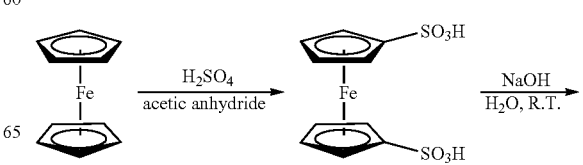

-continued

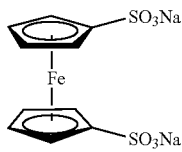

As shown in scheme 3, disodium (ferrocenyl)sulfurtrioxide may be synthesized by sulfonation of ferrocene, followed by treatment with sodium hydroxide.

b. Second Redox Active Material in Combination with Metallocene Compounds

The second redox active material may be included as part of the anolyte of the disclosed metallocene-based AORFBs. The second redox active material used in combination with Metallocene compounds may include a viologen, a pyridinium, a quinone, an anthraquinone, $(CH_2)_3(CMe_2)_2NO$ (TEMPO), a nitroxyl radical, $Fe^{3+/2+}$, $^-[Fe(CN)_6]^{3+/2+}$, $Br_2/Br^-$, $S_4^-/S_2$, $Cr^{3+/2+}$, $Ce^{4+/3+}$, $Zn^{2+/0}$, $V^{5+/4+}$, $V^{4+3+}$, $V^{3+/2+}$, $Pb^{2+/0}$, $PbO_2/Pb^{2+}$, $Cu^{2+/0}$, $Ti^{3+}/TiO^{2+}$, $Li^{+/0}$, $Na^{+/0}$, $mg^{2+/0}$, $Ar^{3+/0}$, $Ca^{2+/0}$ or a combination thereof. In certain embodiments, the second redox active material may be methyl viologen.

In certain embodiments, the viologen may have formula (V):

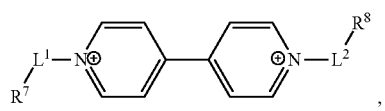

(V)

or a salt thereof, wherein $L^1$ and $L^2$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_m$, $R^7$ and $R^8$ are each independently selected from the group consisting of —$CH_3$, —$NO_2$, —$OR^d$, —$N(R^d)_m$, —$C(O)R^d$, —$C(O)OR^d$, —$S(O)_m$, —$PO_3$, —$S(O)_m$ $R^d$, —$S(O)_mOR^d$, —$OP(O)(OR^d)_2$, —$OCH_3$, —$(CR^d_2)_mCN$, substituted aryl, and substituted heteroaryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; and m, at each occurrence, is independently 2 or 3.

In certain embodiments, the viologen may have formula (V-a):

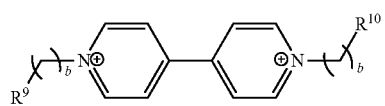

(V-a)

or a salt thereof, wherein $R^9$ and $R^{10}$ are each independently selected from the group consisting of —$CH_3$, —$N(R^d)_m$, —$S(O)_m$, —$PO_3$, —$S(O)_m$ $R^d$; —$(OCH_2CH_2)_m$—$OCH_3$, and substituted aryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; m, at each occurrence, is independently 2 or 3; and b, at each occurrence, is independently 0, 1, 2 or 3.

In certain embodiments, the viologen may have formula (V-b):

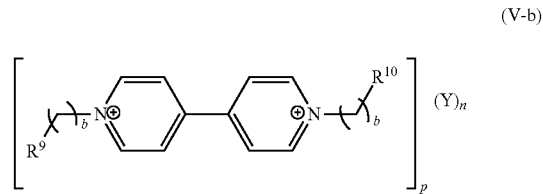

(V-b)

wherein $R^9$ and $R^{10}$ are each independently selected from the group consisting of —$CH_3$, —$N(R^d)_m$, —$S(O)_m$, —$PO_3$, —$S(O)_m$ $R^d$, —$(OCH_2CH_2)_m$—$OCH_3$, substituted aryl, and substituted heteroaryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; Y, at each occurrence, is independently $Na^+$, $K^+$, $Li^+$, $NR^f_4{}^+$, $Br^-$, $I^-$, $SO_4{}^{2-}$, $OH^-$, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, $CN^-$, $N(CN)_2{}^-$, $SCN^-$, or a combination thereof; $R^f$, at each occurrence, is independently selected from the group consisting of hydrogen, alkyl, cycloalkyl, heterocyclyl, aryl, and heteroaryl; m, at each occurrence, is independently 2 or 3; n is 1, 2, 3 or 4; p is 1, 2, 3 or 4; and b, at each occurrence, is independently 0, 1, 2 or 3. In certain embodiments, $R^9$ and $R^{10}$ are each independently —$CH_3$, —$N(CH_3)_3{}^+$, —$SO_3{}^-$, —$(OCH_2CH_2)_m$—$OCH_3$, or substituted aryl; Y, at each occurrence, is independently $Na^+$, $Cl^-$, $Br^-$, or a combination thereof; n is 2, 3 or 4; and p is 1.

The viologen compounds may exist in various salt forms. Generally, the description of salt forms for metallocenes can be applied to the viologen compounds. For the purposes of brevity, this description will not be repeated here. In addition to the description above, viologen compounds may exist in salts forms that have suitable counterions that are anionic, cationic or combinations thereof. For example, where a disclosed viologen compound has an aryl group substituted with —$SO_3$ groups as $R^7$ and/or $R^8$, a suitable cation can be $Na^+$, or any other suitable positive charged species.

In certain embodiments, the viologen may be selected from the group consisting of:

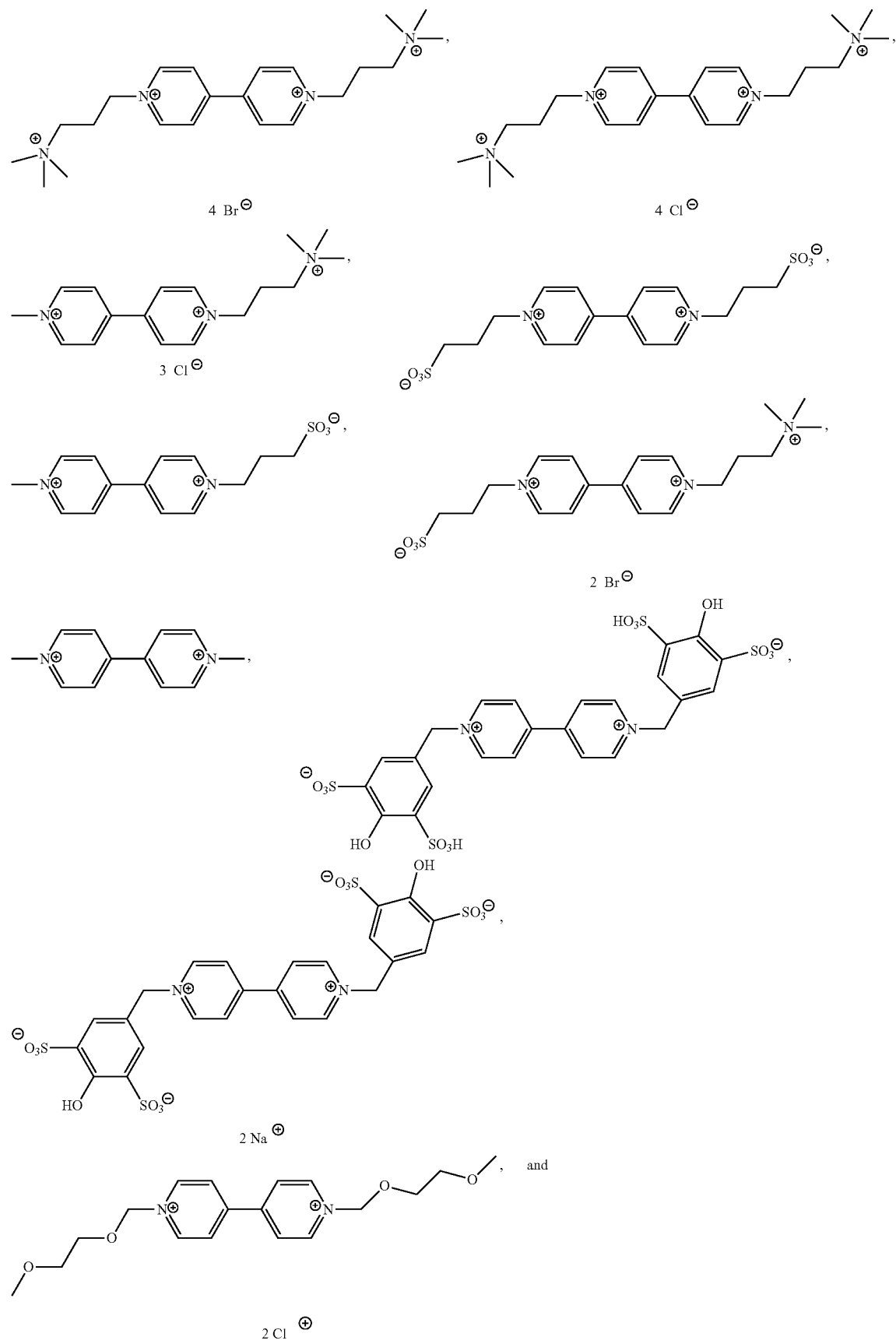

-continued

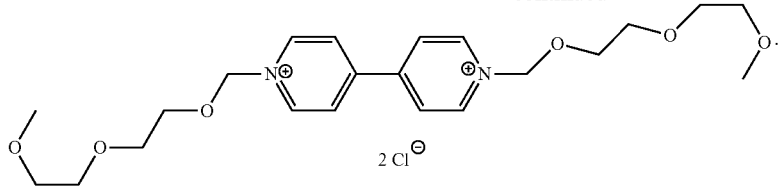 [SMILES: COCCOCCOC[n+]1ccc(-c2cc[n+](COCCOCCOC)cc2)cc1]

2 Cl⊖ ii. Viologen Compounds

Also disclosed herein are AORFBs that include viologen compounds having formula (VI):

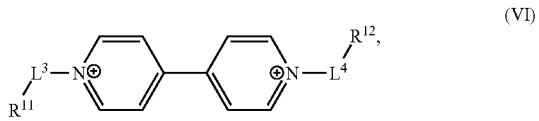

or a salt thereof, wherein $L^3$ and $L^4$ are each independently selected from the group consisting of bond, $C_1$-$C_{12}$ alkylenyl, $C_1$-$C_{12}$ alkenylenyl, $C_1$-$C_{12}$ alkynylenyl, and $C_1$-$C_4$ alkylenyl-$(OCH_2CH_2)_m$; $R^{11}$ is selected from the group consisting of, —$NO_2$, —$OR^g$, —$N(R^g)_q$, —$C(O)R^g$, —$C(O)OR^g$, —$S(O)_q$, —$PO_3$, —$S(O)_qR^g$, —$S(O)_qOR^g$, —$OP(O)(OR^g)_2$, —$OCH_3$, —$(CR^g_2)_mCN$, substituted aryl, and substituted heteroaryl; $R^{12}$ is selected from the group consisting of —$CH_3$, —$NO_2$, —$OR^g$, —$C(O)R^g$, —$C(O)OR^g$, —$S(O)_q$, —$PO_3$, —$S(O)_qR^g$, —$S(O)_qOR^g$, —$OP(O)(OR^g)_2$; $OCH_3$, —$(CR^g_2)_mCN$, substituted aryl, and substituted heteroaryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; and q, at each occurrence, is independently 2 or 3.

In certain embodiments, the substituted aryl and/or the substituted heteroaryl may be substituted with 1, 2 or 3 of the following: —$SO_3^-$, —$SO_3H$, —$PO_3^{-2}$, —$PO_3H$, —COOH, —OH, cyano and a combination thereof.

The viologen compounds of formula (VI) may serve as the first redox active material or the second redox active material, where viologen compounds of formula (VI) may or may not be coupled with metallocene compounds as the other corresponding redox active material. Accordingly, the viologen compounds of formula (VI) may be used as part of the anolyte solution or the catholyte solution within the AORFB. In addition, the viologen compounds of formula (VI) may have two redox couples that can be utilized (e.g., two-electron storage capability), which can enhance energy density of AORFB's.

The viologen compounds of formula (VI) have useful aqueous solubility for application in AORFB's. For example, the viologen or salt thereof may have an aqueous solubility of ≥1 M, ≥1.5 M, ≥2 M, ≥2.5 M, ≥3 M, ≥3.5 M, or ≥4 M. In certain embodiments, the viologen or salt thereof may have an aqueous solubility of from about 1M to about 10 M, such as from about 1M to about 8 M, from about 2M to about 6 M, or from about 3 M to about 5 M. In addition, disclosed viologen compounds having two useable redox couple can remain soluble in aqueous solution in both redox states.

In certain embodiments, the viologen may have formula (VI-a):

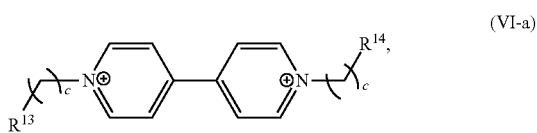

or a salt thereof, wherein $R^{13}$ is selected from the group consisting of —$N(R^g)_q$, —$S(O)_q$, —$PO_3$, —$S(O)Ag$, —$(OCH_2CH_2)_m$—$OCH_3$, and substituted aryl; $R^{14}$ is selected from the group consisting of —$CH_3$, —$S(O)_q$, —$PO_3$, —$S(O)_qR^g$, —$(OCH_2CH_2)_m$—$OCH_3$, and substituted aryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; q, at each occurrence, is independently 2 or 3; and c, at each occurrence, is independently 0, 1, 2 or 3. In certain embodiments, the substituted aryl may be substituted with 1, 2 or 3 of the following: —$SO_3^-$, —$SO_3H$, —$PO_3^{-2}$, —$PO_3H$, —COOH, —OH, cyano or a combination thereof.

In certain embodiments, the viologen may have formula (VI-b):

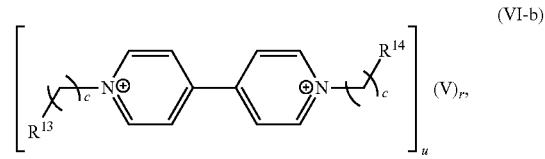

wherein $R^{13}$ is selected from the group consisting of —$N(R^g)_q$, —$S(O)_q$, —$PO_3$, —$S(O)_qR^g$, —$(OCH_2CH_2)_m$—$OCH_3$, and substituted aryl; $R^{14}$ is selected from the group consisting of —$CH_3$, —$S(O)_q$, —$PO_3$, —$S(O)_qR^g$, —$(OCH_2CH_2)_m$—$OCH_3$, and substituted aryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; V, at each occurrence, is independently $Na^+$, $K^+$, $NR^i_4{}^+$, $F^-$, $Cl^-$, $Br^-$, $I^-$, $SO_4{}^{2-}$, $OH^-$, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, $CN^-$, $N(CN)_2{}^-$, $SCN^-$ or a combination thereof; $R^i$, at each occurrence, is independently selected from the group consisting of hydrogen, alkyl, cycloalkyl, heterocyclyl, aryl, and heteroaryl; q, at each occurrence, is independently 2 or 3; r is 1, 2, 3 or 4; u is 1, 2, 3 or 4; and c, at each occurrence, is independently 0, 1, 2 or 3. In certain embodiments, $R^{13}$ is —SO$_3^-$, —(OCH$_2$CH$_2$)$_m$—OCH$_3$, or substituted aryl; $R^{14}$ is —SO$_3^-$, —(OCH$_2$CH$_2$)$_m$—OCH$_3$, or substituted aryl; V, at each occurrence, is independently Na$^+$, K$^+$, Cl$^-$, Br$^-$ or a combination thereof; r is 2, 3 or 4; u is 1; and c, at each occurrence, is independently 1, 2 or 3. In certain embodiments, the substituted aryl may be substituted with 1, 2 or 3 of the following: —SO$_3^-$, —SO$_3$H, —PO$_3^{-2}$, —PO$_3$H, —COOH, —OH, cyano or a combination thereof.

The viologen compounds of formula (VI, VI-a and VI-b) may exist in various salt forms. Generally, the description of salt forms for metallocenes and the above-listed viologen compounds of formula (V) can be applied to the viologen compounds of formula (VI, VI-a and VI-b). For the purposes of brevity, this description will not be repeated here.

In certain embodiments, the viologen may be selected from the group consisting of:

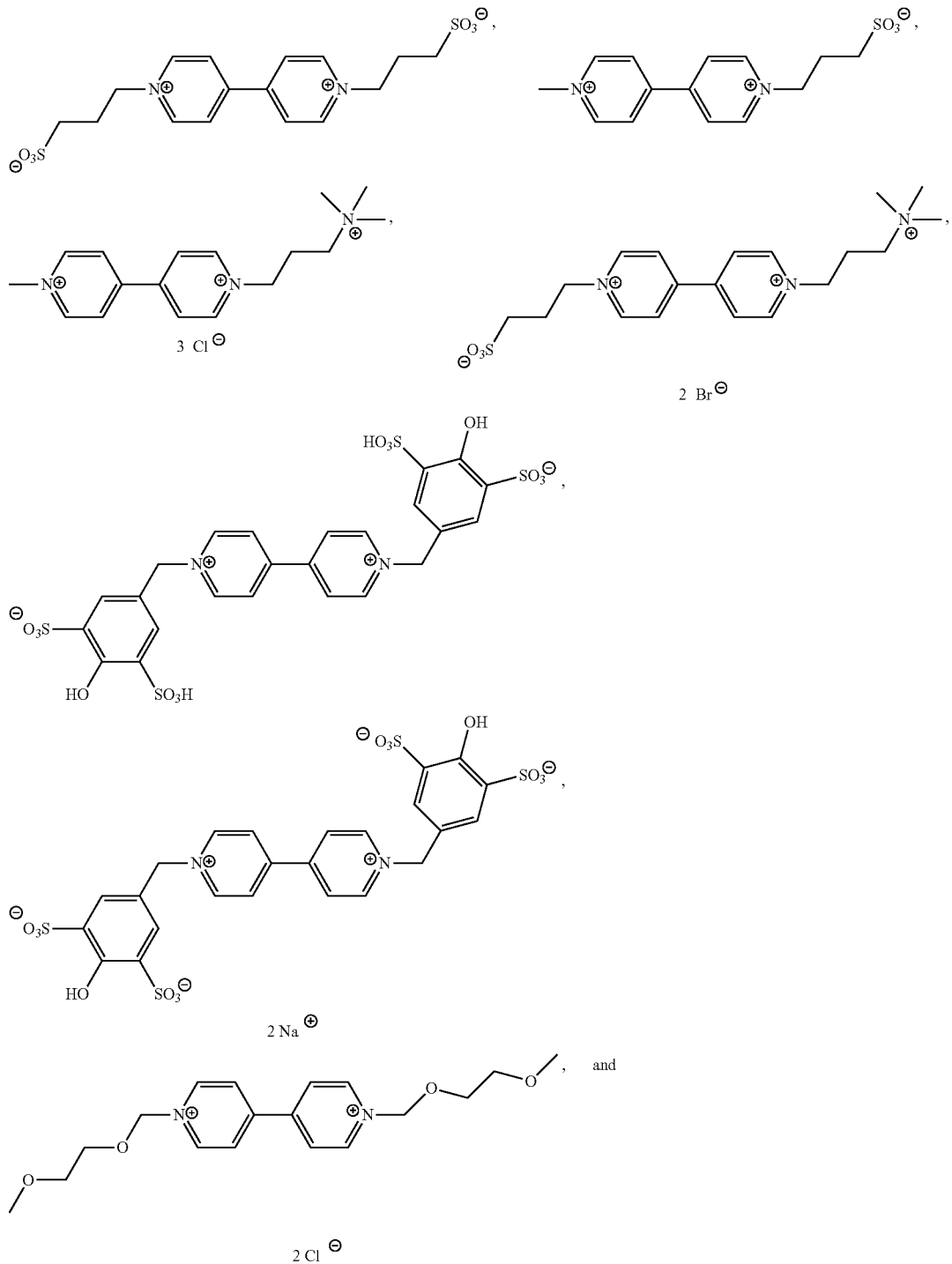

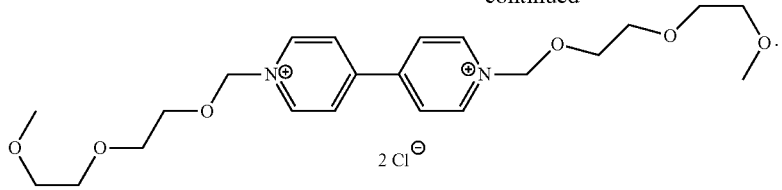

AORFBs that include viologen compounds of formula (VI, VI-a and VI-b) as the second redox active material may include a first redox material that comprises KBr, NaBr, NH$_4$Br, NR$_4$Br (R=alkyl, aryl, alkyl hydroxyl, alkyl ammonium), KI, NaI, NH$_4$I, NR$_4$I (R=alkyl, aryl, alkyl hydroxyl, alkyl ammonium)FeCl$_2$, FeBr$_2$, Ce$^{4+/3+}$, Mn$^{3+/2+}$, PbO$_2$/PbSO$_4$, quinines, anthraxquinines, K$_4$[Fe(CN)$_6$], N$_4$[Fe(CN)$_6$], (NH$_4$)$_4$[Fe(CN)$_6$], NR$_4$[Fe(CN)$_6$], (R=alkyl, aryl, alkyl hydroxyl, alkyl ammonium), V$^{5+4+}$, derivatives of (2,2,6,6-Tetramethylpiperidin-1-yl)oxyl (TEMPO), such as 4-trimethylammonium-(2,2,6,6-Tetramethylpiperidin-1-yl)oxy (4-N$^{Me}$-TEMPO), 4-dimethyl(propyl-3-N,N,N,-trimethylammonium)-(2,2,6,6-Tetramethylpiperidin-1-yl)oxy ((4-N$^{NPr}$-TEMPO), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-SO$_3$-TEMPO), 4-amino-(2,2,6,6-Tetramethylpiperidin-1-yl)oxy (4-NH$_2$-TEMPO), or combination thereof.

In certain embodiments, the derivative of TEMPO may have formula (VIII-a):

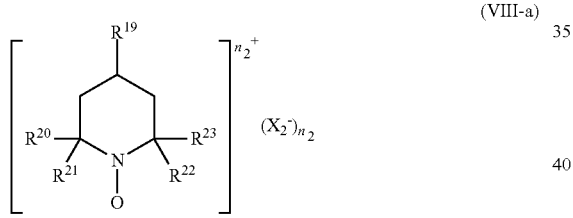

(VIII-a)

wherein R$^{19}$, R$^{20}$, R$^{21}$, R$^{22}$ and R$^{23}$ are each independently selected from the group consisting of hydrogen, halogen, alkyl, cycloalkyl, heterocyclyl, aryl, heteroaryl, —CN, —NO$_2$, —OR$^k$, —SR$^k$, -alkyl-N(R$^k$)$_w$, —N(R$^k$)$_w$, —C(O)R$^k$, —C(O)OR$^k$, —S(O)$_w$R$^k$, —S(O)$_w$OR$^k$, and —OP(O)(OR$^k$)$_2$; R$^k$, at each occurrence, is independently selected from the group consisting of hydrogen, alkyl, cycloalkyl, heterocyclyl, aryl, heteroaryl, alkyl-N(R$^l$)$_w$, an oxygen protecting group, and a nitrogen protecting group; R', at each occurrence, is independently selected from the group consisting of hydrogen, alkyl, cycloalkyl, heterocyclyl, aryl, heteroaryl, an oxygen protecting group, and a nitrogen protecting group; X$_2^-$ can be Cl$^-$, Br$^-$, I$^-$, SO$_4^{2-}$, —NO$_3^-$ and other anions; n$_2$ is 1, 2, 3, 4, or 5, and w, at each occurrence, is independently 2 or 3.

In certain embodiments, R$^{20}$ and R$^{21}$ may together form a cycloalkyl. In certain embodiments, R$^{22}$ and R$^{23}$ may together form a cycloalkyl.

When n$_2$ is further denoted with a "+", it refers to a compound being n$_2^+$. For example, when n$_2$ is 2, the derivative of TEMPO carries a positive charge of 2$^+$. This charge may be countered by a suitable counterion, e.g., X$_2^-$.

In certain embodiments, R$^{19}$ may be alkyl-N(R$_k$)$_w$, or N(R$^k$)$_w$, and R$^{20}$, R$^{21}$, R$^{22}$ and R$^{23}$ may be each independently be C$_1$-C$_6$ alkyl, or together form a cycloalkyl as discussed above; and n$^2$ is 1, 2, or 3.

In certain embodiments, the derivative of TEMPO of formula (VIII-a) may be selected from the group consisting of:

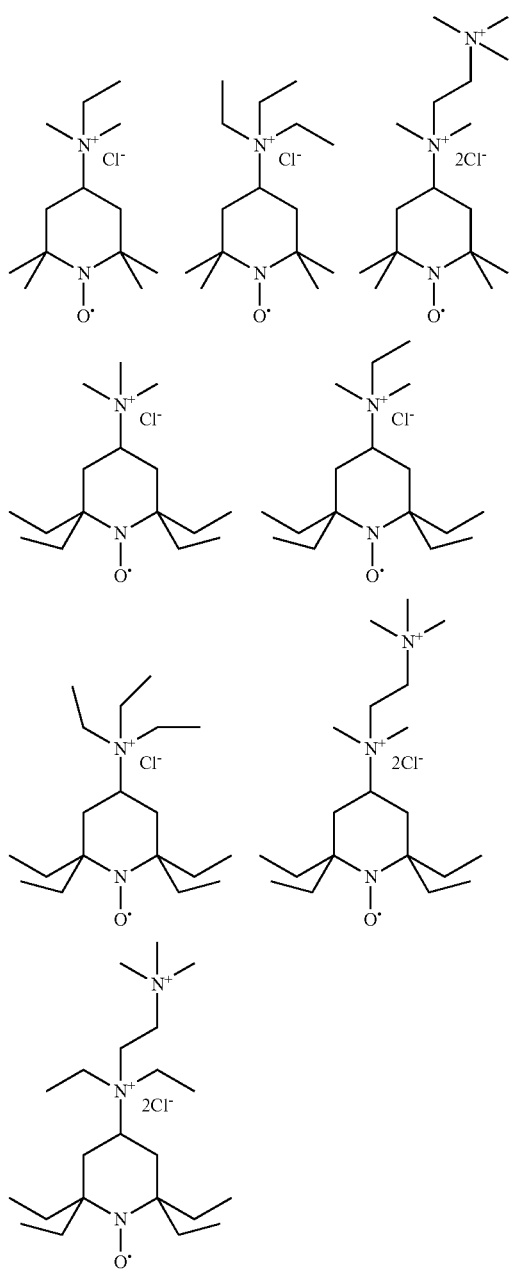

-continued

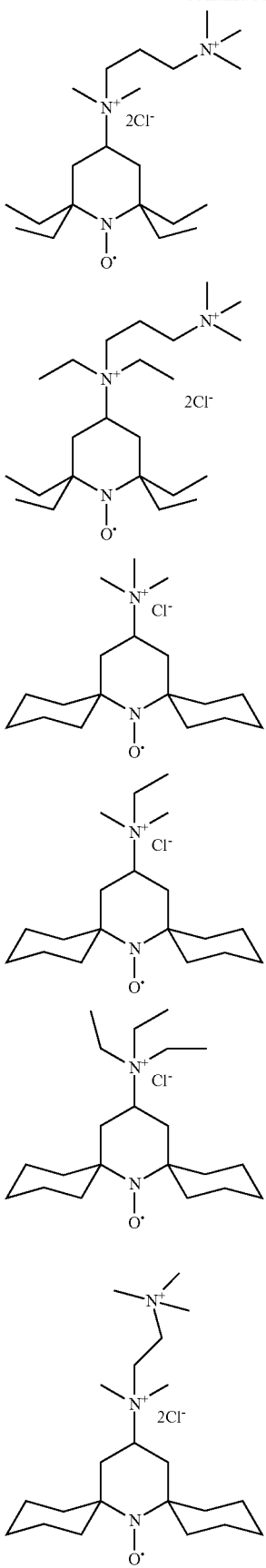

-continued

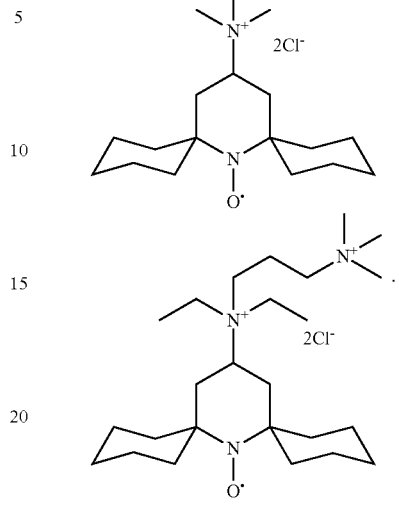

In certain embodiments, the derivative of TEMPO may have formula (VIII-b):

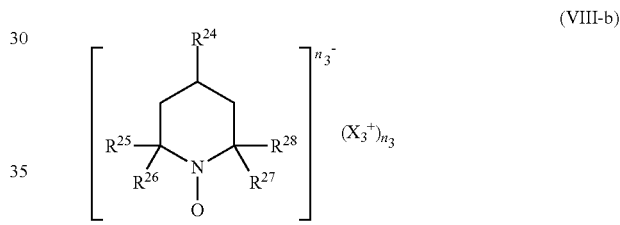

(VIII-b)

wherein $R^{24}$, $R^{25}$, $R^{26}$, $R^{27}$ and $R^{28}$ are each independently selected from the group consisting of hydrogen, halogen, alkyl, cycloalkyl, heterocyclyl, alkylaryl, aryl heteroaryl, —CN, —$NO_2$, —$OR'''$, —$SR'''$, -alkyl-$N(R''')_q$, —$N(R''')_q$, —$C(O)R'''$, —$C(O)OR'''$, —$S(O)_qR'''$, —$S(O)_qOR'''$, and —$OP(O)(OR''')_2$; $R'''$, at each occurrence, is independently selected from the group consisting of hydrogen, alkyl, cycloalkyl, heterocyclyl, aryl, heteroaryl, alkyl-$N(R'')_q$, an oxygen protecting group, and a nitrogen protecting group; $R''$, at each occurrence, is independently selected from the group consisting of hydrogen, alkyl, cycloalkyl, heterocyclyl, aryl, heteroaryl, an oxygen protecting group, and a nitrogen protecting group; $X_3^+$ can be $H^+$, $Li^+$, $Na^+$, $K^+$, $NH_4^+$ and other cations; $n_3$ is 1, 2, 3, 4, or 5; and w, at each occurrence, is independently 2 or 3.

In certain embodiments, $R^{25}$ and $R^{26}$ may together form a cycloalkyl. In certain embodiments, $R^{27}$ and $R^{28}$ may together form a cycloalkyl.

When $n_3$ is further denoted with a "-", it refers to a compound being $n_3^-$. For example, when $n_3$ is 2, the derivative of TEMPO carries a negative charge of $2^-$. This charge may be countered by a suitable counterion, e.g., $X_3^+$.

In certain embodiments, $R^{24}$ may be substituted $C_1$-$C_6$ alkylaryl; and $R^{25}$, $R^{26}$, $R^{27}$ and $R^{28}$ may each independently be $C_1$-$C_6$ alkyl, or form a cycloalkyl as discussed above; and $n^3$ is 1, 2, or 3. In certain embodiments, alkylaryl and/or aryl may be substituted with 1, 2 or 3 of the following: —$SO_3^-$, —$SO_3H$, —$PO_3^{-2}$, —$PO_3H$, —COOH, —OH, —$CH_3$, cyano or a combination thereof.

In certain embodiments, the derivative of TEMPO of formula (VIII-b) may be selected from the group consisting of:

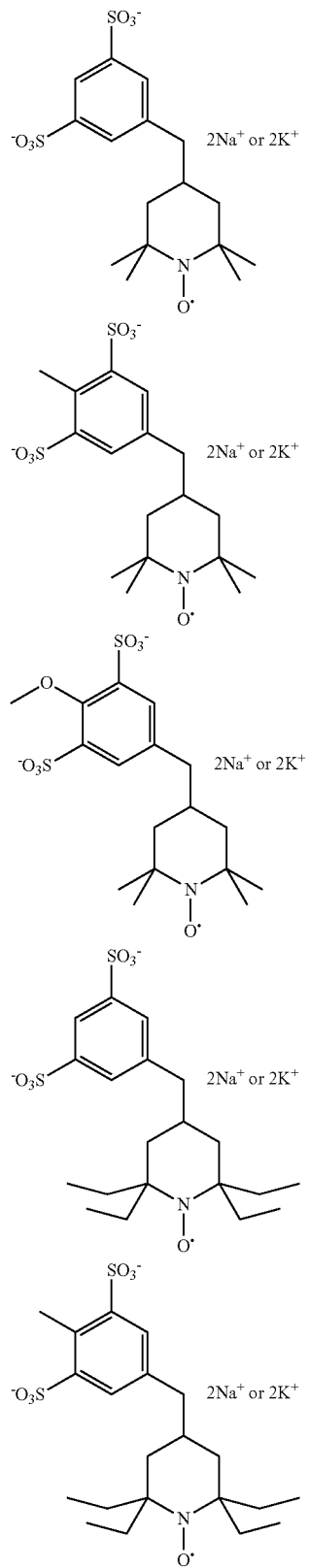

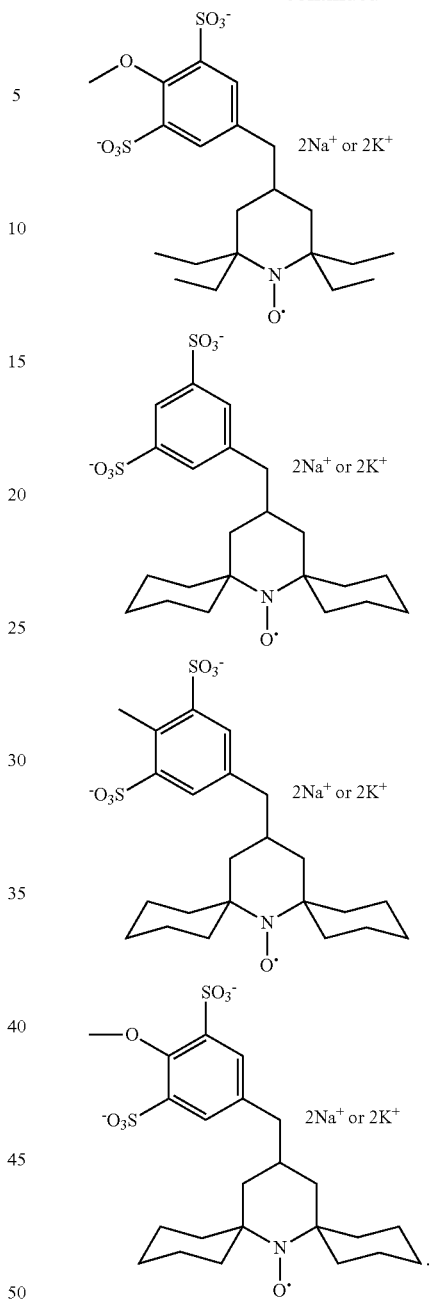

The derivatives of TEMPO of formula (VIII-a and VIII-b) may exist in various salt forms. Generally, the description of salt forms as described above for the metallocene and viologen compounds can be applied to the derivatives of TEMPO. For the purposes of brevity, this description will not be repeated here.

a. Synthesis Methods of Viologen Compounds

Compounds of formula (V) and (VI) can be synthesized as shown in schemes 4 and 5. Abbreviations which have been used in the descriptions of Schemes 4 and 5 that follow are: $CH_3CN$ and/or MeCN for acetonitrile; R.T. for room temperature; $H_2SO_4$ for sulfuric acid; and NaOH for sodium hydroxide; DMF for dimethylformamide, and DMSO for dimethyl sulfoxide.

Scheme 4:

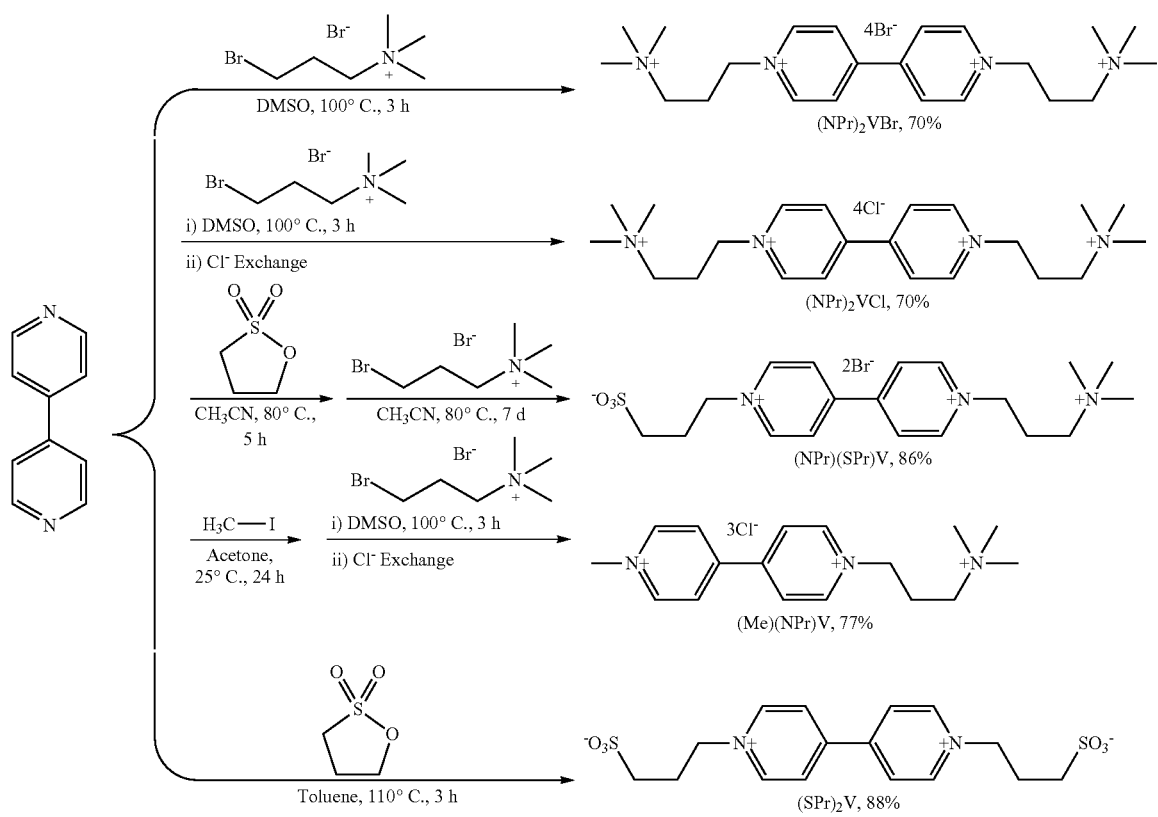

As shown in scheme 4, different viologen compounds may be synthesized by a single and/or two-step alkylation, sulfonation or combination thereof.

Scheme 5:

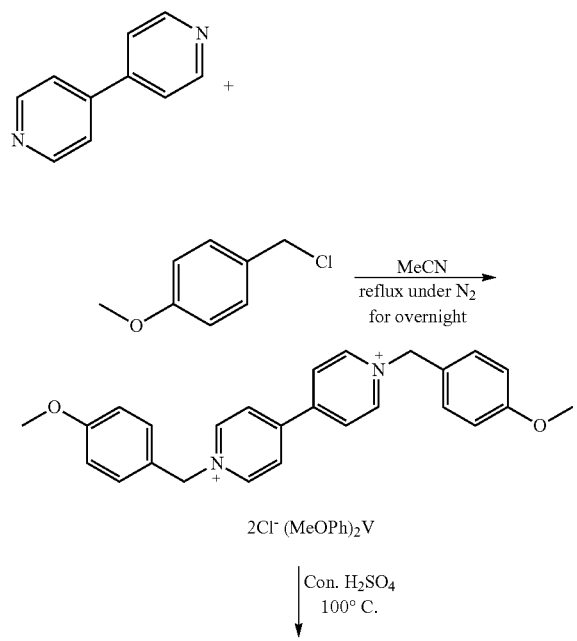

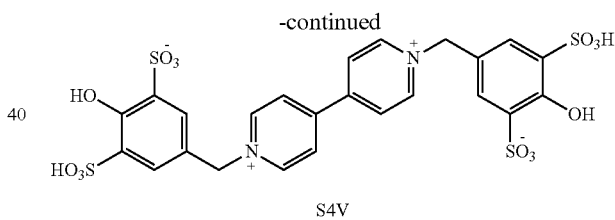

As shown in scheme 5, S4V may be synthesized via a two-step process with (MeOPh)$_2$V being an intermediate compound.

b. Neutral Viologen Compounds

Compounds of formula (VI, VI-a and VI-b) may have an overall neutral charge (e.g., where the substituents balance the positive charge of the bipyridyl-core structure, such as when $R^{11}$ and $R^{12}$ are $SO_3^-$). Neutral viologen compounds may be used in disclosed AORFBs as the second redox active material and such AORFBs may employ a cation exchange mechanism.

In certain embodiments, a neutral viologen may have formula (VII):

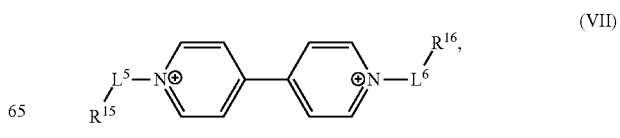

or a salt thereof, wherein $L^5$ and $L^6$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_j$; $R^{15}$ and $R^{16}$ are each independently selected from the group consisting of —$OR^j$, —$C(O)R^j$, —$C(O)OR^j$, —$S(O)_j$, —$PO_3$—$S(O)_j R^j$, —$S(O)_j OR^j$, —$OP(O)(OR^j)_2$, —$(CR^j_2)_j CN$, substituted aryl, and substituted heteroaryl; $R^1$, at each occurrence, is independently selected from the group consisting of alkyl-$S(O)_j$, and an oxygen protecting group; and j, at each occurrence, is independently 2 or 3. In certain embodiments, the substituted aryl and/or the substituted heteroaryl may be substituted with 1, 2 or 3 of the following: —$SO_3^-$, —$SO_3H$, —$PO_3^{-2}$, —$PO_3H$, —COOH, —OH, cyano and a combination thereof.

In certain embodiments, $R^{14}$ and $R^{15}$ may be each independently a sulfonate substituted phenyl groups. In certain embodiments, the phenyl group may be substituted with 1, 2 or 3 sulfonate groups.

In certain embodiments, $L^5$ and $L^6$ may be each independently $C_1$-$C_4$ alkylenyl and $R^{15}$ and $R^{16}$ may be each independently —$S(O)_j$, —$S(O)_j R^j$, —$S(O)_j OR^j$, or substituted aryl.

In certain embodiments, the compound of formula (VII) may be selected from the group consisting of:

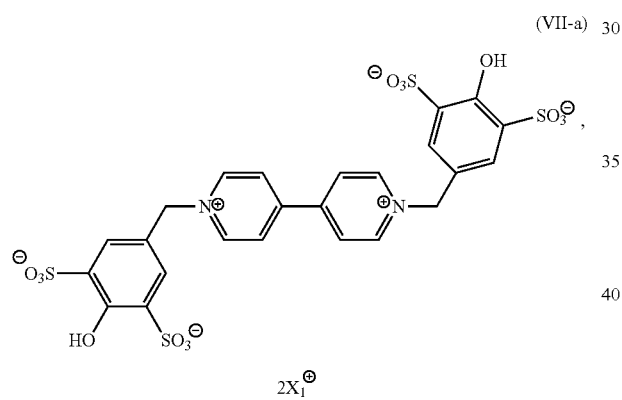
(VII-a)

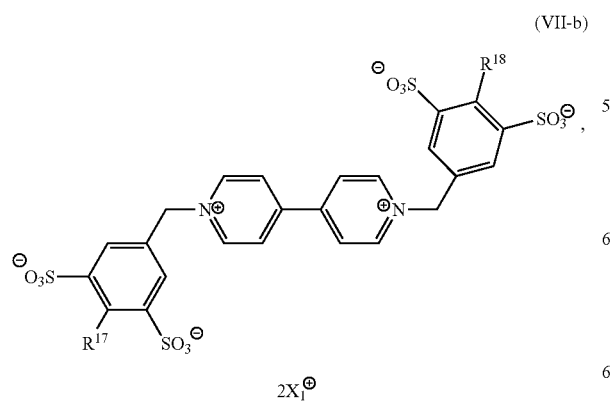
(VII-b)

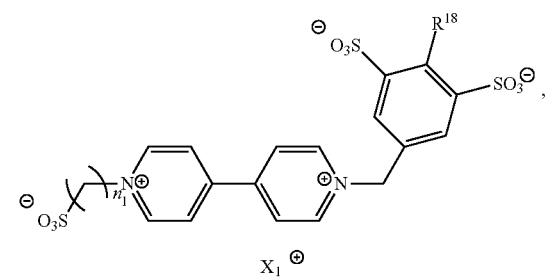
(VII-c)

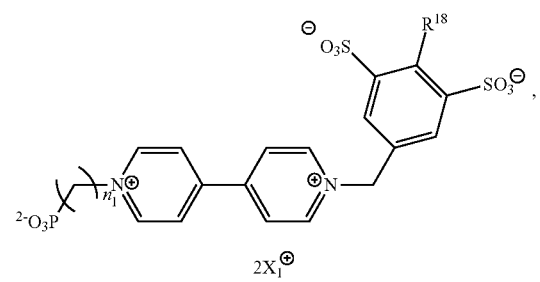
(VII-d)

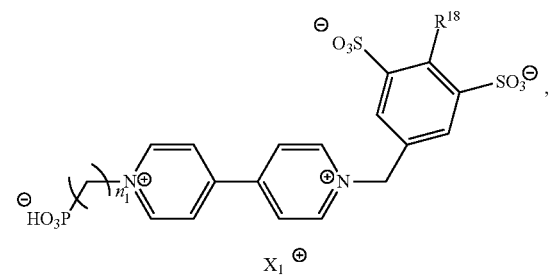
(VII-e)

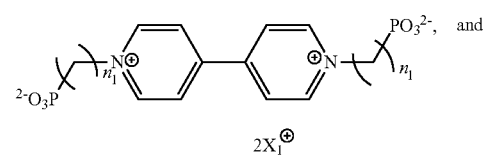
(VII-f)

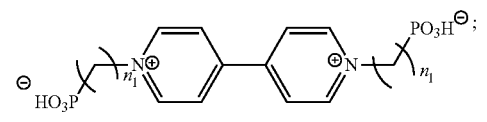
(VII-g)

wherein $X_1$ is $H^+$, $Na^+$, $K^+$ or $NH_4^+$; $R^{17}$ and $R^{18}$ are each individually H, hydroxyl, alkyl, aryl, alkyl oxide, hydroxyalkyl, or aryl hydroxyl; $n_1$ at each occurrence is independently 1, 2 or 3;

In certain embodiments, the neutral viologen may be selected from the group consisting of

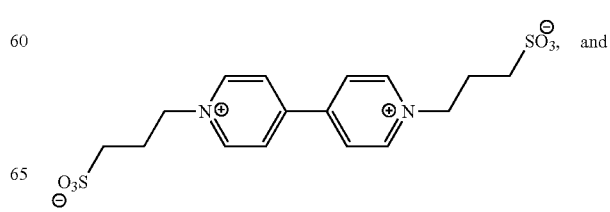

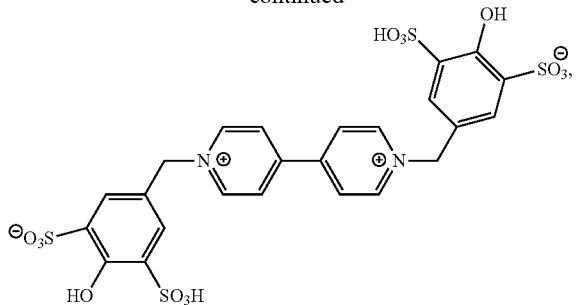

or salts thereof.

In certain embodiments, an AORFB that includes a neutral viologen as the second redox active material, may include a first redox active material comprising KBr, NaBr, NH$_4$Br, NR$_4$Br (R=alkyl, aryl, alkyl hydroxyl, alkyl ammonium), KI, NaI, NH$_4$I, NR$_4$I (R=alkyl, aryl, alkyl hydroxyl, alkyl ammonium)FeCl$_2$, FeBr$_2$, Ce$^{4+/3+}$, Mn$^{3+/2+}$, PbO$_2$/PbSO$_4$, quinines, anthraxquinines, K$_4$[Fe(CN)$_6$], N$_4$[Fe(CN)$_6$], (NH$_4$)$_4$[Fe(CN)$_6$], NR$_4$[Fe(CN)$_6$], (R=alkyl, aryl, alkyl hydroxyl, alkyl ammonium), V$^{5+4+}$, derivatives of (2,2,6,6-Tetramethylpiperidin-1-yl)oxyl (TEMPO), such as 4-trimethylammonium-(2,2,6,6-Tetramethylpiperidin-1-yl)oxy (4-N$^{Me}$-TEMPO), 4-dimethyl(propyl-3-N,N,N,-trimethylammonium)-(2,2,6,6-Tetramethylpiperidin-1-yl)oxy ((4-N$^{NPr}$-TEMPO), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-SO3-TEMPO), 4-amino-(2,2,6,6-Tetramethylpiperidin-1-yl)oxy (4-NH$_2$-TEMPO), or combinations thereof.

In certain embodiments, the neutral viologen compounds of formulas (VII and VIIa-g) can be coupled with a derivative of TEMPO (as the second and first redox active material, respectively) for a disclosed AORFB. Generally, the description of TEMPO derivatives for viologen compounds of formulas (VI, VI-a and VI-b) can be applied to the neutral viologen compounds. For the purposes of brevity, this description will not be repeated here.

In certain embodiments, an AORFB that includes a neutral viologen as the second redox active material, may include a first redox active material comprising $^-$[Fe(CN)$_6$]$^{3+/2+}$, I$_3^-$/I$^-$, Br$_2$/Br$^-$, S$_4^-$/S$_2$, TEMPO or a combination thereof. In certain embodiments, an AORFB that includes a neutral viologen as the second redox material may also include K$_4$[Fe(CN)$_6$], KI or a combination thereof as the first redox active material. In certain embodiments, the first redox active material may include K$_4$[Fe(CN)$_6$], Na$_4$[Fe(CN)$_6$], (NH$_4$)[Fe(CN)$_6$] or a combination thereof. In certain embodiments, the first redox active material may include KI, NaI, (NH$_4$)I or a combination thereof.

B. Aqueous Electrolyte

The disclosed AORFBs may include an aqueous electrolyte(s). The redox active materials may be present in the aqueous electrolyte(s). For example, the first redox active material may be present in a first aqueous electrolyte and the second redox active material may be present in a second aqueous electrolyte. The first and second aqueous electrolytes may be the same or different. In certain embodiments, the first aqueous electrolyte is the positive electrolyte and the second aqueous electrolyte is the negative electrolyte. In other embodiments, the first aqueous electrolyte is the negative electrolyte and the second aqueous electrolyte is the positive electrolyte.

The first and second redox active materials may be present in the first and second aqueous electrolytes, respectively, at a concentration of ≥1 M, ≥1.5 M, ≥2 M, ≥2.5 M, ≥3 M, ≥3.5 M, or ≥4 M. In certain embodiments, the first and second redox active materials may be present in the first and second aqueous electrolytes, respectively, at a concentration of from about 1M to about 10 M, such as from about 1M to about 8 M, from about 2M to about 6 M, or from about 3 M to about 5 M.

The first and second aqueous electrolytes may include a salt. In certain embodiments, the first and second electrolytes may include a salt having the formula (IV):

$$A\text{-}B \quad (IV),$$

wherein A is Na$^+$, K$^+$, Li$^+$, or NR$^c_4{}^+$, pyridinium, pyrrolidium, or imidazolium; R$^c$, is selected from the group consisting of hydrogen, an alkyl, a cycloalkyl, a heterocyclyl, an aryl, and a heteroaryl; and B is selected from the group consisting of a halide anion, SO$_4^{2-}$, OH$^-$, CO$_3^{2-}$, ClO$_4^-$, H$_2$PO$_4^-$, HPO$_4^{2-}$, PO$_4^{3-}$, NO$_3^-$, N$_3^-$, CN$^-$, N(CN)$_2^-$, or SCN$^-$. In certain embodiments, the first and second aqueous electrolytes include NaCl, KCl, or NH$_4$C$_1$.

In embodiments that include neutral viologen compounds as redox active materials, the first and second electrolyte each may individually include a salt where A is potassium. In certain embodiments, AORFBs that include neutral viologen compounds may also have first and second electrolytes that include KCl.

The salt may be present in the first and second aqueous electrolytes at a concentration of from about 0.5 M to about 5 M, such as from about 0.5 M to about 4 M, from about 1 M and about 3 M, or from about 0.5 M to about 2.5 M. In certain embodiments, the first and second aqueous electrolytes include from about 0.5 M to about 5 M NaCl, KCl, or NH$_4$C$_1$. In another embodiment, the first and second aqueous electrolytes include about 2 M NaCl, KCl, or NH$_4$C$_1$.

The first and second aqueous electrolytes may further include acids, bases, supporting electrolytes, additives, co-solvents or combinations thereof.

C. Separator

The disclosed AORFBs may include a separator. The separator may be a porous separator. The separator may not be permeable to metallocenes and/or viologens (or salts thereof). In certain embodiments, the term separator is synonymous with membrane. Separators may be classified as permeable, semi-permeable, or non-permeable. The degree of permeability is dependent on the size of pores in the separator, the character (e.g., charge, hydrophobicity) of the pores, and the character of the electrolyte or electrolyte component which is to be transported across the separator. A porous separator is considered permeable to all electrolyte components, though the degree of permeability may differ for different component species of the electrolyte (e.g., based on size). A semi-permeable separator typically is selectively permeable to certain materials (e.g., small cations, small anions, H$_2$O) while being substantially non-permeable to other materials (e.g., large molecules, neutral species, a type of redox active material). In certain embodiments, the separator is a non-porous separator permeable to ions.

The separator may be ion permeable. In certain embodiments, the separator is selectively permeable to permit the flux of cations with low resistance, and may be termed "cation permeable" or "cation conductive". In certain embodiments, the separator is selectively permeable to permit the flux of anions with low resistance, and may be termed "anion permeable" or "anion conductive". Accordingly, the separator may be cation permeable or anion permeable. An ion selective separator may comprise functional groups of opposite charge to the permitted ion, such that the charge of the functional group repels ions of like charge. In certain embodiments, the separator is a cation exchange membrane. In certain embodiments, the separator is an anion exchange membrane. In other embodiments, the separator is a sulfonate containing fluoropolymer, such as NAFION®. In still other embodiments, the separator is a sulfonated poly(ether ether ketone), polysulfone, polyethyelene, polypropylene, ethylene-propylene copolymer, polyimide, or polyvinyldifluoride. In some embodiments, the separator is functionalized with ammonium, $SO_3H$, OH, COOH or a combination thereof.

The separator may include an ion conductive ceramic, zeolite, or glass. Ion conductive ceramics, zeolites, and glasses are solid materials in which certain ions have high mobility. In certain embodiments, an ion conductive ceramic, zeolite, or glass is permeable to a flux of a certain ion (e.g., $Li^+$, $Na^+$, $K^+$) but may be substantially non-permeable to a flux of another ion (e.g., $H^+$). In certain embodiments, an ion conductive solid ceramic, zeolite, or glass is utilized to maintain a pH imbalance between the first and second electrolytes. In certain embodiments, the separator includes a cation conducting ceramic, zeolite, or glass. In certain embodiments, the separator includes an anion conducting ceramic, zeolite, or glass.

The separator may include one or more separator materials. In certain embodiments, the separator includes multiple components. For example, the separator may include two or more layered membranes or a coated membrane. In certain embodiments, the separator includes a porous membrane coated with a cation or anion conducting ceramic, zeolite, or glass. In other embodiments, the separator comprises an ionic exchange membrane coated with a cation or anion conducting ceramic, zeolite, glass.

The separator may have a thickness of ≤200 microns, ≤100 microns, ≤50 microns, or ≤25 microns. In certain embodiments, the separator has a thickness of ≥10 microns, ≥15 microns, ≥25 microns or ≥50 microns. In certain embodiments, the separator has a thickness of from about 10 microns to about 200 microns, such as from about 10 microns to about 100 microns or from about 25 microns to about 100 microns.

D. Electrodes

The disclosed AORFBs may include one or more electrodes. In certain embodiments, the disclosed AORFBs include a first electrode and a second electrode. The first and second electrode may be the same material, or they may be different materials. In certain embodiments, the electrodes may include a carbon felt, carbon mesh, carbon foam, carbon cloth, carbon paper, or carbon plate. The electrode or electrodes may be coated with a catalyst to improve the efficiency of charge transfer at the electrode, for example, to reduce the charging and/or discharging overpotential. The electrode or electrodes may be coated with a poison, such as lead, to reduce the efficiency of current transfer, for example to reduce the current density of the hydrogen evolution reaction.

E. Properties of the Aqueous Organic Redox Flow Batteries

The disclosed AOFRBs have advantageous electrochemical properties. Some of these exemplary properties are listed below.

The AOFRB may have an energy density of ≥5 Wh/L, ≥10 Wh/L, ≥20 Wh/L, ≥30 Wh/L, ≥40 Wh/L≥50 Wh/L, ≥75 Wh/L, ≥100 Wh/L, or ≥150 Wh/L. In certain embodiments, the AOFRB may have an energy density of from about 10 Wh/L to about 200 Wh/L, such as from about 40 Wh/L to about 150 Wh/L or from about 60 Wh/L to about 100 Wh/L.

The AOFRB may have from about 90% capacity retention to about 99.9% capacity retention after at least 400 cycles at 60 $mA/cm^2$, such as from about 92% capacity retention to about 99.9% capacity retention, from about 93% capacity retention to about 99.9% capacity retention, or from about 95% capacity retention to about 99.9% capacity retention after at least 400 cycles at 60 $mA/cm^2$. In certain embodiments, the AOFRB may have 95% capacity retention after at least 400 cycles at 60 $mA/cm^2$.

The AOFRB may be operated at a current density of ≥50 $mA/cm^2$, ≥75 $mA/cm^2$, ≥100 $mA/cm^2$, ≥125 $mA/cm^2$, ≥150 $mA/cm^2$, or ≥200 $mA/cm^2$. In addition, the AOFRB may be operated at a power density of ≥100 $mW/cm^2$, ≥125 $mW/cm^2$, ≥150 $mW/cm^2$, ≥175 $mW/cm^2$, ≥200 $mW/cm^2$, ≥225 $mW/cm^2$, or ≥250 $mW/cm^2$.

The AOFRB may have an energy efficiency of about 80% to about 99.9%, such as from about 85% to about 99.9%, from about 85% to about 95%, or from about 87% to about 93%. In certain embodiments, the AOFRB has an energy efficiency of about 90%.

In certain embodiments, the AOFRB has a coulombic efficiency of about 100%.

3. Methods of Use

The disclosed metallocene and viologen compounds (and salts thereof) can be used in several applications. For example, the metallocene and viologen compounds (and salts thereof) can be used as redox mediators in batteries, solar cells, electrocatalysis, electrochromism, electrochemical tests, and/or chemical reactions.

4. Examples

Materials and Methods for the Examples 1-5

Chemicals and Materials. All chemicals were purchased from Aldrich or TCI, stored in an Argon glovebox, and used directly. Solubility of substituted ferrocene compounds was measured in water by preparing a super-saturated solution in a volumetric cylinder. Deionized water was purged overnight using $N_2$ before use. All experimental operations were conducted under a $N_2$ atmosphere. Conductivity of the electrolyte solutions was measured using a Mettler Toledo conductivity meter at R.T. NMR studies were conducted using a Bruker 500 MHz NMR spectrometer. UV-Vis was collected using an Ocean Optic spectrometer. Elemental analysis was done at Atlantic Microlab.

Electrochemical Cyclic voltammetry (CV) studies. All electrochemical CV experiments were carried out in 0.5 M NaCl electrolyte solutions. Cyclic voltammetry experiments were performed with a Gamry 1000E potentiostat. All potentials were referenced to NHE according to the known $MV^{2+/1+}$ redox couple (−0.45 V vs NHE). The working electrode (1 mm PEEK-encased glassy carbon, Cypress Systems EE040) was polished using $Al_2O_3$(BAS CF-1050, dried at 150° C. under vacuum) suspended in deionized $H_2O$, then rinsed with deionized $H_2O$ and dried with an air flow. The reference electrode was a silver wire coated with a layer of AgCl and suspended in a solution of 0.5 M NaCl electrolyte. A glassy carbon rod (Structure Probe, Inc.) was used as the counter electrode.

Electrochemical RDE studies: All linear sweep voltammetry (LSV) studies were conducted using a Gamry 1000E potentiostat in a three-electrode configuration, a glassy carbon disk working electrode (5 mm Teflon encased glassy carbon disk, Pine Research Instrumentation) along with a glassy carbon counter electrode and a Ag/AgCl reference electrode same as used in CV studies. Before data collection, the disk electrode was prepared using the procedure described in the CV studies. The electrode was then rotated at from 300 to 2400 rpm with an increment of 300 rpm, which was controlled by a Pine MSR rotator system. LSV scans were recorded at a rate of 5 mV/s from 0.3 V to 0.8 V vs NHE. At each rotation rate, the LSV were recorded 3 times to ensure repeatability. The limiting currents (i.e. the mass transport-limited current intensity) were taken at 0.7 V vs NHE for FcNCl and plotted over the square root of the rotation rate (rad/s). The data were fitted to yield a straight Levich plot, with the slope defined by the Levich equation (equation 1 below), where n=1 for one electron process, Faraday's constant F=96485 C/mol, electrode area A=0.1935 cm$^2$, FcNCl concentration Co=1.0 mM, D is diffusion coefficient, kinematic viscosity n=0.009 cm$^2$/s for 0.5 M NaCl solution. The calculations yielded the diffusion coefficients of FcNCl as 3.25×10$^{-6}$ cm$^2$/s. A plot of overpotential versus $\log_{10}(i_K)$ was constructed for the LSV data collected at 3000 rpm for FcNCl where $i_K$ is the kinetic current for the oxidation of FcNCl. The X-intercept of the fitted Tafel plot gives the log of the exchange current $i_0$ (0.7 μA), which equals to $FAC_Ok_0$ (equation 2), and gives electron transfer rate constant $k_0$=2.29×10$^{-5}$ cm/s for FcNCl.

Levich plot slope=$0.620nFAC_OD^{2/3}v^{-1/6}$      (equation 1)

$i_0=FAC_Ok_0$      (equation 2)

Flow cell tests: The flow cell was constructed with two carbon electrolyte chambers, two graphite felt electrodes (SGL Carbon Group, Germany) and a piece of anion exchange membrane (AME 115, 120 μm thickness, pore size <10 Å, Selemion, Japan) sandwiched between graphite felts, and two copper current collectors. The active area of the electrode and the membrane was 10 cm$^2$. A Masterflex® L/S® peristaltic pump (Cole-Parmer, Vernon Hills, Ill.) was used to circulate the electrolytes through the electrodes at a flow rate of 60 mL/min. In each reservoir, the balanced flow cell employed approximately 12 mL of the NaCl electrolytes containing 0.5 or 0.7 M active materials. Both reservoirs were purged with nitrogen to remove 02 and then sealed before cell cycling. The flow cell was galvanostatically charged/discharged at room temperature on a battery tester (Land Instruments) in the voltage range of 1.5-0.1 V at current densities ranging from 40 to 100 mA/cm$^2$. Polarization curve was recorded using a Gamry 1000E potentiostat. The discharged and charged states of FcNCl and MV were measured using UV-Vis spectroscopy. Post cell studies using $^1$H NMR and CV were conducted for both electrolytes at the end of the cell tests.

Calculation of theoretical energy density: The theoretical energy density of the FcNCl/MV AORFB was calculated using equation 3 below, where n is the number of electrons involved into the cell reaction, C is the concentration of active materials, F is Faraday constant, 26.8 Ah/mol, V is the cell voltage, and 2 represents a factor considering both volumes of anolyte and catholyte. Solubility of FcNCl and MV was measured in water respectively by preparing a super-saturated solution. Similar solubility tests in water were applied for ferrocenecarboxylic acid, 1-1'-ferrocenedicarboxylic acid, ferrocenecarboxylic acid, and 1,1'-ferrocenedimethanol.

Energy density (Wh/L)=$nCFV/2$      (equation 3)

Example 1. Synthesis and Characterization of (Ferrocenylmethyl)Trimethylammonium Chloride (FcNCl)

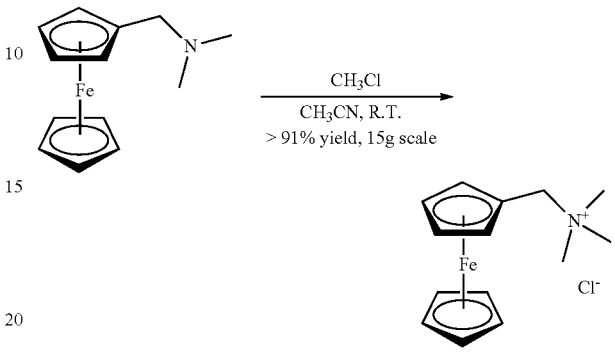

Scheme 6. Synthesis of FcNCl

A 250 mL Schlenk flask was degassed with Na and maintained under N$_2$. (ferrocenylmethyl)dimethylamine (15 g, 61.7 mmol) and methyl chloride (1 M in t-Butylether, 61.7 mL for 61.7 mmol, used 70 mL) were combined in 50 mL CH$_3$CN in the 250 mL flask. The reaction mixture was stirred at R.T. overnight. The orange precipitate was formed and collected by filtration. 100 mL ether was added to the supernatant solution to precipitate a second crop of the product. The combined product was washed with 40 mL ether twice and dried under vacuum. The product was hydroscopic and stored in a dry desiccator. The yield was approximately 91% (16.5 g). $^1$H NMR (D$_2$O, 300 MHz): δ (in p.p.m.), 2.91 (s, 9H), 4.24 (s, 5H), 4.35 (s, 2H), 4.39 (s, 2H), 4.47 (d, 2H). Anal. calcd for C$_{14}$H$_2$O NClFe.0.5 H$_2$O: C, 55.53, H, 6.94, N, 4.63; found C, 55.26, H, 7.05, N, 4.61. UV-Vis: 440 nm.

Figure 13:
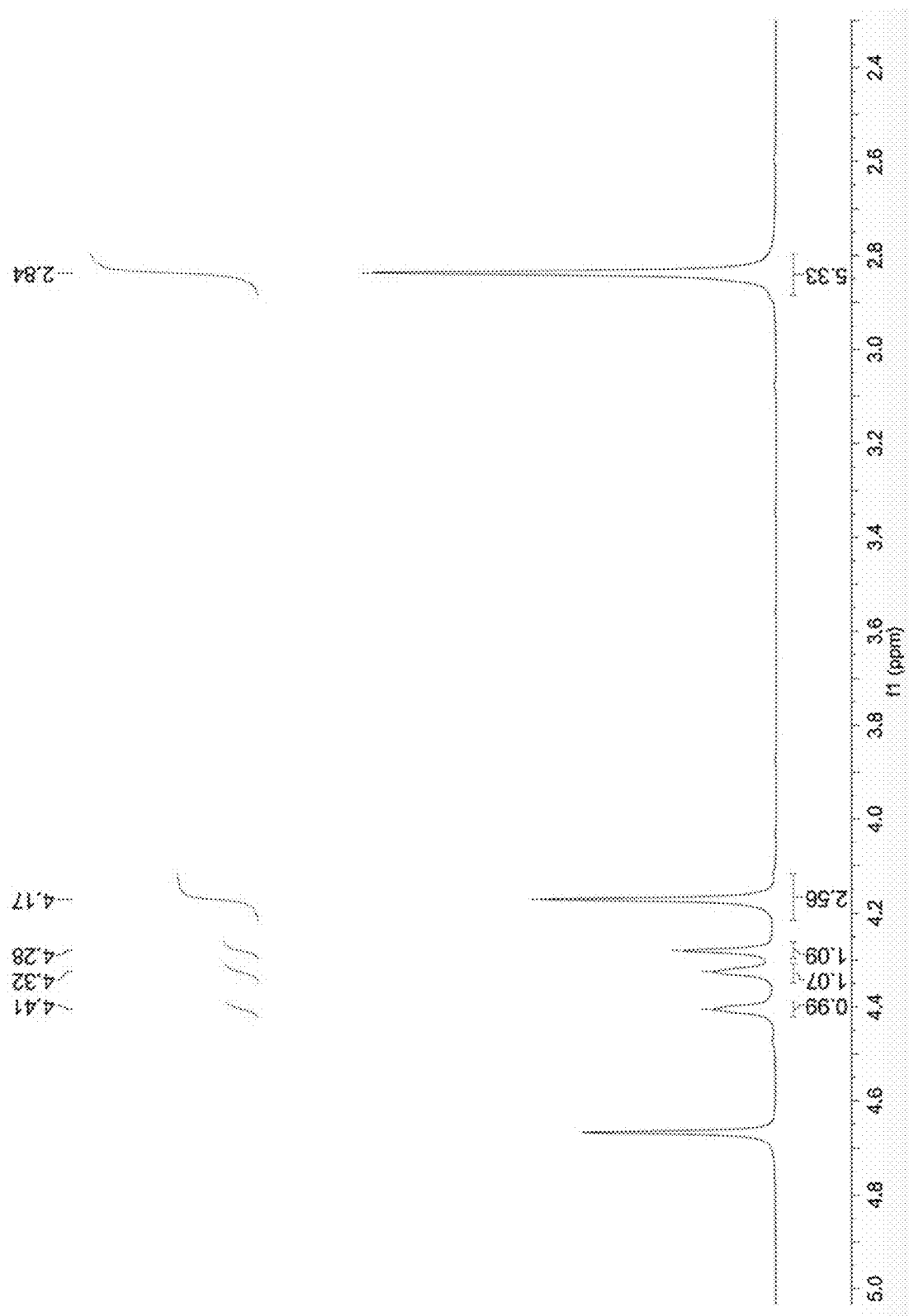
FIG. 13 shows the $^1$H NMR of FcNCl recorded in $D_2O$ at room temperature.

Mixing of (ferrocenylmethyl)dimethylamine with CH$_3$C$_1$ in CH$_3$CN at R.T. resulted in the formation of red-orange FcNCl precipitates with a yield greater than 91% (see above). The one-step N-alkylation reaction was demonstrated on a 15 g lab scale based on (ferrocenylmethyl) dimethylamine. FcNCl was fully characterized by $^1$H NMR (FIG. 13), UV-VIS (FIGS. 16 & 17), and elemental analysis to establish its identity and purity. The $^1$H NMR spectrum was recorded in D$_2$O, the compound displayed a singlet at 4.24 ppm for the non-substituted cyclopentadienide (Cp) ring, 2 singlets at 4.35 and 4.39 ppm for the substituted Cp ring, a singlet at 4.47 ppm for the methylene group, and a singlet at 2.91 ppm for three N-methyl groups.

FcNCl is surprisingly highly soluble in H$_2$O with a solubility of approximately 4.0 M, corresponding to a theoretical capacity 114.4 Ah/L, a desired character for redox flow battery applications. It is hypothesized, without being bound to a particular theory, such high solubility is derived from its hydrophilic pendant ammonium functionality and counter ion.

Example 2. Characterization of FcNCl as a Redox Active Material

Figure 2:
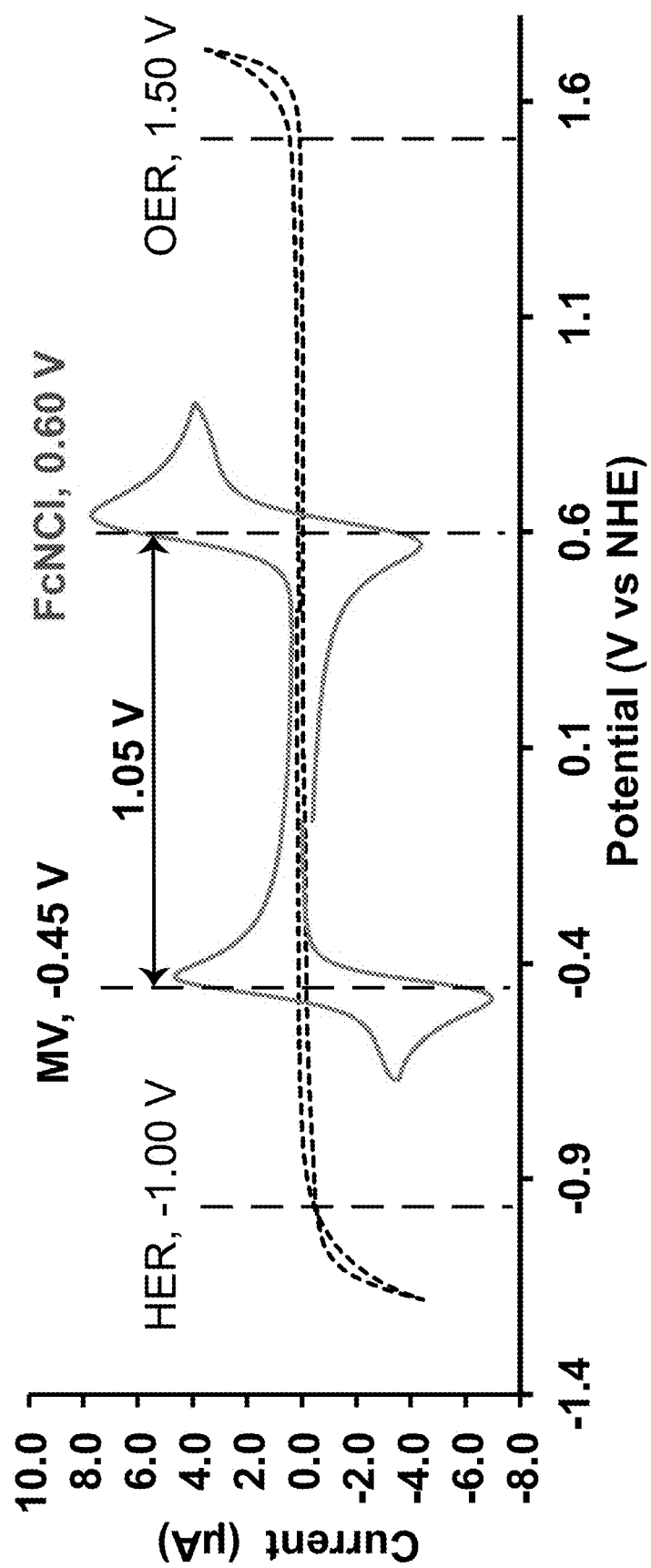
FIG. 2 shows the cyclic voltammogram (CV) of a disclosed AORFB that includes (ferrocenylmethyl)trimethylammonium chloride (FcNCl) (4 mM, 0.60 V) and methyl viologen (MV) (4 mM, −0.45 V) in 0.5 M NaCl solution.
Figure 14:
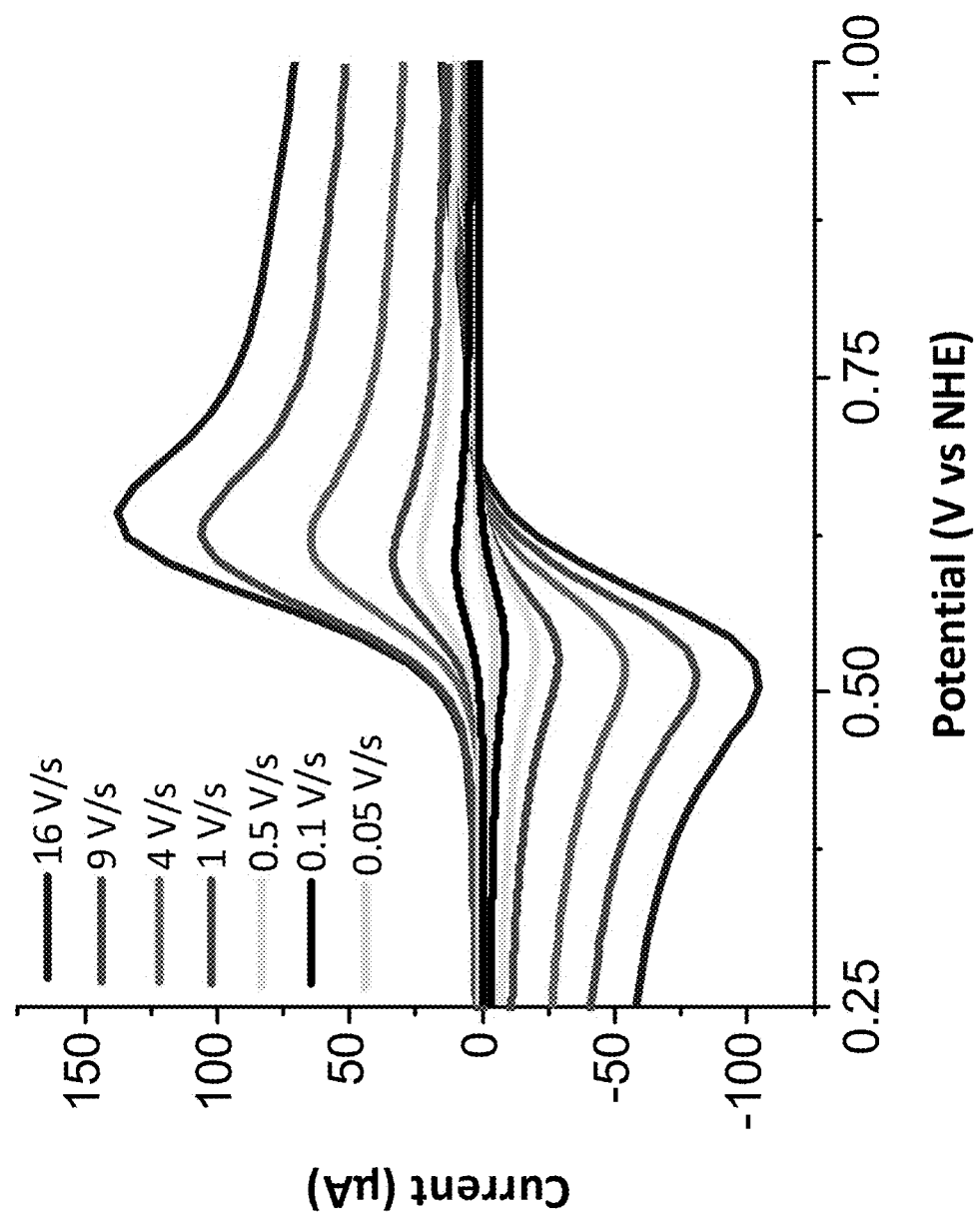
FIG. 14 shows the cyclic voltammograms of a disclosed metallocene compound at various scan rates from 0.05 V/s to 16 V/s
Figure 15:
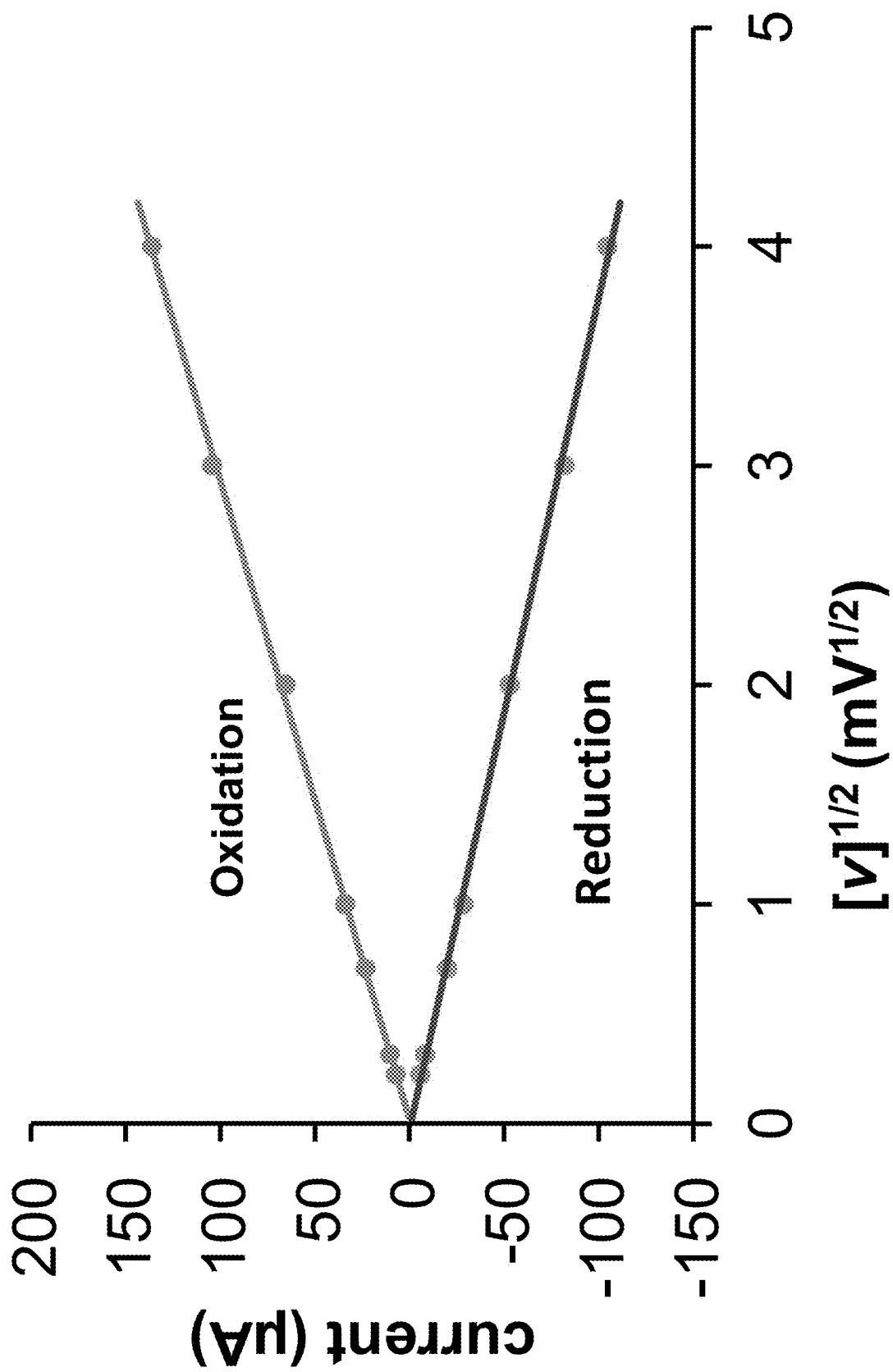
FIG. 15 shows the plot of is and is over the square root of scan rates for a disclosed metallocene compound in oxidation and reduction reactions.

Cyclic voltammetry studies revealed that the metallocene compound displayed a reversible Fe$^{3+/2+}$ redox couple at 0.60 V vs NHE at 50 mV/s in 0.5 M NaCl electrolyte (FIG. 2), which is high enough for AORFB applications. Scan rate dependence studies of FcNCl (FIGS. 14 & 15) demonstrated that its reversible oxidation reaction is a diffusion controlled process.

Figure 3:
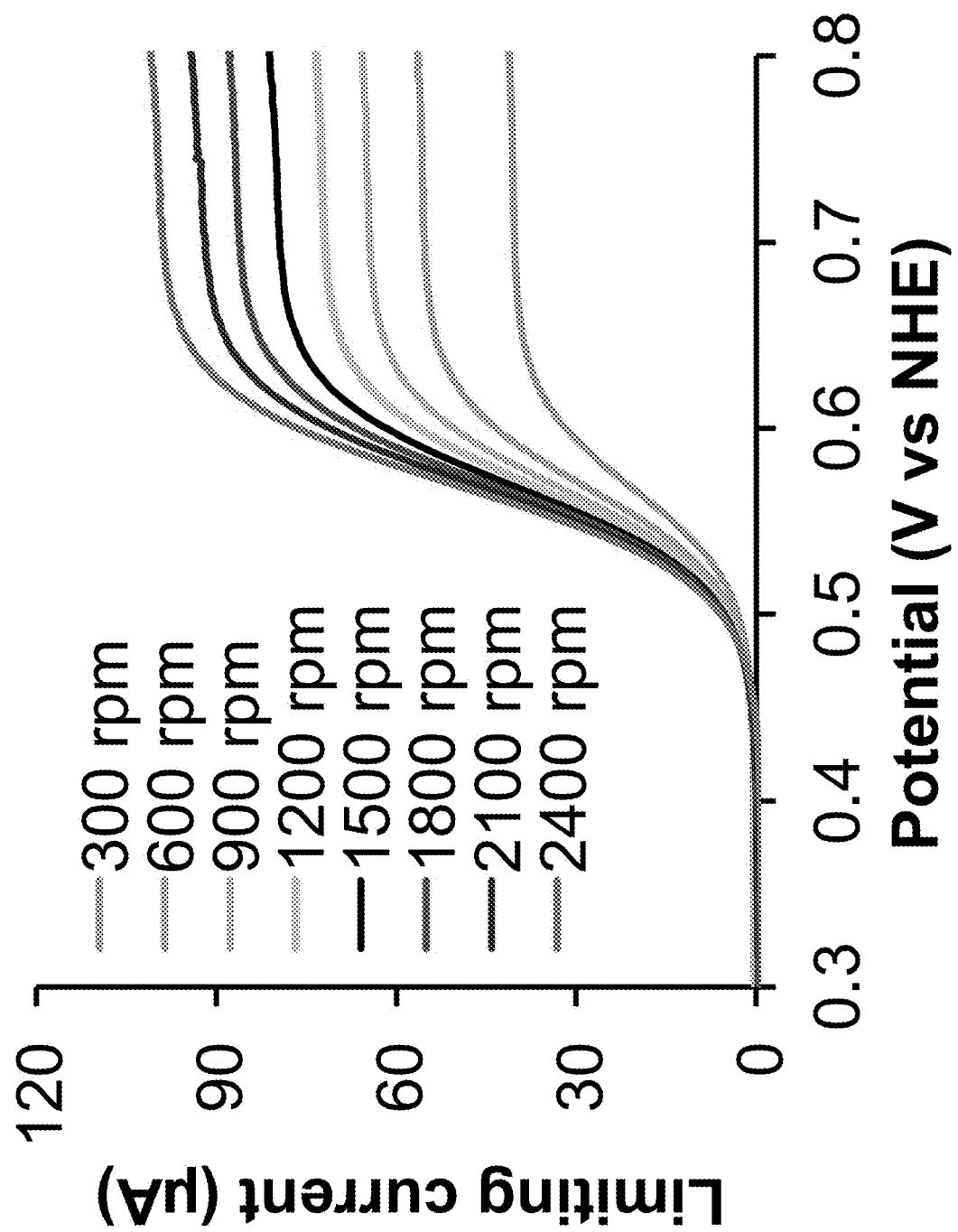
FIG. 3 shows the linear sweep voltammograms (LSV) of FcNCl in a disclosed AORFB at 1.0 mM analyte in 0.5 M NaCl electrolyte.
Figure 4:
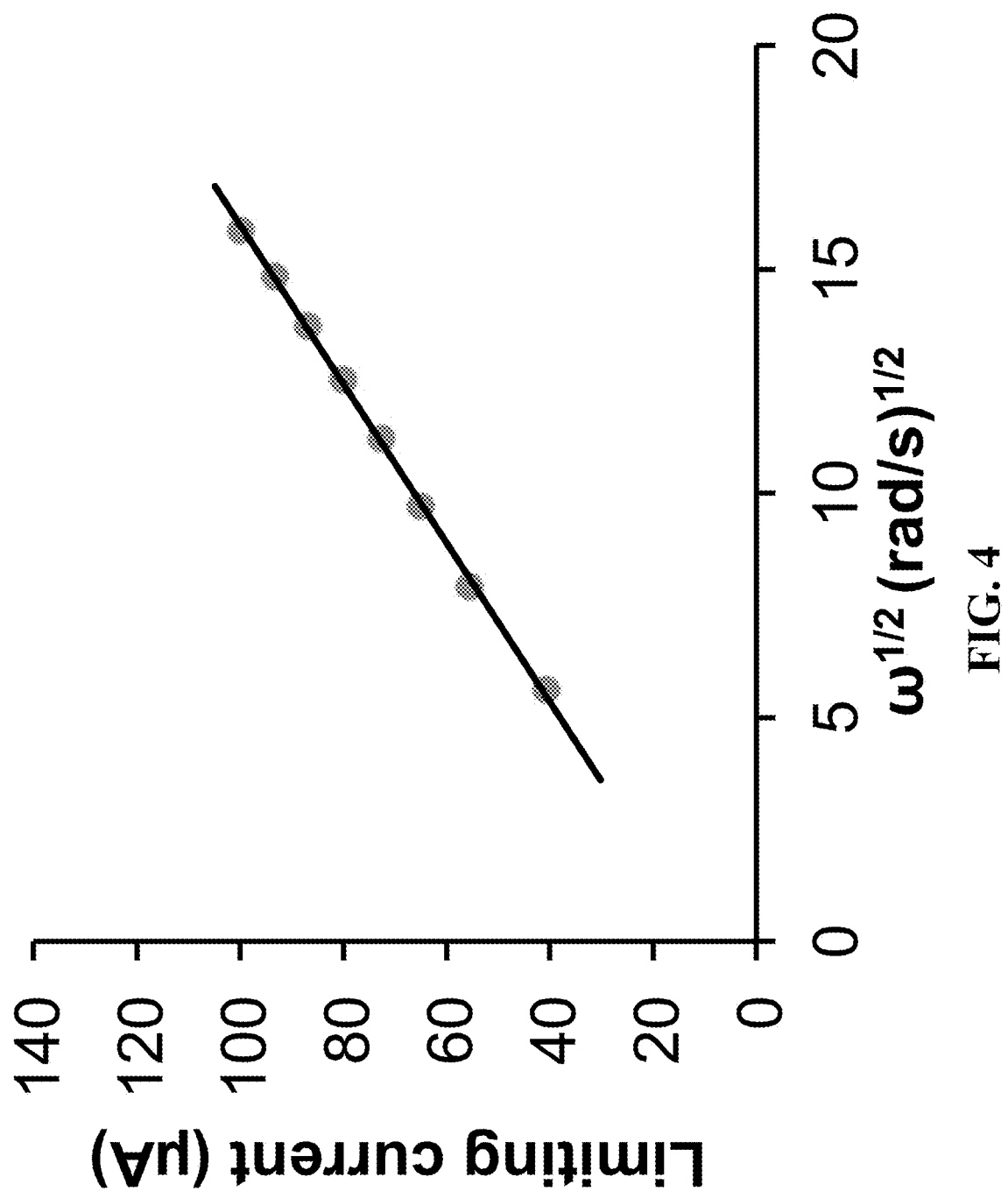
FIG. 4 shows the Levich plots of the limiting current vs the square root of rotation rates for FcNCl in a disclosed AORFB at 1.0 mM analyte in 0.5 M NaCl electrolyte.
Figure 5:
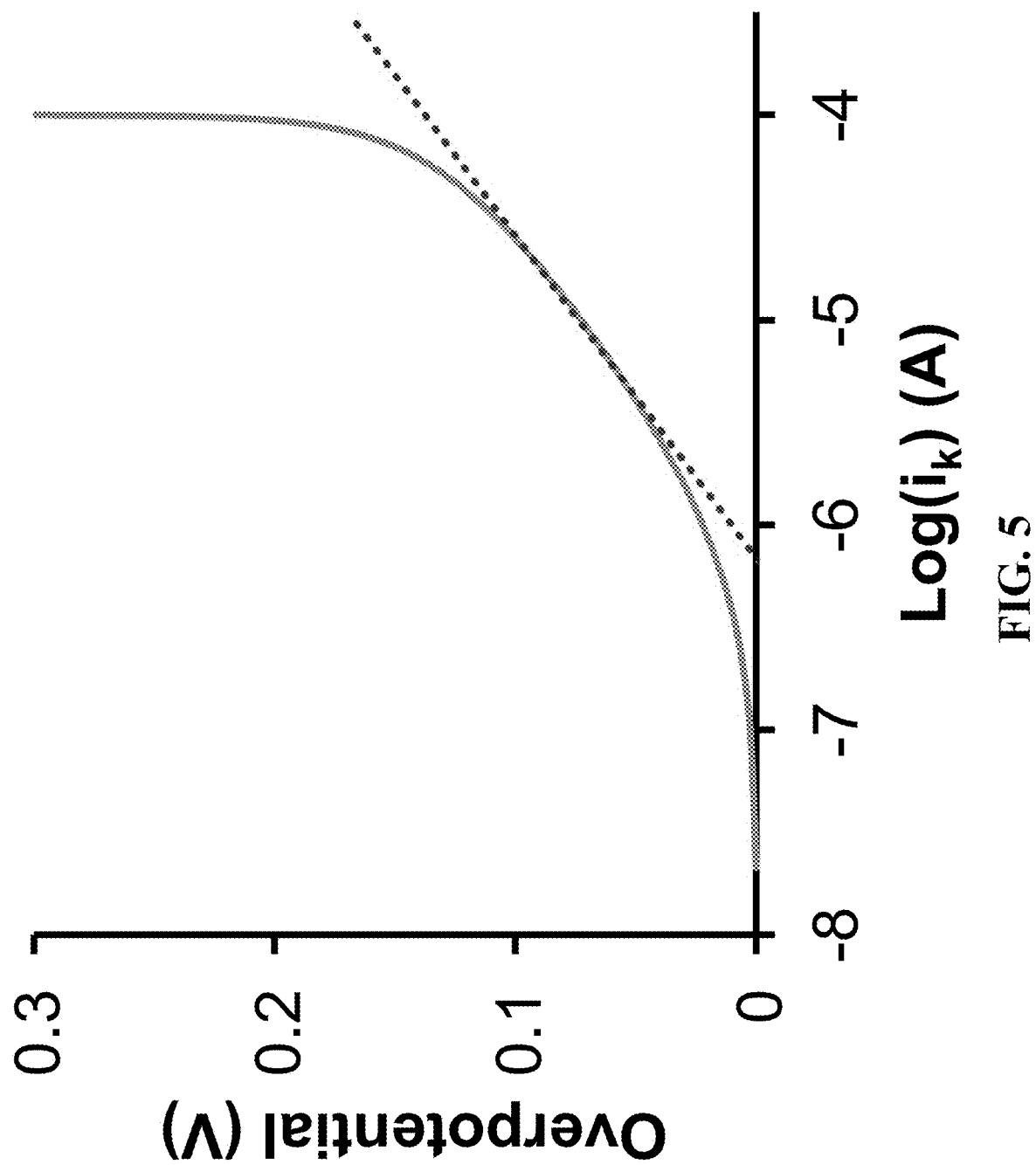
FIG. 5 shows the plot of overpotential over the logarithm of kinetic current and the corresponding fitted Tafel plots for FcNCl in a disclosed RFB at 1.0 mM analyte in 0.5 M NaCl electrolyte.

To further understand electrochemical kinetics of the compound, the compound was studied by linear sweep voltammetry (LSV) using a glassy carbon rotation disc electrode. The results are shown in FIGS. 3-5. The rotation speed was increased from 300 rpm to 2400 rpm to gain different mass-transport limited current with a scan rate at 5 mV/s (FIG. 3). From the well-defined LSV curves, a linear relationship between limiting current and square root of the rotation speed was established (FIG. 4). The diffusion coefficient of FcNCl was calculated to be $3.74 \times 10^{-6}$ cm$^2$/s (using equation 1) from the slope of the Levich plot using Levich equation. Subsequently, a plot of oxidation overpotential over the logarithm of the kinetic current (FIG. 5) was constructed to determine the rate constant for the charge transfer process for the oxidation of FcNCl. The Tafel equation is applicable over 45 mV overpotential and the fitted Tafel plot (shown as the blue dotted line in FIG. 5) yielded a rate constant of $3.66 \times 10^{-5}$ cm/s (calculated using equation 1). The fast electrochemical kinetic results further indicate that FcNCl may be a useful redox active material in AORFBs.

Example 3. Synthesis and Characterization of N$^1$-ferrocenylmethyl-N$^1$, N$^1$, N$^2$, N$^2$, N$^2$-pentamethylpropane-1,2-diaminium dibromide (FcN$_2$)

Scheme 2 (as Shown Above). Synthesis of FcN$_2$

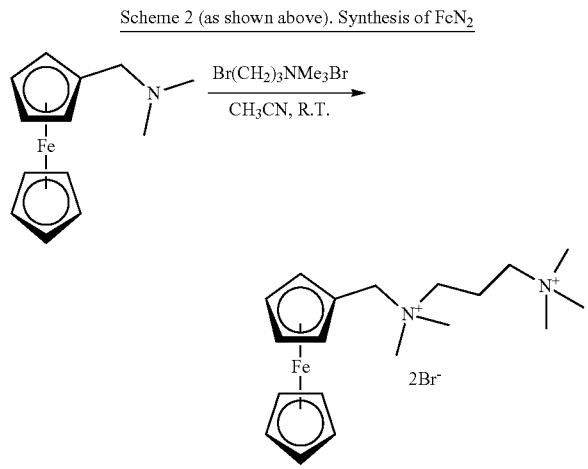

Scheme 2 (as shown above). Synthesis of FcN$_2$

A 100 mL Schlenk flask was degassed with N$_2$ and maintained under N$_2$. (Ferrocenylmethyl)dimethylamine (3.4 g, 14 mmol) in 20 mL CH$_3$CN and (3-Bromopropyl) trimethylammonium bromide (3.4 g, 13 mmol) in 10 mL DMSO were combined in the 100 mL flask. The reaction mixture was stirred at room temperature for 18 h. The formed dark orange precipitate was collected by filtration. Afterward, 50 mL of ether was added to the supernatant solution to precipitate a second crop of product. The combined product was washed with 50 mL ether twice and dried under vacuum. The product was hygroscopic and stored in a dry desiccator. The yield is approximately 68.4% (4.65 g). $^1$H NMR (D$_2$O) δ (in p.p.m.), 2.25 (m, 2H), 2.94 (s, 6H), 3.12 (s, 9H), 3.19 (t, 2H), 3.31 (t, 2H), 4.26 (s, 5H), 4.42 (d, 2H), 4.46 (s, 2H), 4.48 (s, 2H).

Figure 25:
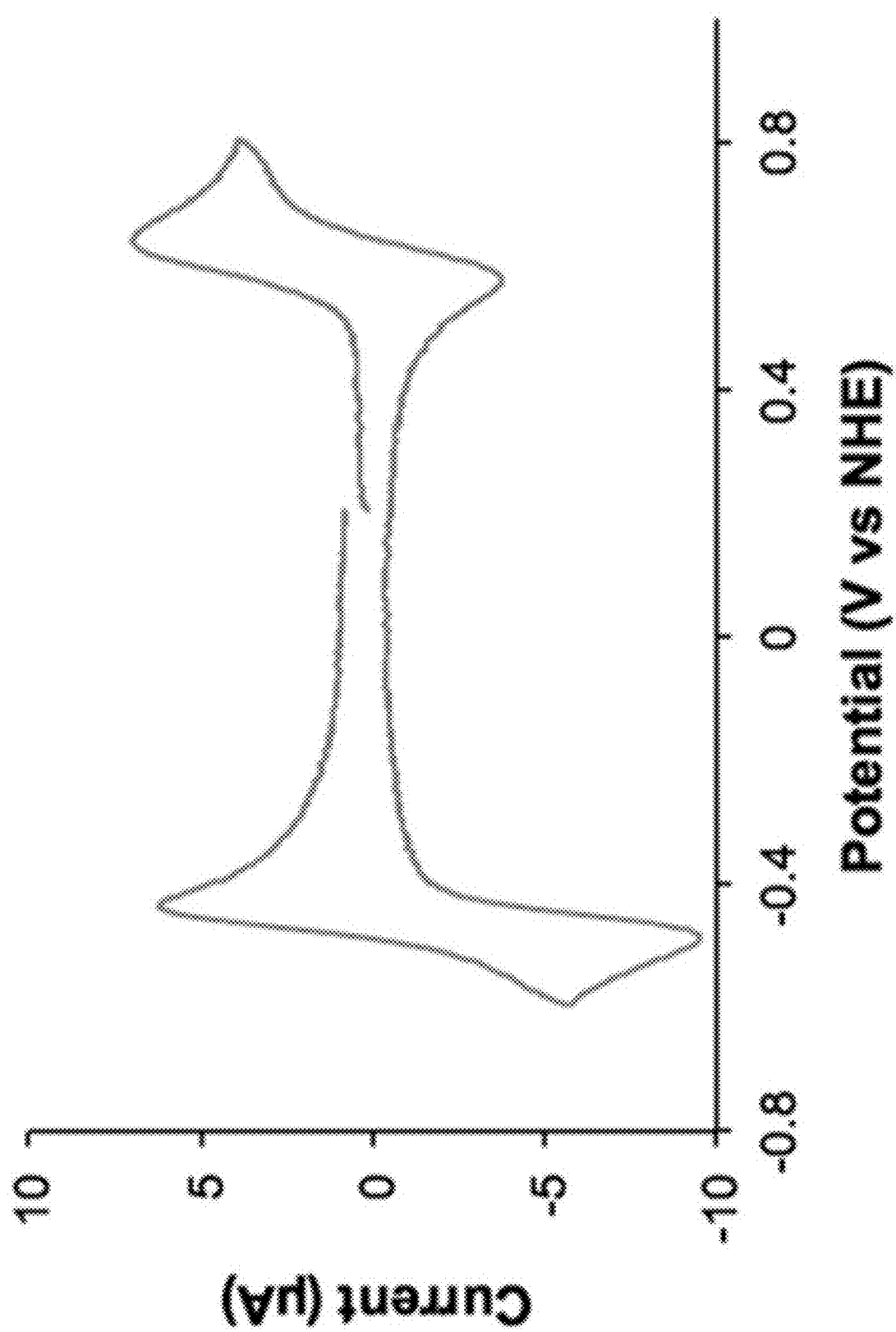
FIG. 25 shows the cyclic voltammogram of a disclosed AORFB that includes $N^1$-ferrocenylmethyl-$N^1$, $N^1$, $N^2$, $N^2$, $N^2$-pentamethylpropane-1,2-diaminium dibromide ($FcN_2$) (4 mM, 0.62 V vs NHE (normal hydrogen electrode)) and MV (4 mM, −0.45 V cvs NHE) in NaCl (0.5 M) solution.
Figure 26:
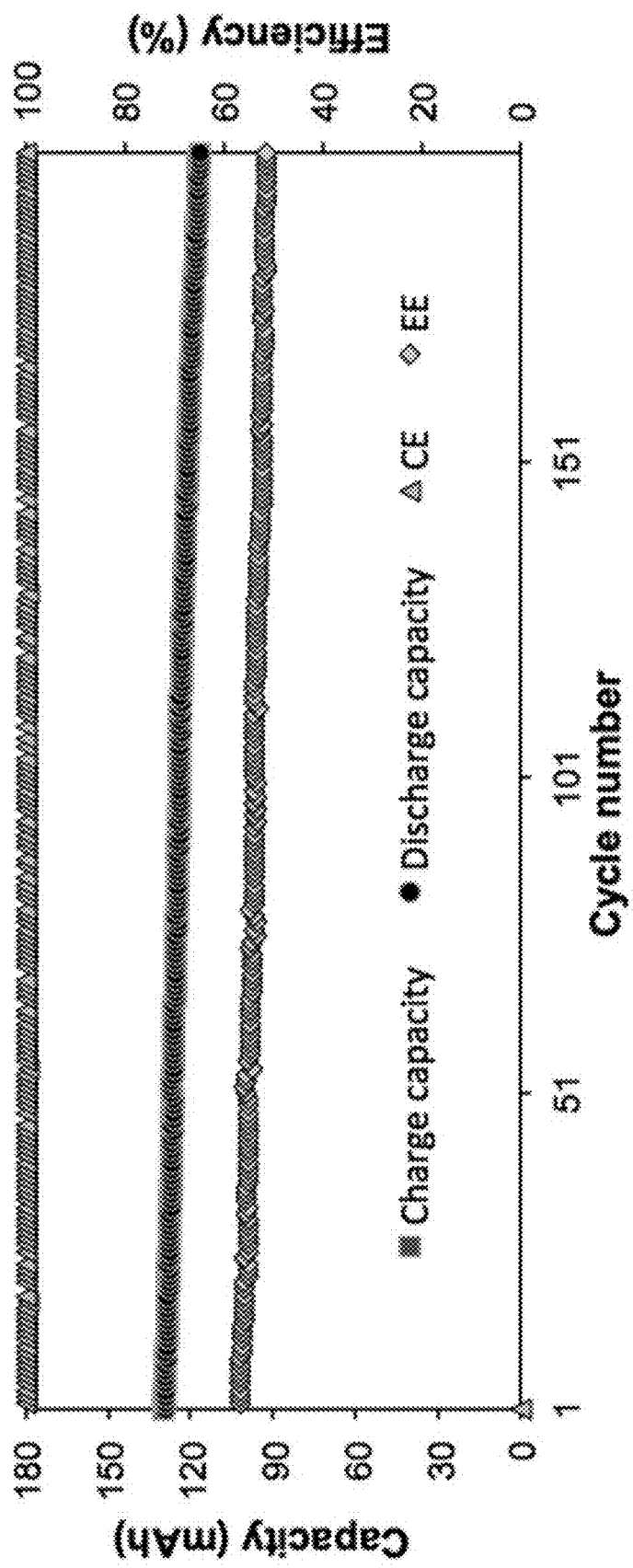
FIG. 26 shows the battery cycling performance of a disclosed $FcN_2$ AORFB.

FcN$_2$ was further characterized for use as a redox active material in an AORFB. Cyclic voltammogram of FcN$_2$ displayed at a Fe$^{3+/2+}$ redox wave at 0.62 V vs NHE using MV (−0.45 V vs NHE) as reference in NaCl (0.5 M) solution (FIG. 25). Also, it gave 1.07 V cell voltage for the FcN$_2$/MV redox flow battery. The prototype cell study of the FcN$_2$/MV redox flow battery was performed using 0.5 M FcN$_2$ in 2.0 M NaCl solution and 0.5 M MV in 2.0 M NaCl solution. The cell was tested for 200 cycles at 60 mA/cm$^2$ using Selemion AMV membrane with excellent capacity retention above 93% (FIG. 26). Coulombic efficiency stays approximately 100% while energy efficiency remained above 51%.

Example 4. Synthesis and Characterization of DiSodium (Ferrocenyl)Sulfurtrioxide (FcS)

Scheme 3 (as shown above). Synthesis of FcS

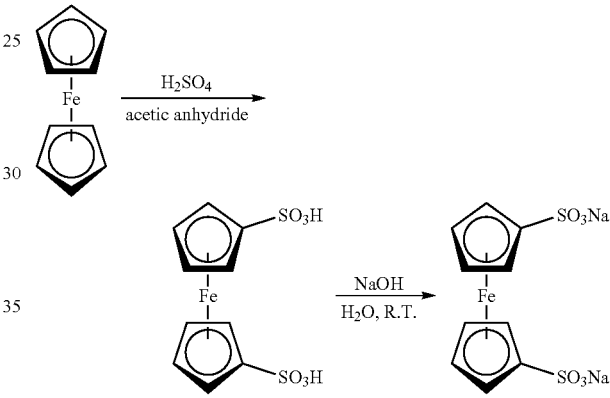

Under N$_2$ atmosphere, 5 mmol (0.93 g) ferrocene and 20 mL acetic anhydride were added into a 100 mL round bottle and cooled to 0° C. for 15 min. H$_2$SO$_4$ was added in to the suspension drop-wise and elevated the temperature to room temperature. Yellow suspension turned into dark brown solution. 5 min later, the solution turned green; 10 min later, yellow precipitant appeared. After reacting for 2 h, precipitant was filtered on a sintered glass funnel and washed with acetic anhydride and petroleum ether. The coarse product was dissolved in ethanol, and NaOH (ethanol solution) was added until pH turned into 7.5. Yellow precipitant appeared and was filtered. Drying in vacuum gave 1.4 g yellow powder (yield: 64%). $^1$H NMR (MeOD) δ (in p.p.m.) 4.70 (s, 2H), 4.44 (s, 2H).

Figure 27:
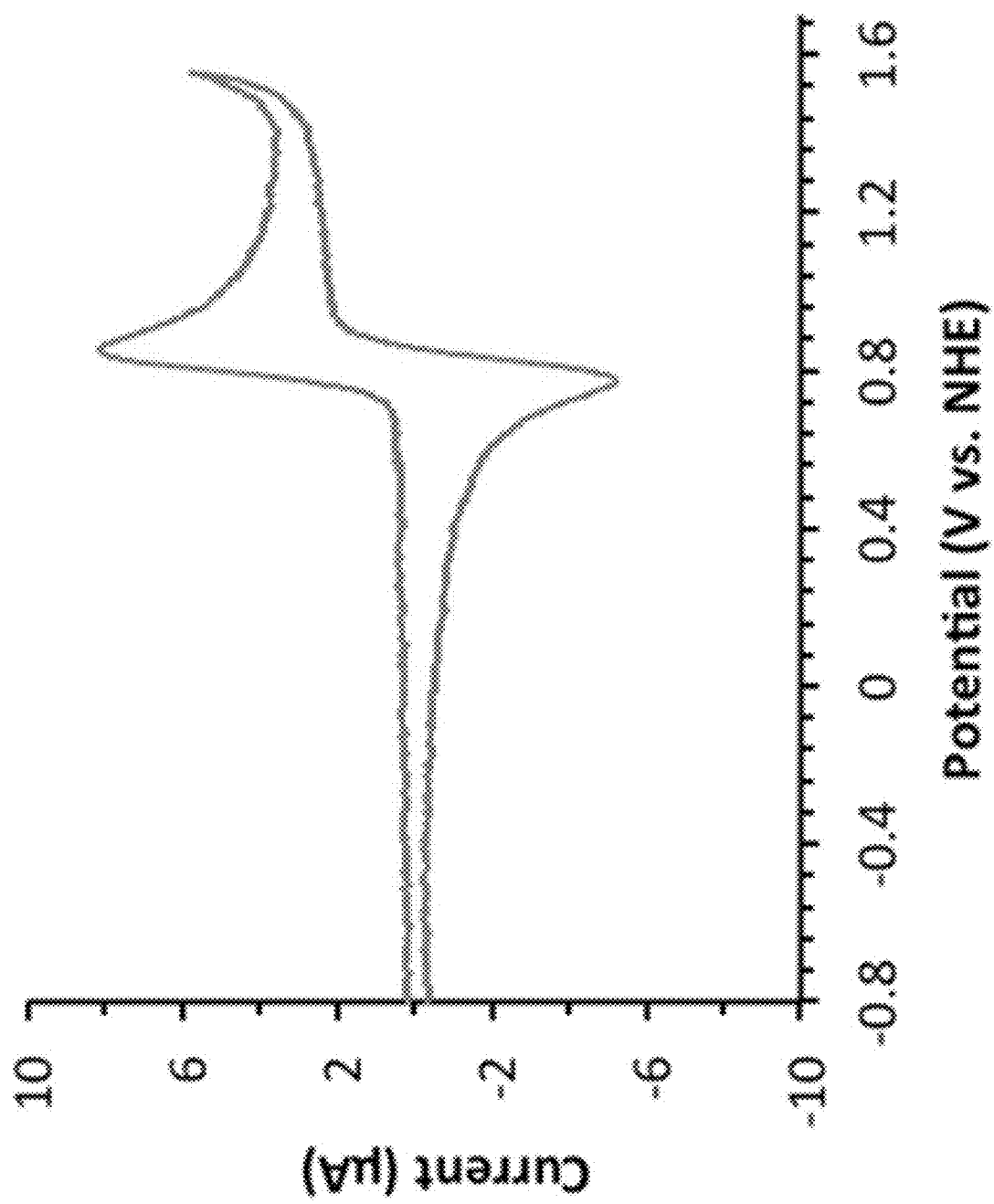
FIG. 27 shows the cyclic voltammogram of a disclosed AORFB that includes disodium (ferrocenyl)sulfurtrioxide (FcS) (4 mM, 1.0 V vs NHE) and $ZnBr_2$ (4 mM, −1.2 V cvs NHE) in a NaCl (0.5 M) solution.
Figure 28:
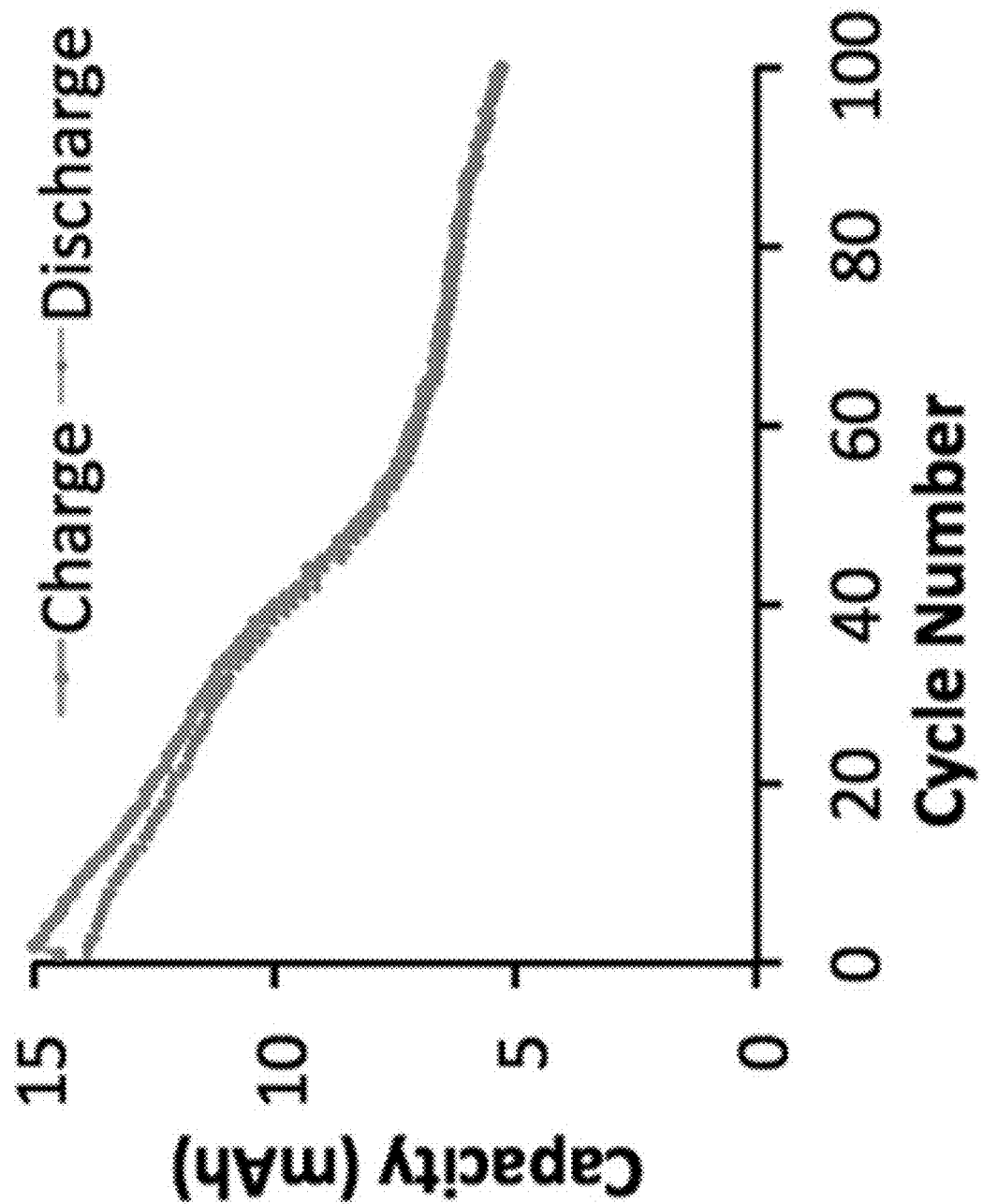
FIG. 28 shows battery cycling performance of a disclosed FcS-Zn AORFB.

FcS was further characterized for use as a redox active material in an AORFB. Cyclic voltammogram of FcS displayed at a Fe$^{3+/2+}$ redox wave ca. at 0.77 V vs NHE in NaCl (0.5 M) solution (FIG. 27). Also, it gave 1.55 V cell voltage for the FcS/Zn redox flow battery. The prototype cell study of the FcS/Zn redox flow battery was performed using 0.1 M FcS in 0.5 M NaCl solution and 0.05 M ZnBr$_2$ in 0.5 M NaCl solution. The cell was tested for 100 cycles at 10 mA/cm$^2$ using a Nafion 212 membrane (FIG. 28). The capacity decay is mainly due to insufficient cycling of the Zn anode.

Example 5. Synthesis and Characterization of FcN₂

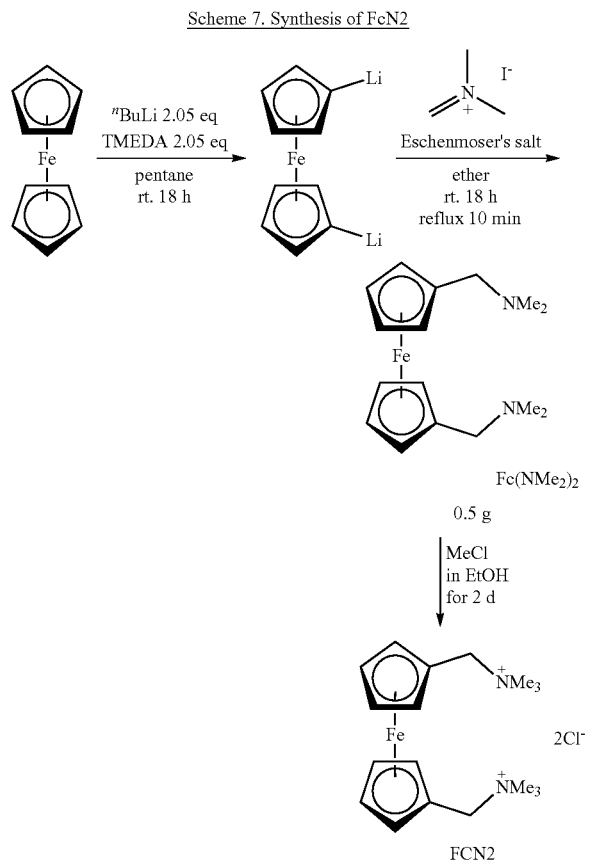

Scheme 7. Synthesis of FcN2

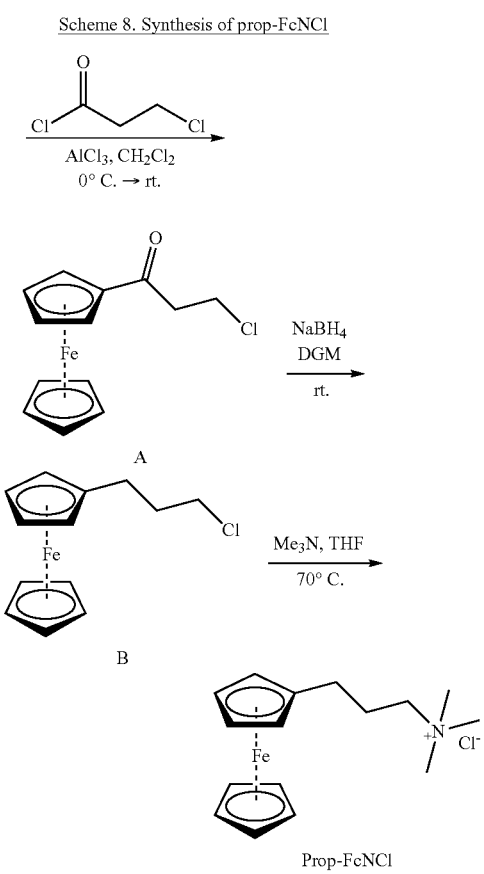

Scheme 8. Synthesis of prop-FcNCl

Synthesis of Fc(NMe₂)₂: The solution of n-BuLi (2.5 M, 7.2 mL, 18.0 mmol) in hexane was added into the mixture of Fc (1.62 g, 8.7 mmol) and TMEDA (2.68 mL, 18.0 mmol) in 80 mL dry pentane. After stirred at room temperature for 4 h, orange precipitate was observed. The dark orange solution was stirred at room temperature for another 18 h, 80 mL of dry ether was added to dilute the reaction mixture. Solid Eschenmoser's salt was added in one portion, the mixture was stirred at room temperature for another 18 h and heated up under reflux for 10 min. 2 mL H₂O was added to quench the reaction, and then, the organic phase was washed with 50 mL H₂O and 50 mL brine, dried with Na₂SO₄. The product was purified by flash column chromatography with neutral alumina (ethyl acetate:MeOH=10:1). The pure product was obtained as an orange oil (1.44 g, 55% yield). ¹H NMR (CDCl₃, 500 MHz, ppm): δ 2.18 (s, 12H), 3.27 (s, 4H), 4.08 (s, 4H), 4.11 (s, 4H).

Synthesis of FcN2: The titled compound was synthesized by reacting Fc(NMe₂)₂ (0.5 g, 1.7 mmol, 1.0 eq.) with MeCl (5.1 mmol, 3.0 eq.) in EtOH (10 mL) at room temperature under N₂ atmospheres for 2 days. The solvent was removed under vacuum. The crude product was washed with 15 mL ether for 5 times to get pure product as brown oil (0.58 g, 89% yield). ¹H NMR (D₂O, 500 MHz, ppm): δ 2.93 (s, 18H), 4.35 (s, 4H), 4.46 (s, 4H), 4.55 (s, 4H).

Cyclic voltammogram of FcN2 (4 mM) in NaCl (0.5 M) solution can be seen in FIG. 55. Conditions: scan rate, 100 mV/s; working electrode, glassy carbon; reference electrode, Ag/AgCl; counter electrode, glassy carbon. In addition, Cycling performance of a FcN₂-MV RFB can be seen in FIG. 56. Conditions: 0.15 M FcN in 2.0 M NaCl solution; 0.15 mM MV in 2.0 M NaCl solution; charge and discharge rate, 20 mA/cm².

Example 6. Synthesis and Characterization of Prop-FcNCl

Synthesis of (3-chloropropyl)ferrocene (B): Under a N₂ atmosphere, 3-chloropropanoyl chloride (4.89 mL, 51 mmol) in 25 mL CH₂Cl₂ was added into the solution of AlCl₃ (7.33 g, 55 mmol) in 50 mL CH₂Cl₂ dropwise and the mixture was stirred at room temperature for 2 h. And then, the mixture was added into the solution of ferrocene (Fc) (9.3 g, 50 mmol) in 50 mL CH₂Cl₂ at 0° C. under N₂ atmosphere. After stirring at room temperature for overnight, the mixture was cooled down to 0° C. again. A solution of NaBH₄ (1.9 g, 50 mmol) in 10 mL diglyme was added into the reaction mixture. The reaction was continued for 4 h and 100 mL of 1M HCl aq. solution was added to quench the reaction. The mixture was extracted with CH₂Cl₂ (100 mL×3). The organic phase was combined and dried under vacuum to get the product as a brown oil (12.5 g, 95% yield). 1H NMR (CDCl₃, 500 MHz, ppm): δ 1.99 (s, 2H), 2.52 (s, 2H), 3.57 (s, 2H), 4.05~4.36 (m, 9H).

Synthesis of prop-FcNCl: 1.05 g of B (4.0 mmol) and 10 mL of 2.0 M NMe₃ in THF (20 mmol) was mixed in a 20 mL stainless steel reaction kettle with Teflon liner. The reactor was kept at 80° C. for 3 days and then cooled down to room temperature. The yellow product was obtained by filtration and washed with acetone (10 mL×3) (0.97 g, 76% yield). ¹H NMR (D$_2$O, 500 MHz, ppm): δ 1.85~1.96 (m, 2H), 2.33~2.46 (m, 2H), 3.02 (s, 9H), 3.15~3.30 (m, 2H), 4.00~4.33 (m, 9H). CV analysis of prop-FcNCl can be seen in FIG. 57.

Example 7. Use of FcNCl in an Aqueous Organic Redox Flow Battery

Figure 6:
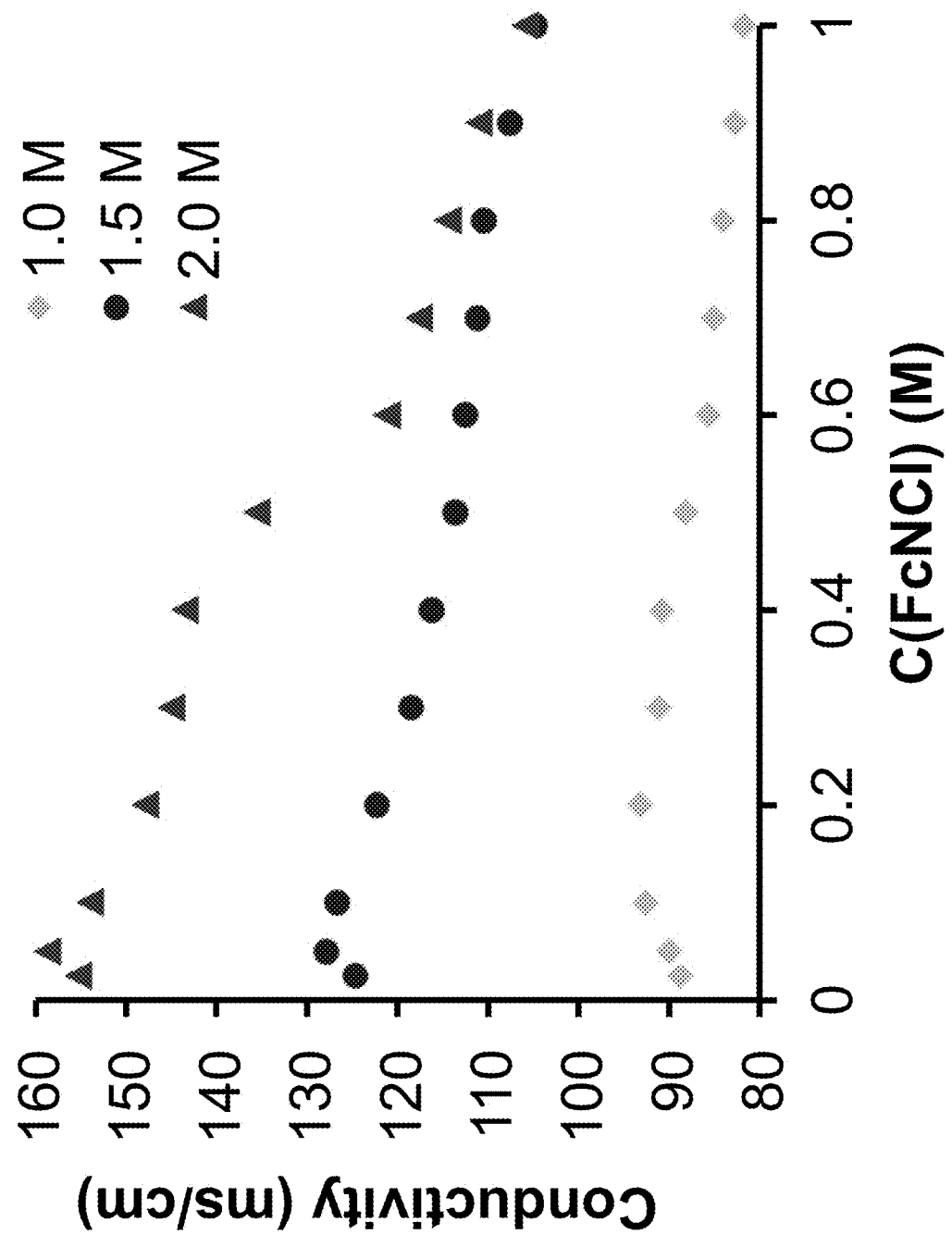
FIG. 6 shows the conductivity measurements of a disclosed metallocene compound at different concentrations (from 1.0 to 2.0 M) at room temperature in NaCl solution.
Figure 7:
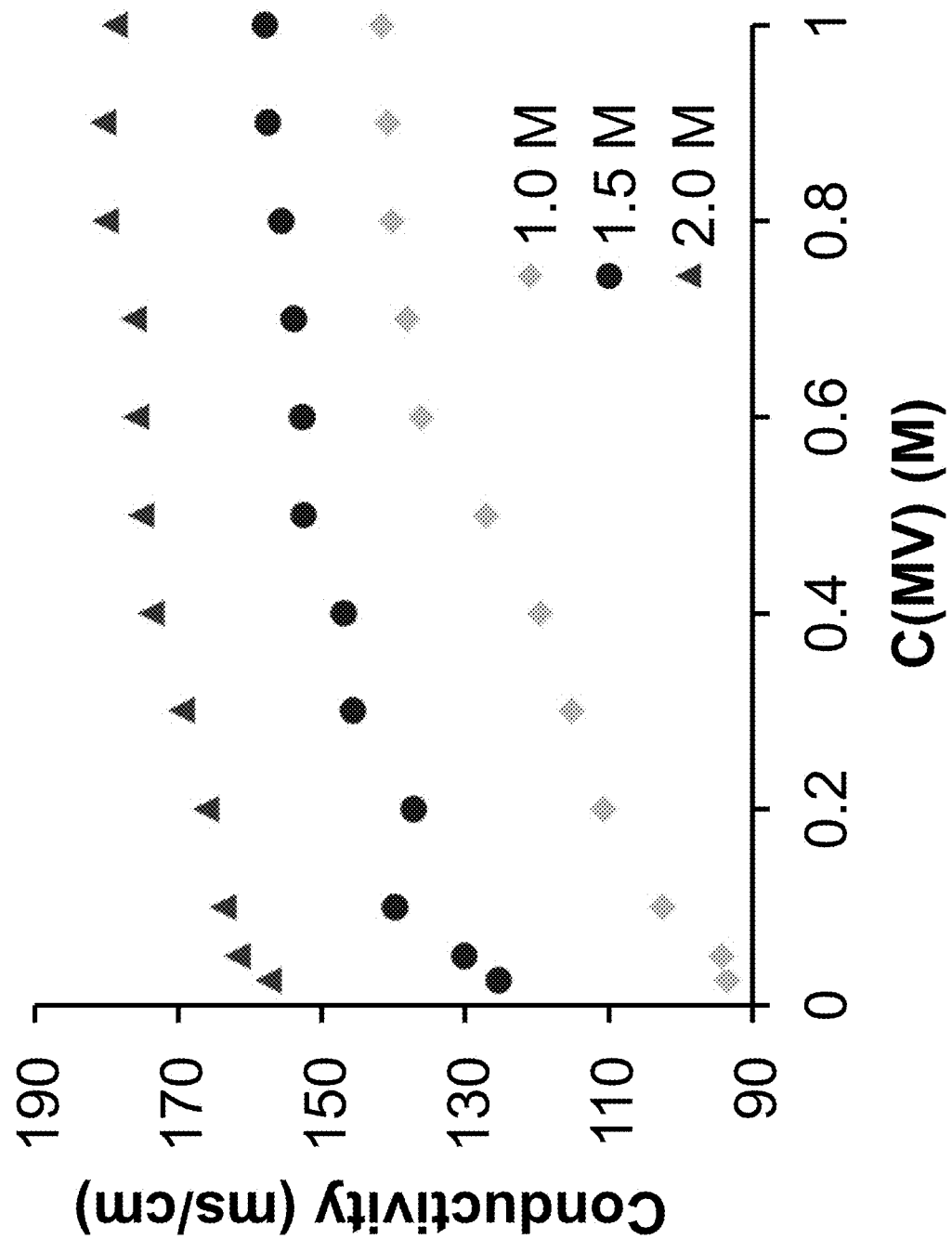
FIG. 7 shows the conductivity measurements of MV at different concentrations (from 1.0 to 2.0 M) at room temperature in NaCl solution.

FcNCl was further investigated for its ability to perform within an AORFB (FIG. 1). Paired with methyl viologen (MV, −0.45 V vs NHE, 3.5 M solubility in water), an established anolyte material for AORFBs, the FcNCl/MV AORFB can deliver 1.05 V cell voltage. Together with their high charge capacities, the AORFB has a theoretical energy density, 49.25 Wh/L, (calculated using equation 3), which is the highest number reported presently for AORFBs. To gain guidance for flow battery tests, comprehensive conductivity tests were conducted for both FcNCl and MV in NaCl supporting electrolyte at different concentrations (FIGS. 6 & 7). The electrolyte conductivity was simultaneously affected by the concentrations of the redox-active compound and the supporting electrolyte, NaCl. For a given NaCl concentration, the FcNCl electrolyte first displayed increased conductivity and then decreased conductivity with increasing concentration of FcNCl. In contrast, the conductivity of the MV electrolyte kept increasing with the concentration of MV. For both electrolytes, conductivity was increased with increasing NaCl concentrations from 1.0 M to 2.0 M. At 2.0 M NaCl concentration, both electrolytes displayed conductivities above 105 mS/cm.

Because of the cation nature of the redox-active moieties of FcNCl and MV, a piece of anion exchange membrane (AEM, Selemin 115) was employed. The AEM was incorporated with pendant ammonium cation functionality that only permits selective transport while suppressing the crossover of the active catholyte and anolyte materials. As the conductivity measurements indicated, 0.5 M concentration of the electrolytes in 2.0 M NaCl could give optimal energy efficiency in terms of overall electrolyte conductivity (135 ms/cm$^2$ for FcNCl and 175 ms/cm$^2$ for MV) while maintaining high electrolyte concentrations. Thus, the flow cell study was conducted at 0.5 M for both active materials in 2.0 M NaCl electrolyte (corresponding to 7.0 Wh/L energy density) at 20° C. The current rate performance was investigated from 40 mA/cm$^2$ to 100 mA/cm$^2$ with an increment of 20 mA/cm$^2$. For each current density, 5 charge and discharge cycles were tested with cutoff voltages at 1.5 V for the charge process and 0.1 V for the discharge process. It should be noted the redox potentials of both active materials are bracketed within the water splitting voltage window (FIG. 2, 1.5 V vs NHE for 02 evolution reaction (OER), and −1.2 V vs NHE for H$_2$ evolution reaction (HER)), indicating OER and HER side reactions are not thermodynamically accessible within the cycling voltage window of the FcNCl/MV AORFB. Furthermore, the voltage gap between OER and HER is approximately 2.5 volts. That leaves space to develop high voltage AORFBs up to 2.0 V, which can be achieved by synthetic tuning of redox potentials of organic materials, and is expected to further enhance the energy density of AORFB.

Figure 16:
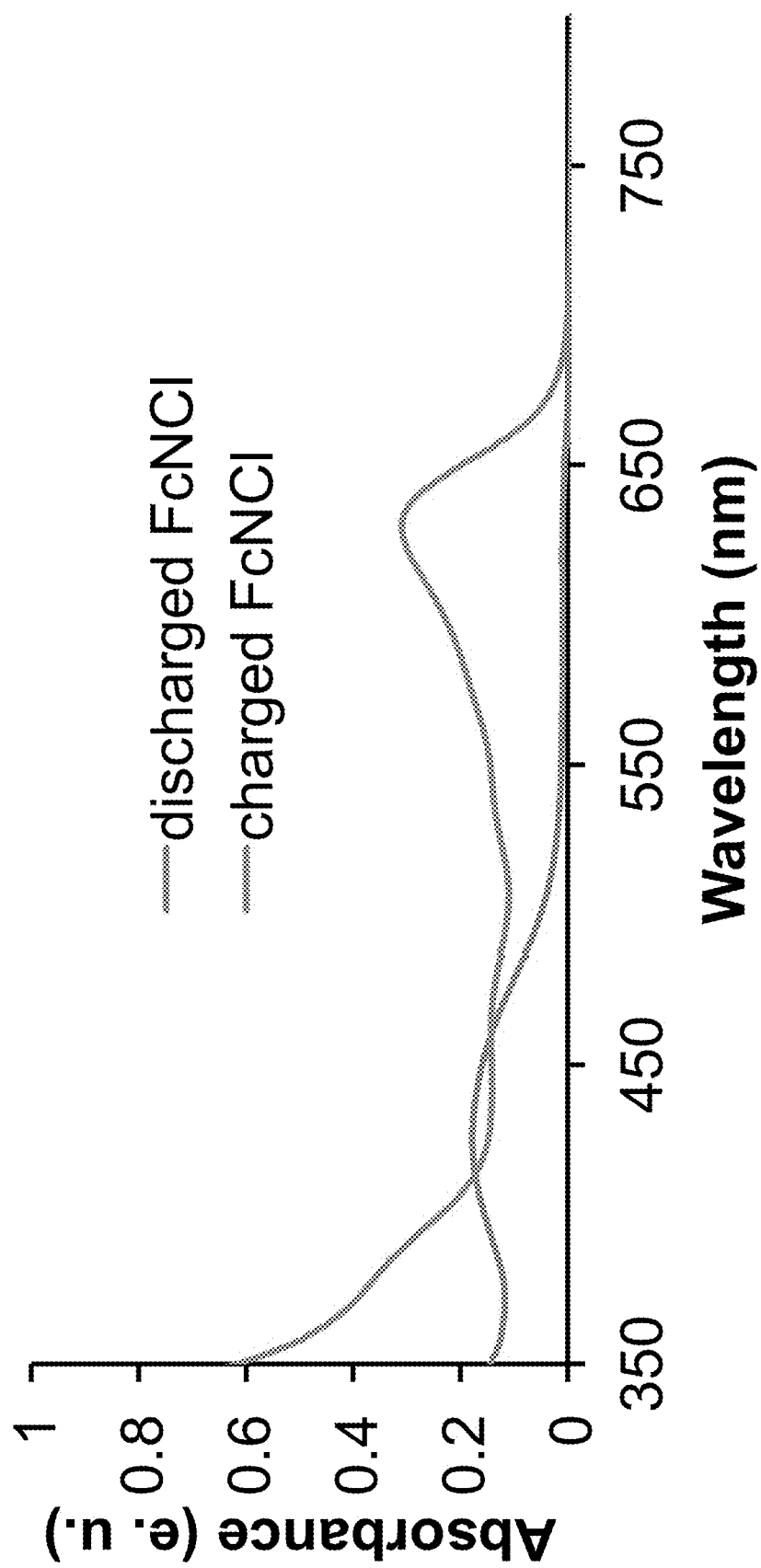
FIG. 16 shows the UV-Vis spectroscopy of FcNCl during charging and discharging in a disclosed AORFB.
Figure 17:
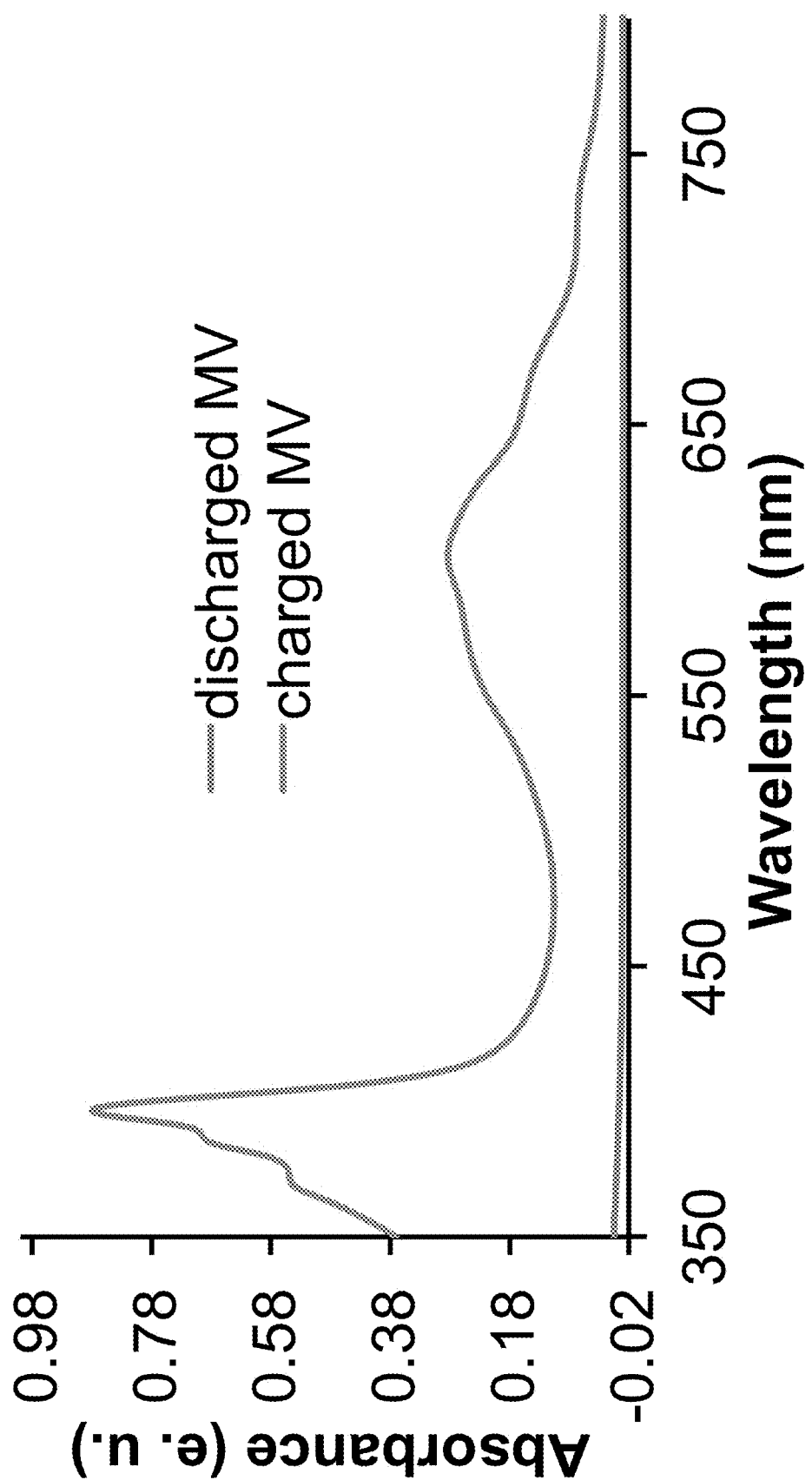
FIG. 17 shows the UV-Vis spectroscopy of MV during charging and discharging in a disclosed AORFB.

Upon charging, both electrolyte solutions underwent immediate color changes, from red-orange to deep green for FcNCl, and from colorless to deep purple for MV. The observed color changes were consistent with the UV-Vis spectrum of FcNCl and MV in their charged and discharged states (FIGS. 16 & 17). FcNCl, in its discharged state, exhibits absorbance at 440 nm, and its charged state, FcNCl$_2$, shows major absorption at 630 nm. The discharged state (MV$^{2+}$) of MV has no absorption in the visible region while its charged state (MV$^+$) exhibits strong waves at 400 nm and 600 nm.

Figure 8:
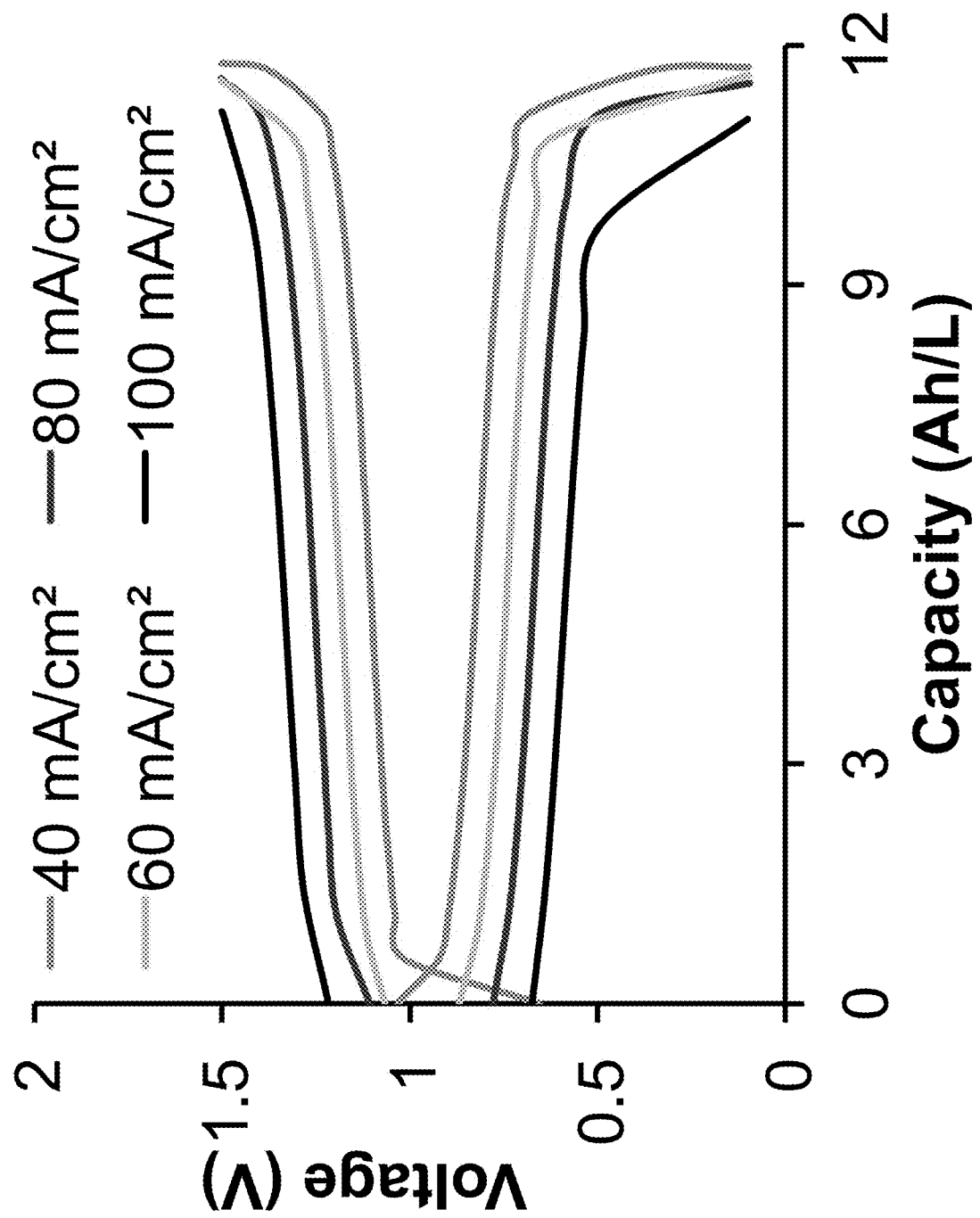
FIG. 8 shows the capacity and coulombic efficiency vs cycling number from 40 mA/cm² to 100 mA/cm² for a disclosed AORFB that includes FcNCl and MV.
Figure 9:
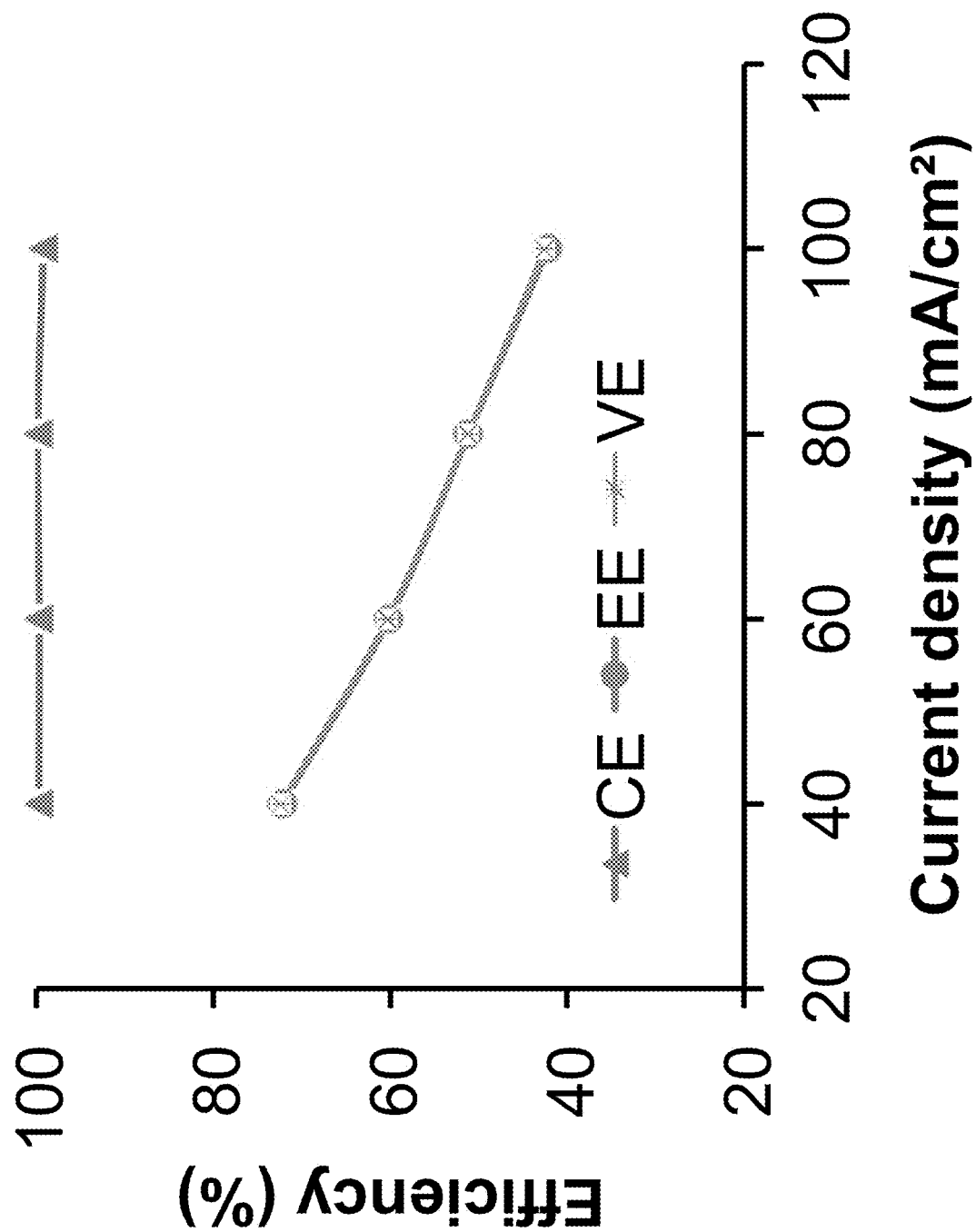
FIG. 9 shows the plots of averaged coulombic efficiency (ce), energy efficiency (ee), and voltage efficiency (ye) versus current density of a disclosed AORFB.

Representative charge/discharges profiles are displayed in FIG. 8. With the increase of the current density, the cell capacity keeps decreasing, mainly due to increased overpotential and reduced charge/discharge time at higher current densities. At 40 mA/cm$^2$, averaged charge and discharge voltage occurred at 1.12 V and 0.82 V. At 100 mA/cm$^2$, the averaged cell voltages for charge and discharge were observed at 1.32 V and 0.61 V. The trend of coulombic efficiency and energy efficiency are depicted in FIG. 9. Coulombic efficiency stayed above 99% for all current densities while energy efficiency decreased from 72% for 40 mA/cm$^2$ to 43% for 100 mA/cm$^2$ due to increased ohmic energy loss. Stable capacity retention was observed for continuous 24 cycles at four current densities.

Figure 10:
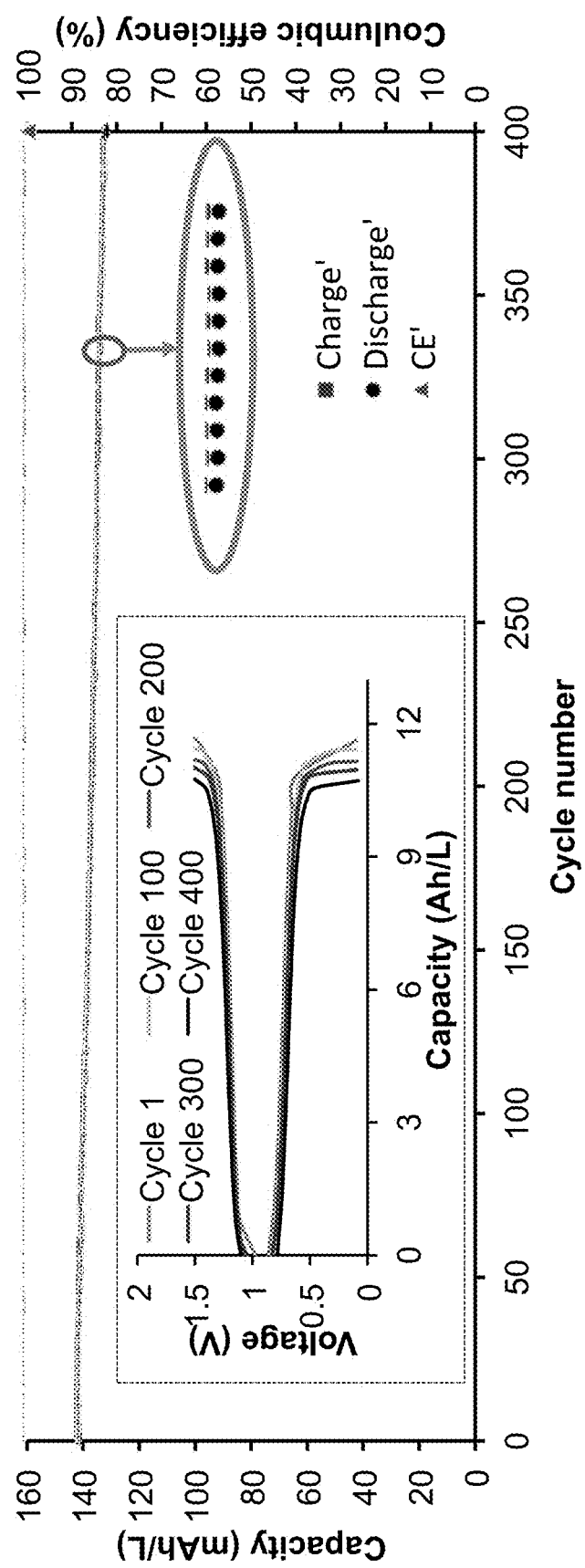
FIG. 10 shows the extended 400 cycle test data of a disclosed AORFB (0.5 M analyte) at 60 mA/cm², which includes analysis of capacity and coulombic efficiency vs cycling number. Inset shows the representative charge and discharge profiles of selected cycles.
Figure 11:
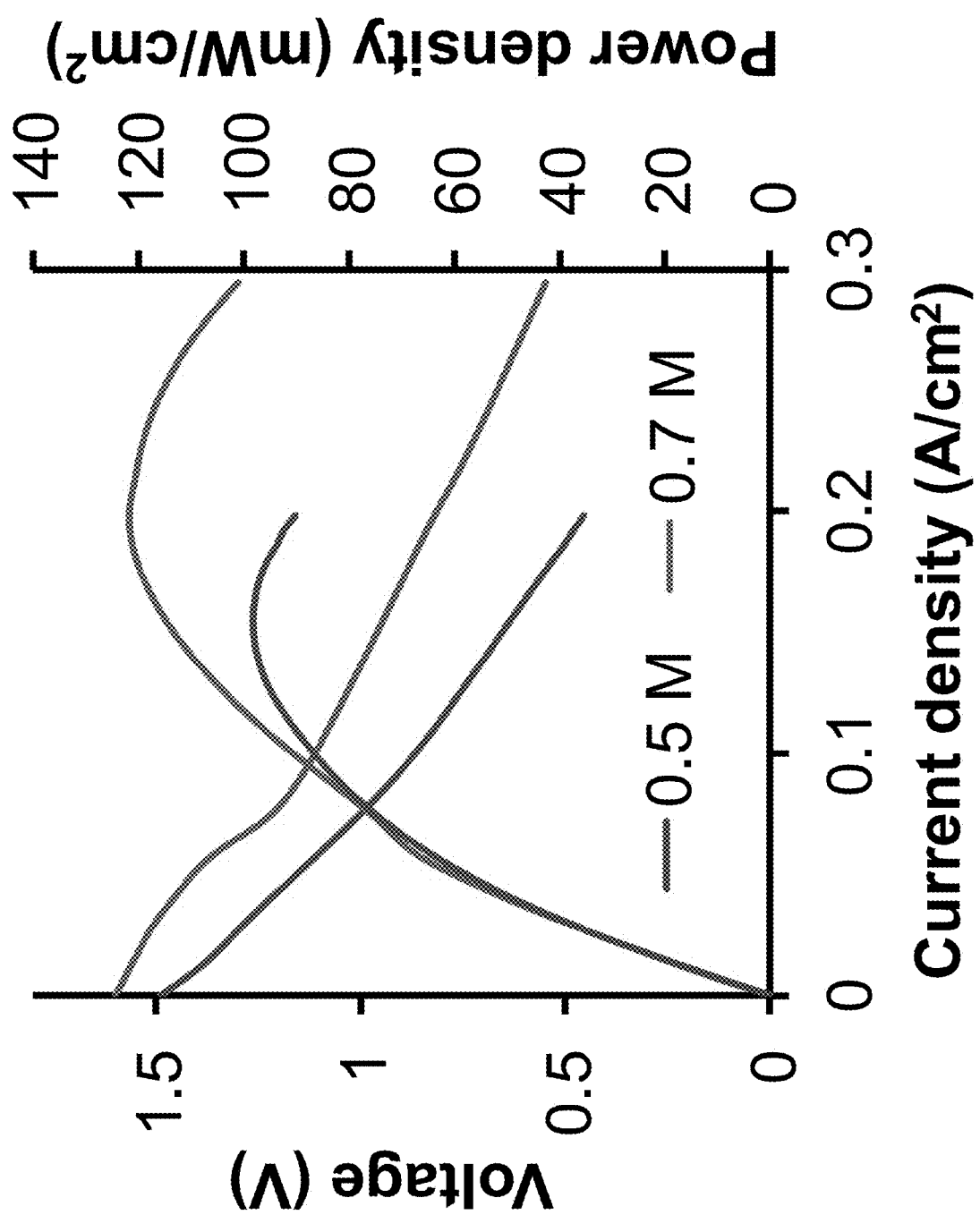
FIG. 11 shows the polarization and power density curves of a disclosed AORFB that includes FcNCl and MV at 0.5 M or 0.7M after full charge using 10 mA/cm².
Figure 12:
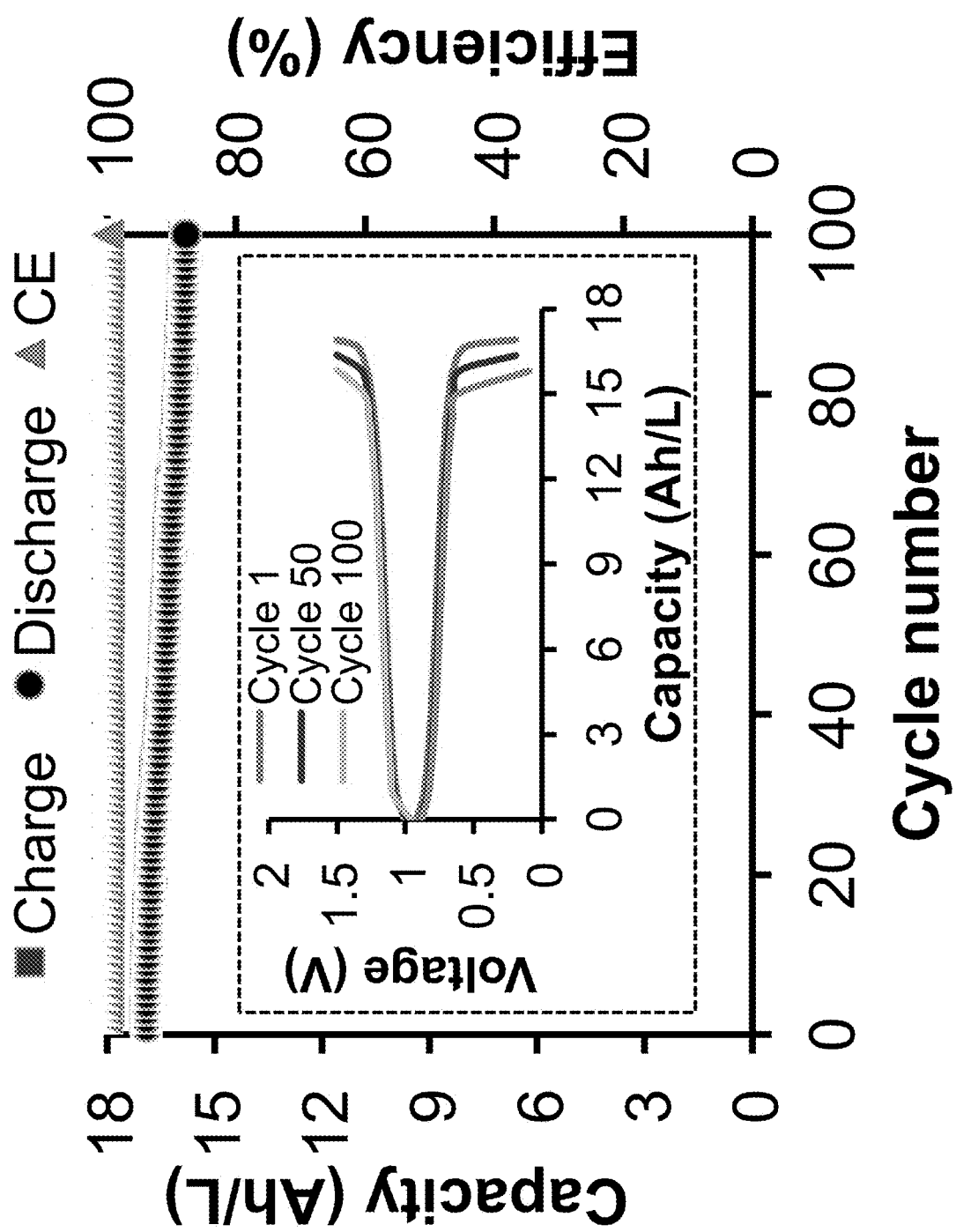
FIG. 12 shows the extended 124 cycle test data at 60 mA/cm², which includes analysis of capacity, coulombic efficiency, and energy efficiency vs cycling number of a disclosed AORFB that includes FcNCl and MV at 0.7 M. Inset shows the plots of average coulombic efficiency, energy efficiency, and voltage efficiency versus current density of a disclosed AORFB.
Figure 18:
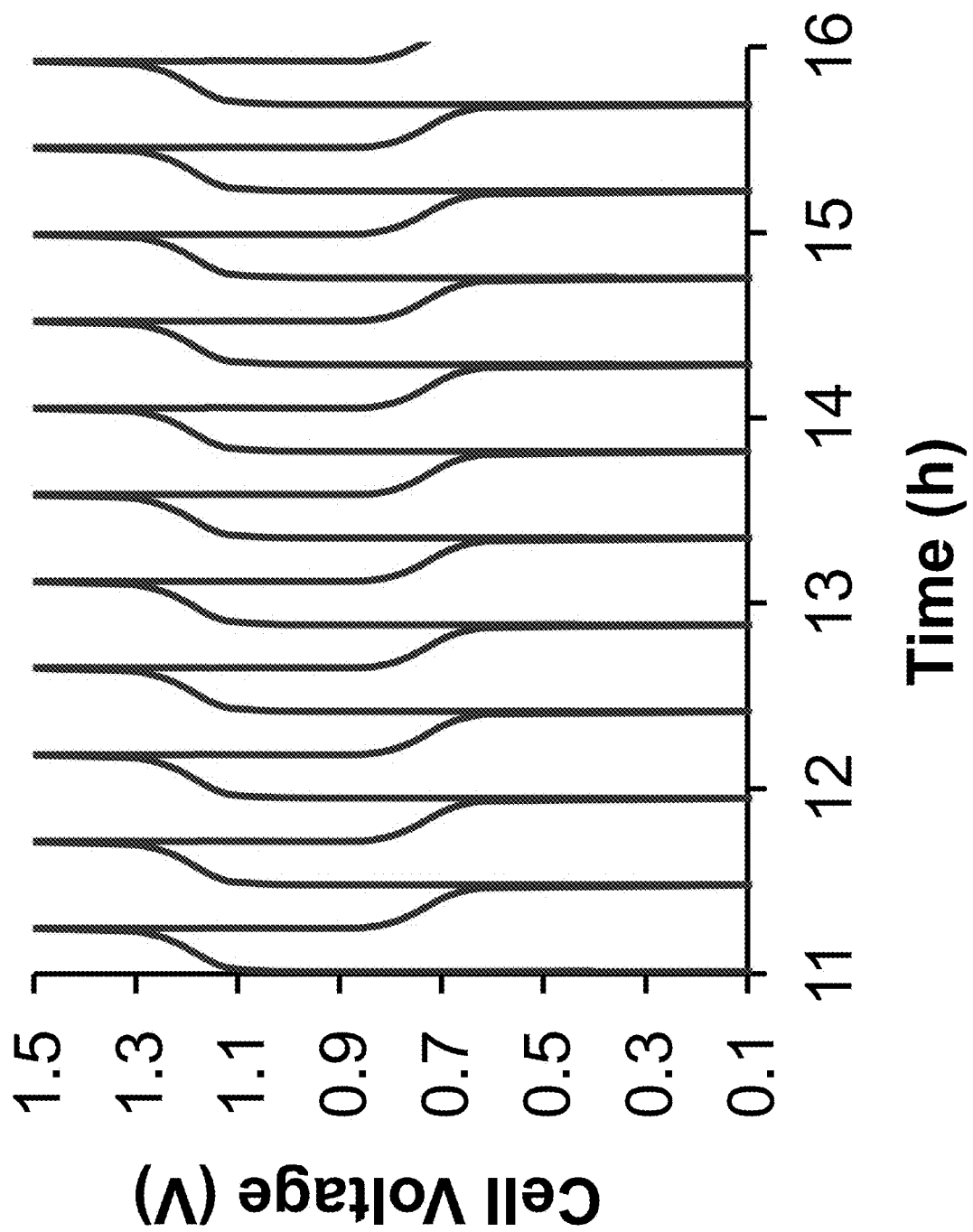
FIG. 18 shows the representative charge/discharge voltage profiles over time of a disclosed AORFB that includes 0.5 M FcNCl/MV at 60 mA/cm².
Figure 19:
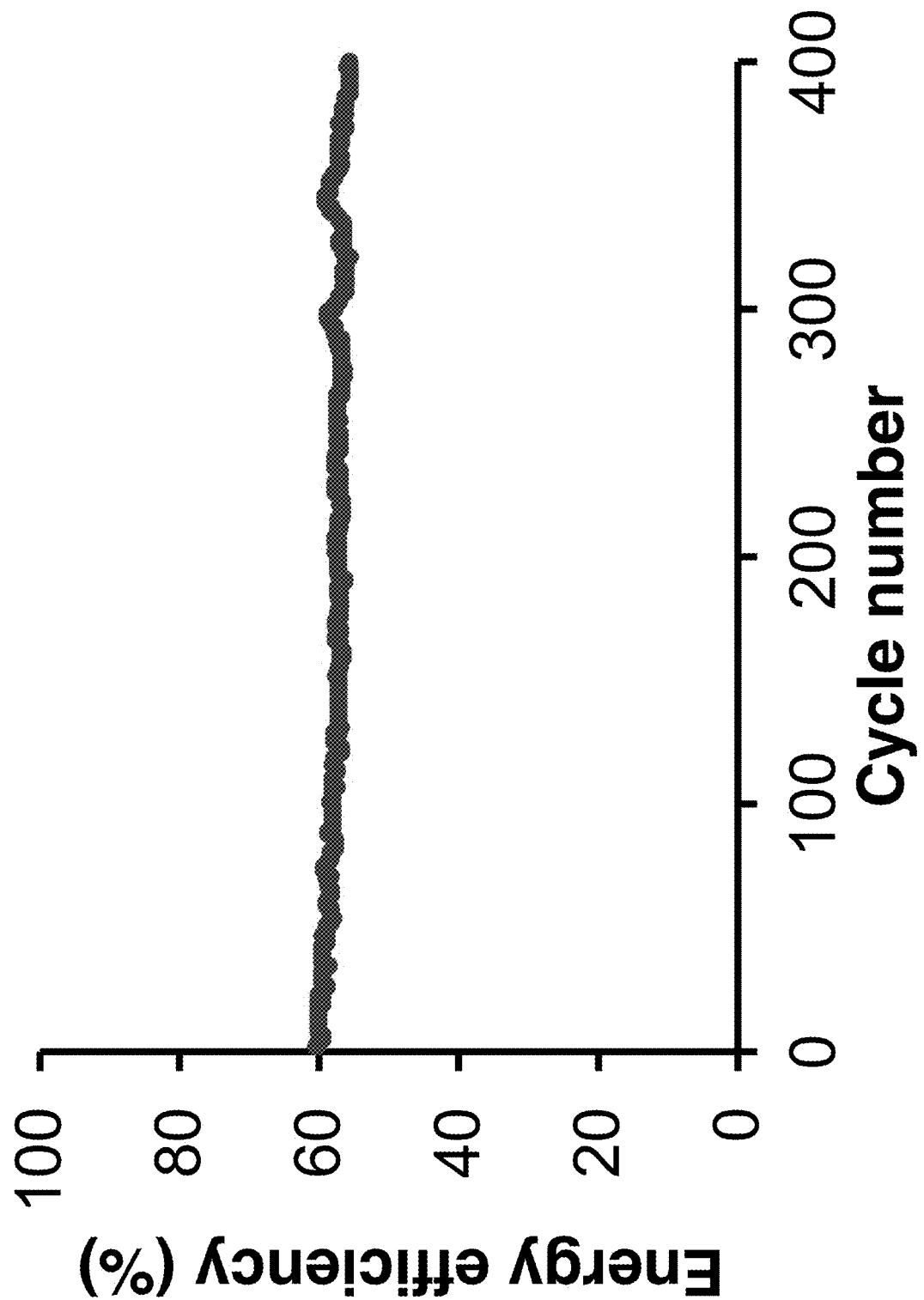
FIG. 19 shows the energy efficiency plot vs cycling number for a disclosed AORFB that includes 0.5 M FcNCl/MV at 60 mA/cm².
Figure 20:
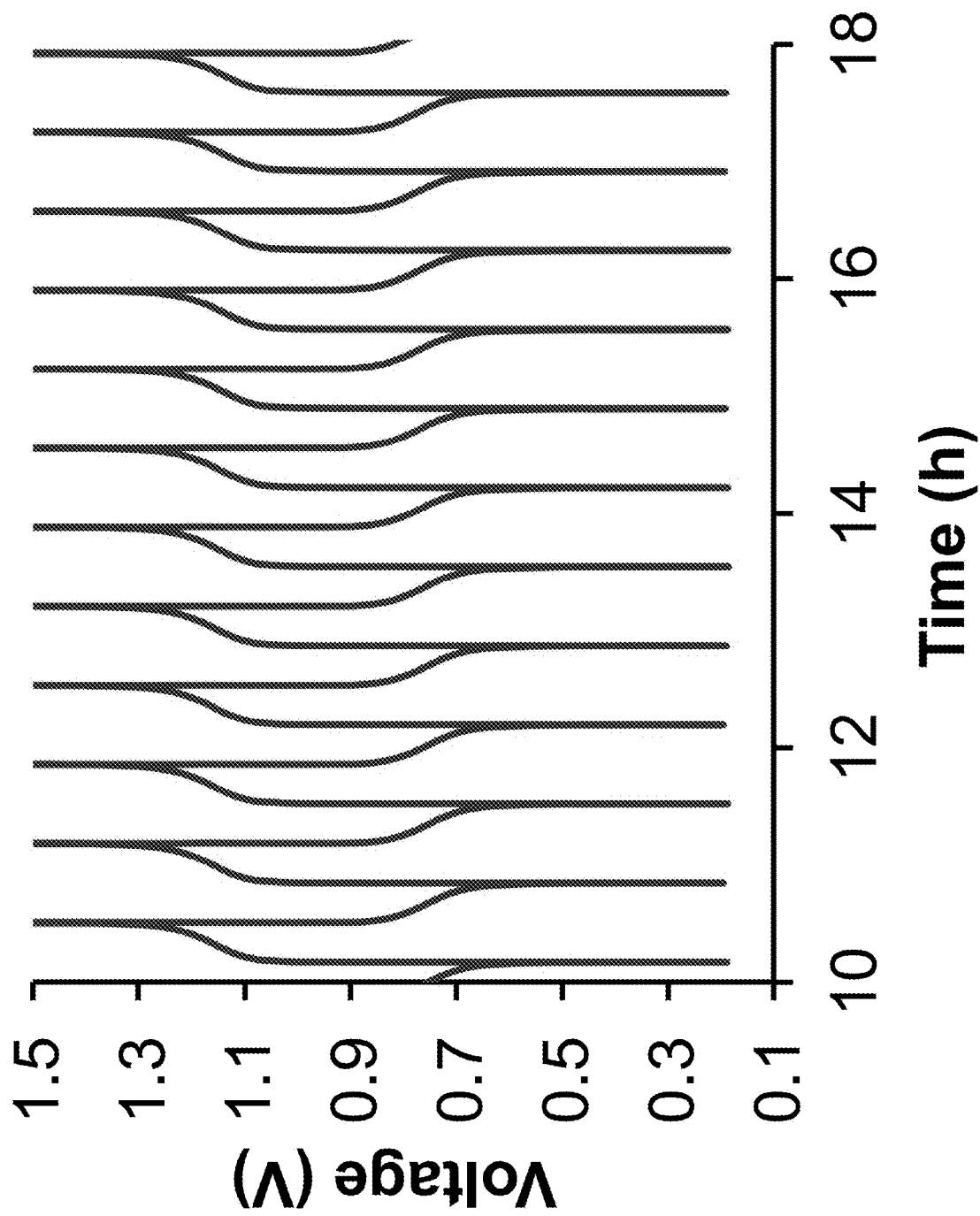
FIG. 20 shows the representative charge/discharge voltage profiles over time of a disclosed AORFB that includes 0.7 M FcNCl/MV at 60 mA/cm².
Figure 21:
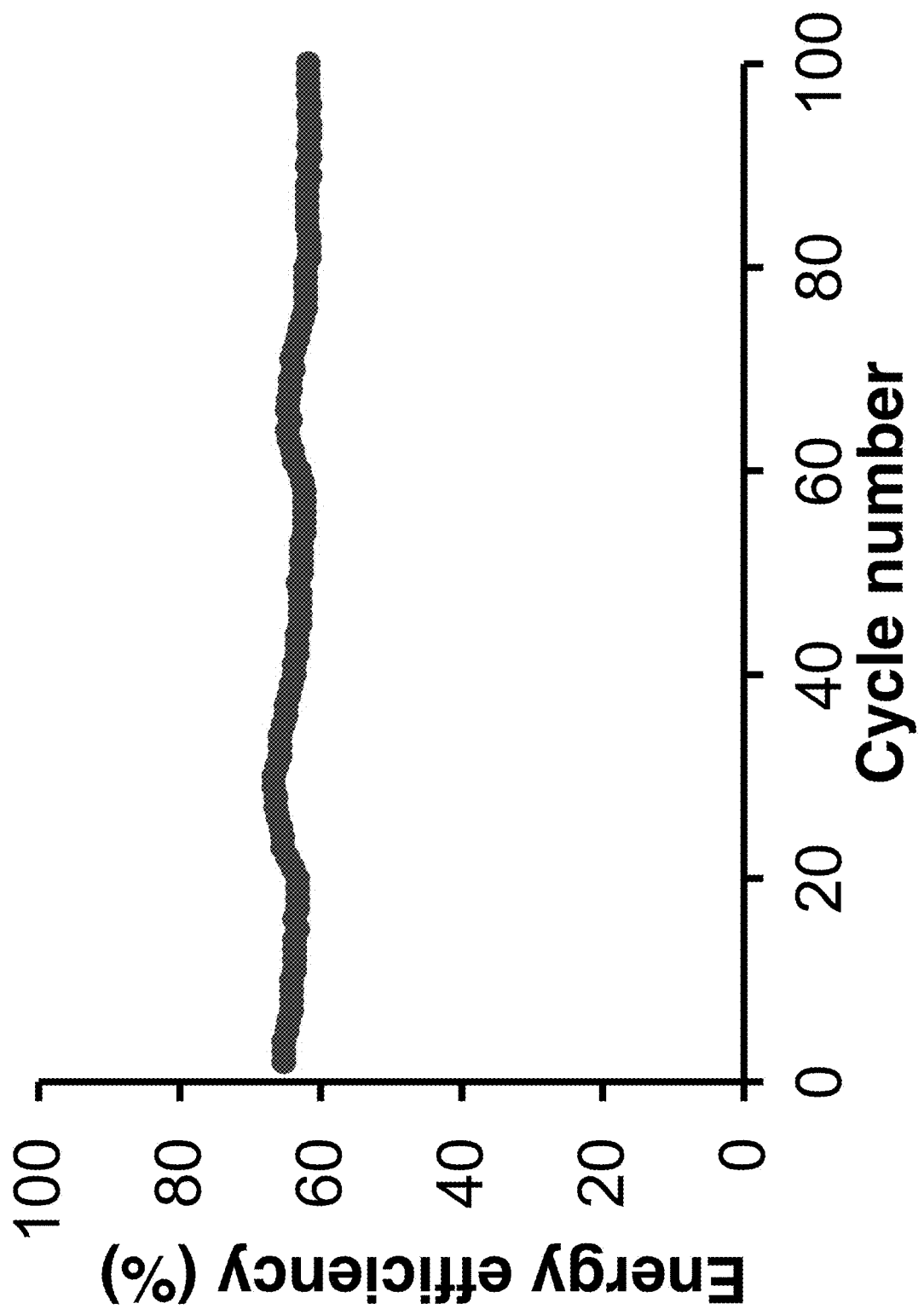
FIG. 21 shows the energy efficiency plot vs cycling number for a disclosed AORFB that includes 0.7 M FcNCl/MV at 60 mA/cm².

To further validate cycling performance of the FcNCl/MV AORFB at 0.5 M, long time cycling was examined at 60 mA/cm$^2$ (FIG. 10), which showed a high energy efficiency, 61%. The 0.5 M cell tested at 60 mA/cm$^2$ delivered stable capacity retention. After 400 cycles tested in 8 days, capacity still remained above 95%. The charge/discharge voltage profiles over time are provided in FIG. 18. On average, the capacity retention was approximately 99.98% for a single charge/discharge cycle. The averaged energy efficiency stayed approximately 60% with small fluctuations over 400 cycles (FIG. 19). The robust cycling performance is provided by the excellent electrochemical and thermal stability of both active materials. For the same long cycling cell, polarization curve was recorded at a full charge state using a small current density, 10 mA/cm$^2$ (FIG. 11, 0.5 M). The resulting power density curve revealed a peak output power density at 85 mW/cm$^2$ (FIG. 11, 0.5 M). To demonstrate higher energy density performance, a flow cell was tested at 0.7 M (9.9 Wh/L energy density) for 100 cycles (FIG. 12) with stable capacity retention at 94%. The 0.7 M cell delivered increased energy efficiency at 65% at 60 mA/cm$^2$ (FIGS. 20 & 21). Correspondingly, an increased peak power density was measured at 120 mW/cm$^2$ (FIG. 11, 0.7 M), which is in the same order of peak power outputs observed for acidic and alkaline AORFBs known within the art.

Figure 22:
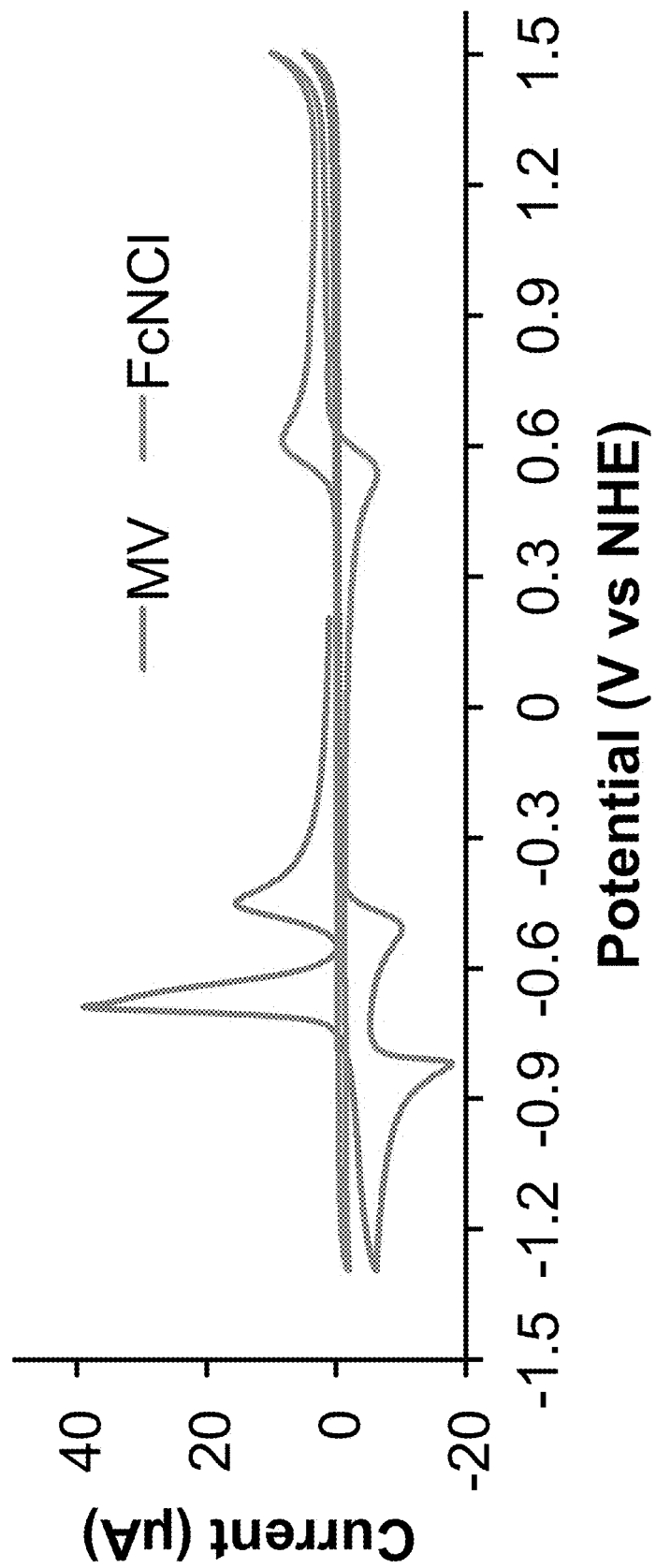
FIG. 22 shows the post-cell CV analysis for FcNCl and MV after 400 cycles of a disclosed AORFB.
Figure 23:
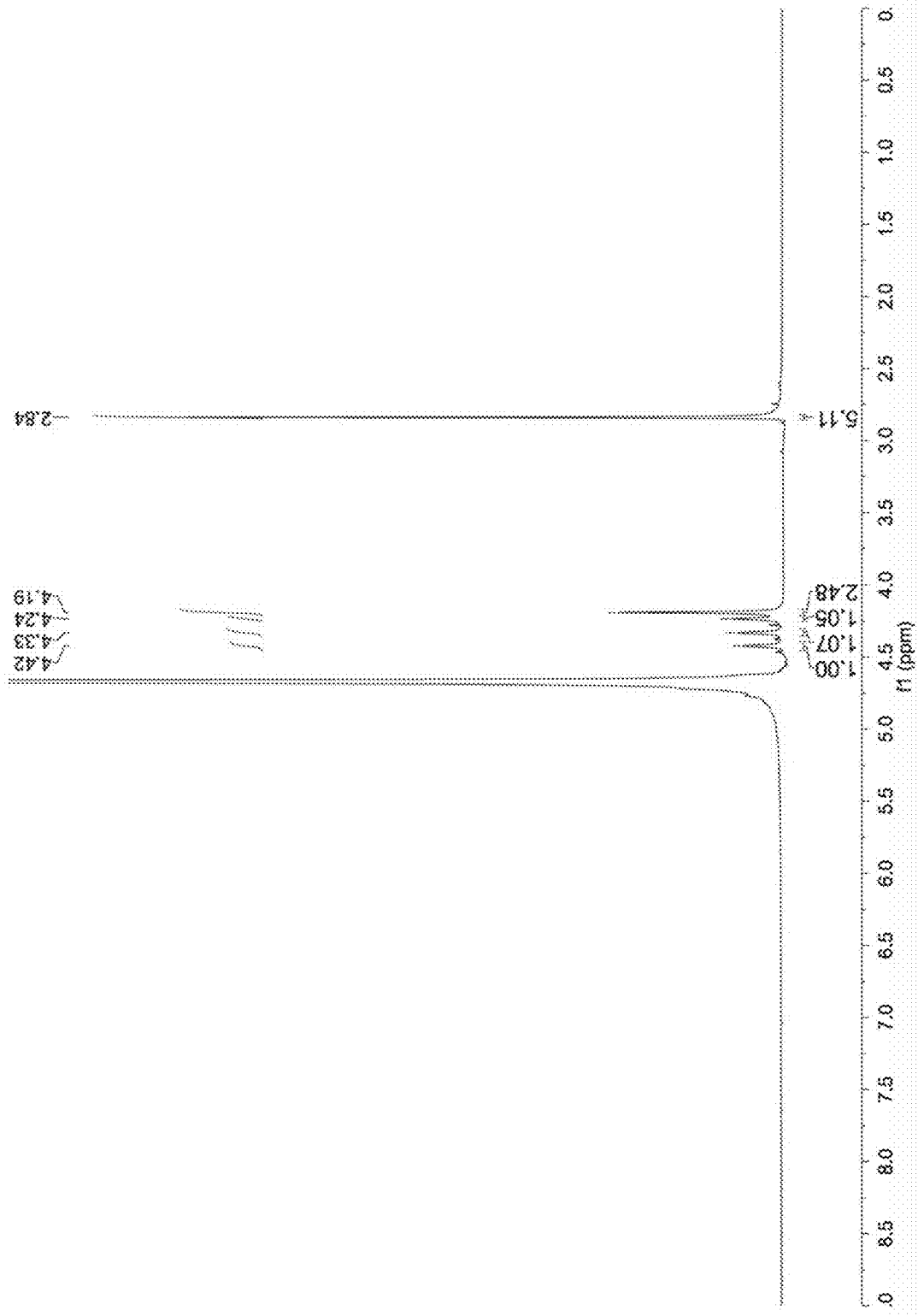
FIG. 23 shows the post-cell $^1$H NMR analysis for FcNCl after 400 cycles of a disclosed AORFB.
Figure 24:
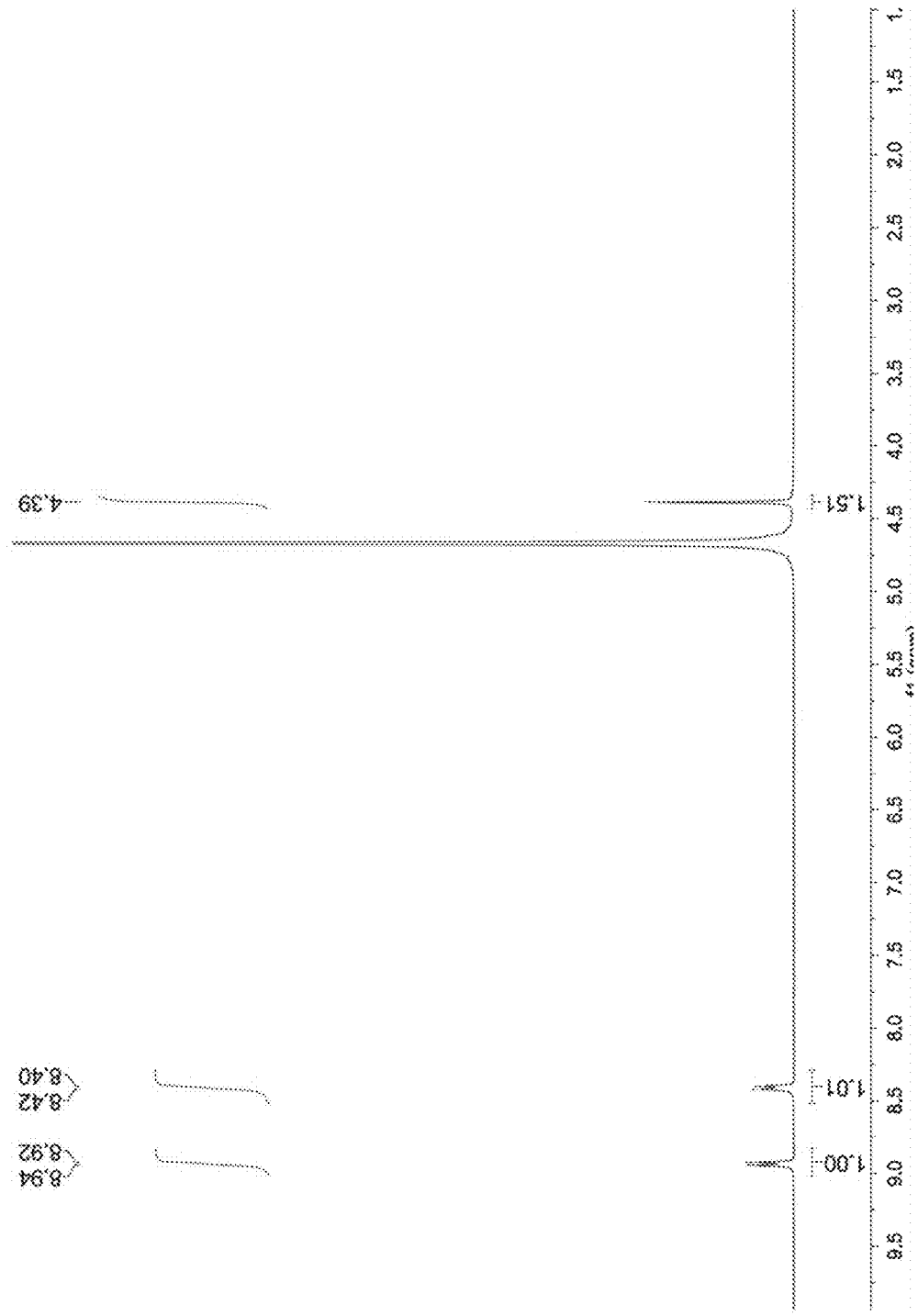
FIG. 24 shows the post-cell $^1$H NMR analysis for MV after 400 cycles of a disclosed AORFB.

Post-cell analysis for the 0.5 M cell after 400 cycles were conducted using cyclic voltammetry and $^1$H NMR (FIGS. 22-24). Both CV and $^1$H NMR and studies indicated that there is no chemical degradation for the catholyte and anolyte. Also the post-analysis studies indicated there was no crossover between catholyte and anolyte as no FcNCl was detected in the $^1$H NMR spectrum and CV of MV, and vice versa, highlighting the excellent compatibility of both catholyte and anolyte with the AEM membrane. Identical results were obtained for the 0.7 M cell.

In summary, disclosed in this example is a FcNCl/MV AORFB, having a high theoretical energy density, 49.25 Wh/L, for sustainable and safe large scale and residential energy storage. The battery is built from abundant elements, including an organic catholyte based on a ferrocene compound, a methyl viologen anolyte, neutral and non-corrosive NaCl supporting electrolyte, and low-cost anion exchange membrane. The batteries exhibit outstanding electrochemical performance, for example 400 cycles with 95% capacity retention and 65% energy efficiency at 60 mA/cm$^2$, and high power supply (up to 125 mW/cm$^2$). Accordingly, the disclosed AORFB technology underlines great promise of soluble redox-active organic molecules for renewable energy storage.

Example 8. Synthesis and Characterization of Two-Electron Storage Viologens

Materials & Methods

Chemicals and instrumentation: All chemicals were purchased from either TCI or Sigma Aldrich, stored in an argon glovebox, and used as received. All experiments were conducted under an $N_2$ or Ar atmosphere. Elemental Analysis was performed by Atlantic Microlab. NMR data were collected with a Bruker 500 MHz spectrometer. EPR data were collected with a Bruker EMX spectrometer. UV-Vis data were collected with an Ocean Optics flame spectrometer. Battery performance data were collected with a Landt battery testing system.

Synthesis of 1,1'-bis[3-(trimethylamonium)propyl]-4,4'-bipyridinium, tetrabromide ($(NPr)_2V$): In a 250 mL $N_2$ purged Schlenk flask, 4,4'-bipyridine (2.5 g, 16 mmol) was combined with (3-bromopropyl)trimethylammonium bromide (8.35 g, 32 mmol) in 25 mL DMSO, and stirred at 100° C. for 2 h. The resulting light yellow precipitate was filtered and washed with 50 mL acetonitrile, then dried under vacuum. 70% yield. The light yellow powder $(NPr)_2V$ was stored in a dry desiccator. $^1$H NMR ($D_2O$, 25° C., 500 MHz): δ (ppm), 2.61 (pentet 4H), 3.11 (singlet 18H), 3.50 (triplet 4H), 4.78 (triplet 4H), 8.55 (doublet, 4H), 9.12 (doublet 4H) (See FIG. 34). Elemental Analysis for $C_{22}H_{38}Br_4N_4 \cdot H_2O$, Calculated: C, 37.95, H, 5.79, N, 8.05. Found: C, 37.21, H, 5.93, N, 7.72.

Synthesis of 4'-pyridine-[3-sulfonatopropyl-4-pyrdinium (SPy): In a 250 mL $N_2$ purged Schlenk flask, 4,4'-bipyridine (2.5 g 16 mmol) was combined with propane sultone (1.96 g 16 mmol) in 25 mL acetonitrile, and refluxed at 80° C. for 24 h. The resulting white precipitate was filtered and dried under vacuum. 90% yield. $^1$H NMR ($D_2O$, 25° C., 500 MHz): δ (ppm), 2.39 (pentet 2H), 2.90 (triplet 2H), 4.70 (triplet 2H), 7.78 (doublet 2H), 8.30 (doublet 2H), 8.64 (doublet 2H), 8.88 (doublet 2H) (See FIG. 35). Elemental analysis for $C_{13}H_{14}N_2O_3S$, Calculated: C, 56.1, H, 5.07, N, 10.07. Found: C, 55.49, H, 5.16, N, 9.84.

Synthesis of 1'-[3-(trimethylammonium)propyl]-4'-pyridinium-1-[3-sulfonatopropyl]-4-pyridinium dibromide ($(NPr)(SPr)V$): In a 250 mL $N_2$ purged Schlenk flask, SPy (1.2 g, 4.3 mmol) was combined with (3-bromopropyl) trimethylammonium bromide (1.1 g, 4.3 mmol) in 50 mL of —$CH_3CN$, and refluxed at 80° C. for 7 days. The resulting yellow precipitate was filtered and washed with 10 mL MeOH. 95% yield. $^1$H NMR ($D_2O$, 25° C., 500 MHz): δ (ppm), 2.43 (pentet 2H), 2.56 (pentet 2H), 2.92 (triplet 2H), 3.08 (singlet 9H), 3.47 (triplet 2H), 4.77 (multiplet 4H), 8.48 (triplet 4H), 9.07 (singlet 4H) (See FIG. 36). Elemental analysis of $C_{19}H_{29}Br_2N_3O_3S \cdot H_2O$, Calculated: C, 40.95, H, 5.61, N, 7.54. Found: C, 40.58, H, 5.41, N, 7.25.

Synthesis of 4'-pyridine-methyl-4-pyrdinium Iodide (MeBpy): In a 250 mL $N_2$ purged Schlenk flask, 4,4'-bipyridine (5.0 g 32 mmol) was combined with methyl iodide (4.54 g 32 mmol) in 80 mL acetone and stirred at room temperature for 24 h. The resulting yellow precipitate was filtered and stored in a dry desiccator. Yield 95%. $^1$H NMR ($D_2O$, 25° C., 500 MHz): δ (ppm), 4.36 (singlet 3H), 7.84 (doublet 2H), 8.31 (doublet 2H), 8.70 (doublet 2H), 8.82 (doublet 2H) (See FIG. 37). Elemental analysis for $C_{11}H_{11}IN_2$, Calculated: C, 44.32, H, 3.72, N, 9.40. Found: C, 44.07, H, 3.61, N, 9.34.

Synthesis of 1'-methyl-4'-pyridinium-1-[3-(trimethylaminium)propyl]-4-pyridinium trichloride ((Me)(NPr)V): In a 250 mL $N_2$ purged Schlenk flask, MeBpy (1 g, 3.4 mmol) was combined with (3-bromopropyl)trimethylammonium bromide (0.88 g 3.4 mmol) in 30 mL DMF, and heated to 95° C. for 24 h. The resulting orange precipitate was filtered and washed with 10 mL diethyl ether before drying at 60° C. in a vacuum oven. The mixed bromide and iodide counter ions were exchanged for chloride by column anion exchange. 82% yield. $^1$H NMR ($D_2O$, 25° C., 500 MHz): δ (ppm), 2.61 (pentet 2H), 3.12 (singlet 9H), 3.51 (triplet 2H), 4.43 (singlet 3H), 4.78 (triplet 2H), 8.46 (doublet 2H), 8.54 (doublet 2H), 8.99 (doublet 2H), 9.11 (doublet 2H) (See FIG. 38). Elemental analysis for $C_{17}H_{26}C_{13}N_3 \cdot 2H_2O$, Calculated: C, 49.22, H, 7.29, N, 10.13. Found: C, 49.49, H, 7.24, N, 9.95.

Synthesis of 1,1'-bis[3-sulfonatopropyl]-4,4'-bipyridinium ($(SPr)_2V$): In a 250 mL $N_2$ purged Schlenk flask, 4,4'-bipyridine (3 g, 19.2 mmol) was dissolved in 35 mL toluene and brought to reflux. Propane sultone (4.7 g, 38.4 mmol) was dissolved in 25 mL toluene, and added dropwise to the refluxing solution. After 3 h at 110° C., the flask was cooled to room temperature. The resulting white precipitate was filtered, washed with 30 mL acetonitrile, and dried under vacuum. 88% yield. $^1$H NMR ($D_2O$, 25° C., 500 MHz): δ (ppm), 2.41 (pentet 4H), 2.91 (triplet 4H), 4.78 (triplet 4H), 8.45 (doublet 4H), 9.04 (doublet 4H) (See FIG. 39). Elemental analysis for $C_{16}H_{20}N_2O_6S_2$, Calculated: C, 47.99, H, 5.03, N, 7.00. Found: C, 47.97, H, 5.06, N, 6.86.

Synthesis of (ferrocenylmethyl)ethyldimethylammonium bromide ($[FcN^{Et}]Br$): In a 250 mL $N_2$ purged Schlenk flask, (ferrocenylmethyl)dimethylamine (10 g, 41.13 mmol) was combined with bromoethane (4.48 g, 41.13 mmol) in 25 mL $CH_3CN$, and stirred at 25° C. for 24 h. The resulting orange precipitate was filtered and washed with 2×25 mL diethyl ether and dried under vacuum. The orange powder $[FcN^{Et}]$Br product was stored in a dry desiccator. $^1$H NMR ($D_2O$, 25° C., 500 MHz): δ (ppm), 1.24 (triplet 3H), 2.78 (singlet 6H), 3.15 (quartet 2H), 4.21 (singlet 5H), 4.29 (singlet 2H), 4.36 (singlet 2H), 4.43 (singlet 2H) (See FIG. 40). Elemental Analysis for $C_{15}H_{22}BrFeN$, Calculated: C, 51.17, H, 6.30, N, 3.98. Found: C, 50.97, H, 6.17, N, 4.16.

Cyclic and square wave voltammetry studies: All experiments were conducted in an Na purged, 0.5 M NaCl aqueous solution, and performed with a Gamry 1000E potentiostat. A 1 mm PEEK encased glassy carbon disk was used as the working electrode. The working electrode was polished with 0.05 micron $Al_2O_3$ powder and rinsed with deionized $H_2O$. A glassy carbon rod was used as the counter electrode. A silver wire coated with AgCl and suspended in 3.0 M KCl electrolyte was used as the reference electrode.

Electrochemical RDE studies: Linear sweep voltammetry (LSV) experiments were conducted using a Gamry 1000E potentiostat with a three-electrode system. A 5 mm rotating glassy carbon disk encased in Teflon served as the working electrode. A glassy carbon rod was used as the counter electrode. A Ag/AgCl wire served as the reference electrode. The working electrode was cleaned using the same method as in the CV experiments. During the experiments, the working electrode rotated from 300 rpm to 2400 rpm at increments of 300 rpm. Three scans at each rotation rate were collected to ensure accuracy. $(NPr)_2V$: LSV scans were conducted at a rate of 5 mV/s from 0.1 V to −1.2 V versus NHE. The limiting currents (mass transport-limited current intensity) at each rotation rate were recorded at −0.57 V and −0.95 V versus NHE. The Levich plots of limiting current versus square root rotation rate showed linear relationships for both reductions. The slopes of these fitted lines are defined by the Levich equation, $$\text{Levich Plot Slope} = 0.620 n F A C_0 D^{2/3} v^{-1/6} \quad \text{(equation 1)}$$

where n=1 for a single electron process, Faraday's constant F=96485 C/mol, electrode area A=0.1963 cm2, (NPr)

$_2$V concentration Co=1×10-5 mol/cm3, D represents the diffusion coefficient, and the kinematic viscosity of 0.5 M NaCl aqueous solution v=0.009 cm$^2$/s. Plots of overpotential versus $\log_{10}(ik)$ were constructed from the 2400 rpm LSV, where ik is the kinetic current of each reduction of (NPr)$_2$V. The x-intercept of the fitted Tafel plot represents the log of the exchange current $i_0$ that is defined by:

$$i_0 = FAC_0 k^0 \quad \text{(equation 2)}$$

where F, A, and $C_0$ are defined above, and $k^0$ represents the electron transfer rate constant.

(NPr)(SPr)V, (Me)(NPr)V, (SPr)$_2$V, and [FcN$^{Et}$]Br: LSV scans were collected and analyzed using the same techniques described for (NPr)$_2$V.

Flow Cell Tests: The flow cell was constructed from two graphite chambers, each housing a graphite felt electrode (SGL Carbon Group, Germany). Sandwiched between the chambers was a sheet of anion exchange membrane (AME 115, 120 μm thickness, pore size <10 Å, Selemion, Japan). The cell membrane had an active area of 10 cm$^2$. On the exterior of each graphite chamber was a copper current collector. A Masterflex® L/S® peristaltic pump (Cole-Parmer, USA) circulated the electrolyte solutions through the cell and reservoirs at 60 mL/min. Each reservoir contained 12 mL 2.0 M NaCl aqueous solution. The anode reservoir contained 0.25 M (NPr)$_2$V, and the cathode reservoir contained 0.5 M [FcN$^{Et}$]Br. The reservoirs were purged with N$_2$ to displace any 02 in the system, then sealed. The flow cell was galvanostatically charged and discharged at 25° C. on a battery tester (Landt Instruments). When utilizing both redox events from (NPr)$_2$V, the cell operated between 1.8 V and 0.1 V. When isolating only the first redox from (NPr)$_2$V, the cell was operated between 1.35 V and 0.1 V. To isolate only the second redox of (NPr)$_2$V, the battery was first charged from 0 V to 1.8 V, then cycled between 1.8 V and 0.85 V. The flow cell operated at current densities from 40 to 100 mA/cm$^2$. During battery operation, small samples of electrolyte were collected to characterize the different redox states of (NPr)$_2$V and [FcN$^{Et}$]Br by UV-Vis. These color changes are represented in the storage tanks shown in FIG. 30A, and a detailed UV-Vis analysis is given in FIG. 49. To monitor the battery resistance, electrochemical impedance data were recorded at 25%, 75%, and 100% state of charge (charged with 10 mA/cm$^2$ charge current density) using a Gamry 1000E potentiostat.

Calculation of theoretical energy density: The theoretical energy density of the (NPr)$_2$V/[FcN$^{Et}$]Br AORFB is calculated using equation 4 below, where n=the number of electrons involved in the cell reaction, C=the concentration of active materials, F=Faraday's constant 26.8 Ah/mol, V=the cell voltage, μv=the factor that represents the overall volumes of anolyte and catholyte.

$$\text{Energy density (Wh/L)} = nCFV / \mu_v \quad \text{(equation 4)}$$

$$\mu_v = 1 + \frac{[\text{max solubility, less soluble electrolyte}]}{[\text{max solubility, more soluble electrolyte}]}$$

For the [FcN$^{Et}$]Br/(NPr)$_2$V AORFB, v=1+[(NPr)$_2$V]/[FcN]=1+1.6/3.75=1.43. So, utilizing only the first redox couple of (NPr)$_2$V, the energy density=(1×1.6×26.8×0.97)/1.43=28.5 Wh/L. Utilizing only the second redox couple of (NPr)$_2$V, the energy density=(1×1.6×26.8×1.34)/1.43=39.6 Wh/L. To calculate the energy density of the two-electron AORFB, the operational voltages for the two electron transfers were averaged, and the energy density as a two-electron system was calculated: energy density=(2×1.6×26.8×1.155)/1.43=68.1 Wh/L. The sum of the two energy densities for the individual redox is equal to the energy density of the full two-electron system.

Computational Methods: Calculations for the theoretical redox potentials of viologen compounds were performed using the Gaussian 09 package. All compounds were modeled as isolated molecules at 298 K. For all candidates, the ground state structure was optimized for the initial oxidation state, one-electron reduced oxidation state, and two-electron reduced oxidation state. Basis sets consisted of 6-31+G(d) and the electron correlation method was calculated M06-2x: Minnesota '06 2x global hybrid functional with 54% HF exchange. All geometries were optimized in water as the implicit solvent. To model the implicit solvent the universal solvation model SMD was used, which is based on the quantum mechanical charge density of a solute molecule interacting with a continuum description of the solvent. Energy minimum of each optimized structure was confirmed by frequency calculation.

The redox potentials were calculated directly versus MV which was derived from the Born-Haber method. This calculation predicts the redox potential of the viologen by comparing it to the experimentally determined potentials for MV. Square wave voltammetry was employed to most accurately measure $E_{1/2}$ for the two reductions of viologen compounds (FIG. 42). The calculation of the theoretical redox potential vs MV can be simplified as shown below:

(a) Calculation of the first reduction of a viologen, abbreviated as $[V]^{2+/+}$:

$$[MV]^{2+} + [V]^{+} \rightarrow [MV]^{+} + [V]^{2+}$$

$$\Delta G° = G°([MV]^{+}) + G°([V]^{2+}) - G°([MV]^{2+}) - G°([V]^{+}) \quad \text{(equation 5)}$$

The calculated free energy of the redox couple is then used in the Nernst Equation:

$$\Delta G° = -nF([MV]^{2+/+} - [V]^{2+/+}) \quad \text{(equation 6)}$$

therefore, $$[V]^{2+/+} = \Delta G°/nF + [MV]^{2+/+} \quad \text{(equation 7)}$$

where n=1, F=23.061 kcal/mol·V, $[MV]^{2+/+}$=0.45 V vs NHE.

(b) Similarly, the second reduction ($[V]^{+/0}$) of a viologen was calculated by reference to the experimental value of $[MV]^{+/0}$.

$$[MV]^{+} + [V]^{0} \rightarrow [MV]^{0} + [V]^{+}$$

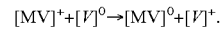

$$\Delta G° = G°([MV]^{0}) + G°([V]^{+}) - G°([MV]^{+}) - G°([V]^{0}) \quad \text{(equation 8)}$$

$$\Delta G° = -nF([MV]^{+/0} - [V]^{+/0}) \quad \text{(equation 9)}$$

therefore, $$[V]^{+/0} = \Delta G°/nF + [MV]^{+/0} \quad \text{(equation 10)}.$$

Results & Discussion

Figure 29:
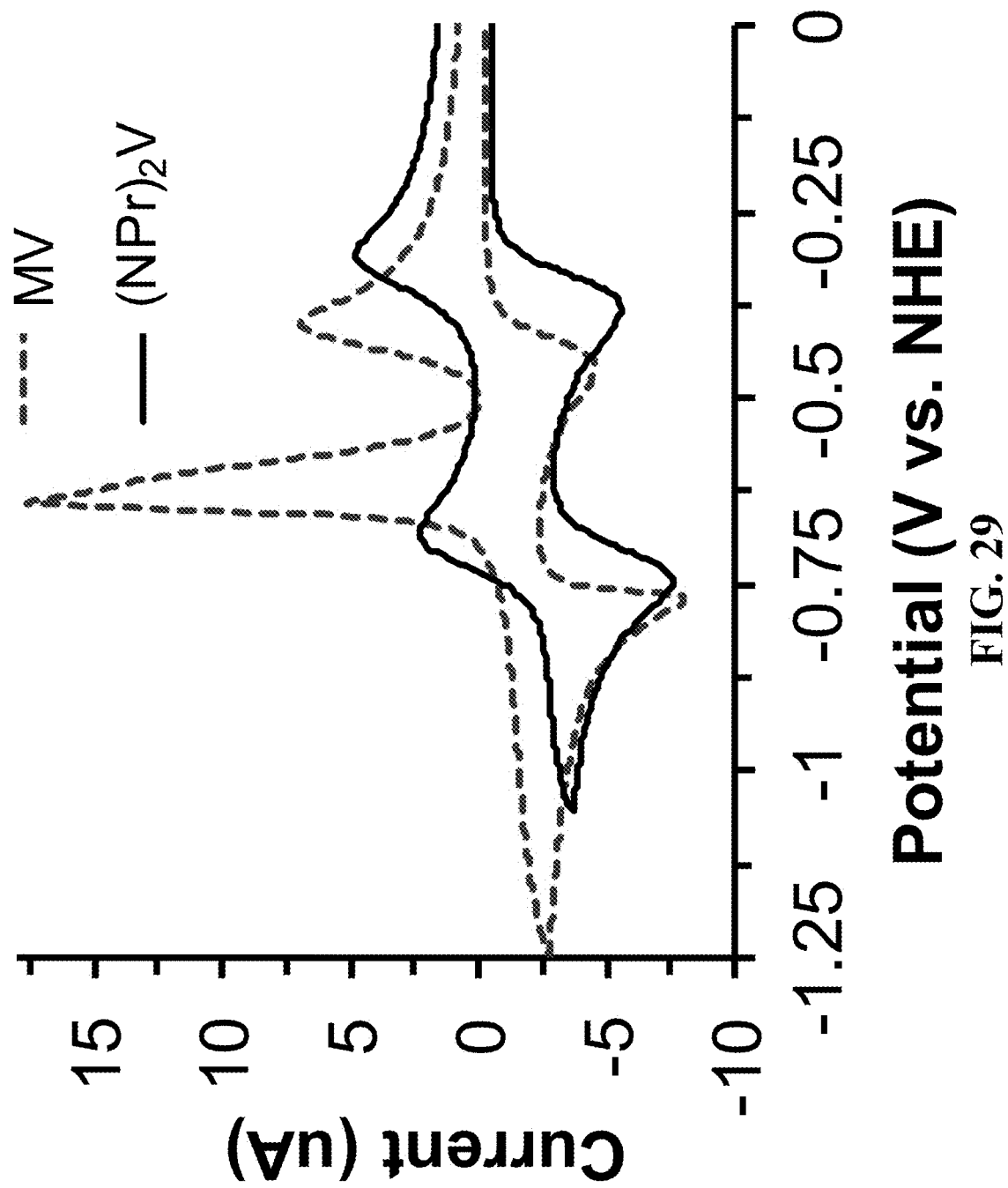
FIG. 29 shows cyclic voltammograms of MV and 1,1'-bis[3-(trimethylamonium)propyl]-4,4'-bipyridinium, tetrabromide (($NPr)_2V$). Experiment conditions: 4 mM MV or $(NPr)_2V$, 0.5 M NaCl supporting electrolyte, 100 mV/s scan rate, glassy carbon working and counter electrodes, Ag/AgCl reference electrode.

Design, Synthesis, and Electrochemical Properties of a Two-Electron Storage Viologen, (NPr)$_2$V: As mentioned above, methyl viologen (MV) via its stable MV$^{2+/+}$ redox couple functioned can perform as a high performance anode material in MV/TEMPO and MV/ferrocene AORFBs. MV is a useful candidate of the viologen class for AORFB via its solubility in H$_2$O (ca. 2.5 M in H$_2$O, above 2.0 M in 2.0 M NaCl solution), redox stability, and a highly negative redox potential at −0.45 V vs. NHE as its first redox potential. However, its second redox couple, MV$^{+/0}$ could not be utilized because of insolubility of the charge-neutral MV$^0$ state in aqueous solution. MV⁰'s insolubility manifests as deposition and stripping behaviors in the cyclic voltammogram of the second redox couple at −0.76 V (FIG. 29). The stripping behavior of the MV$^{+/0}$ redox couple is typical for viologen compounds. It was hypothesized that if the second reduction is reversible and utilized, viologen compounds could achieve two-electron storage and a more negative averaged reduction potential simultaneously.

Consequently, both improvements can contribute to boost the energy density of AORFBs. It was further hypothesized that the insolubility of MV⁰ in the aqueous NaCl electrolyte is ascribed to its charge neutrality and thus a decreased molecular polarity/hydrophilicity. To overcome the solubility issue of the MV⁰ oxidation state, it was attempted to increase the hydrophilicity of the MV⁰ state using a more hydrophilic functional group to replace the methyl group on the N atoms. To this end, 1,1'-bis[3-(trimethylaminium)propyl]-4,4'-bipyridinium tetrabromide ((NPr)$_2$V) was synthesized, a viologen exhibiting a hydrophilic ammonium functional group on each pendant arm by combining 4,4'-bipyridine and (3-bromopropyl)trimethylammonium bromide (see Scheme 4a). The reaction was conducted in DMSO at 100° C. and stirred for 3 h to produce (NPr)$_2$V as white-yellow powder precipitates. The synthesis of (NPr)$_2$V was demonstrated up to a 10 g scale with a moderate isolated yield of 70%. The structure and purity of (NPr)$_2$V was characterized by 41 NMR, UV-Vis, and elemental analysis (FIGS. 34, 49, and 50).

bility of the two-electron reduced [(NPr)$_2$V]$^{2+}$ state (FIG. 29). The two reductions of (NPr)$_2$V were observed at −0.35 V vs NHE and −0.72 V vs NHE. Further, scan rate dependence studies indicated that both redox of (NPr)$_2$V are diffusion controlled processes (FIG. 43). (NPr)$_2$V has relatively lower solubility in aqueous solution compared to MV (2.5 M, see Table 1 below), but (NPr)$_2$V's ability to store two electron's per molecule, i.e. 3.2 mole electron per liter and equivalent to 85.7 Ah/L charge capacity, places it among the most energy dense organic anolytes currently available. In addition, its lower effective redox potential −0.54 V (the average of −0.35 and −0.72 V) than MV (−0.45 V) can further increase the energy density of AORFBs when paired with a same catholyte.

To better investigate this compound as an anolyte candidate in an AORFB, its electrochemical kinetics were investigated using linear sweep voltammetry with a glassy carbon rotating disk electrode. LSV plots, derived Levich plots and Tafel plots for (NPr)$_2$V are shown in FIG. 44. Two linear Levich plots (FIG. 44B) were constructed for the two reductions of (NPr)$_2$V using limiting currents (FIG. 44A) and the square root of rotation speeds. The corresponding slopes from the linear relationships were transformed using the Levich equation to calculate the diffusion coefficients for (NPr)$_2$V: $3.88 \times 10^{-6}$ and $3.84 \times 10^{-6}$ cm$^2$/s for the 1$^{st}$ and 2$^{nd}$ electron reductions, respectively. (NPr)$_2$V shows no significant change in diffusion coefficient between the first and Scheme 4 (as shown above). Synthesis of Viologens

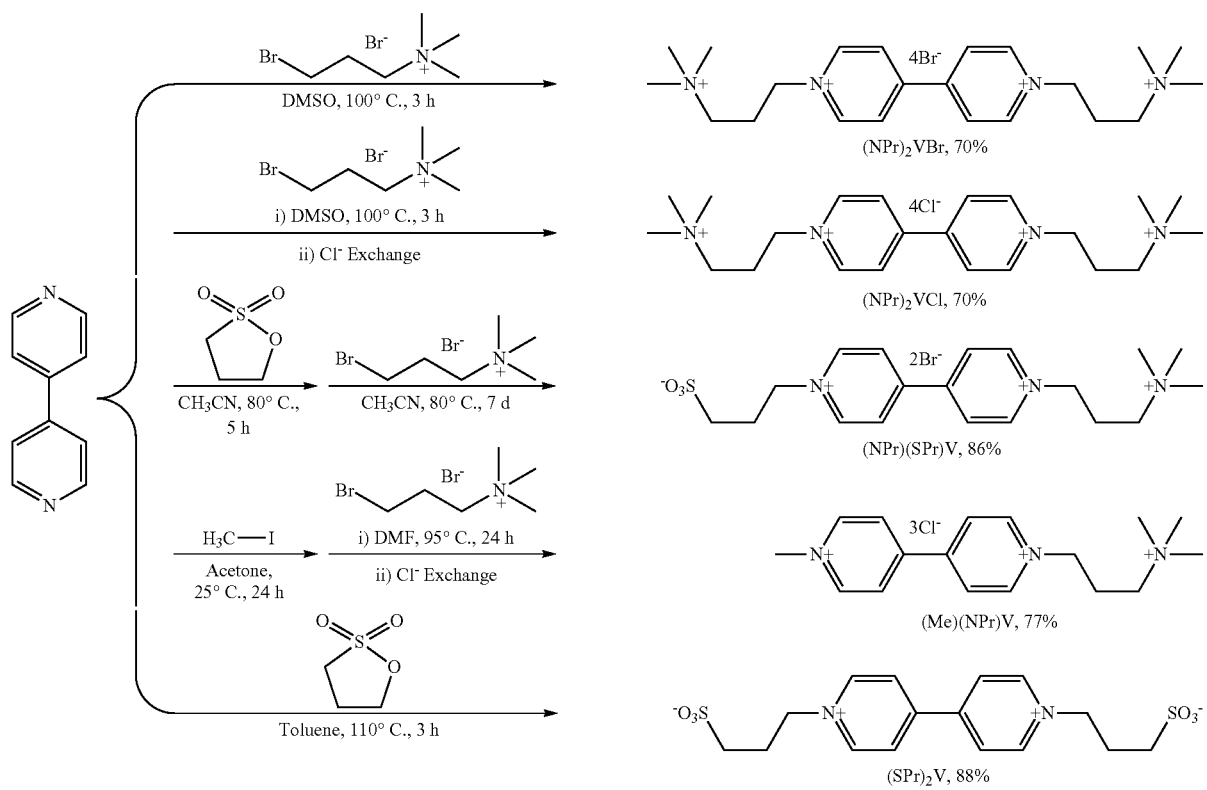

The highly charged ionic (NPr)$_2$V exhibited high solubility in H$_2$O (1.6 M), and more importantly, cyclic voltammetry studies showed both redox couples [(NPr)$_2$V]$^{4+/3+}$ and [(NPr)$_2$V]$^{3+/2+}$ were fully reversible, confirming the solusecond reduction, suggesting a comparable molecular size of [(NPr)$_2$V]$^{4+}$ and [(NPr)$_2$V]$^{3+}$. Furthermore, plots of overpotential versus the logarithm of kinetic current (FIGS. 44C and 44D) and corresponding Tafel plots were constructed to calculate the rate constants for the electron transfers of (NPr)$_2$V, 4.32×10$^{-6}$ for the 1$^{st}$ reduction and 2.46×10$^{-6}$ cm/s for the 2$^{nd}$ reduction.

Flow Battery Studies of (NPr)$_2$V: The two-electron storage capability of (NPr)$_2$V was examined using redox flow battery tests. To match the high charge capacity of (NPr)$_2$V, a highly water soluble compound was identified, [FcN$^{Et}$]Br (FIG. 30A) as the catholyte material (3.75 M and 100.5 Ah/L in water). Cyclic voltammetry data were collected on a mixture of (NPr)$_2$V and [FcN$^{Et}$]Br to determine the cell voltage: −0.35 V and −0.72 V vs. NHE for (NPr)$_2$V and 0.60 V vs. NHE for [FcN$^{Et}$]Br (FIG. 30B). The three redox potentials observed for (NPr)$_2$V and [FcN$^{Et}$]Br are suitably distanced from the onset potentials for the hydrogen and oxygen evolution reactions at neutral pH (FIG. 30B). These onset potentials delineate the traditional voltage extrema for designing neutral aqueous redox flow batteries. Aqueous battery systems should strike a balance between maximizing voltage, while avoiding these energy-wasting side reactions. As (NPr)$_2$V undergoes two distinct reductions at two different potentials both with favorable kinetics, a battery constructed with (NPr)$_2$V can take advantage of either or both of these single-electron reductions. Based on the solubility of these new electrolytes, (NPr)$_2$V and [FcN$^{Et}$]Br have impressive theoretical capacities of 85.8 Ah/L and 100.5 Ah/L respectively. When utilizing only the first redox couple of (NPr)$_2$V paired with [FcN$^{Et}$]Br, the battery would have an energy density of 28.5 Wh/L at a 0.95 V cell voltage. Utilizing only the second higher voltage redox couple of (NPr)$_2$V, the battery would have an energy density of 39.6 Wh/L at 1.32 V. Operating the battery utilizing both redox couples would have an energy density of 68.1 Wh/L at a cell voltage of 1.14 V, which represents the highest theoretical energy density known for aqueous organic redox flow batteries.

Figure 30A:
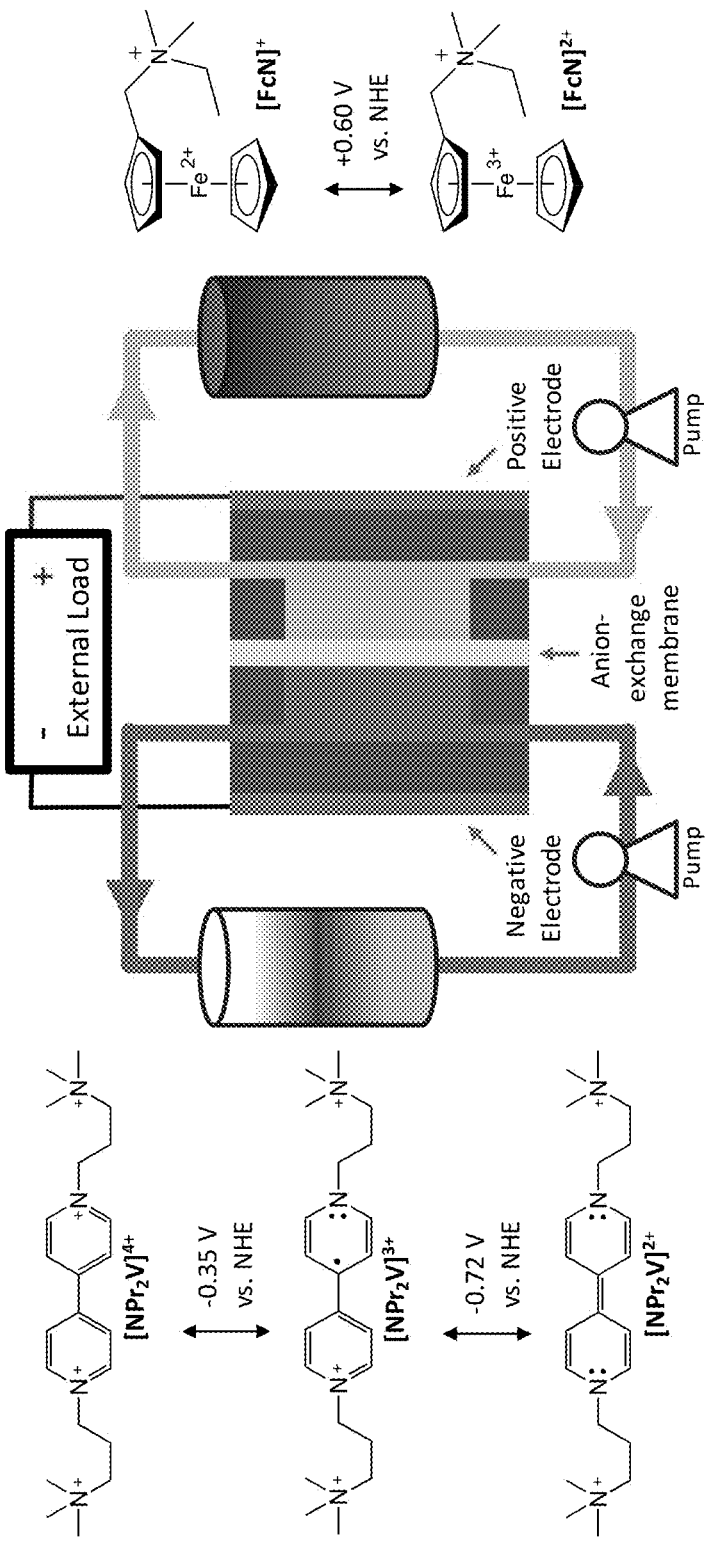
FIGS. 30(A) and 30(B) show the design of a $(NPr)_2V/[FcN^{Et}]Br$ AORFB and electrochemical data of $(NPr)_2V$ and (ferrocenylmethyl)ethyldimethylammonium bromide ($[FcN^{Et}]Br$) catholyte.
Figure 30B:
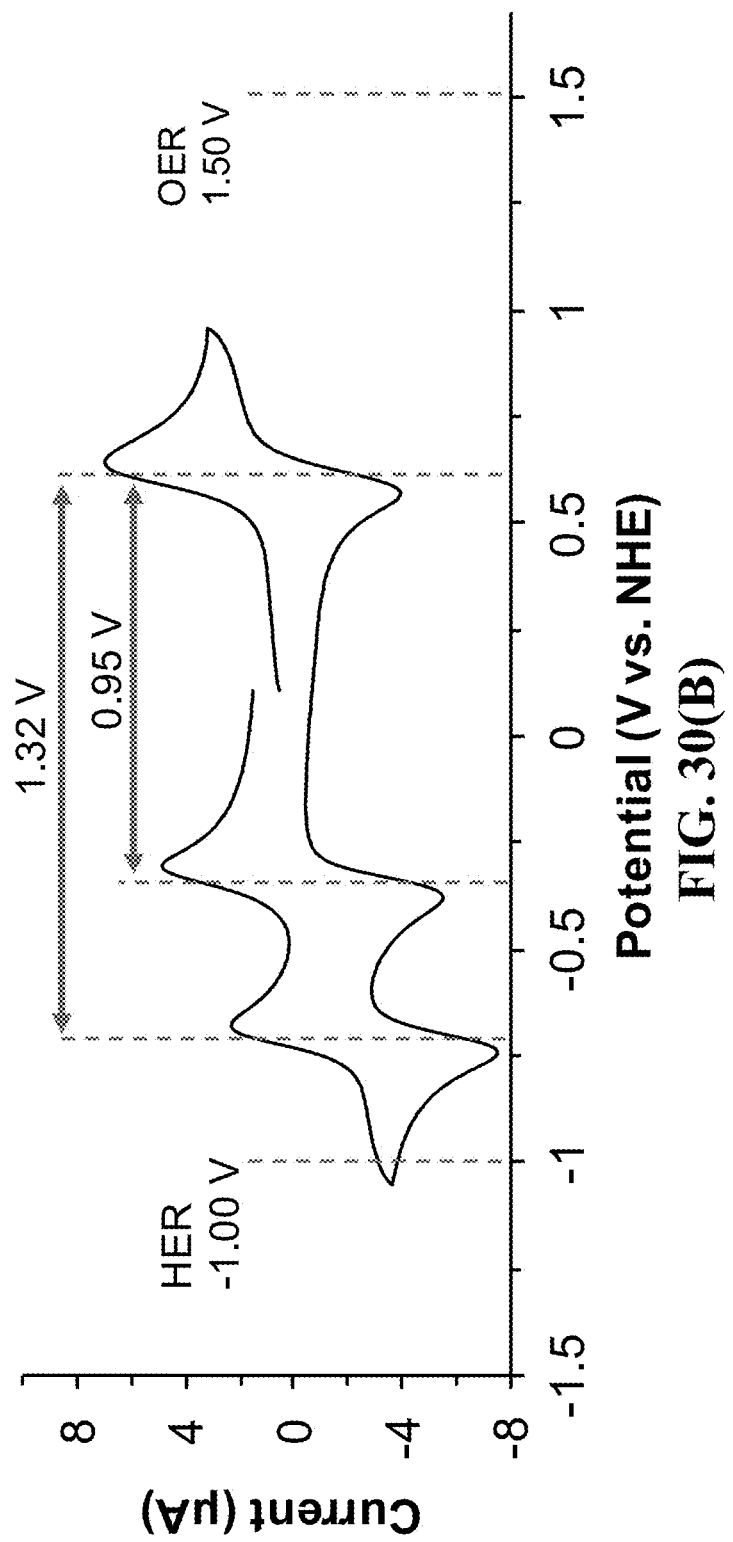

A flow cell was constructed using 0.25 M (NPr)$_2$V and 0.5 M [FcN$^{Et}$]Br in 2.0 M NaCl supporting electrolyte, as shown in FIG. 30A. Both active materials are cationically charged, so a sheet of anion-exchange membrane (AMV, Selemion) was employed for selective Cl charge transfer. Taking advantage of both redox couples of (NPr)$_2$V, the cell was galvanostatically charged and discharged between 1.8 V and 0.1 V. In this configuration, the cell had a capacity of 13.4 Ah/L, and an energy density of 7.8 Wh/L.

Figure 31A:
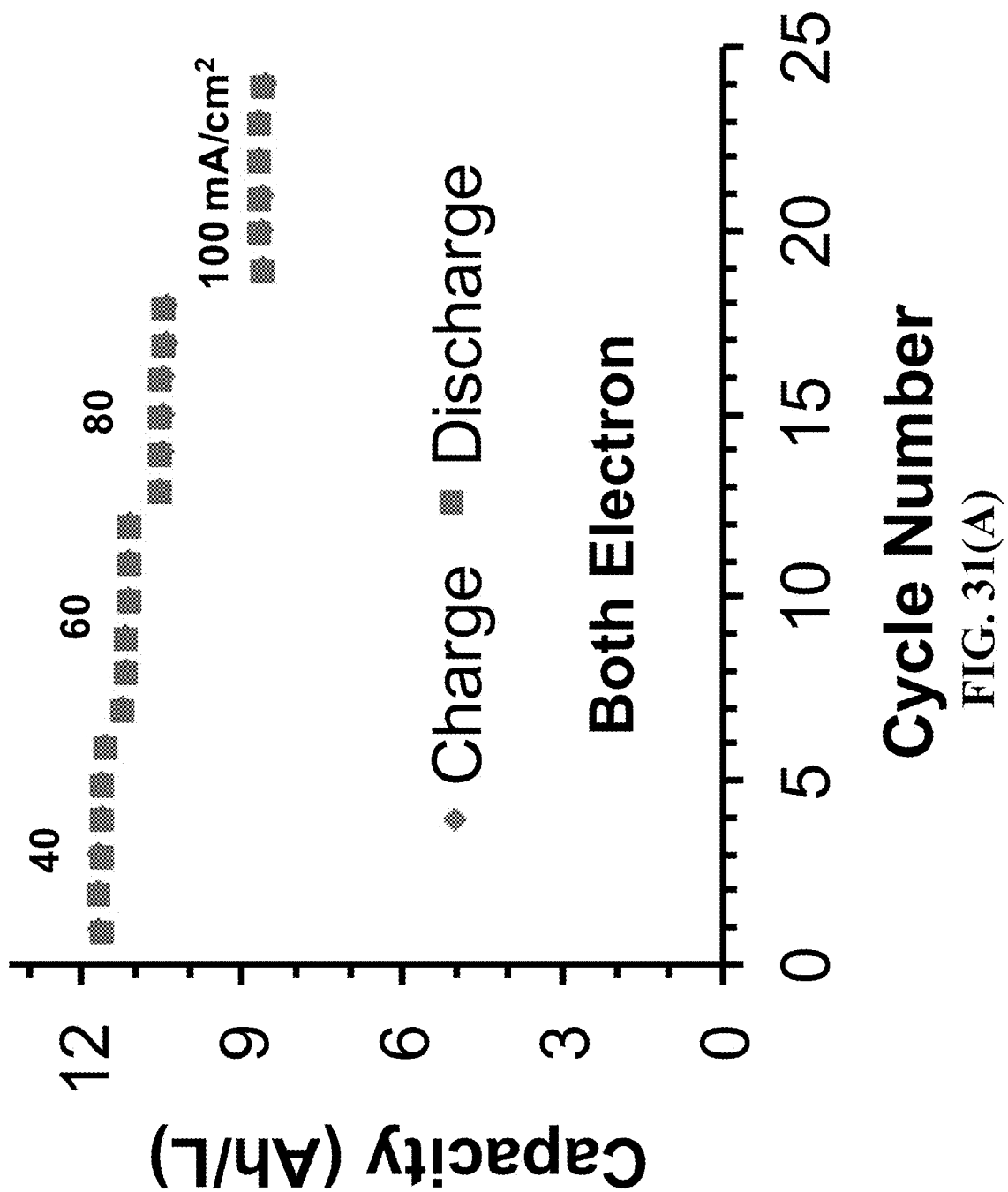
Figure 31B:
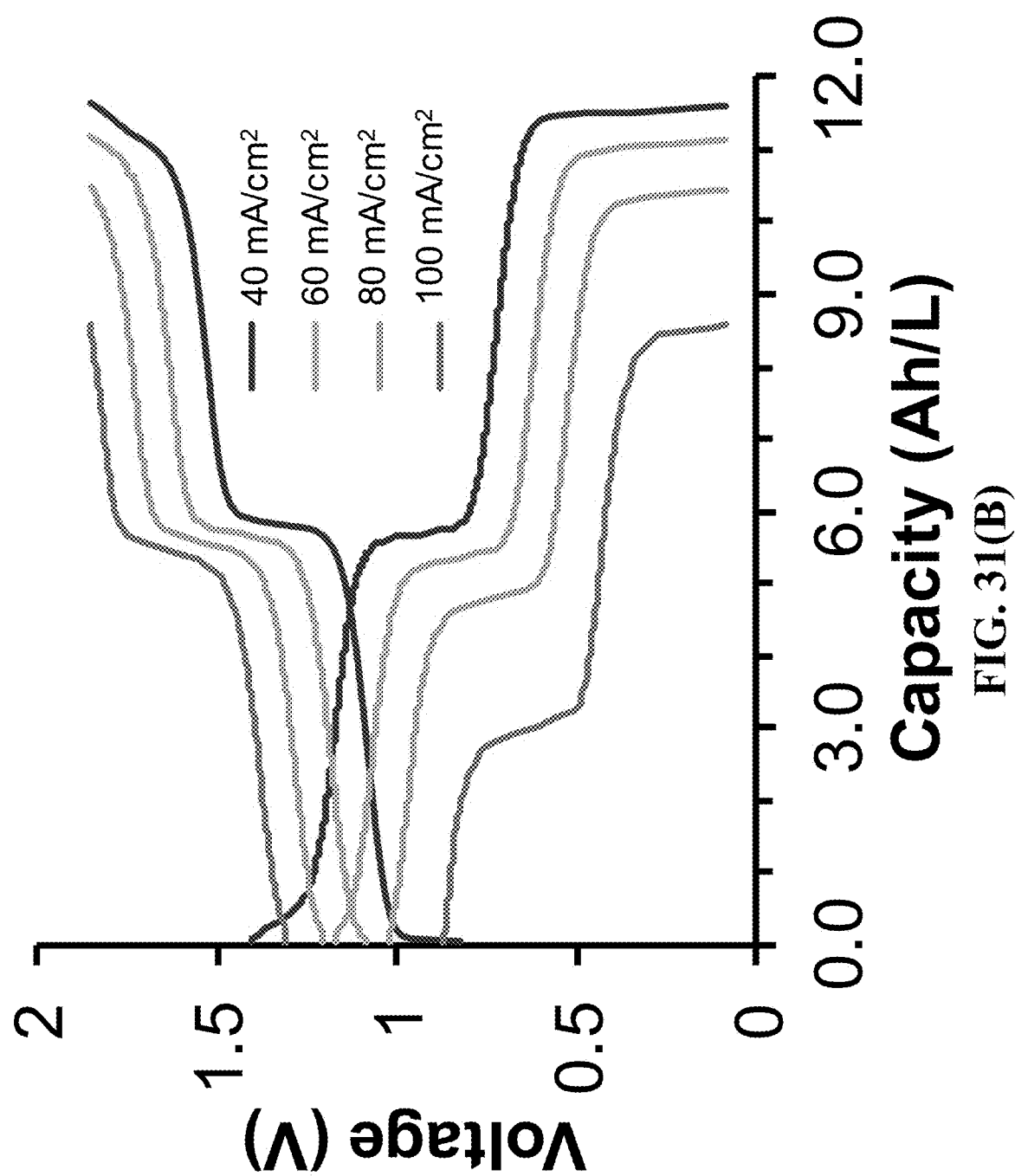
Figure 31C:
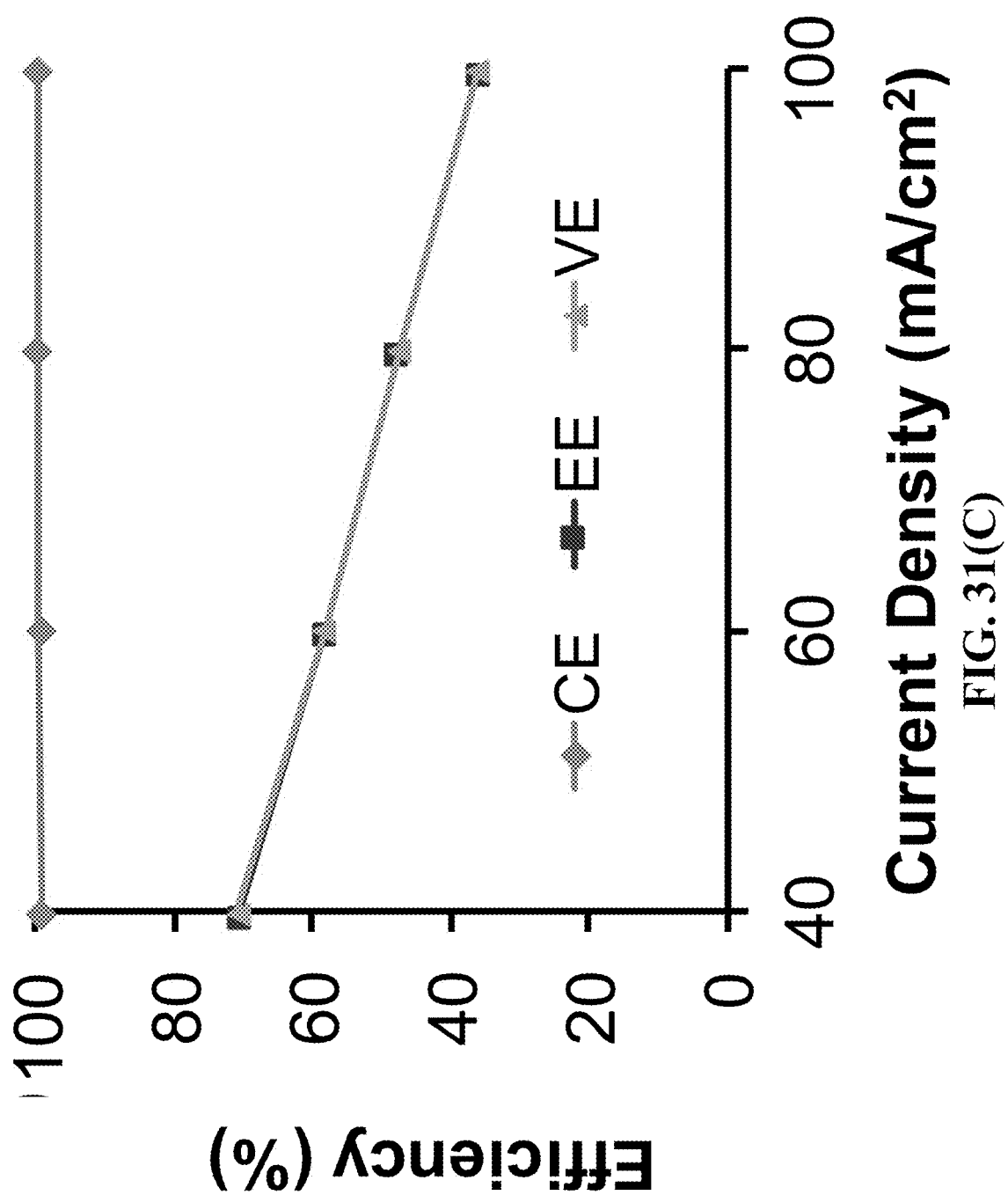
Figure 31D:
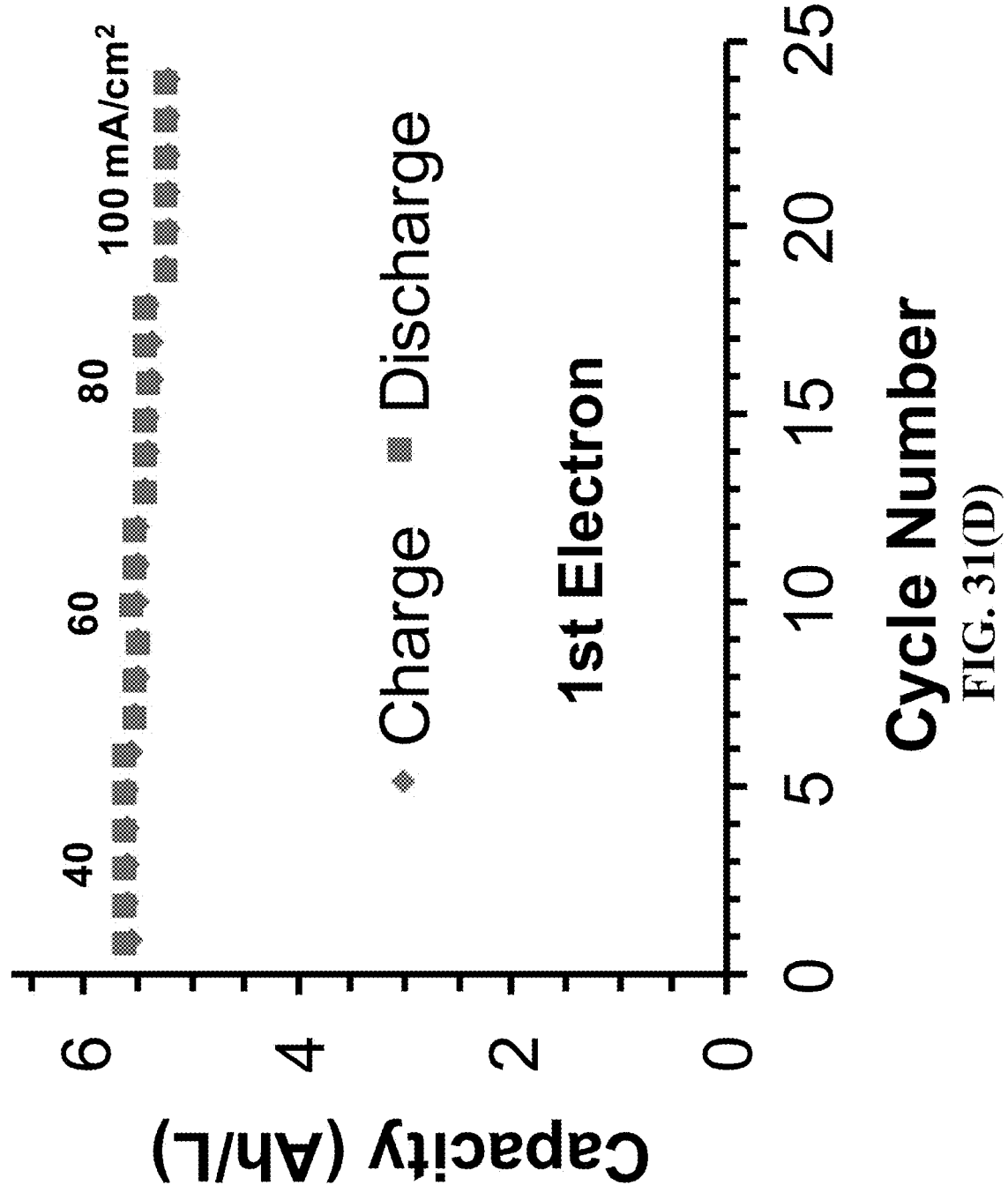
Figure 31E:
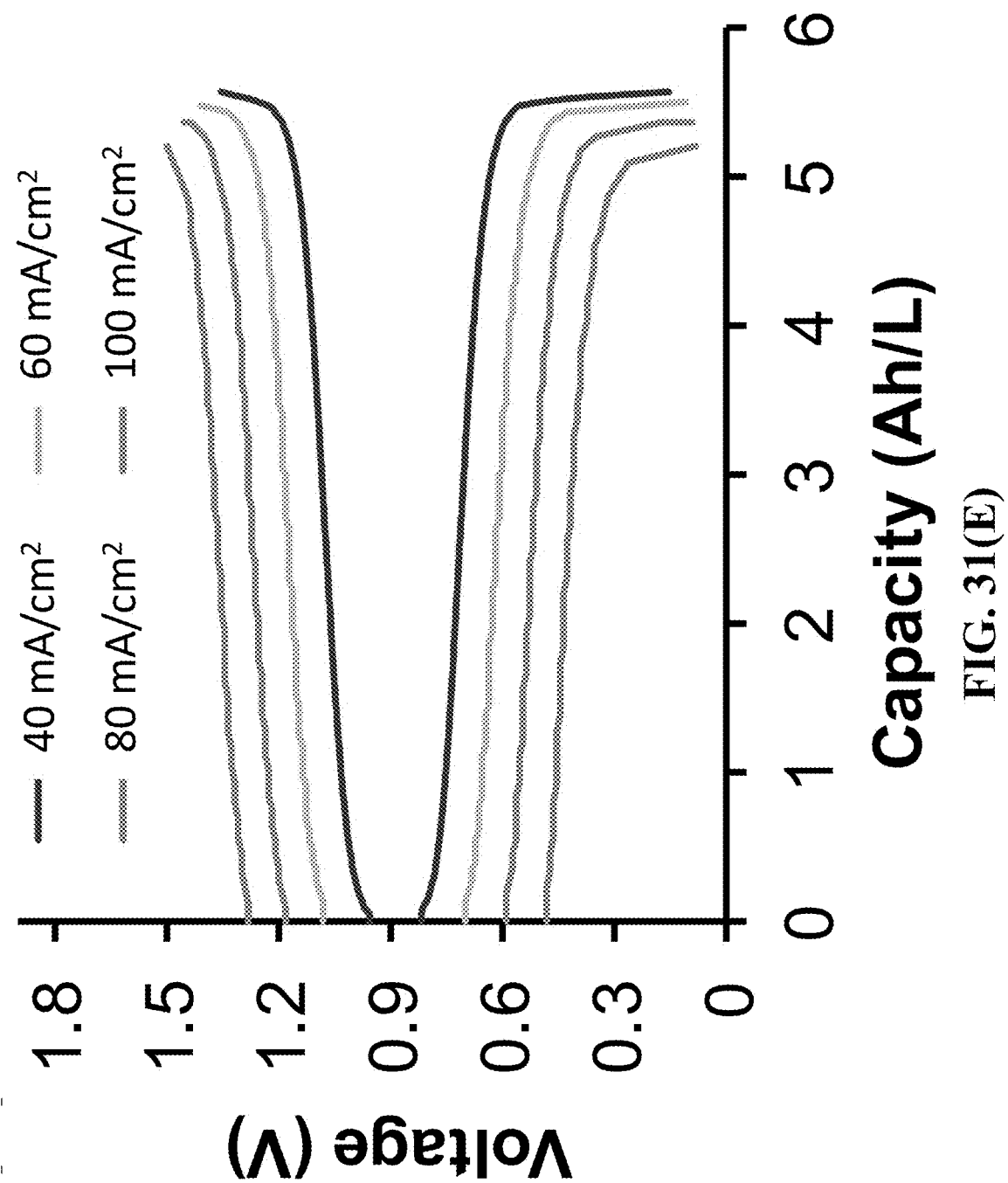
Figure 31F:
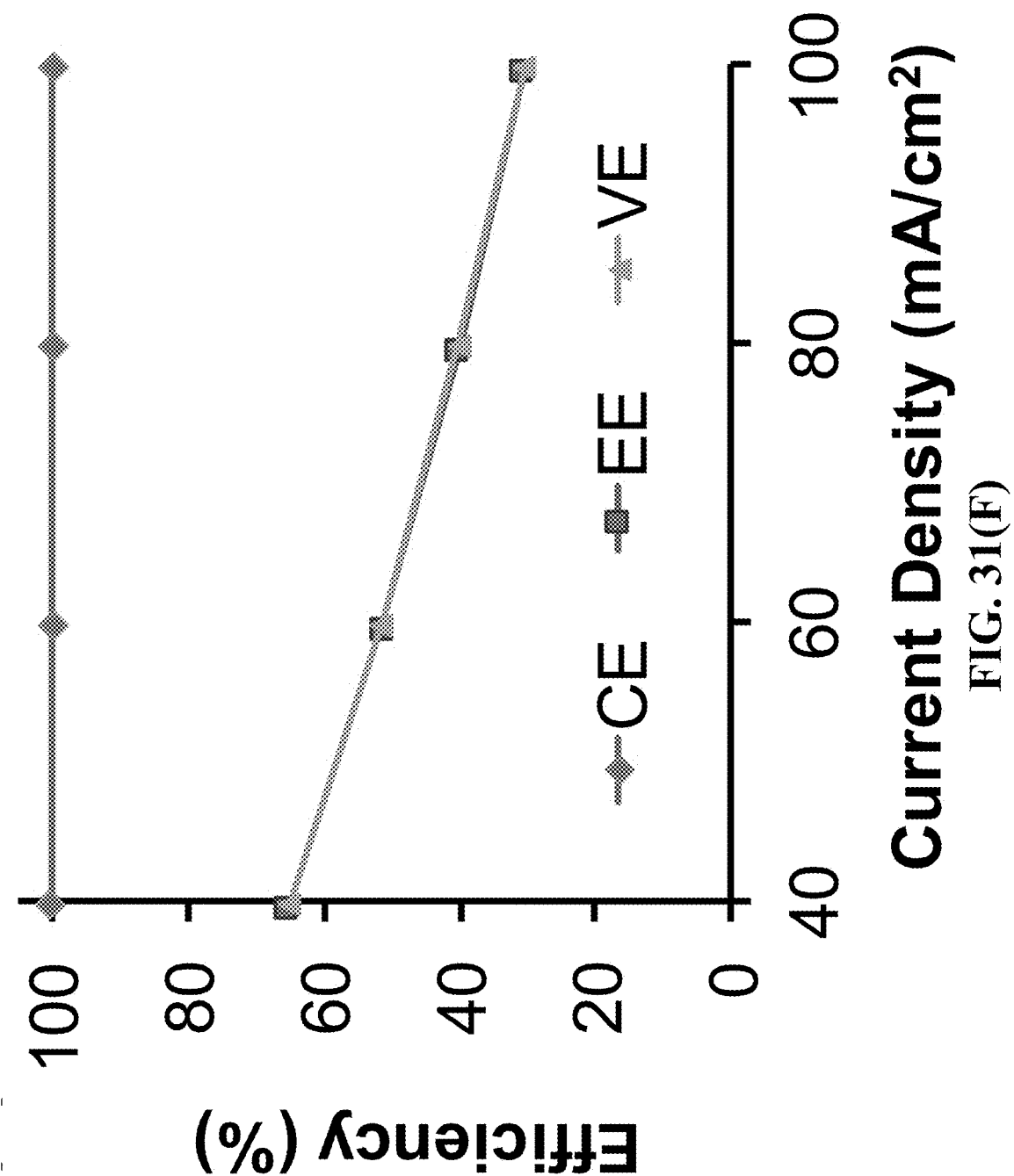
Figure 31G:
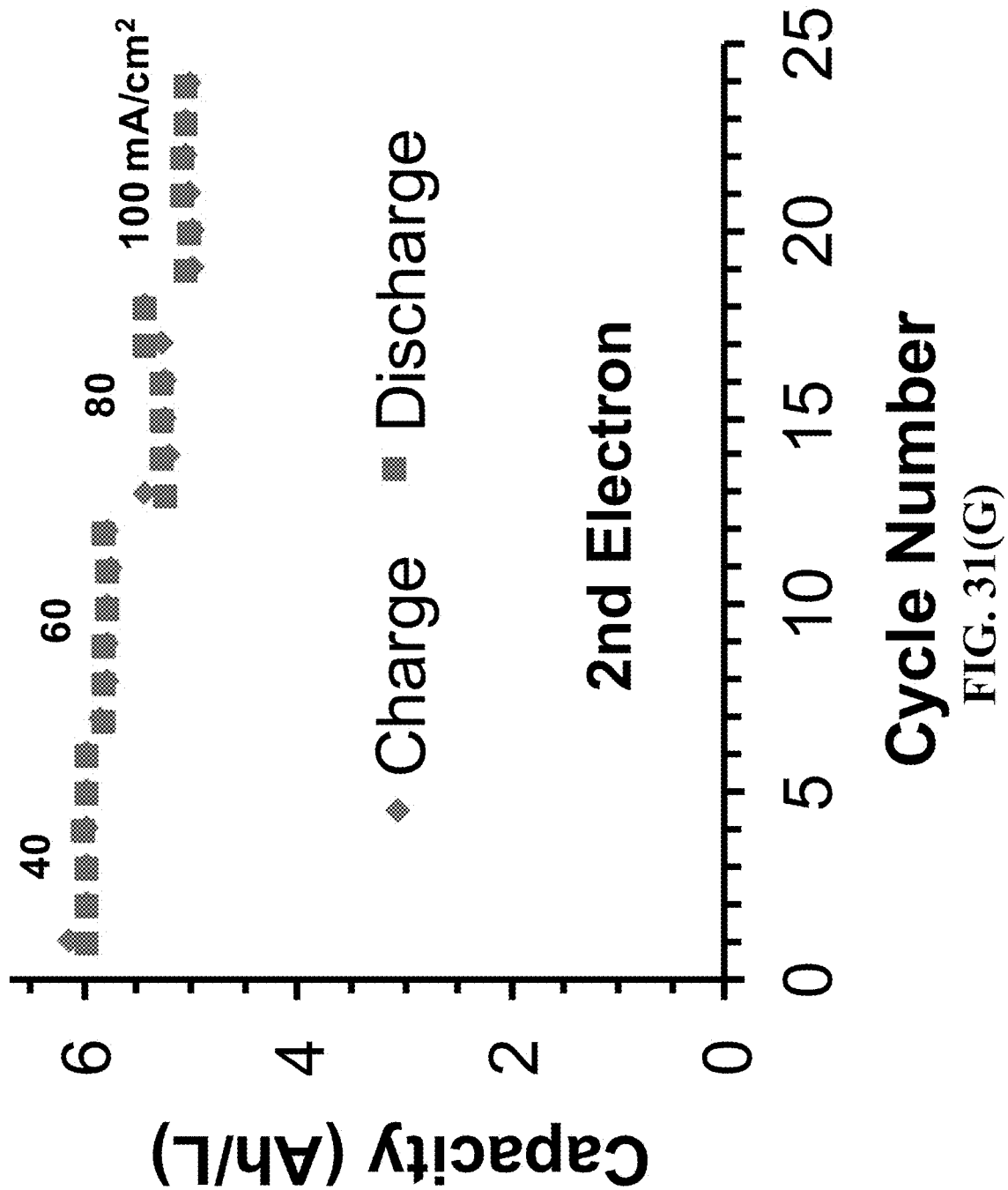
Figure 31H:
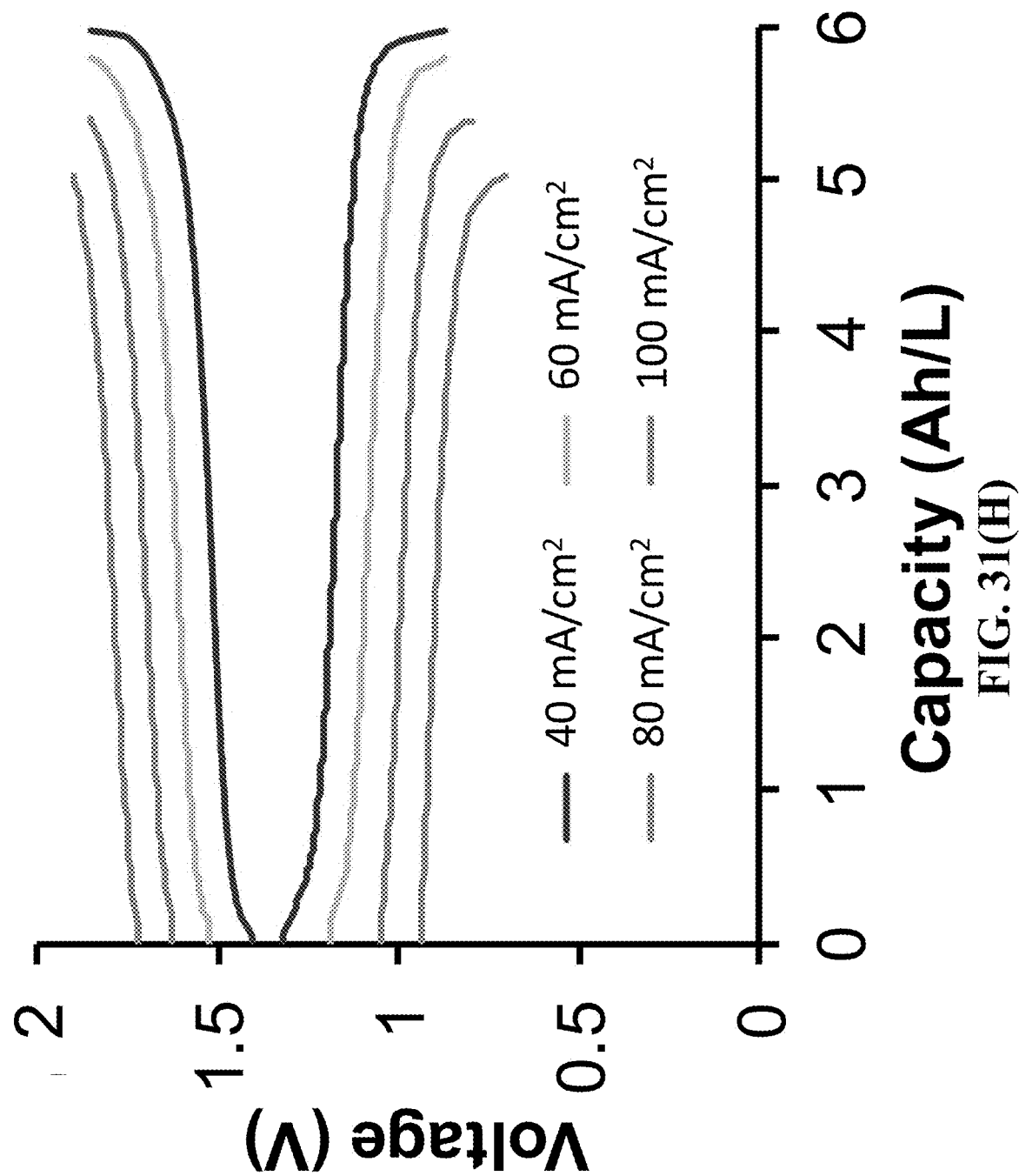
Figure 31I:
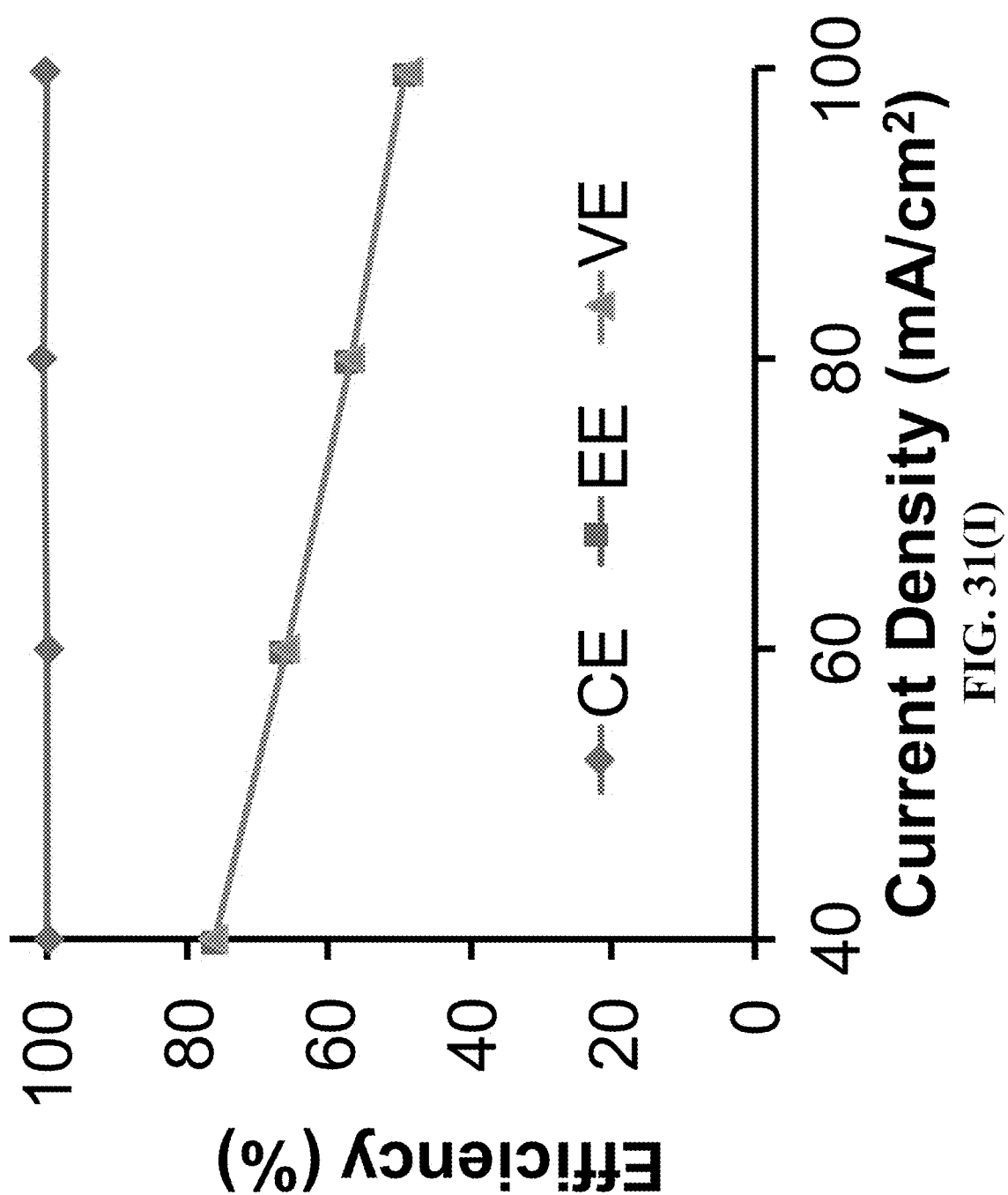

The rate performance of the battery was tested by operating at increasing current densities from 40 mA/cm$^2$ to 100 mA/cm$^2$ at increments of 20 mA/cm$^2$ (FIG. 31A-C). The battery was cycled 6 times at each current density to ensure consistent data. Owing to the two distinctive redox processes of (NPr)$_2$V, each cycle consisted of two charge plateaus and two discharge plateaus (FIG. 31B). For each current density, capacity remained nearly constant (FIG. 31A). The observed capacity of the cell decreased with increasing current density due to increased ohmic loss within the cell and decreased cycling time (FIG. 31A). Compared to 40 mA/cm$^2$, capacity retention was 96% at 60 mA/cm$^2$, 90% at 80 mA/cm$^2$, and 74% at 100 mA/cm$^2$ (FIG. 31A). Similarly, the energy efficiency and the voltage efficiency decreased linearly with increasing current density from 70% at 40 mA/cm$^2$ to 36% at 100 mA/cm$^2$ (FIG. 31C). The coulombic efficiency remained above 99% for all tests. The state of charge for this cell was simple to visualize thanks to distinct color changes (see FIG. 30A) in the electrolyte solution during the cycling process. The anode solution was nearly colorless at full discharge, very deep blue at 50% charge ($\lambda_{max}$ 601 nm, see FIG. 49 for UV-vis spectra), and yellow-brown at 100% charge ($\lambda_{max}$ 410 nm).

The cathode solution changed from yellow-orange at full discharge ($\lambda_{max}$ 452 nm), to deep blue-green at full charge ($\lambda_{max}$ 630 nm). The radical nature of the one-electron reduced state, [(NPr)$_2$V]$^{3+}$ (S=½, g=2.0064) was confirmed by an EPR study (FIG. 50).

The long-term stability of this system was measured by operating the battery at 60 mA/cm$^2$ for 100 cycles using the two-electron process for (NPr)$_2$V (FIG. 31J). The coulombic efficiency remained above 99% throughout testing, and the battery showed impressive 99.96% capacity retention per cycle. The two charge plateaus occur near 1.2 V and 1.6 V, while the two discharge plateaus occur near 1.1 and 0.6 V. A graph of representative battery cycles versus time is shown in FIG. 51 which further emphasizes the stability of the (NPr)$_2$V/[FcN$^{Et}$]Br system.

To investigate how each redox process affects the battery performance, the (NPr)$_2$V/[FcN$^{Et}$]Br cell was operated with restricted charge and discharge cutoff voltages (FIG. 31D-I). By limiting the voltage range of 0.1 V to 1.35 V, the cell was tested using the lower voltage redox couple of (NPr)$_2$V from 40 mA/cm$^2$ to 100 mA/cm$^2$. At four current densities, this lower-voltage cell showed lower energy efficiency compared to the full two-electron system. For instance, just 53% energy efficiency was observed at 60 mA/cm$^2$. With the cycling voltage between 0.85 V and 1.8 V, the cell using the higher voltage showed higher energy efficiency, nearly 70% at a current density of 60 mA/cm$^2$. The observation also applies to the voltage efficiency. The energy efficiency of the two-electron process is right about the average of the energy efficiency of two individual one-electron processes. The results indicated that the first electron process is a limiting step for the battery energy efficiency. Further studies using electrochemical impedance spectroscopy revealed that the second electron process with higher energy efficiency was attributed to a lower area specific resistance than that of the first electron process. Specifically, at 25% and 75% state of charge corresponding to the first electron and second electron processes, the area specific resistances were recorded as ca. 4.8 and 5.0 Ω·cm$^2$, respectively (see Nyquist plots in FIG. 52).

Computational Prediction and Experimental Verification of New Two Electron Storage Viologens: To expand the concept of two-electron storage viologens, a number of designed two-electron storage viologen candidates (as shown below) were surveyed using DFT calculations to predict their redox potentials.

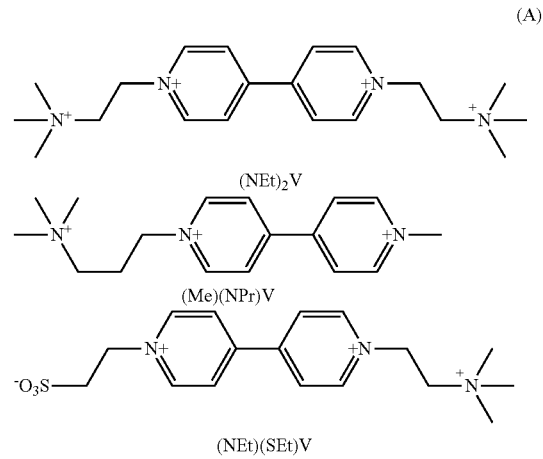

(A)

(NEt)$_2$V (Me)(NPr)V (NEt)(SEt)V

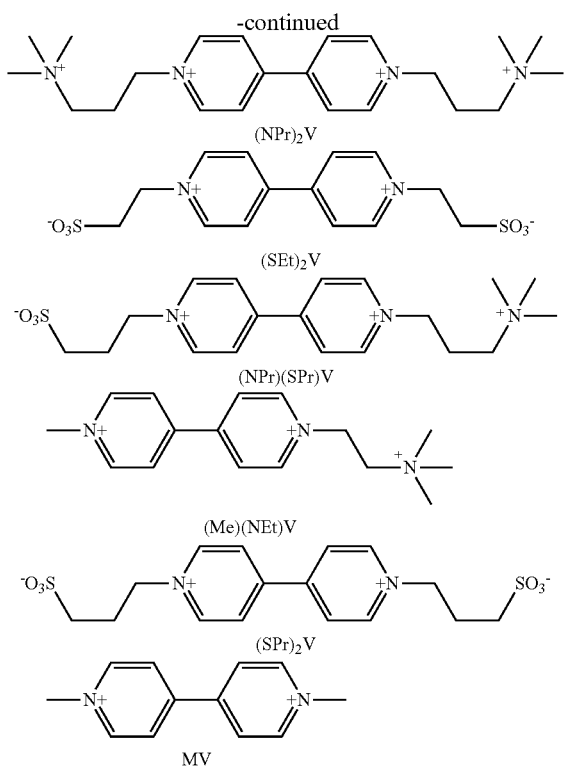

These candidates were designed with at least one polar N-substituent, and a varied substituent on the second N atom. DFT calculations were conducted using M06-2× functional and 6-31+G(d) bases sets with the SMD solvation model. For all candidates, the ground state structure was optimized for the initial oxidation state, one-electron reduced oxidation state, and two-electron reduced oxidation state. The redox potentials of the first and second redox couples (designated as $[V]^{2+/+}$ and $[V]^{+/0}$, respectively) of the candidates were calculated using equations 5-10 by referencing to the experimental values of $MV^{2+/+}$ and $MV^{+/0}$. The predicted redox potentials are plotted in FIG. 42. $[(NEt)_2V]^{4+}$ with two NEt electron-withdrawing substituents has the most positive predicted redox potentials at −0.22 and −0.54 V vs. NHE for the first and second reductions respectively. $(SPr)_2V$ has the most negative predicted redox potential values at −0.46 and −0.74 V vs. NHE, comparable to those of MV. Viologens with mixed substituents possess negative redox potential values in between. The calculated redox potentials (−0.33 and −0.64 V vs. NHE) of $(NPr)_2V$ match well with the experimental (−0.35 V and −0.72 V), giving only 80 mV difference for the more negative redox couple.

TABLE 1

A summary of physical and chemical properties of MV, $(NPr)_2V$, (NPr)(SPr)V, (Me)(NPr)V and $(SPr)_2V$: solubility in water, [C]; charge capacity, CC; redox potentials, experimental and calculated $E_{1/2}$ (V vs. NHE); diffusion constants, D, and electron transfer rate constants, $k^0$.

| Compounds | [C] (mol/L) | CC (Ah/L) | Exp. $E_{1/2}$ (Calc.) | D (cm²/s) | $k^0$ (cm/s) |
|---|---|---|---|---|---|
| MV | 2.5 | 67.0 | −0.45 | 2.57 × 10⁻⁵ | 2.8 × 10⁻⁴ |
| $(NPr)_2V$ | 1.6 | 85.8 | −0.35 (−0.33) | 3.88 × 10⁻⁶ | 4.32 × 10⁻⁵ |
| | | | −0.72 (−0.64) | 3.84 × 10⁻⁶ | 2.46 × 10⁻⁵ |
| (NPr)(SPr)V | 1.6 | 85.8 | −0.37 (−0.36) | 4.96 × 10⁻⁶ | 3.50 × 10⁻⁵ |
| | | | −0.74 (−0.72) | 5.04 × 10⁻⁶ | 2.09 × 10⁻⁵ |
| (Me)(NPr)V | 1.8 | 96.5 | −0.39 (−0.34) | 5.40 × 10⁻⁶ | 2.39 × 10⁻⁵ |
| | | | −0.78 (−0.73) | 5.29 × 10⁻⁶ | 1.84 × 10⁻⁵ |
| $(SPr)_2V$ | 2.0 | 107.2 | −0.43 (−0.46) | 3.26 × 10⁻⁶ | 1.49 × 10⁻⁵ |
| | | | −0.79 (−0.73) | 2.81 × 10⁻⁶ | 3.96 × 10⁻⁵ |

To further verify the DFT prediction, we prepared 1'-[3-(trimethylaminium)propyl]-4'-pyridinium-1-[3-sulfonatopropyl]-4-pyridinium dibromide, (NPr)(SPr)V, 1'-methyl-4'-pyridinium-1-[3-(trimethylaminium)propyl]-4-pyridinium trichloride, (Me)(NPr)V, and 1,1'-bis[3-sulfonatopropyl]-4,4'-bipyridinium, $(SPr)_2V$, in good yields (Scheme 4B-D as shown above). $(NEt)_2V$ and (NEt)(SEt)V were also prepared. Cyclic voltammetry studies confirmed that (NPr)(SPr)V, (Me)(NPr)V and $(SPr)_2V$ demonstrated two successive fully reversible redox waves (FIG. 41). (NPr)(SPr)V exhibited two reversible reduction events at −0.37 V and −0.74 V (FIG. 41B and Table 1). (NPr)(SPr)V has a solubility of 1.6 M in $H_2O$, and thus can provide 3.2 mole electron/L or 85.8 Ah/L charge capacity. (Me)(NPr)V exhibited reductions at −0.39 and −0.78 V with a solubility of 1.8 M, and charge capacity of 96.5 Ah/L. $(SPr)_2V$ undergoes reversible reductions at −0.43 V and −0.79 V (FIG. 41D and Table 1). Even as a neutral compound, the solubility of $(SPr)_2V$ is 2.0 M in $H_2O$. $(SPr)_2V$ can provide 4.0 mole electron/L or 107 Ah/L charge capacity. As can be seen from FIG. 42 and Table 1, the experimental redox potentials of the synthesized viologens match very well with their calculated values. The largest potential discrepancy between the experimental and calculated values is only 80 mV. The excellent agreement highlights the applicability of the adopted DFT model to predict the redox potentials of viologen compounds.

Diffusion constants and electron transfer rate constants for (NPr)(SPr)V, (Me)(NPr)V, and $(SPr)_2V$ (see FIG. 45-47) are summarized in Table 1. These compounds exhibit faster diffusion and have larger rate constants than most inorganic compounds and are on par with organic compounds applied in ARFBs. Regarding the physical and chemical properties of (NPr)(SPr)V, (Me)(NPr)V, and $(SPr)_2V$, they are all promising anolyte candidates for AORFBs. It is worth noting that $(NPr)_2V$ and (Me)(NPr)V, when paired with a TEMPO catholyte, can deliver a cell voltage more than 1.5 V. $(SPr)_2V$ holds a potential as an anolyte material in an AORFB employing a cation exchange membrane.

In summary, functionalization of 4,4'-bypyridine with hydrophilic substituents offers opportunities to develop new two-electron storage viologen compounds with low reduction potential and high charge capacity for AORFBs that are among the most energy dense organic anolyte materials. Synthesis of these viologen compounds are convenient from the bis-alkylation of 4,4'-bypyridine with commercially available alkylation reagents. Paired with a selected water soluble ferrocene catholyte, 1,1'-bis[3-(trimethylaminium) propyl]-4,4'-bipyridinium, tetrabromide $((NPr)_2V)$ demonstrated rather stable AORFB performance. A reliable DFT model was also developed to accurately predict the redox potentials of viologen compounds. The presented synthetic and computational chemistry have opened a new avenue of viologen derivatization to build neutral AORFBs with high voltage and high energy density.

Example 9. Synthesis and Characterization of 1,1'-bis[(3, 5,-bisulfonato-4-hydroxyphenyl) methyl]-4,4'-Bipyridinium (S4V)

Scheme 5 (as shown above). The synthesis route for S4V.

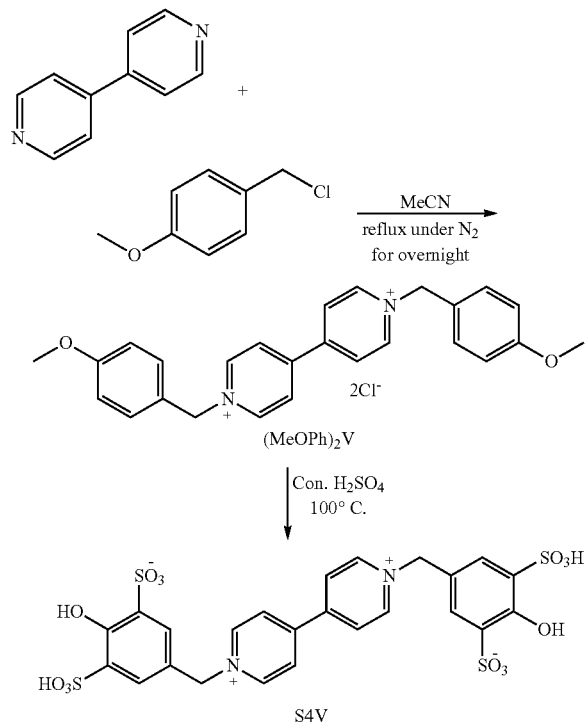

Synthesis of (MeOPh)$_2$: The titled compound was synthesized by refluxing 4,4'-bpy (1.56 g, 10 mmol, 1.0 eq.) with 4-methoxybenzyl chloride (3.90 g, 25 mmol, 2.5 eq.) in 30 mL MeCN under N$_2$ atmosphere for overnight. When the reaction mixture was cooled down to room temperature, filter and wash with CH$_2$Cl$_2$ (10 mL×3) to get the product as light yellow powder (4.30 g, 92% yield). $^1$H NMR (D$_2$O, 500 MHz, ppm): δ 3.78 (s, 6H), 5.78 (s, 4H), 7.03 (d, J=10.0 Hz, 4H), 7.44 (d, J=10.0 Hz, 4H), 8.43 (d, J=5.0 Hz, 4H), 9.04 (d, J=5.0 Hz, 4H).

Synthesis of S4V: The titled compound was synthesized by heating the (MeOPh)$_2$V (2.0 g) in concentrated H$_2$SO$_4$ (30 mL) for 10 days. When the reaction mixture was cooled down to room temperature, the reaction mixture was diluted to 100 mL by DI-H$_2$O. Saturated NaHCO$_3$ aq. solution was added to neutralize the solution under 0° C. Water was removed under vacuum to obtain the mixture of product and inorganic salt. DMSO (5 mL) was added to dissolve the organic product and filtration was conducted to remove the inorganic salt. The filtrate was poured into 50 mL acetone, white precipitate generated immediately. The product was obtained after filtration and vacuum dry (1.41 g, 48% yield). $^1$H NMR (D$_2$O, 500 MHz, ppm): δ 5.83 (s, 4H), 7.95 (s, 4H), 8.45 (s, 4H), 9.07 (s, 4H). CV analysis of S4V can be seen in FIG. 54.

Example 10. Neutral Aqueous Viologen-Based Redox Flow Batteries with Cation Exchange Mechanism In this example, a neutral viologen AORFB operating in a cation charge transfer mechanism (FIG. 58). The new design is demonstrated with a sulfonate functionalized viologen (1,1'-bis[3-sulfonatopropyl]-4,4'-bipyridinium, (SPr)$_2$V) anolyte and enables the use of low cost inorganic redox active catholyte materials such as K$_4$[Fe(CN)$_6$] and KI. The demonstrated (SPr)$_2$V/K$_4$[Fe(CN)$_6$] AORFB delivered outstanding battery performance including 71% energy efficiency at 60 mA/cm$^2$ and 99.96% capacity retention per cycle for 300 cycles. The exemplary cation exchange viologen AORFBs expand the application of viologen compounds in redox flow batteries and offer new opportunities to develop low cost and high performance viologen redox flow batteries that promise sustainable and green energy storage of renewable energy.

1,1'-bis[3-sulfonatopropyl]-4,4'-bipyridinium, (SPr)$_2$V (FIG. 58), is a bis-sulfonate functionalized viologen compound. It was hypothesized that the flanged negative charged sulfonate groups of (SPr)$_2$V and its large molecular size could be compatible with a cation exchange membrane with minimized crossover in a cation exchange AROFB. (SPr)$_2$V was synthesized by one step alkylation of 4,4'-bipyridine with propane sultone in high yield (88%). The compound was characterized by $^1$H NMR and elemental analysis. Even as a neutral compound, the solubility of (SPr)$_2$V is 2.0 M in H$_2$O (53.5 Ah/L charge capacity) or 1.7 M in 1.5 M KCl (42.9 Ah/L charge capacity). In terms of the raw materials and simple synthesis, (SPr)$_2$V is expected to have a similar cost as commercial methyl viologen in large scale production.

Figure 59:
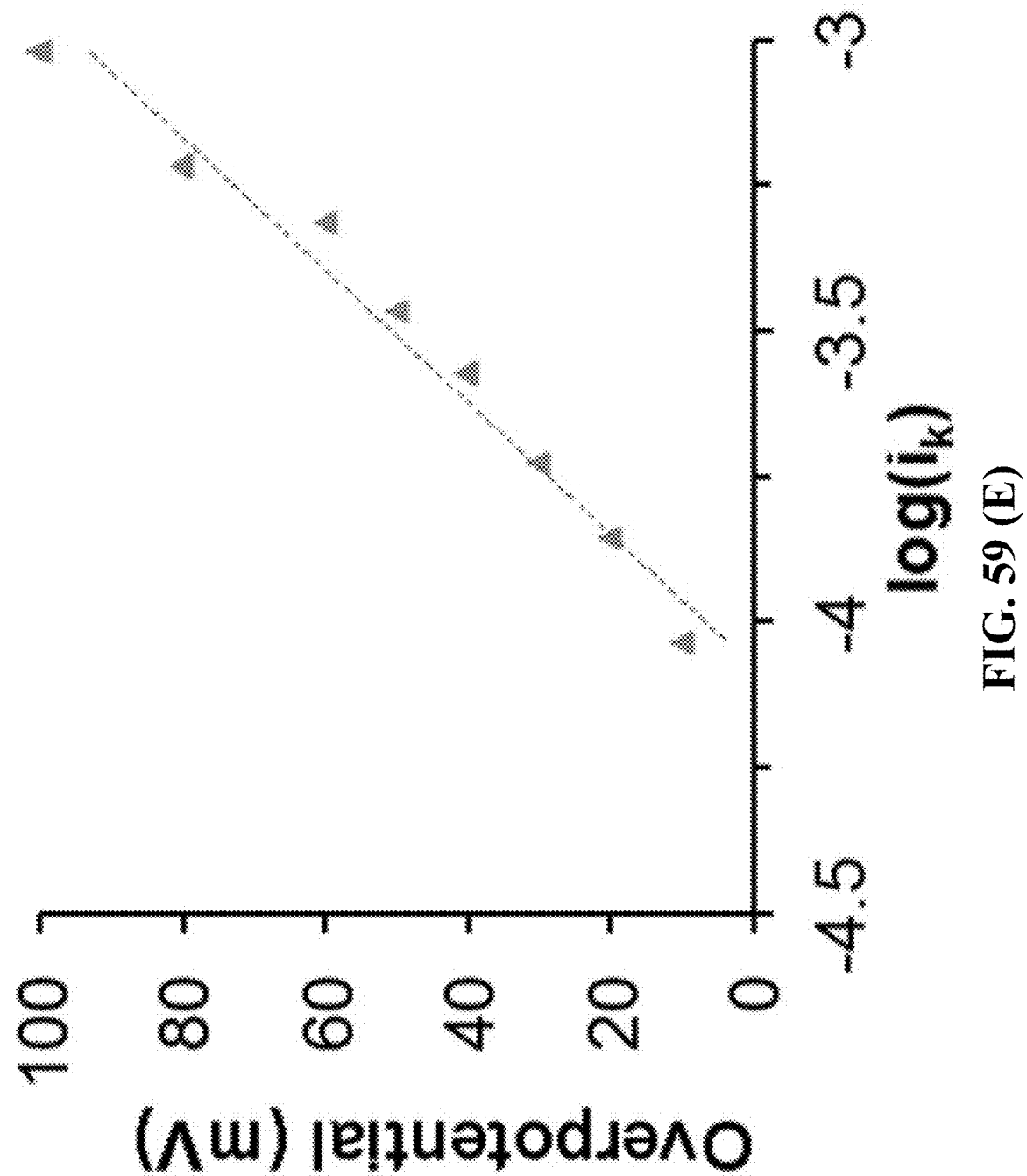

Fundamental electrochemical properties of (SPr)$_2$V were examined by cyclic voltammetry (CV) and rotation disc electrode (RDE) linear scan voltammetry (LSV). In its CV plot (FIG. 59), (SPr)$_2$V displayed a reversible one electron reduction at −0.44 V vs NHE that is comparable to that of methyl viologen (−0.45 V). LSV plots, derived Levich plots and Tafel plots for (SPr)$_2$V are shown in FIG. 59B. A linear Levich plot (FIG. 59C) was constructed for the reduction of (SPr)$_2$V using limiting currents (FIG. 59A) and the square root of rotation speeds. The diffusion coefficient (D) of (SPr)$_2$V was calculated as 3.26×10$^{-6}$ cm$^2$/s by the Levich equation using the slope of the Levich plot. Koutechy-Levich analysis (FIG. 59D) was applied to gain the kinetic current without the influence of mass transport at overpotential from 10 to 100 mV for the reduction. Subsequently, a plot of overpotential versus the logarithm of kinetic current (FIG. 59E) and the corresponding Tafel plot was fitted to calculate the rate constant for the electron transfer of (SPr)$_2$V as 1.49×10$^{-5}$ cm/s. The diffusion coefficient and electron transfer rate constant of (SPr)$_2$V are comparable to reported viologen compounds applied in AORFB s.

Flow battery demonstration of (SPr)$_2$V was investigated with K$_4$[Fe(CN)$_6$]$_6$. K$_4$[Fe(CN)$_6$]$_6$ undergoes a one electron oxidation at 0.47 V vs NHE (FIG. 59A). The combination of (SPr)$_2$V and K$_4$[Fe(CN)$_6$]$_6$ enables 0.9 V cell voltage. The voltage window of the (SPr)$_2$V/K$_4$[Fe(CN)$_6$]$_6$ AORFB is bracketed within the water splitting window (1.5 V for oxygen evolution and 1.2 V for hydrogen evolution) at the neutral condition thus water electrolysis side reactions are unlikely to occur. In fact, K$_4$[Fe(CN)$_6$]$_6$ is highly conductive by itself at 0.6 M (177.6 mS/cm), nearly saturated in H$_2$O. And thus a 0.6 M K$_4$[Fe(CN)$_6$]$_6$ aqueous solution (16 Ah/L) was used as catholyte without additional supporting electrolyte for the ensuing flow battery studies. (SPr)$_2$V, 0.6 M in 1.5 M KCl, was used as catholyte with a conductivity of 103.2 mS/cm. Equations 11 and 12 below give the anode and cathode half-cell reactions for the flow battery. As shown in FIG. 58, the (SPr)$_2$V/K$_4$[Fe(CN)$_6$]$_6$ AORFB engages a cation exchange membrane, e.g., Nafion 211 membrane, which mediates K$^+$ cation charge transfer.

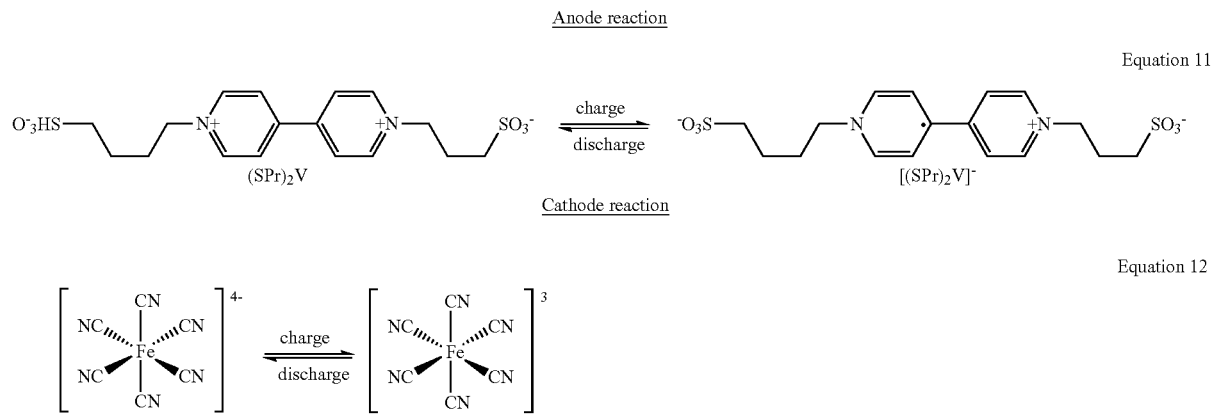

Anode reaction

Equation 11

Cathode reaction

Equation 12

The flow battery was cycled between 1.1 V and 0.1 V. Rate performance of the battery was studied from 40 mA/cm$^2$ to 100 mA/cm$^2$ with an increment of 20 mA/cm$^2$. Representative charge and discharge profiles are shown in FIG. 60A. At all tested current densities, the battery delivered nearly 100% coulombic efficiency. Even at neutral conditions, the battery exhibited exceptional energy efficiency recorded as 80%, 71%, 63, and 54% at 40, 60, 80 and 100 mA/cm$^2$, respectively (FIG. 60B). Regarding energy efficiency (FIG. 60C), the present cation exchange (SPr)$_2$V/K$_4$[Fe(CN)$_6$]$_6$ AORFB presents a significant performance improvement. It was hypothesized that the enhanced energy efficiency may be partly attributed to the higher ion conductivity of the Nafion 211 cation exchange membrane compared to those of anion exchange membranes. The current performance and energy efficiency at a same current density of the (SPr)$_2$V/K$_4$[Fe(CN)$_6$]$_6$ AORFB are comparable with acidic vanadium flow batteries and much better than Zn-Bra flow batteries. Furthermore, the high capacity utilization of the (SPr)$_2$V/K$_4$[Fe(CN)$_6$]$_6$ AORFB (16 Ah/L theoretical capacity) was observed, e.g. 15 Ah/L at 40 mA/cm$^2$ to 13 Ah/L at 100 mA/cm$^2$. Long cycling performance was examined at 60 mA/cm$^2$ for 300 cycles (FIG. 60D). The flow battery delivered rather stable cycling performance, e.g., more than 91% total capacity retention after 200 cycles, equivalent to 99.96% capacity retention per cycle. Polarization curve of the battery was collected at 100% state of charge and yielded a peak power density of 83 mW/cm$^2$ (FIG. 60E). The high current and high power performance of the flow battery was demonstrated using an LED array (FIG. 60G).

Post-CV analysis after 300 cycles revealed there was a small amount of (SPr)$_2$V observed in the K$_4$[Fe(CN)$_6$]$_6$ catholyte. Considering the charge mismatch of neutral (SPr)$_2$ V with the cation exchange membrane, the observed crossover of (SPr)$_2$V in the battery test is rather negligible. To understand the exceptional compatibility of the charge neutral (SPr)$_2$V with the cation exchange membrane, DFT modeling was applied to calculate the formal charge distribution of the neutral (SPr)$_2$V and its charged state, [(SPr)$_2$V]$^-$. Shown in FIGS. 61A and 61B are the optimized structures of (SPr)$_2$V and [(SPr)$_2$V]$^-$ encased with their electrostatic charge surface. The space-filling models of (SPr)$_2$V (FIGS. 61C and 61D) and [(SPr)$_2$V]$^-$ have a 3-dimensional size of approximately 0.6×0.8×2.2 nm$^3$. For the neutral (SPr)$_2$V, negative charge represented by red color is concentrated on the two terminal SO$_3^-$ groups while the positive charge represented by blue color is delocalized throughout the bipyridine fragment. [(SPr)$_2$V]$^-$ displays a dominant negative charge surface while the positive charge density centered on the bipyridine fragment is significantly decreased. According to the parallel water channel model of Nafion membranes, ion transport nano-channels of hydrated Nafion membranes have an averaged size around 2.4 nm (FIGS. 61C and 61D). Regarding the probability of crossover, (SPr)$_2$V can adopt two basic orientations when approaching the nano-channels of a Nafion cation exchange membrane, namely perpendicular orientation and parallel orientation, as displayed in FIGS. 61C and 61D, respectively. When (SPr)$_2$V adopts the perpendicular orientation, the native charge repulsion between both SO$_3^-$ groups of (SPr)$_2$V and the SO$_3^-$ groups of the cation exchange membrane also applies, and also such orientation (2.2 nm) renders an unfavorable size match with the channel (2.4 nm) of the membrane to move in. When (SPr)$_2$V adopts the parallel orientation, the native charge repulsion between the SO$_3^-$ group of (SPr)$_2$V and the SO$_3^-$ groups of the cation exchange membrane disfavors the crossover of (SPr)$_2$V. The perpendicular orientation (0.8 nm) can fit into the channel of the membrane and may have a higher chance than the parallel orientation to cross over. Overall, the proposed charge repulsion and size exclusion may explain the observed low crossover of (SPr)$_2$V during the long cycling battery testing. [(SPr)$_2$V]$^-$ has a one more net negative charge, the chance to crossover is even lower. It was hypothesized that introduction of additional negative charge functionalities such as —SO$_3^-$ or —PO$_4^{2-}$ group can further reduce the crossover of the derivatives of (SPr)$_2$V and lead to more stable cation exchange redox low batteries.

To further expand the concept of the cation exchange viologen AORFBs, KI (0.65 V vs NHE) was also investigated as a catholyte. The corresponding (SPr)$_2$V/KI AORFB has a cell voltage of 1.1 V. The flow battery using 0.5 M (SPr)$_2$V anolyte and 2.0 M KI and 2.0 M KCl catholyte was cycled between 1.2 V and 0.1 V at 60 mA/cm$^2$ for 300 cycles (FIG. 60F). To minimize the crossover of electrolytes, a thicker Nafion 212 membrane was used in the flow battery.

The battery delivered even more stable cycling performance, 99.99% capacity retention per cycle with energy efficiency of 57% and coulombic efficiency of nearly 100%.

In summary, a new design of viologen AORFBs has been demonstrated that employs a cation transfer mechanism. The cation viologen AORFBs were demonstrated through 1,1'-bis[3-sulfonatopropyl]-4,4'-bipyridinium, (SPr)$_2$V, as anolyte, and low cost K$_4$[Fe(CN)$_6$]$_6$ or KI as catholyte. Both (SPr)$_2$V/K$_4$[Fe(CN)$_6$]$_6$ and (SPr)$_2$V/KI AORFB AORFBs delivered outstanding battery performance. The presented cation exchange viologen AORFBs further advance the application of viologen molecules in redox flow batteries and broadly expands the design of neutral viologen redox flow batteries by coupling with negatively charged catholytes. The reliable performance, tunability, sustainability and benignity of the cation exchange viologen AORFBs mark them as a promising RFB technology for renewable energy storage.

Example 11. Synthesis of Ammonium Functionalized TEMPO (4-NMe-TEMPO and 4-NNPr-TEMPO) as Catholyte Materials and their Application in Anion Exchange AORFBs solution was dried by anhydrous sodium sulfate. After removing the solvent under vacuum, the product was obtained as colorless oil (15.8 g, 85.9%). $^1$H NMR (500 MHz, CDCl$_3$): δ=2.68 (t, 1H, N—CH), 2.30 (s, 6H, N—CH$_3$), 1.76 (d, 2H, CH), 1.2 (d, 12H, CH$_3$), 1.03 (t, 2H, CH).

Synthesis of N, N, N, 2, 2, 6, 6-Heptamethylpiperidin-4-ammonium chloride (2): Methyl iodide (8.5 g, 60 mmol in 100 mL diethyl ether) was added into 4-Dimethylamino-2,2,6,6-tetramethylpiperidine (12 g, 65 mmol, in 50 mL diethyl ether) dropwise. Then the mixture was stirred for 8 hours. White precipitate was collected by filtration and washed with 20 mL diethyl ether three times. The obtained white salt was dissolved in 20 mL deionized water and flushed over a anion exchange column. Cyclic voltammetry was applied to validate the replacement of iodide. When the water was evaporated under vacuum, the product was obtained as white hygroscopic powder (12.8 g, 90.5%). $^1$H NMR (500 MHz, D$_2$O): δ=3.74 (t, 1H, N—CH), 3.01 (s, 9H, N—CH$_3$), 2.08 (d, 2H, CH), 1.35 (t, 2H, CH), 1.16 (d, 12H, CH$_3$).

Synthesis of N, N, N, 2, 2, 6, 6-Heptamethylpiperidinyloxy-4-ammonium chloride (3, 4-N$^{Me}$-TEMPO): the chlo- Scheme 9. Synthesis of ammonium functionalized TEMPO (4-NMe-TEMPO and 4-NNPr-TEMPO)

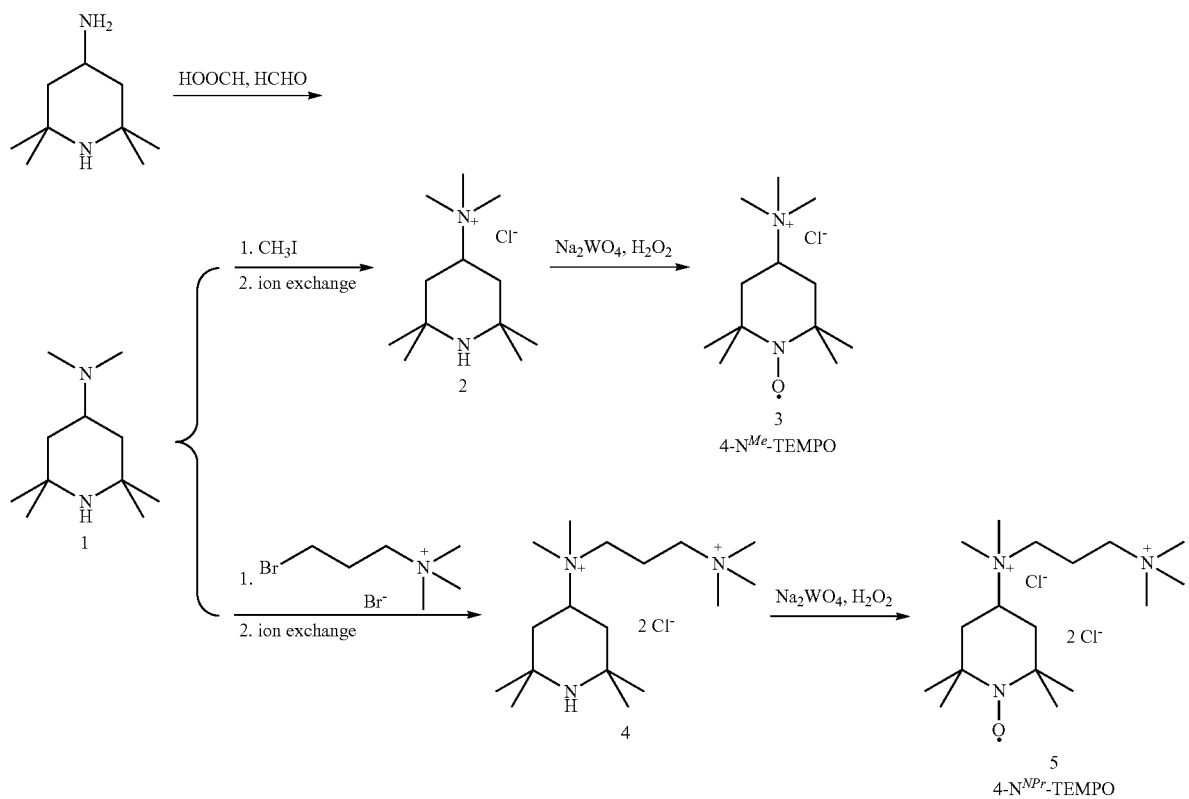

Synthesis of 4-Dimethylamino-2,2,6,6-tetramethylpiperidine(1): 4-Amino-2,2,6,6-tetramethylpiperidine (15.6 g, 0.1 mol) and formaldehyde aqueous solution (17.0 g, 0.21 mol) was added into ice cooled formic acid (23.0 g, 0.5 mol) dropwise. Then solution was stirred overnight. After cooling down the solution, sodium hydroxide was added until oil layer generated. The orange oil layer was extracted by 30 mL diethyl ether and washed by NaCl saturate solution. The ride salt 2 was dissolved in 100 mL water. Sodium hydroxide was added to tune pH value to 12. Then sodium tungstate (230 mg) and 8.1 mL hydrogen peroxide was added. The solution was stirred for 3 days at room temperature. Then another 4.3 mL hydrogen peroxide was added and stirred for 3 days. TLC (CH$_3$CN/H$_2$O/KNO$_3$:10/1/0.1) was used to monitor the reaction. Then water was removed. The product was obtained as orange solid (13.3 g, 96.3%). $^1$H NMR (500

MHz, D₂O with one drop of phenylhydrazine): δ=3.52 (t, 1H, N—CH), 2.90 (s, 9H, N—CH₃), 2.01 (d, 2H, CH), 1.59 (d, 12H, CH₃), 1.13 (t, 2H, CH).

Synthesis of N¹, N¹, N¹, N³, N³, 2, 2, 6, 6-nonamethyl-N³-(piperidin-4-yl)propane-1,3-bis(ammonium) dichloride (4): Compound 4 was prepared similar as compound 2 from compound 1 (10.5 g, 57 mmol) and (3-Bromopropyl)trimethylammonium bromide (13.4 g, 51.3 mmol) were dissolved in 100 mL mixed solvent of DMSO/acetone (V/V: 5/1). The product was obtained as a transparent gel (12.7 g, 67.2%). ¹H NMR (500 MHz, D₂O): δ=3.78 (t, 1H, N—CH), 3.36 (m, 4H, N—CH₂), 3.13 (s, 9H, N—CH₃), 3.03 (s, 6H, N—CH₃), 2.26 (m, 2H, CH₂), 2.04 (d, 2H, CH), 1.42 (t, 2H, CH), 1.15 (d, 12H, CH₃).

Synthesis of N¹, N¹, N¹, N³, N³, 2, 2, 6, 6-nonamethyl-N³-(piperidinyloxy)propane-1,3-bis(ammonium) dichloride (5, 4-N$^{NPr}$-TEMPO): The same method for compound 3 synthesis was applied to compound 5 from compound 4 (13.1 g, 37 mmol). The product was obtained as orange solid. (13.0 g, 95.5%) ¹H NMR (500 MHz, D₂O with one drop of phenylhydrazine): δ=3.79 (t, 1H, N—CH), 3.37 (m, 4H, N—CH₂), 3.14 (s, 9H, N—CH₃), 3.04 (s, 6H, N—CH₃), 2.27 (m, 2H, CH₂), 2.06 (d, 2H, CH), 1.44 (t, 2H, CH), 1.16 (d, 12H, CH₃).

Both 4-N$^{Me}$-TEMPO (2.5 M in H₂O) and 4-N$^{NPr}$-TEMPO (2.3 M in H₂O) exhibit a reversible oxidation potential at 1.06 V vs NHE. 1,1'-bis[3-(trimethylaminium)propyl]-4,4'-bipyridinium tetrachloride, (NPr)₂VCl (see Schemes 10 &11), in NaCl supporting electrolyte, and 4-trimethylammounium-TEMPO (4-N$^{Me}$-TEMPO) or 4-(propanyl-1-amminum) dimethylammounium-TEMPO (4-N$^{NPr}$-TEMPO) in NaCl as catholyte were applied for aqueous redox flow battery applications that has a cell voltage of ca. 1.5 V. The (NPr)₂VCl/4-N$^{Me}$-TEMPO AORFB (0.5 M, 16.1 Ah/L) manifested a cycling performance at 60 mA/cm², 47.8% energy efficiency, and outstanding 99.985% capacity retention per cycle for 500 charge/discharge cycle (see FIGS. 62(A)-(C)). The (NPr)₂VCl/4-N$^{NPr}$-TEMPO AORFB delivered a higher energy efficiency at 60% at 60 mA/cm² and an even higher cycling stability at 99.997% capacity retention per cycle for 500 charge/discharge cycle (see FIGS. 63(A)-(C)). These AORFBs may represent a more stable high voltage neutral AORFBs.

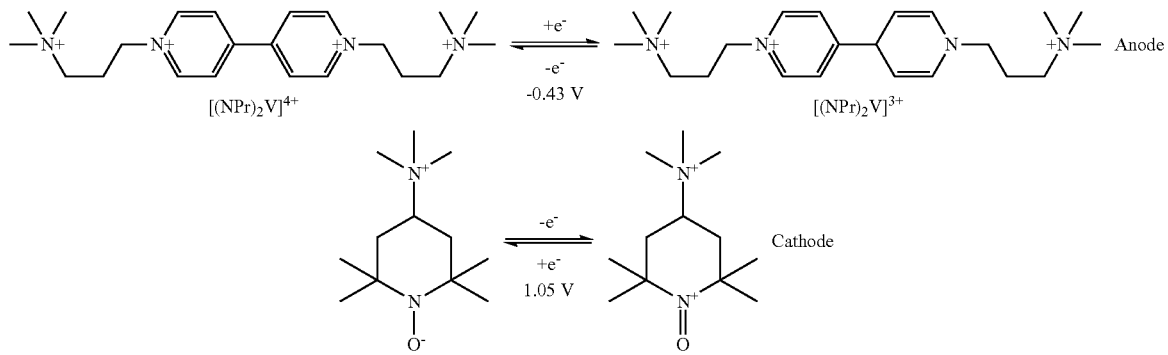

Scheme 10. TEMPO catholyte in AORFBs

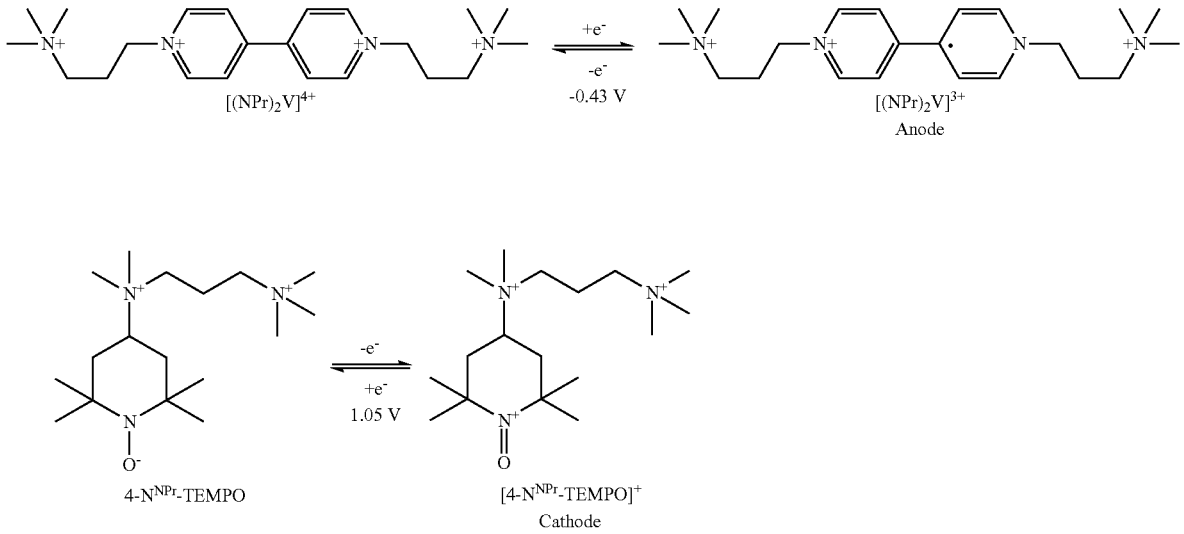

Scheme 11. TEMPO catholyte in AORFBs

For reasons of completeness, various aspects of the present disclosure are set out in the following numbered clauses:

Clause 1. A redox flow battery comprising: a first redox active material comprising a metallocene or a salt thereof; and a second redox active material.

Clause 2. The redox flow battery of clause 1, wherein the metallocene is water soluble.

Clause 3. The redox flow battery of clause 1 or clause 2, wherein the metallocene has an aqueous solubility of ≥1 M.

Clause 4. The redox flow battery of any one of clauses 1-3, wherein the metallocene comprises a hydrophilic functional group.

Clause 5. The redox flow battery of any one of clauses 1-4, wherein the metallocene comprises a hydrophilic functional group that is a quaternary ammonium salt.

Clause 6. The redox flow battery of any one of clauses 1-5, where the metallocene is a ferrocene.

Clause 7. The redox flow battery of any one of clauses 1-6, wherein the metallocene has formula (I):

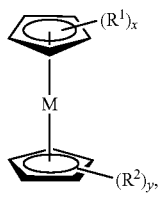

(I)

or a salt thereof, wherein: M is Fe, Co, Ni, Mn, Cr, Ti, Mo, V, or W; $R^1$ and $R^2$, at each occurrence, are each independently selected from the group consisting of hydrogen, halogen, alkyl, cycloalkyl, heterocyclyl, aryl, heteroaryl, —CN, —NO$_2$, —OR$^a$, —SR$^a$, -alkyl-N(R$^a$)$_z$, —N(R$^a$)$_z$, —C(O)R$^a$, —C(O)OR$^a$, —S(O)$_z$R$^a$, —S(O)$_z$OR$^a$, and —OP(O)(OR$^a$)$_2$; R$^a$, at each occurrence, is independently selected from the group consisting of hydrogen, alkyl, cycloalkyl, heterocyclyl, aryl, heteroaryl, alkyl-N(R$^b$)$_z$, an oxygen protecting group, and a nitrogen protecting group; R$^b$, at each occurrence, is independently selected from the group consisting of hydrogen, alkyl, cycloalkyl, heterocyclyl, aryl, heteroaryl, an oxygen protecting group, and a nitrogen protecting group; x is 1, 2, 3, 4, or 5; y is 0, 1, 2, 3, 4, or 5; and z, at each occurrence, is independently 2 or 3.

Clause 8. The redox flow battery of any one of clauses 1-7, wherein the metallocene has formula (I-a):

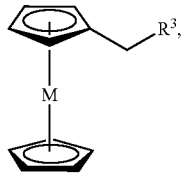

(I-a)

or a salt thereof, wherein: M is Fe, Co, Ni, Mn, Cr, Ti, Mo, V, or W; $R^3$ is —NO$_2$, —OR$^a$, —N(R$^a$)$_z$, —C(O)R$^a$, —C(O)OR$^a$, —S(O)$_z$R$^a$, —S(O)$_z$OR$^a$, or —OP(O)(OR$^a$)$_2$; R$^a$, at each occurrence, is independently selected from the group consisting of hydrogen, alkyl, cycloalkyl, heterocyclyl, aryl, heteroaryl, alkyl-N(R$^b$)$_z$, an oxygen protecting group, and a nitrogen protecting group; R$^b$, at each occurrence, is independently selected from the group consisting of hydrogen, alkyl, cycloalkyl, heterocyclyl, aryl, heteroaryl, an oxygen protecting group, and a nitrogen protecting group; and z, at each occurrence, is independently 2 or 3.

Clause 9. The redox flow battery of any one of clauses 1-8, wherein the metallocene has formula (I-b):

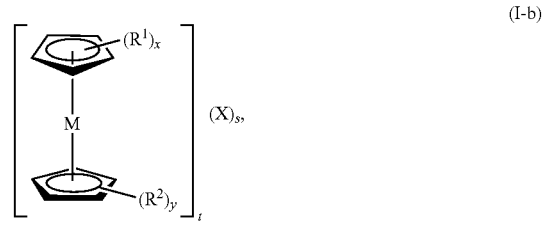

(I-b)

wherein: M is Fe, Co, Ni, Mn, Cr, Ti, Mo, V, or W; $R^1$ and $R^2$, at each occurrence, are each independently selected from the group consisting of hydrogen, halogen, alkyl, cycloalkyl, heterocyclyl, aryl, heteroaryl, —CN, —NO$_2$, —OR$^a$, —SR$^a$, -alkyl-N(R$^a$)$_z$, —N(R$^a$)$_z$, —C(O)R$^a$, —C(O)OR$^a$, —S(O)$_z$R$^a$, —S(O)$_z$OR$^a$, and —OP(O)(OR$^a$)$_2$; R$^a$, at each occurrence, is independently selected from the group consisting of hydrogen, alkyl, cycloalkyl, heterocyclyl, aryl, heteroaryl, alkyl-N(R$^b$)$_z$, an oxygen protecting group, and a nitrogen protecting group; R$^b$, at each occurrence, is independently selected from the group consisting of hydrogen, alkyl, cycloalkyl, heterocyclyl, aryl, heteroaryl, an oxygen protecting group, and a nitrogen protecting group; x is 1, 2, 3, 4, or 5; y is 0, 1, 2, 3, 4, or 5; z, at each occurrence, is independently 2 or 3; X, at each occurrence, is independently F$^-$, Cl$^-$, Br$^-$, I$^-$, SO$_4^{2-}$, OH$^-$, CO$_3^{2-}$, ClO$_4^-$, H$_2$PO$_4^-$, HPO$_4^{2-}$, PO$_4^{3-}$, NO$_3^-$, N$_3^-$, CN$^-$, N(CN)$_2^-$, SCN$^-$, or a combination thereof; s is 1, 2, or 3; and t is 1, 2, or 3.

Clause 10. The redox flow battery of any one of clauses 1-9, wherein the metallocene has formula (I-b-1):

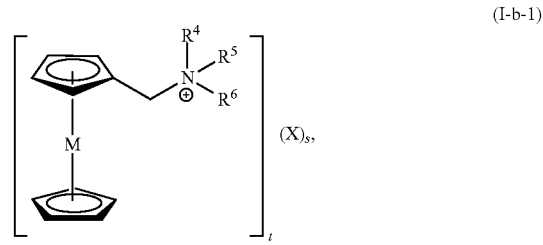

(I-b-1)

wherein: M is Fe, Co, Ni, Mn, Cr, Ti, Mo, V, or W; $R^4$, $R^5$, and $R^6$ are each independently selected from the group consisting of hydrogen, C$_1$-C$_6$-alkyl, and alkyl-N(R$^b$)$_z$; R$^b$, at each occurrence, is independently selected from the group consisting of hydrogen, alkyl, cycloalkyl, heterocyclyl, aryl, heteroaryl, an oxygen protecting group, and a nitrogen protecting group; X, at each occurrence, is independently F$^-$, Cl$^-$, Br$^-$, I$^-$, or a combination thereof; s is 1, 2, or 3; and t is 1, 2, or 3.

Clause 11. The redox flow battery of any one of clauses 1-10, wherein the metallocene has formula (I-c):

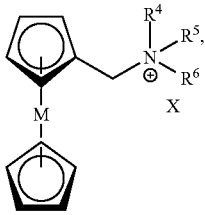
(I-c)

wherein: M is Fe, Co, Ni, Mn, Cr, Ti, Mo, V, or W; $R^4$, $R^5$, and $R^6$ are each independently selected from the group consisting of hydrogen and $C_1$-$C_6$-alkyl; and X is $F^-$, $Cl^-$, $Br^-$, $I^-$, or a combination thereof.

Clause 12. The redox flow battery of clause 1, wherein the metallocene has formula (I-d), (I-e), (I-f), (I-g), (I-h), (I-i), or (I-j):

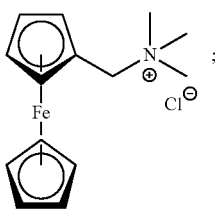
(I-d)

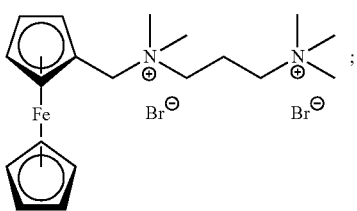
(I-e)

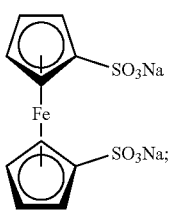
(I-f)

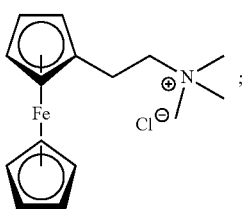
(I-g)

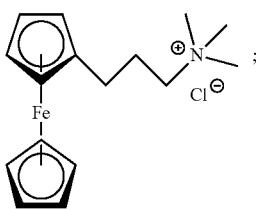
(I-h)

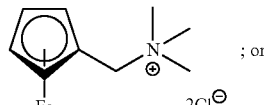
(I-i)

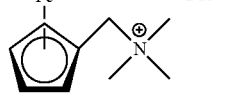
; or

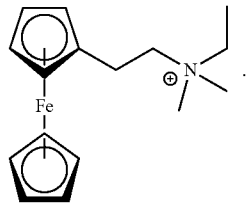
(I-j)

Clause 13. The redox flow battery of any one of clauses 1-12, wherein the second redox active material comprises viologen, pyridinium, quinone, anthraquinone, $(CH_2)_3(CMe_2)_2NO$, nitroxyl radicals, $Fe^{3+/2+}$, $^-[Fe(CN)_6]^{3+/2+}$, $I_3^-/I^-$, $Br_2/Br^-$, $S_4^-/S_2^-$, $Cr^{3+/2+}$, $Ce^{4+/3+}$, $Zn^{2+/0}$, $V^{5+/4+}$, $V^{4+/3+}$, $V^{3+/2+}$, $Pb^{2+/0}$, $pbO_2/Pb^{2+}$, $Cu^{2+/0}$, $Ti_3^+/TiO^{2+}$, $Li^{+/0}$, $Na^{+/0}$, $Mg^{2+/0}$, $Al^{+3+/0}$, $Ca^{2+/0}$ or a combination thereof.

Clause 14. The redox flow battery of any one of clauses 1-13, wherein the second redox active material comprises methyl viologen.

Clause 15. The redox flow battery of clause 13, wherein the viologen has formula (V):

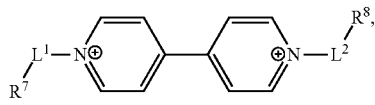
(V)

or a salt thereof, wherein: $L^1$ and $L^2$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_m$, $R^7$ and $R^8$ are each independently selected from the group consisting of —$CH_3$, —$NO_2$, —$OR^d$, —$N(R^d)_m$, —$C(O)R^d$, —$C(O)OR^d$, —$S(O)_m$, —$PO_3$, —$S(O)_m$ $R^d$, —$S(O)_mOR^d$, —$OP(O)(OR^d)_2$, —$OCH_3$, —$(CR^d_2)_mCN$, substituted aryl, and substituted heteroaryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; and m, at each occurrence, is independently 2 or 3.

Clause 16. The redox flow battery of clause 13 or clause 15, wherein the viologen has formula (V-a):

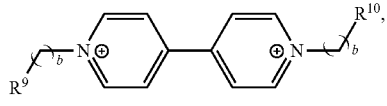
(V-a)

or a salt thereof, wherein: $R^9$ and $R^{10}$ are each independently selected from the group consisting of —$CH_3$, —$N(R^d)_m$, —$S(O)_m$, —$PO_3$, —$S(O)_m$ $R^d$; —$(OCH_2CH_2)_m$—$OCH_3$, and substituted aryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; m, at each occurrence, is independently 2 or 3; and b, at each occurrence, is independently 0, 1, 2 or 3.

Clause 17. The redox flow battery of any one of clauses 13 or 15-16, wherein the viologen has formula (V-b):

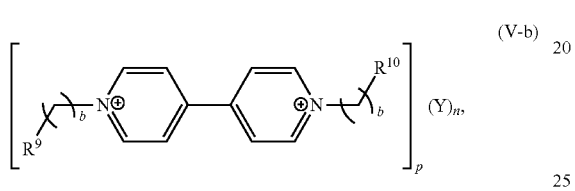

wherein: $R^9$ and $R^{10}$ are each independently selected from the group consisting of —$CH_3$, —$N(R^d)_m$, —$S(O)_m$, —$PO_3$, —$S(O)_m$ $R^d$, —$(OCH_2CH_2)_m$—$OCH_3$, substituted aryl, and substituted heteroaryl; $R^d$, at each occurrence, is independently selected from the group consisting of hydrogen, alkyl, cycloalkyl, heterocyclyl, aryl, heteroaryl, alkyl-$N(R^e)_m$, alkyl-$S(O)_m$, an oxygen protecting group, and a nitrogen protecting group; $R^e$, at each occurrence, is independently selected from the group consisting of hydrogen, alkyl, cycloalkyl, heterocyclyl, aryl, heteroaryl, an oxygen protecting group, and a nitrogen protecting group; Y, at each occurrence, is independently $Na^+$, $K^+$, $Li^+$, $NR^f_4{}^+$, $F^-$, $Cl^-$, $Br^-$, $I^-$, $SO_4{}^{2-}$, $OH^-$, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, $CN^-$, $N(CN)_2{}^-$, $SCN^-$, or a combination thereof; $R^f$, at each occurrence, is independently selected from the group consisting of hydrogen, alkyl, cycloalkyl, heterocyclyl, aryl, and heteroaryl; m, at each occurrence, is independently 2 or 3; n is 1, 2, 3 or 4; p is 1, 2, 3 or 4; and b, at each occurrence, is independently 0, 1, 2 or 3.

Clause 18. The redox flow battery of clause 17, wherein: $R^9$ and $R^{10}$ are each independently —$CH_3$, —$N(CH_3)_3{}^+$, —$SO_3{}^-$, —$(OCH_2CH_2)_m$—$OCH_3$, or substituted aryl; Y, at each occurrence, is independently $Na^+$, $Cl^-$, $Br^-$, or a combination thereof; n is 2, 3 or 4; and p is 1.

Clause 19. The redox flow battery of any one of clauses 13 or 15-18, wherein the viologen is selected from the group consisting of

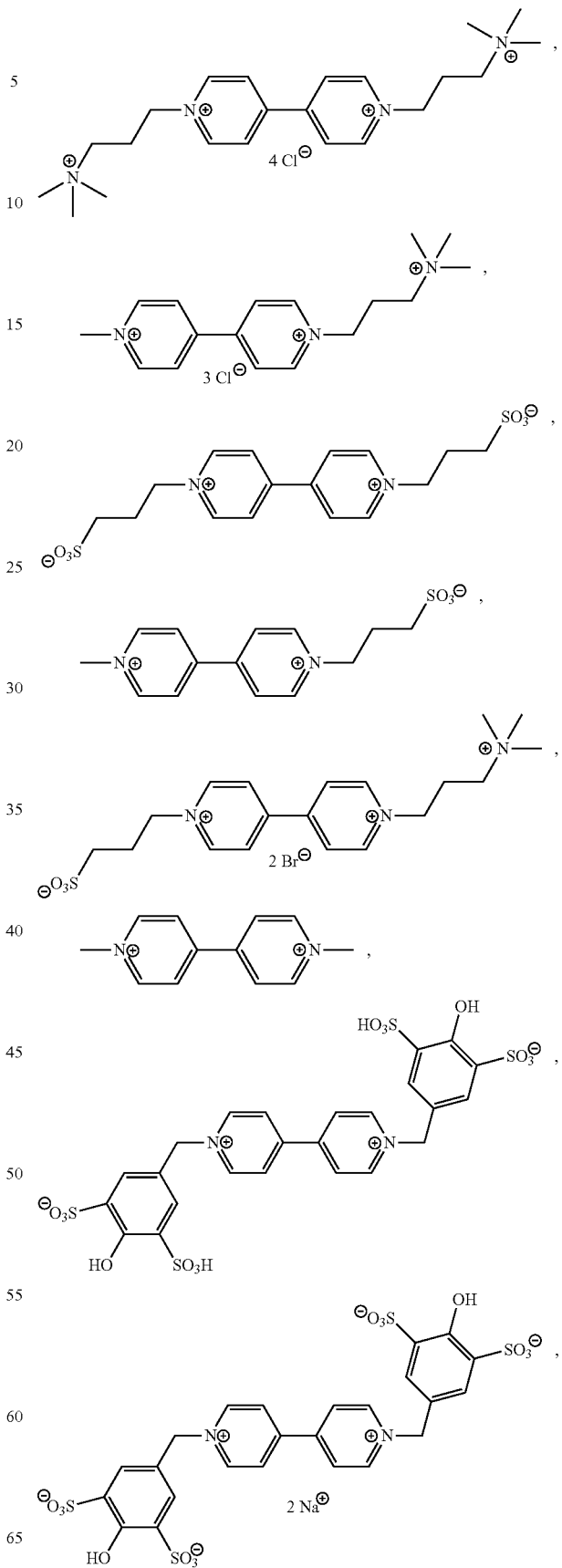

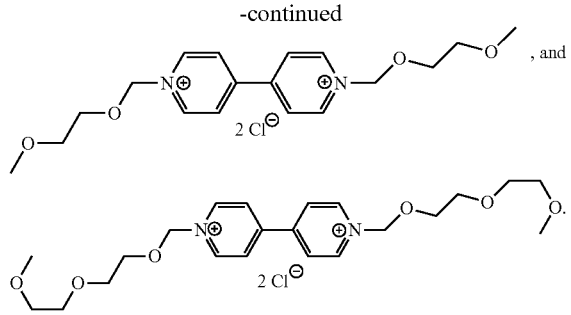

Clause 20. A redox flow battery comprising: a first redox active material; and a second redox active material comprising a viologen or a salt thereof, wherein the viologen has formula (VI):

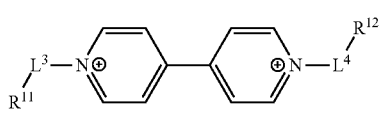

(VI)

or a salt thereof, wherein: $L^3$ and $L^4$ are each independently selected from the group consisting of bond, $C_1$-$C_{12}$ alkylenyl, $C_1$-$C_{12}$ alkenylenyl, $C_1$-$C_{12}$ alkynylenyl, and $C_1$-$C_4$ alkylenyl-$(OCH_2CH_2)_m$; $R^{11}$ is selected from the group consisting of, —$NO_2$, —$OR^g$, —$N(R^g)_q$, —$C(O)R^g$, —$C(O)OR^g$, —$S(O)_q$, —$PO_3$, —$S(O)_qR^g$, —$S(O)_qOR^g$, —$OP(O)(OR^g)_2$, —$OCH_3$, —$(CR^g_2)_mCN$, substituted aryl, and substituted heteroaryl; $R^{12}$ is selected from the group consisting of —$CH_3$, —$NO_2$, —$OR^g$, —$C(O)R^g$, —$C(O)OR^g$, —$S(O)_q$, —$PO_3$, —$S(O)_qR^g$, —$S(O)_qOR^g$, —$OP(O)(OR^g)_2$; $OCH_3$, —$(CR^g_2)_mCN$, substituted aryl, and substituted heteroaryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; and q, at each occurrence, is independently 2 or 3.

Clause 21. The redox flow battery of clause 20, wherein the viologen has formula (VI-a):

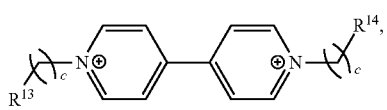

(VI-a)

or a salt thereof, wherein: $R^{13}$ is selected from the group consisting of —$N(R^g)_q$, —$S(O)_q$, —$PO_3$, —$S(O)_qR^g$, —$(OCH_2CH_2)_m$—$OCH_3$, and substituted aryl; $R^{14}$ is selected from the group consisting of —$CH_3$, —$S(O)_q$, —$PO_3$, —$S(O)_qR^g$, —$(OCH_2CH_2)_m$—$OCH_3$, and substituted aryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; q, at each occurrence, is independently 2 or 3; and c, at each occurrence, is independently 0, 1, 2 or 3.

Clause 22. The redox flow battery of clause 20 or clause 21, wherein the viologen has formula (VI-b):

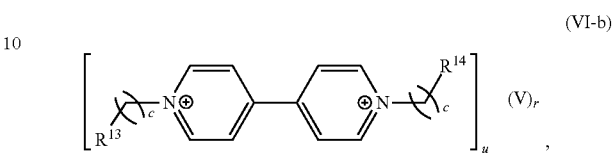

(VI-b)

wherein: $R^n$ is selected from the group consisting of —$N(R^g)_q$, —$S(O)_q$, —$PO_3$, —$S(O)_qR^g$, —$(OCH_2CH_2)_m$—$OCH_3$, and substituted aryl; $R^{14}$ is selected from the group consisting of —$CH_3$, —$S(O)_q$, —$PO_3$, —$S(O)_qR^g$, —$(OCH_2CH_2)_m$—$OCH_3$, and substituted aryl; $R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group; $R^h$, at each occurrence, is independently selected from the group consisting of hydrogen, alkyl, cycloalkyl, heterocyclyl, aryl, heteroaryl, an oxygen protecting group, and a nitrogen protecting group; V, at each occurrence, is independently $Na^+$, $K^+$, $Li^+$, $NR^i_4{}^+$, $F^-$, $Cl^-$, $Br^-$, $I^-$, $SO_4{}^{2-}$, $OH^-$, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, $CN^-$, $N(CN)_2{}^-$, $SCN^-$ or a combination thereof; $R^i$, at each occurrence, is independently selected from the group consisting of hydrogen, alkyl, cycloalkyl, heterocyclyl, aryl, and heteroaryl; q, at each occurrence, is independently 2 or 3; r is 1, 2, 3 or 4; u is 1, 2, 3 or 4; and c, at each occurrence, is independently 0, 1, 2 or 3.

Clause 23. The redox flow battery of clause 22, wherein: $R^{13}$ is —$SO_3{}^-$, —$(OCH_2CH_2)_m$—$OCH_3$, or substituted aryl; $R^{14}$ is —$SO_3{}^-$, —$(OCH_2CH_2)_m$—$OCH_3$, or substituted aryl; V, at each occurrence, is independently $Na^+$, $K^+$, $Cl^-$, $Bf$ or a combination thereof; r is 2, 3 or 4; u is 1; and c, at each occurrence, is independently 1, 2 or 3.

Clause 24. The redox flow battery of any one of clauses 20-23, wherein the viologen is selected from the group consisting of

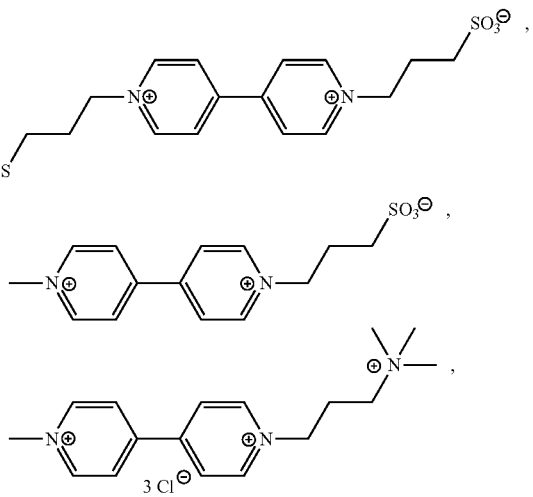

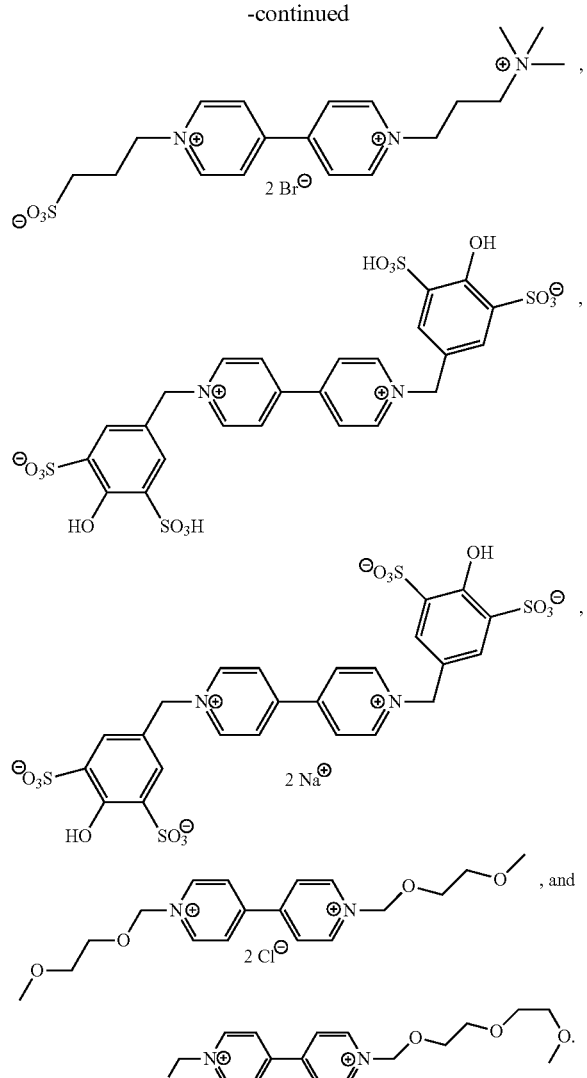

Clause 25. The redox flow battery of any of clauses 20-24, wherein the viologen has formula (VII):

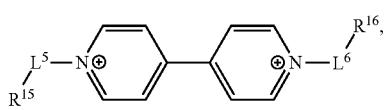

(VII)

or a salt thereof, wherein: $L^5$ and $L^6$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_j$, $R^{15}$ and $R^{16}$ are each independently selected from the group consisting of $OR^1$, —$C(O)R^j$, —$C(O)OR^j$, —$S(O)_j$, —$PO_3$, —$S(O)_jR^j$, —$S(O)_jOR^j$, —OP$(O)(OR^j)_2$, —$(CR^j{}_2)_jCN$, substituted aryl, and substituted heteroaryl; $R^j$, at each occurrence, is independently selected from the group consisting of alkyl-$S(O)_j$, and an oxygen protecting group; and j, at each occurrence, is independently 2 or 3.

Clause 26. The redox flow battery of clause 25, wherein the viologen is selected from the group consisting of

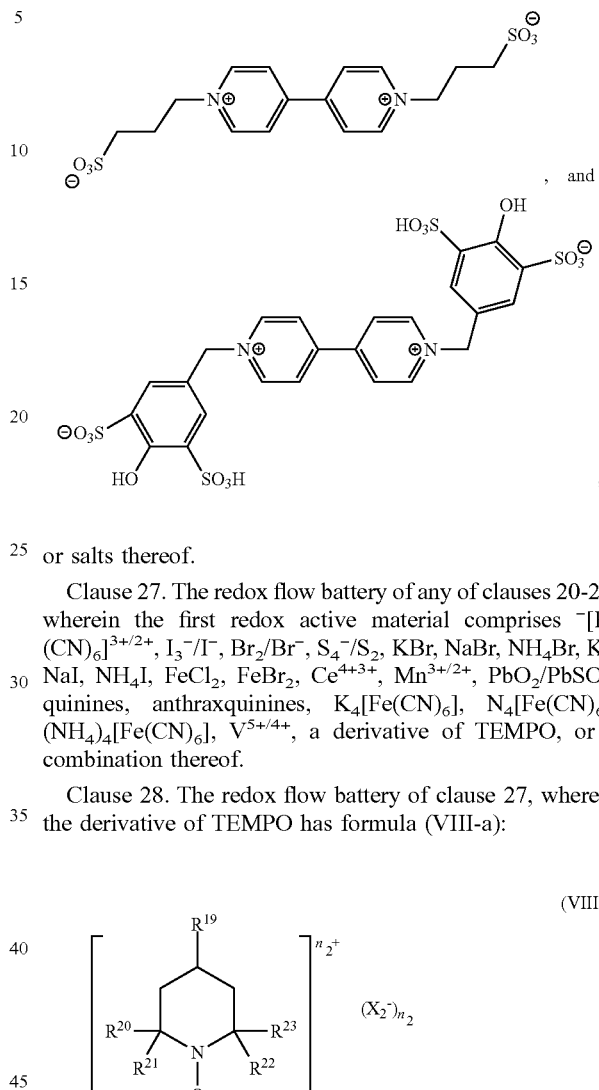

or salts thereof.

Clause 27. The redox flow battery of any of clauses 20-26, wherein the first redox active material comprises $^-$[Fe(CN)$_6$]$^{3+/2+}$, $I_3^-/I^-$, $Br_2/Br^-$, $S_4^-/S_2$, KBr, NaBr, NH$_4$Br, KI, NaI, NH$_4$I, FeCl$_2$, FeBr$_2$, Ce$^{4+/3+}$, Mn$^{3+/2+}$, PbO$_2$/PbSO$_4$, quinines, anthraxquinines, K$_4$[Fe(CN)$_6$], N$_4$[Fe(CN)$_6$], (NH$_4$)$_4$[Fe(CN)$_6$], V$^{5+/4+}$, a derivative of TEMPO, or a combination thereof.

Clause 28. The redox flow battery of clause 27, wherein the derivative of TEMPO has formula (VIII-a):

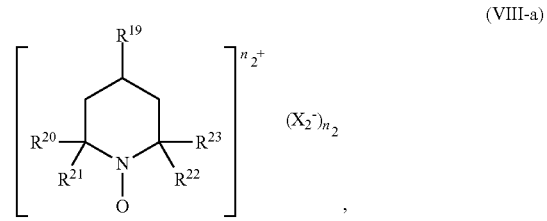

(VIII-a)

wherein: $R^{19}$, $R^{20}$, $R^{21}$, $R^{22}$ and $R^{23}$ are each independently selected from the group consisting of hydrogen, halogen, alkyl, cycloalkyl, heterocyclyl, aryl, heteroaryl, —CN, —NO$_2$, —OR$^k$, —SR$^k$, -alkyl-N(R$^k$)$_w$, —N(R$^k$)$_w$, —C(O)R$^k$, —C(O)OR$^k$, —S(O)$_w$R$^k$, —S(O)$_w$OR$^k$, and —OP(O)(OR$^k$)$_2$; $R^k$, at each occurrence, is independently selected from the group consisting of hydrogen, alkyl, cycloalkyl, heterocyclyl, aryl, heteroaryl, alkyl-N(R$^1$)$_w$, an oxygen protecting group, and a nitrogen protecting group; $R^1$, at each occurrence, is independently selected from the group consisting of hydrogen, alkyl, cycloalkyl, heterocyclyl, aryl, heteroaryl, an oxygen protecting group, and a nitrogen protecting group; $X_2^-$ is Cl$^-$, Br$^-$, I$^-$, SO$_4^{2-}$, —NO$_3^-$ or a combination thereof; $n_2$ is 1, 2, 3, 4, or 5; and w, at each occurrence, is independently 2 or 3.

Clause 29. The redox flow battery of clause 27, wherein the derivative of TEMPO has formula (VIII-b):

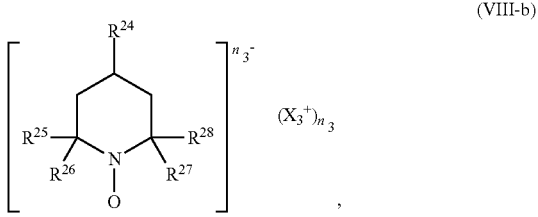

(VIII-b)

wherein: $R^{24}$, $R^{25}$, $R^{26}$, $R^{27}$ and $R^{28}$ are each independently selected from the group consisting of hydrogen, halogen, alkyl, cycloalkyl, heterocyclyl, aryl, heteroaryl, —CN, —NO$_2$, —OR''', —SR''', -alkyl-N(R''')$_q$, —N(R''')$_q$, —C(O) R''', —C(O)OR''', —S(O)$_q$R''', —S(O)$_q$OR''', and —OP(O) (OR''')$_2$; R''', at each occurrence, is independently selected from the group consisting of hydrogen, alkyl, cycloalkyl, heterocyclyl, aryl, heteroaryl, alkyl-N(R'')$_q$, an oxygen protecting group, and a nitrogen protecting group; R'', at each occurrence, is independently selected from the group consisting of hydrogen, alkyl, cycloalkyl, heterocyclyl, aryl, heteroaryl, an oxygen protecting group, and a nitrogen protecting group; $X_3^+$ is H$^+$, Li$^+$, Na$^+$, K$^+$, NH$_4^+$ or a combination thereof; $n_3$ is 1, 2, 3, 4, or 5; and w, at each occurrence, is independently 2 or 3.

Clause 30. The redox flow battery of clause 27, wherein the derivative of TEMPO is selected from the group consisting of 4-trimethylammonium-(2,2,6,6-Tetramethylpiperidin-1-yl)oxy (4-N$^{Me}$-TEMPO), 4-dimethyl(propyl-3-N, N,N,-trimethylammonium)-(2,2,6,6-Tetramethylpiperidin-1-yl)oxy ((4-N$^{NPr}$-TEMPO), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-S03-TEMPO), 4-amino-(2,2,6,6-Tetramethylpiperidin-1-yl)oxy (4-NH$_2$-TEMPO), and a combination thereof.

Clause 31. The redox flow battery of any one of clauses 1-30, further comprising: a first aqueous electrolyte; a second aqueous electrolyte; and a separator between the first and second aqueous electrolytes.

Clause 32. The redox flow battery of clause 31, wherein the first redox active material is present in the first aqueous electrolyte at a concentration of ≥0.1 M.

Clause 33. The redox flow battery of clause 31 or clause 32, further comprising a first electrode in contact with the first aqueous electrolyte and a second electrode in contact with the second aqueous electrolyte.

Clause 34. The redox flow battery of any one of clauses 31-33, wherein the separator is a porous separator.

Clause 35. The redox flow battery of any one of clauses 21-34, wherein the separator is an anion exchange membrane or a cation exchange membrane.

Clause 36. The redox flow battery of any one of clauses 31-35, wherein the separator is functionalized with ammonium or sulfonate.

Clause 37. The redox flow battery of any one of clauses 31-36, wherein the first and second aqueous electrolytes comprise a salt having the formula (IV):

A-B  (IV), wherein: A is Na$^+$, K$^+$, Li$^+$, NR$^c_4{}^+$, pyridinium, pyrrolidium, or imidazolium; R$^c$, at each occurrence, is independently selected from the group consisting of hydrogen, alkyl, cycloalkyl, heterocyclyl, aryl, and heteroaryl; and B is halide anion, SO$_4^{2-}$, OH$^-$, CO$_3^{2-}$, ClO$_4^-$, H$_2$PO$_4^-$, HPO$_4^{2-}$, PO$_4^{3-}$, NO$_3^-$, N$_3^-$, CN$^-$, N(CN)$_2^-$, or SCN$^-$.

Clause 38. The redox flow battery of any one of clauses 31-38, wherein the first and second aqueous electrolytes comprise between about 0.5 M to about 5 M NaCl, KCl, or NH$_4$C$_1$.

Clause 39. The redox flow battery of any one of clauses 31-38, wherein the first and second aqueous electrolytes comprise between about 0.5 M to about 5 M NaCl, KCl, or NH$_4$C$_1$.

Clause 40. The redox flow battery of any one of clauses 31-39, wherein the first and second aqueous electrolytes comprise about 2 M NaCl, KCl or NH$_4$C$_1$.

Clause 41. The redox flow battery of any one of clauses 1-40, wherein the battery has an energy density of ≥10 Wh/L.

Clause 42. The redox flow battery of any one of clauses 1-41, wherein the battery has at least 95% capacity retention after 400 cycles at 60 mA/cm$^2$.

Clause 43. The redox flow battery of any one of clauses 1-42, wherein the battery is operated at ≥50 mA/cm$^2$.

Clause 44. The redox flow battery of any one of clauses 1-43, wherein the battery is operated at ≥100 mW/cm$^2$.

Clause 45. The redox flow battery of any one of clauses 1-44, wherein the battery has an energy efficiency of about 90%.

Clause 46. The redox flow battery of any one of clauses 1-45, wherein the battery has a coulombic efficiency of about 100%.

Clause 47. The redox flow battery of any one of clauses 31-46, further comprising: a first circulation loop comprising a first storage tank containing the first aqueous electrolyte, piping for transporting the first aqueous electrolyte, a chamber in which the first electrode is in contact with the first aqueous electrolyte, and a pump to circulate the first aqueous electrolyte through the first circulation loop; a second circulation loop comprising a second storage tank containing the second aqueous electrolyte, piping for transporting the second aqueous electrolyte, a chamber in which the second electrode is in contact with the second aqueous electrolyte, and a pump to circulate the second aqueous electrolyte through the second circulation loop; and control hardware and software.

Clause 48. A method of storing energy, comprising applying a potential difference across the first and second electrode of the redox flow battery of clause 33, wherein the first redox active material is oxidized.

Clause 49. A method of releasing energy, comprising applying a potential difference across the first and second electrode of the redox flow battery of clause 33, wherein the first redox active material is reduced.

Clause 50. A method of synthesizing a compound of formula (I-c):

(I-c)

wherein M is Fe, Co, Ni, Mn, Cr, Ti, Mo, V, or W; $R^4$, $R^5$, and $R^6$ are each independently selected from the group consisting of C$_1$-C$_6$-alkyl; and X is F$^-$, Cl$^-$, Br$^-$ or I$^-$;

the method comprising alkylating the amine of formula (II) with an alkylhalide of formula (III), wherein $X^1$ is F, Cl, Br, or I;

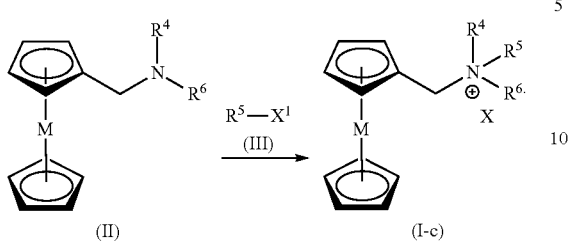

Clause 51. The method of clause 50, wherein $R^4$, $R^5$, and $R^6$ are each methyl; and X is Cl⁻.

Clause 52. The method of clause 50 or clause 51, wherein the alkylation is conducted in a solvent comprising acetonitrile.

Clause 53. The method of any one of clauses 50-52, wherein the alkylation is conducted at room temperature.

Clause 54. The method of any one of clauses 50-53, wherein the yield of the compound of formula (I-c) is 90% or greater.

Clause 55. The method of any one of clauses 50-53, wherein the yield of the compound of formula (I-c) is 90% or greater, and wherein the scale is 15 grams or greater.

The invention claimed is:
1. A redox flow battery comprising:
a first redox active material; and
a second redox active material comprising a viologen or a salt thereof, wherein the viologen has formula (VI):

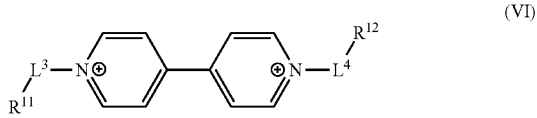

or a salt thereof, wherein:
$L^3$ and $L^4$ are each independently selected from the group consisting of bond, $C_1$-$C_{12}$ alkylenyl, $C_1$-$C_{12}$ alkenylenyl, $C_1$-$C_{12}$ alkynylenyl, and $C_1$-$C_4$ alkylenyl-$(OCH_2CH_2)_m$;
$R^{11}$ is selected from the group consisting of, $-NO_2$, $-OR^g$, $-N(R^g)_q$, $-C(O)R^g$, $-C(O)OR^g$, $-S(O)_q$, $-PO_3$, $-S(O)_qR^g$, $-S(O)_qOR^g$, $-OP(O)(OR^g)_2$, $-OCH_3$, $-(CR^g_2)_mCN$, substituted aryl, and substituted heteroaryl;
$R^{12}$ is selected from the group consisting of $-CH_3$, $-NO_2$, $-OR^g$, $-C(O)R^g$, $-C(O)OR^g$, $-S(O)_q$, $-PO_3$, $-S(O)_qR^g$, $-S(O)_qOR^g$, $-OP(O)(OR^g)_2$; $-OCH_3$, $-(CR^g_2)_mCN$, substituted aryl, and substituted heteroaryl;
$R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group;
$R^h$, at each occurrence, is independently selected from the group consisting of hydrogen, alkyl, cycloalkyl, heterocyclyl, aryl, heteroaryl, an oxygen protecting group, and a nitrogen protecting group; and
q, at each occurrence, is independently 2 or 3.

2. The redox flow battery of claim 1, wherein the viologen has formula (VI-a):

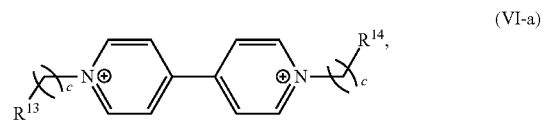

or a salt thereof, wherein:
$R^{13}$ is selected from the group consisting of $-N(R^g)_q$, $-S(O)_q$, $-PO_3$, $-S(O)_qR^g$, $-(OCH_2CH_2)_m-OCH_3$, and substituted aryl;
$R^{14}$ is selected from the group consisting of $-CH_3$, $-S(O)_q$, $-PO_3$, $-S(O)_qR^g$, $-(OCH_2CH_2)_m-OCH_3$, and substituted aryl;
$R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group;
$R^h$, at each occurrence, is independently selected from the group consisting of hydrogen, alkyl, cycloalkyl, heterocyclyl, aryl, heteroaryl, an oxygen protecting group, and a nitrogen protecting group;
q, at each occurrence, is independently 2 or 3; and
c, at each occurrence, is independently 0, 1, 2 or 3.

3. The redox flow battery of claim 1, wherein the viologen has formula (VI-b):

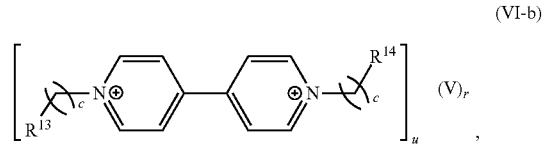

wherein:
$R^{13}$ is selected from the group consisting of $-N(R^g)_q$, $-S(O)_q$, $-PO_3$, $-S(O)_qR^g$, $-(OCH_2CH_2)_m-OCH_3$, and substituted aryl;
$R^{14}$ is selected from the group consisting of $-CH_3$, $-S(O)_q$, $-PO_3$, $-S(O)_qR^g$, $-(OCH_2CH_2)_m-OCH_3$, and substituted aryl;
$R^g$, at each occurrence, is independently selected from the group consisting of hydrogen, alkyl, cycloalkyl, heterocyclyl, aryl, heteroaryl, alkyl-$N(R^h)_q$, alkyl-$S(O)_q$, an oxygen protecting group, and a nitrogen protecting group;
$R^h$, at each occurrence, is independently selected from the group consisting of hydrogen, alkyl, cycloalkyl, heterocyclyl, aryl, heteroaryl, an oxygen protecting group, and a nitrogen protecting group;
V, at each occurrence, is independently Na⁺, K⁺, Li⁺, $NR^i_4{}^+$, F⁻, Cl⁻, Br⁻, I⁻, $SO_4{}^{2-}$, OH⁻, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, CN⁻, $N(CN)_2{}^-$, SCN⁻ or a combination thereof;
$R^i$, at each occurrence, is independently selected from the group consisting of hydrogen, alkyl, cycloalkyl, heterocyclyl, aryl, and heteroaryl;
q, at each occurrence, is independently 2 or 3;
r is 1, 2, 3 or 4;
u is 1, 2, 3 or 4; and
c, at each occurrence, is independently 0, 1, 2 or 3.

4. The redox flow battery of claim 3, wherein:

$R^{13}$ is $SO_3^-$, —$(OCH_2CH_2)_m$—$OCH_3$, or substituted aryl;

$R^{14}$ is $SO_3^-$, —$(OCH_2CH_2)_m$—$OCH_3$, or substituted aryl;

V, at each occurrence, is independently $Na^+$, $K^+$, $Cl^-$, $Br^-$ or a combination thereof;

r is 2, 3 or 4;

u is 1; and c, at each occurrence, is independently 1, 2 or 3.

5. The redox flow battery of claim 1, wherein the viologen is selected from the group consisting of

,

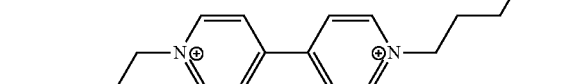,

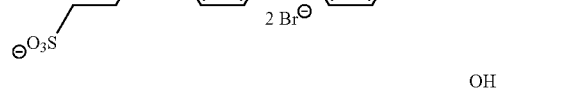,

,

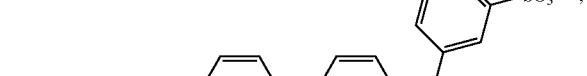,

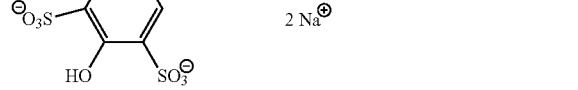,

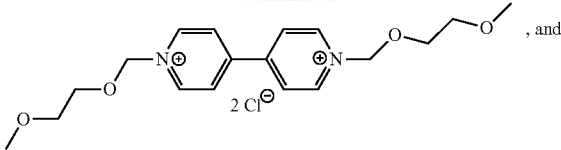, and

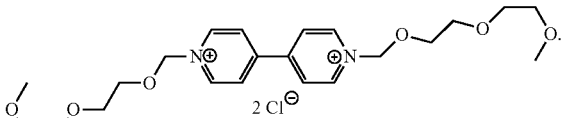.

6. The redox flow battery of claim 1, wherein the viologen has formula (VII):

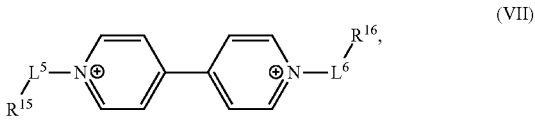

or a salt thereof, wherein:

$L^5$ and $L^6$ are each independently selected from the group consisting of bond, $C_1$-$C_{12}$ alkylenyl, $C_1$-$C_{12}$ alkenylenyl, $C_1$-$C_{12}$ alkynylenyl; and $C_1$-$C_4$ alkylenyl-$(OCH_2CH_2)_j$, $R^{15}$ and $R^{16}$ are each independently selected from the group consisting of $OR^j$, —$C(O)OR^j$, —$S(O)_j$, —$PO_3$, —$S(O)_j$ $R^j$, —$S(O)_jOR^j$, —$OP(O)(OR^j)_2$, —$(CR^j_2)_j$ CN, substituted aryl, and substituted heteroaryl;

$R^j$, at each occurrence, is independently selected from the group consisting of alkyl-$S(O)_j$, and an oxygen protecting group; and j, at each occurrence, is independently 2 or 3.

7. The redox flow battery of claim 6, wherein the viologen is selected from the group consisting of

, and

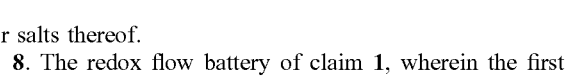, or salts thereof.

8. The redox flow battery of claim 1, wherein the first redox active material comprises $^-[Fe(CN)_6]^{3+/2+}$, $I_3^-/I^-$, $Br_2/Br^-$, $S_4^-/S_2^-$, KBr, NaBr, $NH_4Br$, KI, NaI, $NH_4I$, $FeCl_2$, $FeBr_2$, $Ce^{4+/3+}$, $Mn^{3+/2+}$, $PbO_2/PbSO_4$, quinines, anthraxquinines, $K_4[Fe(CN)_6]$, $N_4[Fe(CN)_6]$, $(NH_4)_4[Fe(CN)_6]$, $V^{5+/4+}$, (2,2,6,6-Tetramethylpiperidin-1-yl)oxyl (TEMPO), a derivative of TEMPO, or a combination thereof.

9. The redox flow battery of claim 8, wherein the derivative of TEMPO has formula (VIII-a):

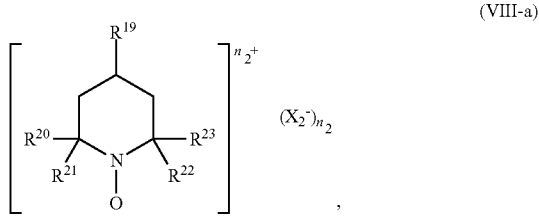

(VIII-a)

wherein:
$R^{19}$, $R^{20}$, $R^{21}$, $R^{22}$ and $R^{23}$ are each independently selected from the group consisting of hydrogen, halogen, alkyl, cycloalkyl, heterocyclyl, aryl, heteroaryl, —CN, —$NO_2$, —$OR^k$, —$SR^k$, -alkyl-$N(R^k)_w$, —$N(R^k)_w$, —$C(O)R^k$, —$C(O)OR^k$, —$S(O)_w R^k$, —$S(O)_w OR^k$, and —$OP(O)(OR^k)_2$;
$R^k$, at each occurrence, is independently selected from the group consisting of hydrogen, alkyl, cycloalkyl, heterocyclyl, aryl, heteroaryl, alkyl-$N(R^l)_w$, an oxygen protecting group, and a nitrogen protecting group;
$R^l$, at each occurrence, is independently selected from the group consisting of hydrogen, alkyl, cycloalkyl, heterocyclyl, aryl, heteroaryl, an oxygen protecting group, and a nitrogen protecting group;
$X_2^-$ is $Cl^-$, $Br^-$, $I^-$, $SO_4^{2-}$, —$NO_3^-$ or a combination thereof;
$n_2$ is 1, 2, 3, 4, or 5; and
w, at each occurrence, is independently 2 or 3.

10. The redox flow battery of claim 8, wherein the derivative of TEMPO has formula (VIII-b):

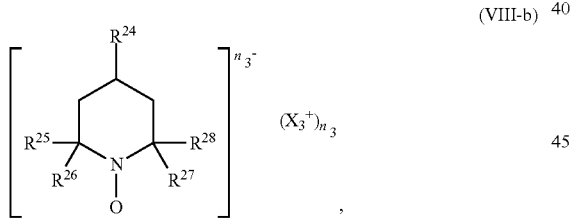

(VIII-b)

wherein:
$R^{24}$, $R^{25}$, $R^{26}$, $R^{27}$ and $R^{28}$ are each independently selected from the group consisting of hydrogen, halogen, alkyl, cycloalkyl, heterocyclyl, alkylaryl, aryl, heteroaryl, —CN, —$NO_2$, —$OR^m$, —$SR^m$, -alkyl-N$(R^m)_q$, —$N(R^m)_q$, —$C(O)R^m$, —$C(O)OR^m$, —$S(O)_q R^m$, —$S(O)_q OR^m$, and —$OP(O)(OR^m)_2$;
$R^m$, at each occurrence, is independently selected from the group consisting of hydrogen, alkyl, cycloalkyl, heterocyclyl, aryl, heteroaryl, alkyl-$N(R^n)_q$, an oxygen protecting group, and a nitrogen protecting group;
$R^n$, at each occurrence, is independently selected from the group consisting of hydrogen, alkyl, cycloalkyl, heterocyclyl, aryl, heteroaryl, an oxygen protecting group, and a nitrogen protecting group;
$X_3^+$ is $H^+$, $Li^+$, $Na^+$, $K^+$, $NH_4^+$ or a combination thereof;
$n_3$ is 1, 2, 3, 4, or 5; and
w, at each occurrence, is independently 2 or 3.

11. The redox flow battery of claim 8, wherein the derivative of TEMPO is selected from the group consisting of 4-trimethylammonium-(2,2,6,6-Tetramethylpiperidin-1-yl)oxy (4-$N^{Me}$-TEMPO), 4-dimethyl(propyl-3-N,N,N,-trimethylammonium)-(2,2,6,6-Tetramethylpiperidin-1-yl)oxy ((4-$N^{NPr}$-TEMP 0), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-S03-TEMPO), 4-amino-(2,2,6,6-Tetramethylpiperidin-1-yl)oxy (4-$NH_2$-TEMPO), and a combination thereof.

12. The redox flow battery of claim 1, further comprising:
a first aqueous electrolyte;
a second aqueous electrolyte; and
a separator between the first and second aqueous electrolytes.

13. The redox flow battery of claim 1, wherein the second redox active material is present in the second aqueous electrolyte at a concentration of ≥0.1 M.

14. The redox flow battery of claim 12, further comprising a first electrode in contact with the first aqueous electrolyte and a second electrode in contact with the second aqueous electrolyte.

15. The redox flow battery of claim 12, wherein the separator is a porous separator.

16. The redox flow battery of claim 12, wherein the separator is an anion exchange membrane or a cation exchange membrane.

17. The redox flow battery of claim 12, wherein the first and second aqueous electrolytes each independently comprise a salt having the formula (IV):

A-B (IV), wherein:
A is $Na^+$, $K^+$, $Li^+$, $NR^c_4{}^+$, pyridinium, pyrrolidium, or imidazolium;
$R^c$, at each occurrence, is independently selected from the group consisting of hydrogen, alkyl, cycloalkyl, heterocyclyl, aryl, and heteroaryl; and
B is halide anion, $SO_4^{2-}$, $OH^-$, $CO_3^{2-}$, $ClO_4^-$, $H_2PO_4^-$, $HPO_4^{2-}$, $PO_4^{3-}$, $NO_3^-$, $N_3^-$, $CN^-$, —$N(CN)_2^-$, or $SCN^-$.

18. The redox flow battery of claim 12, wherein the first and second electrolytes each independently comprise NaCl, KCl, or $NH_4Cl$.

19. The redox flow battery of claim 18, wherein the first and second aqueous electrolytes each independently comprise between about 0.5 M to about 5 M NaCl, KCl, or $NH_4Cl$.

20. The redox flow battery of claim 12, further comprising:
a first circulation loop comprising a first storage tank containing the first aqueous electrolyte, piping for transporting the first aqueous electrolyte, a chamber in which the first electrode is in contact with the first aqueous electrolyte, and a pump to circulate the first aqueous electrolyte through the first circulation loop;
a second circulation loop comprising a second storage tank containing the second aqueous electrolyte, piping for transporting the second aqueous electrolyte, a chamber in which the second electrode is in contact with the second aqueous electrolyte, and a pump to circulate the second aqueous electrolyte through the second circulation loop; and
control hardware and software.

21. A method of storing energy, comprising applying a potential difference across the first and second electrode of the redox flow battery of claim 14, wherein the first redox active material is oxidized.

22. A method of releasing energy, comprising applying a potential difference across the first and second electrode of the redox flow battery of claim 14, wherein the first redox active material is reduced.

* * * * *